United States Patent
Sheng et al.

(10) Patent No.: US 12,404,336 B2
(45) Date of Patent: *Sep. 2, 2025

(54) BISPECIFIC ANTAGONIST COMPRISING A LAG-3 BINDING DOMAIN

(71) Applicant: GENSUN BIOPHARMA, INC., Newbury Park, CA (US)

(72) Inventors: Jackie Sheng, Thousand Oaks, CA (US); Margaret Karow, Santa Rosa Valley, CA (US); Wei Zhang, Thousand Oaks, CA (US)

(73) Assignee: GENSUN BIOPHARMA, INC., Newbury Park, CA (US)

( * ) Notice: Subject to any disclaimer, the term of this patent is extended or adjusted under 35 U.S.C. 154(b) by 259 days.

This patent is subject to a terminal disclaimer.

(21) Appl. No.: 18/306,562

(22) Filed: Apr. 25, 2023

(65) Prior Publication Data

US 2023/0331857 A1    Oct. 19, 2023

Related U.S. Application Data

(63) Continuation of application No. 16/795,804, filed on Feb. 20, 2020, now Pat. No. 11,667,716, which is a continuation of application No. 16/457,421, filed on Jun. 28, 2019, now Pat. No. 10,597,453.

(60) Provisional application No. 62/823,989, filed on Mar. 26, 2019, provisional application No. 62/691,658, filed on Jun. 29, 2018.

(51) Int. Cl.
| | |
|---|---|
| C07K 16/28 | (2006.01) |
| A61P 35/00 | (2006.01) |
| C07K 14/00 | (2006.01) |
| C07K 14/71 | (2006.01) |
| C07K 16/22 | (2006.01) |
| C07K 16/46 | (2006.01) |
| A61K 39/00 | (2006.01) |

(52) U.S. Cl.
CPC .......... *C07K 16/2863* (2013.01); *A61P 35/00* (2018.01); *C07K 14/00* (2013.01); *C07K 14/71* (2013.01); *C07K 16/22* (2013.01); *C07K 16/2803* (2013.01); *C07K 16/2818* (2013.01); *C07K 16/2827* (2013.01); *C07K 16/468* (2013.01); *A61K 2039/505* (2013.01); *C07K 2317/31* (2013.01); *C07K 2317/565* (2013.01); *C07K 2317/622* (2013.01); *C07K 2317/64* (2013.01); *C07K 2317/76* (2013.01); *C07K 2317/92* (2013.01); *C07K 2318/10* (2013.01); *C07K 2319/30* (2013.01); *C07K 2319/32* (2013.01)

(58) Field of Classification Search
None
See application file for complete search history.

(56) References Cited

U.S. PATENT DOCUMENTS

| | | |
|---|---|---|
| 5,837,243 A | 11/1998 | Deo et al. |
| 5,869,046 A | 2/1999 | Presta et al. |
| 5,922,845 A | 7/1999 | Deo et al. |
| 6,054,287 A | 4/2000 | Carter et al. |
| 6,054,297 A | 4/2000 | Carter et al. |
| 6,111,090 A | 8/2000 | Gorman et al. |
| 6,121,022 A | 9/2000 | Presta et al. |
| 6,365,157 B2 | 4/2002 | Rockwell et al. |
| 6,376,653 B1 | 4/2002 | Holmes et al. |
| 6,448,077 B1 | 9/2002 | Rockwell et al. |
| 6,528,959 B2 | 3/2003 | Kitano et al. |
| 6,582,959 B2 | 6/2003 | Kim |
| 6,703,020 B1 | 3/2004 | Thorpe et al. |
| 6,884,879 B1 | 4/2005 | Baca et al. |
| 7,025,962 B1 | 4/2006 | Gorman et al. |
| 7,025,982 B2 | 4/2006 | Gorman et al. |
| 7,060,269 B1 | 6/2006 | Baca et al. |
| 7,060,289 B2 | 6/2006 | Baca et al. |
| 7,067,637 B1 | 6/2006 | Hotten et al. |
| 7,138,370 B2 | 11/2006 | Oliner et al. |
| 7,169,901 B2 | 1/2007 | Baca et al. |
| 7,182,135 B2 | 2/2007 | Szarka |
| 7,227,004 B2 | 6/2007 | Kim |
| 7,297,334 B2 | 11/2007 | Baca et al. |
| 7,338,660 B2 | 3/2008 | Bedian et al. |
| 7,365,166 B2 | 4/2008 | Baca et al. |
| 7,484,654 B2 | 2/2009 | Jones et al. |
| 7,498,414 B2 | 3/2009 | Zhu |
| 7,521,053 B2 | 4/2009 | Oliner |
| 7,527,791 B2 | 5/2009 | Adams et al. |
| 7,575,893 B2 | 8/2009 | Simmons |
| 7,579,186 B1 | 8/2009 | Sakamoto et al. |
| 7,618,632 B2 | 11/2009 | Collins et al. |
| 7,619,069 B2 | 11/2009 | Davies et al. |

(Continued)

FOREIGN PATENT DOCUMENTS

| | | |
|---|---|---|
| EP | 0090505 | 2/1984 |
| EP | 0 920 505 | 6/2008 |

(Continued)

OTHER PUBLICATIONS

Hinton, et al., 2004. J. Biol. Chem. 279(8): 6213-6216.

(Continued)

*Primary Examiner* — Laura B Goddard

(74) *Attorney, Agent, or Firm* — Michael Ye; Kalos Athena Wang PLLC

(57) ABSTRACT

Antitumor antagonists that bind specifically to immune checkpoint regulator are disclosed. Also disclosed is a method of treating proliferative disorders with the antitumor antagonists.

20 Claims, 50 Drawing Sheets

Specification includes a Sequence Listing.

(56) References Cited

U.S. PATENT DOCUMENTS

| | | | |
|---|---|---|---|
| 7,658,924 | B2 | 2/2010 | Oliner et al. |
| 7,691,977 | B2 | 4/2010 | Fuh et al. |
| 7,758,859 | B2 | 7/2010 | Fuh et al. |
| 7,811,785 | B2 | 10/2010 | Fuh et al. |
| 7,812,135 | B2 | 10/2010 | Smith et al. |
| 8,030,025 | B2 | 10/2011 | Boone et al. |
| 8,367,805 | B2 | 2/2013 | Chamberlain et al. |
| 8,388,967 | B2 | 3/2013 | Smith et al. |
| 8,475,798 | B2 | 7/2013 | Patti et al. |
| 8,574,577 | B2 | 11/2013 | Barbas, III |
| 8,581,886 | B2 | 11/2013 | Ponath et al. |
| 8,586,023 | B2 | 11/2013 | Shiku et al. |
| 8,591,886 | B2 | 11/2013 | Ponath et al. |
| 8,992,913 | B2 | 3/2015 | Mader et al. |
| 9,079,965 | B2 | 7/2015 | Zhou et al. |
| 9,200,079 | B2 | 12/2015 | Chamberlain et al. |
| 9,764,038 | B2 | 9/2017 | Dennler et al. |
| 9,890,204 | B2 | 2/2018 | Brinkmann et al. |
| 9,987,500 | B2 | 6/2018 | Papadopoulos et al. |
| 10,112,997 | B2 | 10/2018 | Gurney et al. |
| 10,189,902 | B2 | 1/2019 | Maurer et al. |
| 2003/0190317 | A1 | 10/2003 | Baca et al. |
| 2003/0203409 | A1 | 10/2003 | Kim |
| 2003/0206899 | A1 | 11/2003 | Ferrara et al. |
| 2005/0186208 | A1 | 8/2005 | Fyfe et al. |
| 2006/0009360 | A1 | 1/2006 | Pifer et al. |
| 2006/0280747 | A1 | 12/2006 | Fuh et al. |
| 2007/0020267 | A1 | 1/2007 | Fuh et al. |
| 2007/0059312 | A1 | 3/2007 | Baca et al. |
| 2007/0141065 | A1 | 6/2007 | Fuh et al. |
| 2011/0217318 | A1 | 9/2011 | Takayama et al. |
| 2013/0022601 | A1 | 1/2013 | Brinkmann et al. |
| 2013/0078248 | A1 | 3/2013 | Gschwind et al. |
| 2013/0259859 | A1 | 10/2013 | Ott et al. |
| 2014/0243505 | A1 | 8/2014 | Zhou et al. |
| 2014/0308285 | A1 | 10/2014 | Yan et al. |
| 2014/0356385 | A1 | 12/2014 | Dennler et al. |
| 2015/0197578 | A1 | 7/2015 | Thurston |
| 2015/0225483 | A1 | 8/2015 | Lo |
| 2015/0337033 | A1 | 11/2015 | Kim et al. |
| 2016/0355589 | A1 | 12/2016 | Williams et al. |
| 2017/0044256 | A1 | 2/2017 | Grogan et al. |

FOREIGN PATENT DOCUMENTS

| | | | |
|---|---|---|---|
| EP | 1947183 | | 7/2008 |
| EP | 1866338 | | 5/2013 |
| EP | 1888339 | | 5/2013 |
| WO | 98/023289 | | 6/1998 |
| WO | 99/20758 | | 4/1999 |
| WO | 99/40196 | | 8/1999 |
| WO | 9940198 | | 8/1999 |
| WO | 2001/03720 | | 1/2001 |
| WO | 2005/007190 | | 1/2005 |
| WO | 12005055808 | | 6/2005 |
| WO | 2005/115451 | | 12/2005 |
| WO | 2005/055808 | | 6/2006 |
| WO | 2006/083289 | | 8/2006 |
| WO | 2007/133822 | | 11/2007 |
| WO | 2010/003118 | | 1/2010 |
| WO | 2011/028683 | | 3/2011 |
| WO | 2011/051728 | | 5/2011 |
| WO | 2011051726 | | 5/2011 |
| WO | 2011/090754 | | 7/2011 |
| WO | 2013/039954 | | 3/2013 |
| WO | 2014/062659 | | 4/2014 |
| WO | 2016073282 | | 5/2016 |
| WO | 2016191643 | | 12/2016 |
| WO | WO-2016200782 | A1 * | 12/2016 ............. A61P 31/04 |
| WO | 2017/161976 | | 9/2017 |
| WO | 2017218707 | | 12/2017 |
| WO | 2005/1115451 | | 7/2018 |
| WO | 2018128939 | | 7/2018 |

OTHER PUBLICATIONS

Hinton, et al. 2006 Journal of Immunology 176:346-356.
Shields, et al. (2001) J. Biol. Chem., 276(9):6591-6604.
Dall'Acqua, et al. (2002) J. Immunol., 169:5171-5180.
Dall'Acqua, et al. (2006) J. Biol. Chem., 281:23514-23524.
Yeung, et al. (2009) J. Immunol. 182:7663.
Zalevsky, et al. (2010) Nat. Biotechnol. 28:167.
Petkova, et al. (2006) Int. Immunol. 18:1759.
Joller, et al. (2014) Immunity 40:569.
Johnston, et al. (2014) Cancer Cell 26:923.
He, et al. (2004) J. Immunol. 173:4919-28.
Dranoff, et al. (1993) Proc. Natl. Acad. Sci. U.S.A. 90:3538-43.
Rosenberg, S.A. (1999). A new era for cancer immunotherapy based on the genes that encode cancer antigens. Immunity, 10(3), 281-287.
Kim, et al. (1994) Science 266: 2011-2013.
Karyampudi L., et al. (2014) Cancer Res 74:2974-2985.
Nestle, et al. (1998) Nature Medicine 4:328-332.
Kugler, et al. (2000) Nature Medicine 6:332-336.
Mokyr, et al. (1998) Cancer Research 58: 5301-5304.
Weinberg, et al. (2000) Immunol. 164: 2160-2169.
Melero, et al. (1997) Nature Medicine 3: 682-685.
Hulloff, et al. (1999) Nature 397: 262-266.
Greenberg & Riddell 99 Science 286: 546-51.
Thompson R H et al., Cancer Res 2008, 66(7):3381.
Blood 2009 114(8):1537.
Le Mercier, et al. (2015) Front. Immunol., (6). Article 418.
Kyi, et al. FEBS Letters, 588:368-376 (2014).
Tansey, M.G., et al. (2009) Drug Discovery Today, 14(23-24):1082-1088. Abstract.
128 Wranik, et al., J Biol. Chem., 287(5):43331-43339, 2012.
Ridge, et al. (1998) Nature 393: 474-478.
International Searching Report and The Written Opinion of the International Searching Authority, mail date Nov. 21, 2019, issued in International Application No. PCT/US19/3999.
European Patent Office Search report; PCT/US2019/039994; mail date Jun. 13, 2022.
Ahmadzadeh, M. et al., "Tumor antigen-specific CD8 T cells infiltrating the tumor express high levels of PD-1 and are functionally impaired", Blood, Aug. 20, 2009, 114(8):1537.
Dall'Acqua, et al., "Increasing the Affinity of a Human IgG1 for the Neonatal Fc Receptor: Biological Consequences", The Journal of Immunology, 2002, 169:5171-5180.
Dall'Acqua, et al., "Properties of Human IgG1s Engineered for Enhanced Binding to the Neonatal Fc Receptor (FoRn)", Journal of Biological Chemistry, 2006, 281:23514-23524.
Dranoff, G, et al., "Vaccination with irradiated tumor cells engineered to secrete murine granulocyte-macrophage colony-stimulating factor stimulates potent, specific, and long-lasting anti-tumor immunity", Proc. Natl. Acad. Sci. U.S.A., Apr. 15, 1993, 90(8):3539-3543.
Greenberg, P.D., et al., "Deficient Cellular Immunit-Finding and Fixing the Defects", Science Jul. 23, 1999, 23:285 (546-651).
Harlow, E., et al, "Antibodies, A Laboratory Manual", (1988), Cold Spring Harbor Publications, New York.
He, Y., et al., "Blocking Programmed Death-1 Ligand-PD-1 Interactions by Local Gene Therapy Results in Enhancement of Antitumor Effect of Secondary Lymphoid Tissue Chemokine", The Journal of Immunology, 2004, 173:4919-4928.
Hinton, et al., "An Engineered Human IgG1 Antibody with Longer Serum Half-Life", Journal of Immunology, 2006, 176:346-356.
Hinton, et al., "Engineered Human IgG Antibodies with Longer Serum Half-lives in Primates", Journal of Biological Chemistry, 2004, 279(8): 6213-6216.
Hutloff, A., et el., "ICOS is an inducible T-cell co-stimulator structurally and functionally related to CD28", Nature, Jan. 21, 1999, 397:263-266.
International Search Report and Written Opinion of the International Searching Authority issued on May 10, 2018 in PCT Application No. PCT/US17/69072.
Karyampudi, L., et al., "Accumulation of memory precursor CD8 T cells in regressing tumors following combination therapy with vaccine and anti-PD-1 antibody", Jun. 2014, 74:2974-2985.

(56) References Cited

OTHER PUBLICATIONS

Kim, N.W., et al., "Specific Association of Human Telomerase Activity with Immortal Cells and Cancer", Dec. 1994, vol. 266, pp. 2011-2013.

Kugler, A., et al., "Regression of human metastatic renal cell carcinoma after vaccination with tumor cell-dendrite cell hybrids", Nature Medicine, Mar. 6, 2000, 3:332-336.

Kyi, C., et al., "Checkpoint ocking antibodies in cancer otherapy", FEBS Letters, 2014, 588:368-376.

Le Mercier, L, et al., "Beyond CTLA-4 and PD-1, the Generation Z of Negative Checkpoint Regulators", Front. Immunol., Aug. 2015, (6), Article 418.

Lo, B.K.C., "Antibody engineering: Methods and Protocols, Methods in molecular biology", (2004) vol. 248. Humana Press, Clifton, N.J.

Melero, I., et al., "Monoclonal antibodies against the 4-1 BB T-cell activation molecule eradicate established tumors", Nature Medicine, Jun. 1997, 3(6):682-685.

Mokyr, M.B., et al., Relization of the Therapeutic Potantiai of CTLA-4 Blockage in Low-Dose Chemotherpahy-treated Tumor-bearinq Mice Cancer Research (1998), 58:5304-5304.

Nestle, F.O., et al., "Vaccination of mel anoma patients with peptide-or tumor lysate-pulsed dendritic cells", Nature Medicine, Mar. 1998, (3):328-332.

Petkova, S.B., et al., "Enhanced half-life of genetically engineered human IgG1 antibodies in a humanized FcRn mouse model: potential application in humorally mediated autoimmune disease", Int. Immunol., Dec. 2006, 18(12):1759-1769.

Ridge, J.P., et al., "A conditioned dendritic cell can be a temporal bridge between a CD4+ T-helper and a T-killer cell" Nature, Jun. 4, 1998, 393:474-478.

Rosenberg, S.A., et al., "A New Era for Cancer Immunotherapy Based on the Genes that Encode Cancer Antigens", Immunity, Mar. 1999, vol. 10, pp. 281-287.

Shields, et al., "High Resolution Mapping of the Binding Site on Human IgG1 for FcyRI, FcyRII, FcyRIII, and FcRn and Design of IgG1 Variants with Improved Binding to the FcyR", Journal of Biological Chemistry, 2001, 276(9):6591-6604.

Tansey, M.G., et al., "The TNF superfamily in 2009: new pathways, new indications, and new drugs". Drug Discovery Today, Dec. 2009, 14(23-24):1082-1088.

Thompson, R.H., et al., "Tumor B7-H1 Is Associated with Poor Prognosis in Renal Cell Carcinoma with Long-term Follow-up", (2006), 66(7):3381.

Weinberg, A.D., et al., "Engagement of the OX-40 receptor in vivo e chances antitumor immunity", Journal of Immunology, Feb. 15, 2000, 15:164(4):2160-2169.

Wranik, et al., "LUZ-Y, a Novel Platform for the Mammalian Cell Production of Full-length IgG-bispecific Antibodies", Journal of Biological Chemistry, 2012, 287(52):43331-43339.

Yeung, et al., "Engineering Human IgG1 Affinity to Human Neonatal Fc Receptor: Impact of Affinity Improvement of Pha Primates", The Journal of Immunology, 2009, 182:7663.

Zalevsky, J. et al., "Enhanced antibody life improves in vivo activity", Nat. Biotechnol., Feb. 2010, 28 (2):157-159.

U.S. Appl. No. 18/306,562, filed Apr. 25, 2023, Pending.
U.S. Appl. No. 16/795,804, filed Feb. 20, 2020, Pending.
U.S. Appl. No. 16/457,421, filed Jun. 28, 2019, Patented.

* cited by examiner

Anti-TIGIT mab sequences

| Mab | Heavy Chain CDR1 | | Heavy Chain CDR2 | | Heavy Chain CDR3 | |
|---|---|---|---|---|---|---|
| T-01 | SDYAWN | (SEQ ID:1) | YISYSGSTGYNPSLKS | (SEQ ID:2) | RMIGYAMDY | (SEQ ID:3) |
| T-02 | SDYAWN | (1) | YITYSGGTSYNPSLKS | (SEQ ID:4) | RQIGLGFTY | (SEQ ID:5) |
| T-03 | DHTIH | (SEQ ID:6) | YFYPRDGSTKYNEKFKG | (SEQ ID:7) | GMLRWFAD | (SEQ ID:8) |
| T-04 | DHTIH | (6) | YIYPRDGSSKYNVKFKG | (SEQ ID:9) | GMLRWFAY | (SEQ ID:10) |
| T-05 | DQAIH | (SEQ ID:11) | YIYPRDGSTKYNETFKG | (SEQ ID:12) | GMLRWFAY | (10) |
| T-06 | SDYAWN | (1) | YITYSGSTSYNPSLKS | (SEQ ID:13) | RQVGLGFAY | (SEQ ID:14) |
| T-07 | SDSAWN | (SEQ ID:15) | YITYSGSTNYNPSLRS | (SEQ ID:16) | RQVGLGFAY | (14) |
| T-08 | NYGMN | (SEQ ID:17) | WINTYTGEPTYADDFKG | (SEQ ID:18) | APPYGVDVRFAY | (SEQ ID:19) |
| T-09 | TFAMGVG | (SEQ ID:20) | HIWWDDDKYNPALKS | (SEQ ID:21) | MDYSYFAWFAY | (SEQ ID:22) |
| T-10 (B21-35) | SYYMH | (SEQ ID:23) | INPSGGRTSYAQMFQG | (SEQ ID:24) | DREEQWPVGGFDY | (SEQ ID:25) |

| Mab | Light Chain CDR1 | | Light Chain CDR2 | | Light Chain CDR3 | |
|---|---|---|---|---|---|---|
| T-01 | KASQDVSTVA | (SEQ ID:26) | SASYRYT | (SEQ ID:27) | QQHYSTPWT | (SEQ ID:28) |
| T-02 | KASQDLSTAVA | (SEQ ID:29) | SSSYRYT | (SEQ ID:30) | QQHYSTPWT | (28) |
| T-03 | KASQDVSTTVA | (SEQ ID:31) | SASYRYT | (27) | QQHYSTPLT | (SEQ ID:32) |
| T-04 | KASQDVFTAVA | (SEQ ID:33) | SASYRYT | (27) | QQHYSIPLT | (SEQ ID:34) |
| T-05 | KASQDVSTAVA | (SEQ ID:35) | SASYRYT | (27) | QQHYSTPLT | (32) |
| T-06 | KASQDVSTAVA | (35) | SASYHYT | (SEQ ID:36) | QQHYSTPWT | (28) |
| T-07 | KASQDVSTAVA | (35) | SASYRFT | (SEQ ID:37) | QHHYSTPWT | (SEQ ID:38) |
| T-08 | RSSQSIVHSNGNTYLE | (SEQ ID:39) | KVSDRFS | (SEQ ID:40) | FQGSHVPWT | (SEQ ID:41) |
| T-09 | RSSTGAVTTSNYAN | (SEQ ID:42) | GTNNRAP | (SEQ ID:43) | ALWYSNHWV | (SEQ ID:44) |
| T-10 | RASQSIKRYLN | (SEQ ID:45) | SASNLQS | (SEQ ID:46) | QQSYIIPPT | (SEQ ID:47) |

FIG. 1

Anti-TIGIT Antibody Variable Domain Sequences

T-01
VH (SEQ ID NO: 48)
QVQLQESGPGLVKPSQTLSLTCTVSGYSITSDYAWNWIRQPPGKGLEWIGYISYSGSTGY
NPSLKSRVTISVDTSKNQFSLKLSSVTAADTAVYYCARRMIGYAMDYWGQGTSVTVSS

VL (SEQ ID NO: 49)
DIQMTQSPSSLSASVGDRVTITCKASQDVSTVVAWHQQKPGKAPKLLIYSASYRYTGVP
SRFSGSGSGTDFTLTISSLQPEDFATYYCQQSYSTPQQHYSTPWTFGGGTKLEIKR

T-02
VH (SEQ ID NO: 50)
QVKLQESGPGLVKPSQTLSLTCTVTGYSITSDYAWNWIRQPPGKGLEWIGYITYSGGTSY
NPSLKSRVTISVDTSKNQFSLKLSSVTAADTAVYSCARRQIGLGFTYWGQGTLVTVSA

VL (SEQ ID NO: 51)
DIQMTQSPSSLSASVGDRVTIPCKASQDLSTAVAWYQQKPGKAPKLLIYSSSYRYTGVPS
RFSGSGSGTDFTLTISSLQPEDFATYYCQQSYSTPQQHYSTPWTFGEGTKLEIK

T-03
VH (SEQ ID NO: 52)
EVQLVQSGAEVKKPGATVKISCKVSGYTFTDHTIHWVQQAPGKGLEWMGYFYPRDGST
KYNEKFKGRVTITADTSTDTAYMELSSLRSEDTAVYYCATGMLRWFADWGQGTLITVS
VA

VH (SEQ ID NO: 53)
DIQMTQSPSSLSASVGDRVTITCKASQDVSTTVAWYQQKPGKAPKLLIYSASYRYTGVP
SRFSGSGSGTDFTLTISSLQPEDFATYYCQQHYSTPLTFGAGTKLELK

*FIG. 2A*

T-04
VH (SEQ ID NO: 54):
EVQLVQSGAEVKKPGATVKISCKVSGYTFTDHTIHWVQQAPGKGLEWMGYIYPRDGSS
KYNVKFKGRVTITADTSTDTAYMELSSLRSEDTAVYYCATGMLRWFAYWGQGTLVTV
SS

VL (SEQ ID NO: 55):
DIQMTQSPSSLSASVGDRVTITCKASQDVFTAVAWYQQKPGKAPKLLIYSASYRYTGVP
SRFSGSGSGTDFTFTISSLQPEDIATYYCQQHYSIPLTFGAGTKLEIK

T-05
VH (SEQ ID NO: 56):
EVQLKQSGAEVKKPGATVKISCKVSGYTFTDQAIHWVQQAPGKGLEWMGYIYPRDGST
KYNETFKGRVTITADTSTDTAYMELSSLRSEDTAVYFCARGMLRWFAYWGQGTLVTVS
S

VL (SEQ ID NO: 57):
DIQMTQSPSSLSASVGDRVTITCKASQDVSTAVAWYQQKPGKAPKLLIYSASYRYTGVP
SRFSGSGSGTDFTLTISSLQPEDFATYYCQQHYSTPLTFGAGTKLELK

T-06
VH (SEQ ID NO: 58):
QVQLQESGPGLVKPSQTLSLTCTVSGGSVSSDYAWNWIRQPPGKGLEWIGYITYSGSTS
YNPSLKSRVTISVDTSKNQFSLKLSSVTAADTAVYYCARRQVGLGFAYWGQGTLVTVS
A

VL (SEQ ID NO: 59):
DIQMTQSPSSLSASVGDRVTITCKASQDVSTAVAWYQQKPGKAPKLLIYSASYHYTGVP
SRFSGSGSGTDFTLTISSLQPEDFATYYCQQHYSTPWTFGGGTKLEIK

T-07
VH (SEQ ID NO: 60):
EVQLQESGPGLVKPSDTLSLTCAVSGYSITSDSAWNWIRQPPGKGLEWIGYITYSGSTNY
NPSLRSRVTMSVDTSKNQFSLKLSSVTAVDTAVYYCTRRQVGLGFAYWGQGTLVTVSA

VL (SEQ ID NO: 61):
DIQMTQSPSSLSASVGDRVTITCKASQDVSTAVAWYQQKPGKAPKLLIYSASYRFTGAP
SRFSGSGSGTDFTLTISSLQPEDFGIYYCQHHYSTPWTFGGGTKLEFK

FIG. 2B

T-08
VH (SEQ ID NO: 62):
QVQLVQSGSELKKPGASVKVSCKASGYTFTNYGMNWVRQAPGQGLEWMGWINTYTG
EPTYADDFKGRFVFSLDTSVSTAYLQISSLKAEDTAVYYCARAPPYGYDVRFAYWGQG
TLVTVSS

VL (SEQ ID NO: 63):
DVVMTQSPLSLPVTLGQPASISCRSSQSIVHSNGNTYLEWFQQRPGQSPRVLIYKVSDRF
SGVPDRFSGSGSGTDFTLKISRVEAEDVGVYYCFQGSHVPWTFGRGTKLEIK

T-09
VH (SEQ ID NO: 64):
QVTLKESGPTLVKPTQTLTLTCTFSGFSLSTFAMGVGWIRQPPGKALEWLAHIWWDDD
KYYNPALKSRLTITKDTSKNQVVLTMTNMDPVDTATYYCARMDYSYFAWFAYWGQG
TLVTVSS

VL (SEQ ID NO: 65):
QAVVTQEPSLTVSPGGTVTLTCRSSTGAVTTSNYANWVQQKPGQLFRGLIGGTNNRAP
WVPARFSGSLIGDKAALTLSGVQPEDEAEYFCALWYSNHWVFGGGTKLTVL

T-10 (B21-35)
VH (SEQ ID NO: 66):
QVQLVQSGAEVKKPGASVKVSCKASGYTFTSYYMHWVRQAPGQGLEWMGIINPSGGR
TSYAQMFQGRVTMTRDTSTSTVYMELSSLRSEDTAVYYCARDREEQWPVGGFDYWGQ
GTLVTVSS

VL (SEQ ID NO: 67):
DIQMTQSPSSLSASVGDRVTITCRASQSIRRYLNWYQQKPGKAPKLLIYSASNLQSGVPS
RFSGSGSGTDFTLTISSLQPEDFATYYCQQSYIIPPTFGQGTKVEIK

FIG. 2C

Anti-PD1 mab sequences

| Mab | Heavy Chain CDR1 | | Heavy Chain CDR2 | | Heavy Chain CDR3 | |
|---|---|---|---|---|---|---|
| PD-01 | NFLMS | (SEQ ID:68) | TISGGGRDTYYVDSVKG | (SEQ ID:69) | RTTYSMDY | (SEQ ID:70) |
| PD-02 | NSYLY | (SEQ ID:71) | GINPSNGGTNFNEKFKT | (SEQ ID:72) | RDYNYDGGFDS | (SEQ ID:73) |
| PD-03 | NSYIY | (SEQ ID:74) | GINPSNGGTNFNEKFKT | (72) | RRDYRYDGGFDS | (SEQ ID:75) |
| PD-04 | NSYIY | (74) | GINPSNGGTNFNEKFKT | (72) | RDYNYDGGFDS | (53) |
| PD-05 (2P16) | TYYIY | (SEQ ID:76) | GINPGNGGTNFNEKFKI | (SEQ ID:77) | RYHGVDGGLDY | (SEQ ID:78) |
| PD-06 (2P17) | SYYIH | (SEQ ID:79) | WIFPGSGNSKYNENFKG | (SEQ ID:80) | SETYDVGDY | (SEQ ID:81) |

| Mab | Light Chain CDR1 | | Light Chain CDR2 | | Light Chain CDR3 | |
|---|---|---|---|---|---|---|
| PD-01 | LASQTIGTWLA | (SEQ ID:82) | AATSLAD | (SEQ ID:83) | QQFYSIPWT | (SEQ ID:84) |
| PD-02 | RASSTLYSNYLH | (SEQ ID:85) | RASFLAS | (SEQ ID:86) | QQGSSIPLT | (SEQ ID:87) |
| PD-03 | SASSSLYSSVLH | (SEQ ID:88) | RASFLAS | (86) | QQGSSIPLT | (87) |
| PD-04 | RASSLYSNYLH | (SEQ ID:89) | RASFLAS | (86) | QQGSSIPLT | (87) |
| PD-05 | RASKSVSTSGFSYIH | (SEQ ID:90) | LASNLES | (SEQ ID:91) | QHTWELPNT | (SEQ ID:92) |
| PD-06 | KASQNVGTNVA | (SEQ ID:93) | SASYRYS | (SEQ ID:94) | QQYYSYPYT | (SEQ ID:95) |

FIG. 3 anti-PD-1 Antibody Variable Domain Sequences

PD-01
VH (SEQ ID NO: 96):
EVQLVESGGGLVQPGGSLRLSCAASGFTFSNFLMSWVRQAPGKGLEWVSTISGGGR
DTYYVDSVKGRFTISRDNSKNTLYLQMNSLRAEDTAVYYCAKRTTYSMDYWGQGT
SVTVSS

VL (SEQ ID NO: 97):
DIQMTQSPSSVSASVGDRVTITCLASQTIGTWLAWYQQKPGKAPKLLIYAATSLADG
VPSRFSGSGSGTDFTLTISSLQPEDFATYYCQQFYSIPWTFGGGTKLEIK

PD-02
VH (SEQ ID NO: 98):
QVQLVQSGAEVKKPGASVKVSCKASDYTFTNSYLYWLRQAPGQGLEWMGGINPSN
GGTNFNEKFKTRTTSTRDTSISTAYMELSRLRSDDTVVYYCTRRDYNYDGGFDSWG
QGTLVTVSS

VL (SEQ ID NO: 99):
DIQMTQSPSSLSASVGDRVTFTCRASSTLYSNYLHWYQQKPGKAPKLLIYRASFLAS
GVPSRFSGSGSGTDFTLTISSLQPEDFATYYCQQGSSIPLTFGGGTKVEIK

PD-03
VH (SEQ ID NO: 100)
QVQLVQSGAEVKKPGASVKVSCKASDYTFTNSYIYWVRQAPGQGLEWMGGINPSN
GGTNFNEKFKTRVTSTRDTSISTAYMELSRLRSDDTVVYYCARRDYRYDGGFDSWG
QGTTLTVSS

VL (SEQ ID NO: 101)
DIQMTQSPSSLSASVGDRVTITCSASSSLYSSYLHWYQQKPGKAPKLLIYRASFLASG
VPSRFSGSGSGTDFTLTISSLQPEDFATYYCQQGSSIPLTFGAGTKLDLK

*FIG. 4A*

PD-04
VH (SEQ ID NO: 102):
QVQLVQSGAEVKKPGASVKVSCKASDYTFTNSYIYWVRQAPGQGLEWMGGINPSN
GGTNFNEKFKTRVTSTRDTSISTAYMELSRLRSDDTVVYYCARRDYNYDGGFDSWG
QGTLVTVSS

VL (SEQ ID NO: 103):
DIQMTQSPSSLSASVGDRVTFTCRASSSLYSNYLHWYQQKPGKAPKLLIYRASFLAS
GVPSRFSGSGSGTDFTLTISSLQPEDFATYYCQQGSSIPLTFGGGTKVEIK

PD-05
VH (SEQ ID NO: 104):
QVQLVQSGAEVKKPGASVKVSCKASGYTFTTYYIYWVRQAPGQGLEWMGGINPGN
GGTNFNEKFKIRVTMTRDTSISTAYMELSSLRSEDTAVYYCARRYHGYDGGLDYWG
QGTLVTVSS

VL (SEQ ID NO: 105):
DIVLTQSPASLAVSPGQRATITCRASKSVSTSGFSYIHWYQQKPGQPPKLLIYLASNLE
SGVPARFSGSGSGTDFTLTINPVEANDTANYYCQHTWELPNTFGGGTKVEIK

PD-06
VH (SEQ ID NO: 106):
QVQLVQSGAEVKKPGASVKVSCKASGYTFTSYYIHWVRQAPGQGLEWMGWIFPGS
GNSKYNENFKGRVTLTADTSTSTVYMELSSLRSEDTAVYYCASETYDYGDYWGQGT
LVTVSS

VL (SEQ ID NO: 107):
DIQMTQSPSFLSASVGDRVTITCKASQNVGTNVAWYQQKPGKAPKALIYSASYRYSG
VPSRFSGSGSGTEFTLTISSLQPEDFATYYCQQYYSYPYTFGQGTKLEIK

*FIG. 4B*

Anti-PD-L1 mab sequences

| Mab | Heavy Chain CDR1 | | Heavy Chain CDR2 | | Heavy Chain CDR3 | |
|---|---|---|---|---|---|---|
| PL-01 | NYWMH | (SEQ ID:108) | MIHPNTNYNYNEKFKS | (SEQ ID:109) | SDYGSSPYYFDY | (SEQ ID:110) |
| PL-02 | SYWMH | (SEQ ID:111) | MIHPNVGSTNYNEKFKS | (SEQ ID:112) | SRYGSSPYYFDY | (SEQ ID:113) |
| PL-03 | SYWMH | (111) | MIHPNSGGNNYNEKFKS | (SEQ ID:114) | SWYGSSPYYFDY | (SEQ ID:115) |
| PL-04 | SYWMH | (111) | MIHPTGVSTDYNEKFKS | (SEQ ID:116) | SDYGSSPYYFDY | (110) |
| PL-05 | SDYAWN | (SEQ ID:117) | YISDSGSTSYNPSLKS | (SEQ ID:118) | SFLRLRSYFDH | (SEQ ID:119) |
| PL-06 | SYGIN | (SEQ ID:120) | CIYIGNDYTNYNEKFKG | (SEQ ID:121) | AYYGSRVDY | (SEQ ID:122) |
| PL-07 | SYGIN | (120) | CIYIGNDYTNYNEKFKG | (121) | AYYGSRVDY | (122) |
| PL-08 | SYWMH | (111) | MIHPNSGGNNYNEKFKS | (114) | SWYGSSPYYFDY | (115) |

| Mab | Light Chain CDR1 | | Light Chain CDR2 | | Light Chain CDR3 | |
|---|---|---|---|---|---|---|
| PL-01 | RASQDIDNYLN | (SEQ ID:123) | YTSRLHS | (SEQ ID:124) | QQGYTLPWT | (SEQ ID:125) |
| PL-02 | RASQDISNYLN | (SEQ ID:126) | YTSRLQS | (SEQ ID:127) | QQGNTLPWT | (SEQ ID:128) |
| PL-03 | RASQDISNYLN | (126) | YTSRLHS | (124) | QQGNTLPWT | (128) |
| PL-04 | RASQDISNYLN | (126) | YTSRLHS | (124) | QQGDTLPWT | (SEQ ID:129) |
| PL-05 | KASQDVNVAVA | (SEQ ID:130) | WASTRHI | (SEQ ID:131) | QQHYSTPYT | (SEQ ID:132) |
| PL-06 | KASQDINKYIA | (SEQ ID:133) | YTSTLQP | (SEQ ID:134) | LQYDNLYT | (SEQ ID:135) |
| PL-07 | QSISDYLH | (SEQ ID:136) | CASQSISG | (SEQ ID:137) | QNGHSFPYT | (SEQ ID:138) |
| PL-08 | RASQDIDNYLN | (123) | YTSRLHS | (124) | QQGYTLPWT | (125) |

FIG. 5 anti-PD-L1 Antibody Variable Domain Sequences

PL-01
VH (SEQ ID NO: 139):
QVQLVQSGAEVKKPGASVKVSCKASGYTFTNYWMHWMKQAPGQGLEWMGMIHPNT
NNYNYNEKFKSRVTSTRDTSISTAYMELSRLRSDDTVVYYCARSDYGSSPYYFDYWGQ
GTLVTVSS

VL (SEQ ID NO: 140):
DIQMTQSPSSLSASVGDRVTISCRASQDIDNYLNWYQQKPGKAPKLLIKYTSRLHSGVPS
RFSGSGSGTDFTLTISSLQPEDFATYFCQQGYTLPWTFGGGTKVEIK

PL-02
VH (SEQ ID NO: 141):
QVQLVQSGAEVKKPGASVKVSCKASGYTFTSYWMHWVRQAPGQGLEWMGMIHPNVG
STNYNEKFKSKATMTRDKSSSTVYMELSSLRSEDTAVYYCARSRYGSSPYYFDYWGQG
TLVTVSS

VL (SEQ ID NO: 142):
DIQMTQSPSSLSASVGDRVTISCRASQDISNYLNWYQQKPGKAPKLLIYYTSRLQSGVPS
RFSGSGSGTDFTFTISSLQPEDIATYFCQQGNTLPWTFGQGTKVEIK

PL-03
VH (SEQ ID NO: 143):
QVQLVQSGAEVKKPGASVKVSCKASGYTFTSYWMHWVRQAPGQGLEWMGMIHPNSG
GNNYNEKFKSRVTMTRDTSISTAYMELSRLRSDDTAVYYCARSWYGSSPYYFDYWGQ
GTLVTVSS

VL (SEQ ID NO: 144):
DIQMTQSPSSLSASVGDRVTISCRASQDISNYLNWYQQKPGKAPKLLIYYTSRLHSGVPS
RFSGSGSGTDFTFTISSLQPEDIATYFCQQGNTLPWTFGQGTKVEIK

*FIG. 6A*

PL-04
VH (SEQ ID NO: 145):
QVQLVQSGAEVKKPGASVKVSCKASGYTFTSYWMHWVRQAPGQGLEWMGMIHPTGV
STDYNEKFKSRVTMTRDTSTSTVYMELSSLRSEDTAVYYCARSDYGSSPYYFDYWGQG
TLVTVSS

VL (SEQ ID NO: 146):
DIQMTQSPSSLSASVGDRVTISCRASQDISNYLNWYQQKPGKAPKLLIKYTSRLHSGVPS
RFSGSGSGTDFTLTISSLQPEDFATYFCQQGDTLPWTFGGGTKVEIK

PL-05
VH (SEQ ID NO: 147):
DVQLQESGPGLVKPSQSLSLTCTVTGYSITSDYAWNWIRQFPGNKLEWMGYISDSGSTS
YNPSLKSRISITRDTSKNQFFLQLNSVTTEDTATYYCANSFLRLRSYFDHWGQGTTLTVS
S

VL (SEQ ID NO: 148):
DIVMTQSHKFMSTSVGDRVSITCKASQDVNVAVAWYQQKPGQSPKLLIFWASTRHIGV
PDRFTGSGSGTDYTLTISSVQAEDLALYYCQQHYSTPYTFGGGTKLEIK

PL-06
VH (SEQ ID NO: 149):
QVQLVQSGAEVKKPGASVKVSCKASGYTFTSYGINWVRQAPGQRLEWMGWCIYIGND
YTNYNEKFKGRVTITRDTSASTAYMELSSLRSEDTAVYYCARAYYGSRVDYWGQGTLV
TVSS

VL (SEQ ID NO: 150):
DIQMTQSPSSLSAFVGDRVTITCKASQDINKYIAWYQQKPGKAPKLLIHYTSTLQPGVPS
RFSGSGSGRDFTFTISSLQPEDIATYYCLQYDNLYTFGGGTKVEIK

PL-07
VH (SEQ ID NO: 151):
QVQLVQSGAEVKKPGASVKVSCKASGYTFTSYGINWVRQAPGQRLEWMGWCIYIGND
YTNYNEKFKGRVTITRDTSASTAYMELSSLRSEDTAVYYCARAYYGSRVDYWGQGTLV
TVSS

VL (SEQ ID NO: 152):
EIVLTQSPVTLSLSPGERATLSCQSISDYLHWYLQKPGQAPRLLIKCASQSISGIPARFSGS
GSGSDFTLTISSLEPEDFAVYYCQNGHSFPYTFGGGTKVEIK

*FIG. 6B*

PL-08
VH (SEQ ID NO: 153):
QVQLVQSGAEVKKPGASVKVSCKASGYTFTSYWMHWVRQAPGQGLEWMGMIHPNSG
GNNYNEKFKSRVTMTRDTSISTAYMELSRLRSDDTAVYYCARSWYGSSPYYFDYWGQ
GTLVTVSS

VL (SEQ ID NO: 154):
DIQMTQSPSSLSASVGDRVTISCRASQDIDNYLNWYQQKPGKAPKLLIKYTSRLHSGVPS
RFSGSGSGTDFTLTISSLQPEDFATYFCQQGYTLPWTFGGGTKVEIK

*FIG. 6C*

Anti-PD-1 antibodies with TIGIT scfv

Bi-TPM-93

Bi-TPM-94A

Bi-TPM-94B

Functional Domain Sequences in FIGs. 7A-7C

| VH/VL or Fusion Protein Domain | Amino Acid Sequences of Functional Domains |
|---|---|
| Anti-PD-1 HCVR (PD-01) | EVQLVESGGGLVQPGGSLRLSCAASGFTFSNFLMSWVRQAPGKGLEWVSTISGGGRDTYYV DSVKGRFTISRDNSKNTLYLQMNSLRAEDTAVYYCAKRTTYSMDYWGQGTSVTVSS (SEQ ID NO:96) |
| Anti-PD-1 LCVR (PD-01) | DIQMTQSPSSVSASVGDRVTITCLASQTIGTWLAWYQQKPGKAPKLLIYAATSLADGVPSRFS GSGSGTDFTLTISSLQPEDFATYYCQQFYSIPWTFGGGTKLEIK (SEQ ID NO:97) |
| Anti-PD-1 HCVR (PD-06, 2P17) | QVQLVQSGAEVKKPGASVKVSCKASGYTFTSYYIHWVRQAPGQGLEWMGWIFPGSGNSKY NENFKGRVTLTADTSTSTVYMELSSLRSEDTAVYYCASETYDYGDYWGQGTLVTVSS (SEQ ID NO:106) |
| Anti-PD-1 LCVR (PD-06, 2P17) | DIQMTQSPSFLSASVGDRVTITCKASQNVGTNVAWYQQKPGKAPKALIYSASYRYSGVPSRFS GSGSGTEFTLTISSLQPEDFATYYCQQYYSYPYTFGQGTKLEIK (SEQ ID NO:107) |
| Anti-TIGIT HCVR (B21-35) | QVQLVQSGAEVKKPGASVKVSCKASGYTFTSYYMHWVRQAPGQGLEWMGIINPSGGRTSY AQMFQGRVTMTRDTSTSTVYMELSSLRSEDTAVYYCARDREEQWPVGGFDYWGQGTLVTV SS (SEQ ID NO:66) |
| Anti-TIGIT LCVR (B21-35) | DIQMTQSPSSLSASVGDRVTITCRASQSIRRYLNWYQQKPGKAPKLLIYSASNLQSGVPSRFSG SGSGTDFTLTISSLQPEDFATYYCQQSYIIPPTFGQGTKVEIK (SEQ ID NO:67) |
| IgG4 CH1-CH2-CH3 (hinged stabilized S231P) | ASTKGPSVFPLAPCSRSTSESTAALGCLVKDYFPEPVTVSWNSGALTSGVHTFPAVLQSSGLYS LSSVVTVPSSSLGTKTYTCNVDHKPSNTKVDKRVESKYGPPCPPCPAPEFLGGPSVFLFPPKPK DTLMISRTPEVTCVVVDVSQEDPEVQFNWYVDGVEVHNAKTKPREEQFNSTYRVVSVLTVLH QDWLNGKEYKCKVSNKGLPSSIEKTISKAKGQPREPQVYTLPPSQEEMTKNQVSLTCLVKGFY PSDIAVEWESNGQPENNYKTTPPVLDSDGSFFLYSRLTVDKSRWQEGNVFSCSVMHEALHN HYTQKSLSLSLGK (SEQ ID NO: 155) |
| 3xG4S linker | GGGGSGGGGSGGGGS (SEQ ID NO:188) |
| 6xG4S linker | GGGGSGGGGSGGGGSGGGGSGGGGSGGGGS (SEQ ID NO:191) |

*FIG. 8*

HC and LC Sequences of Antagonists in FIGs. 7A-7C

| Antagonist (HC/LC) | Amino Acid Sequence |
|---|---|
| Bi-TPM-93 HC | EVQLVESGGGLVQPGGSLRLSCAASGFTFSNFLMSWVRQAPGKGLEWVSTISGGG RDTYYVDSVKGRFTISRDNSKNTLYLQMNSLRAEDTAVYYCAKRTTYSMDYWGQGT SVTVSSASTKGPSVFPLAPCSRSTSESTAALGCLVKDYFPEPVTVSWNSGALTSGVHT FPAVLQSSGLYSLSSVVTVPSSSLGTKTYTCNVDHKPSNTKVDKRVESKYGPPCPPCP APEFLGGPSVFLFPPKPKDTLMISRTPEVTCVVVDVSQEDPEVQFNWYVDGVEVHN AKTKPREEQFNSTYRVVSVLTVLHQDWLNGKEYKCKVSNKGLPSSIEKTISKAKGQPR EPQVYTLPPSQEEMTKNQVSLTCLVKGFYPSDIAVEWESNGQPENNYKTTPPVLDSD GSFFLYSRLTVDKSRWQEGNVFSCSVMHEALHNHYTQKSLSLSLGKGGGGSGGGGS QVQLVQSGAEVKKPGASVKVSCKASGYTFTSYYMHWVRQAPGQGLEWMGIINPS GGRTSYAQMFQGRVTMTRDTSTSTVYMELSSLRSEDTAVYYCARDREEQWPVGGF DYWGQGTLVTVSSGGGGSGGGGSGGGGSDIQMTQSPSSLSASVGDRVTITCRASQ SIRRYLNWYQQKPGKAPKLLIYSASNLQSGVPSRFSGSGSGTDFTLTISSLQPEDFATY YCQQSYIIPPTFGQGTKVEIK (SEQ ID NO: 158) (PD-01) |
| TPM-93 LC | DIQMTQSPSSVSASVGDRVTITCLASQTIGTWLAWYQQKPGKAPKLLIDAATSLADG VPSRFSGSGSGTDFTLTISSLQPEDFATYYCQQFYSIPWTFGGGTKLEIKRTVAAPSVFI FPPSDEQLKSGTASVVCLLNNFYPREAKVQWKVDNALQSGNSQESVTEQDSKDSTY SLSSTLTLSKADYEKHKVYACEVTHQGLSSPVTKSFNRGEC (SEQ ID NO: 159) (PD-01) |
| Bi-TPM-94A HC | QVQLVQSGAEVKKPGASVKVSCKASGYTFTSYYIHWVRQAPGQGLEWMGWIFPG SGNSKYNENFKGRVTLTADTSTSTVYMELSSLRSEDTAVYYCASETYDYGDYWGQGT LVTVSSASTKGPSVFPLAPCSRSTSESTAALGCLVKDYFPEPVTVSWNSGALTSGVHTF PAVLQSSGLYSLSSVVTVPSSSLGTKTYTCNVDHKPSNTKVDKRVESKYGPPCPPCPA PEFLGGPSVFLFPPKPKDTLMISRTPEVTCVVVDVSQEDPEVQFNWYVDGVEVHNA KTKPREEQFNSTYRVVSVLTVLHQDWLNGKEYKCKVSNKGLPSSIEKTISKAKGQPRE PQVYTLPPSQEEMTKNQVSLTCLVKGFYPSDIAVEWESNGQPENNYKTTPPVLDSD GSFFLYSRLTVDKSRWQEGNVFSCSVMHEALHNHYTQKSLSLSLGKGGGGSGGGGS QVQLVQSGAEVKKPGASVKVSCKASGYTFTSYYMHWVRQAPGQGLEWMGIINPS GGRTSYAQMFQGRVTMTRDTSTSTVYMELSSLRSEDTAVYYCARDREEQWPVGGF DYWGQGTLVTVSSGGGGSGGGGSGGGGSDIQMTQSPSSLSASVGDRVTITCRASQ SIRRYLNWYQQKPGKAPKLLIYSASNLQSGVPSRFSGSGSGTDFTLTISSLQPEDFATY YCQQSYIIPPTFGQGTKVEIK (SEQ ID NO: 160) |
| Bi-TPM-94A LC | DIQMTQSPSFLSASVGDRVTITCKASQNVGTNVAWYQQKPGKAPKALIYSASYRYSG VPSRFSGSGSGTEFTLTISSLQPEDFATYYCQQYYSYPYTFGQGTKLEIKRTVAAPSVFI FPPSDEQLKSGTASVVCLLNNFYPREAKVQWKVDNALQSGNSQESVTEQDSKDSTY SLSSTLTLSKADYEKHKVYACEVTHQGLSSPVTKSFNRGEC (SEQ ID NO: 161) |

*FIG. 9A*

HC and LC Sequences of Antagonists in FIGs. 7A-7C

| Antagonist (HC/LC) | Amino Acid Sequence |
|---|---|
| Bi-TPM-94B HC | QVQLVQSGAEVKKPGASVKVSCKASGYTFTSYYIHWVRQAPGQGLEWMGWIFPGSGNSKYNENFKGRVTLTADTSTSTVYMELSSLRSEDTAVYYCASETYDYGDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGKGGGGSGGGGSQVQLVQSGAEVKKPGASVKVSCKASGYTFTSYYMHWVRQAPGQGLEWMGIINPSGGRTSYAQMFQGRVTMTRDTSTSTVYMELSSLRSEDTAVYYCARDREEQWPVGGFDYWGQGTLVTVSSGGGGSGGGGSGGGGSGGGGSGGGGSDIQMTQSPSSLSASVGDRVTITCRASQSIRRYLNWYQQKPGKAPKLLIYSASNLQSGVPSRFSGSGSGTDFTLTISSLQPEDFATYYCQQSYIIPPTFGQGTKVEIK (SEQ ID NO: 162) |
| Bi-TPM-94B LC | DIQMTQSPSFLSASVGDRVTITCKASQNVGTNVAWYQQKPGKAPKALIYSASYRYSGVPSRFSGSGSGTEFTLTISSLQPEDFATYYCQQYYSYPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 161) |

*FIG. 9B*

Size-exclusion ultra-high performance liquid chromatography revealed species heterogeneity in Bi-TPM-93 and Bi-TPB-94A, which was eliminated by linker modification in Bi-TPM-94B

Bi-TPM-94B induces more IFN-γ production than the individual combination of antibodies during CMV recall response of human PBMCs

Bi-TPM94B induces more T cell proliferation than the combination of antibodies during CMV recall response of human PBMCs

Anti-LAG-3 mAb CDR1, CDR2 and CDR3 Amino Acid Sequences

| mAb | HCDR1 | HCDR2 | HCDR3 |
|---|---|---|---|
| 2L2A.1 | DYYMN (SEQ ID:163) | VINPYNGDTSYNQKFKG (SEQ ID:164) | DDGYYVHYFDY (SEQ ID:165) |
| 2L2A.6 | DYYMN (SEQ ID:163) | VINPYNGDTSYNQKFKG (SEQ ID:164) | DDGYYVHYFDY (SEQ ID:165) |
| 2L27B | HYYMN (SEQ ID:166) | LINPYNGDTAYNQKFKD (SEQ ID:167) | TRDDGYYVEH (SEQ ID:168) |
| 3L1A | TAYTIH (SEQ ID:169) | WLYPGNDNIMYNENFKD (SEQ ID:170) | HEDWGPLDY (SEQ ID:171) |

*FIG. 19A*

| mAb | LCDR1 | LCDR2 | LCDR3 |
|---|---|---|---|
| 2L2A.1 | RASQDISSRLT (SEQ ID:172) | ATSSLDS (SEQ ID:173) | LQYASSPLT (SEQ ID:174) |
| 2L2A.6 | RASQDISSRLT (SEQ ID:172) | ATSSLDS (SEQ ID:173) | LQYASSPLT (SEQ ID:174) |
| 2L27B | RASQDIGSRLN (SEQ ID:175) | ATSSLDS (SEQ ID:173) | LQYASSPPT (SEQ ID:176) |
| 3L1A | RASQSISS (SEQ ID:177) | RASNLES (SEQ ID:178) | QQSNGLPYT (SEQ ID:179) |

*FIG. 19B*

Anti-LAG-3 mAb Variable Domain Sequences

2L2A.1
VH (SEQ ID NO: 180)
QVQLVQSGAEVKKPGASVKVSCKASGYTLTDYYMNWMRQAPGQGLEWMGVINPYNGDTSYNQKFKG
RVTMTRDTSTSTVYMELSSLRSEDTAVYYCVRDDGYYVHYFDYWGQGTLVTVSS

VL (SEQ ID NO: 181)
DIQMTQSPSSLSASVGDRVTITCRASQDISSRLTWLQQEPEKAPKRLIYATSSLDSGVPKRFSGSGSGTDFTL
TISSLQPEDFATYYCLQYASSPLTFGGGTKVEIK

2L2A.6
VH (SEQ ID NO: 182)
QVQLVQSGAEVKKPGASVKVSCKASGYTFTDYYMNWVRQAPGQGLEWMGVINPYNGDTSYNQKFKGR
VTMTRDTSTSTVYMELSSLRSEDTAVYYCARDDGYYVHYFDYWGQGTLVTVSS

VL (SEQ ID NO: 183)
DIQMTQSPSSLSASVGDRVTITCRASQDISSRLTWLQQKPGKAPKRLIYATSSLDSGVPSRFSGSGSGTDFTL
TISSLQPEDFATYYCLQYASSPLTFGGGTKVEIK

2L27B
VH (SEQ ID NO: 184)
QVQLVQSGAEVKKPGASVKVSCKASGFTFSHYYMNWVRQAPGQGLEWMGLINPYNGDTAYNQKFKDR
VTMTRDTSTSTVYMELSSLRSEDTAVYFCTRDDGYYVEHFDYWDDGYYVEHFDYWGQGTLVTVSS

VL (SEQ ID NO: 185)
DIQMTQSPSSLSASVGDRVTITCRASQDIGSRLNWYQQKPGKAPKRLIYATSSLDSGVPSRFSGSGSGTDFT
LTISSLQPEDFATYYCLQYASSPPTFGGGTKVEIK

3L1A
VH (SEQ ID NO: 186)
QVQLVQSGAEVKKPGASVKVSCKASGYTFTAYTIHWVRQAPGQGLEWMGWLYPGNDNIMYNENFKDR
VTMTRDTSTSTVYMELSSLRSEDTAVYYCARHEDWGPLDYWGQGTLVTVSS

VL (SED ID NO: 187)
DIQMTQSPSTLSASVGDRVTITCRASQSISSWLAWYQQKPGKAPKLLIYRASNLESGVPSRFSGSGSGTEFTL
TISSLQPDDFATYYCQQSNGLPYTFGQGTKLEIK

*FIG. 20*

Mouse anti-LAG-3 mAbs block the interaction between LAG-3 and its MHC II ligand

Anti-LAG-3 mAb 2L2A.1 induces more IFN-γ production than a benchmark (BM) anti-LAG-3 mAb Anti-LAG-3 mAb 2L2A.1 can induce more IFN-γ production than a benchmark (BM) anti-LAG-3 mAb

Anti-LAG-3 mAb 2L2A.1 can induce more primary T cell proliferation than a benchmark (BM) anti-LAG-3 mAb

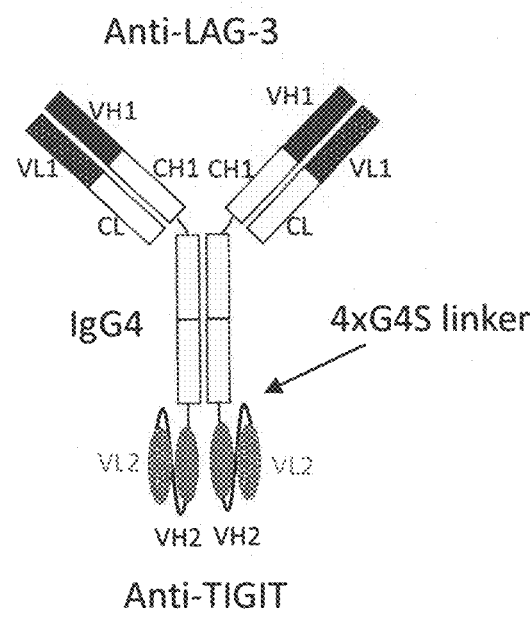
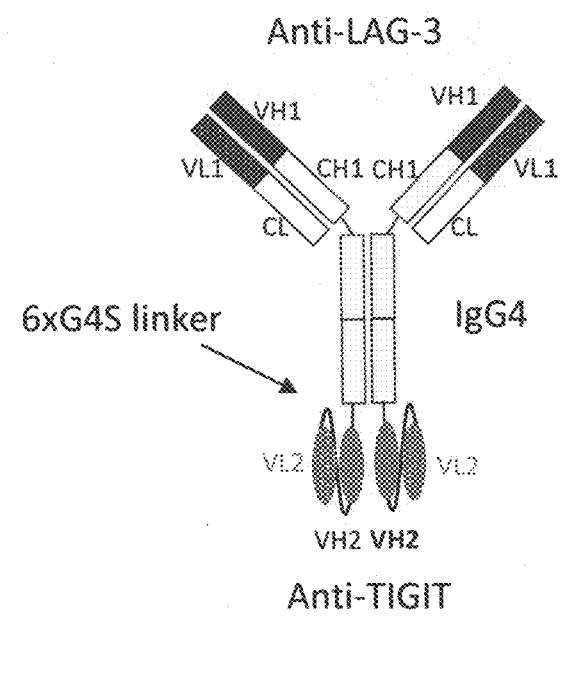
FIG. 30A
FIG. 30B

Functional Domain Sequences in FIGs. 30A-30B

| VH/VL or Fusion Protein Domain | Amino Acid Sequences of Functional Domains |
|---|---|
| Anti-LAG-3 HCVR (2L2A.1) | QVQLVQSGAEVKKPGASVKVSCKASGYTLTDYYMNWMRQAPGQGLEWMGVINPYNGDTSYNQKFKGRVTMTRDTSTSTVYMELSSLRSEDTAVYYCVRDDGYYVHYFDYWGQGTLVTVSS (SEQ ID NO: 180) |
| Anti-LAG-3 LCVR (2L2A.1) | DIQMTQSPSSLSASVGDRVTITCRASQDISSRLTWLQQEPEKAPKRLIYATSSLDSGVPKRFSGSGSGTDFTLTISSLQPEDFATYYCLQYASSPLTFGGGTKVEIK (SEQ ID NO: 181) |
| Anti-TIGIT HCVR (B21-35) | QVQLVQSGAEVKKPGASVKVSCKASGYTFTSYYMHWVRQAPGQGLEWMGIINPSGGRTSYAQMFQGRVTMTRDTSTSTVYMELSSLRSEDTAVYYCARDREEQWPVGGFDYWGQGTLVTVSS (SEQ ID NO: 66) |
| Anti-TIGIT LCVR (B21-35) | DIQMTQSPSSLSASVGDRVTITCRASQSIRRYLNWYQQKPGKAPKLLIYSASNLQSGVPSRFSGSGSGTDFTLTISSLQPEDFATYYCQQSYIIPPTFGQGTKVEIK (SEQ ID NO: 67) |
| IgG4 CH1-CH2-CH3 (hinge stabilized S231P) | ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK (SEQ ID NO: 155) |
| 4xG4S linker | GGGGSGGGGSGGGGSGGGGS (SEQ ID NO: 189) |
| 6xG4S linker | GGGGSGGGGSGGGGSGGGGSGGGGSGGGGS (SEQ ID NO: 191) |

*FIG. 31*

HC and LC Sequences of Antagonists of Bi-LT-1 and Bi-LT-3 in FIGs. 30A-30B

| Antagonist (HC/LC) | Amino Acid Sequence |
|---|---|
| Bi-LT-1 HC | QVQLVQSGAEVKKPGASVKVSCKASGYTLTDYYMNWMRQAPGQGLEWMGVINPYNGDTSYNQKFKGRVTMTRDTSTSTVYMELSSLRSEDTAVYYCVRDDGYYVHYFDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGKGGGGSGGGGSQVQLVQSGAEVKKPGASVKVSCKASGYTFTSYYMHWVRQAPGQGLEWMGIINPSGGRTSYAQMFQGRVTMTRDTSTSTVYMELSSLRSEDTAVYYCARDREEQWPVGGFDYWGQGTLVTVSSGGGGSGGGGSGGGGSGGGGSDIQMTQSPSSLSASVGDRVTITCRASQSIRRYLNWYQQKPGKAPKLLIYSASNLQSGVPSRFSGSGSGTDFTLTISSLQPEDFATYYCQQSYIIPPTFGQGTKVEIK (SEQ ID NO:192) |
| Bi-LT-1 LC | DIQMTQSPSSLSASVGDRVTITCRASQDISSRLTWLQQKPEKAPKRLIYATSSLDSGVPSRFSGSGSGTDFTLTISSLQPEDFATYYCLQYASSPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO:194) |
| Bi-LT-3 HC | QVQLVQSGAEVKKPGASVKVSCKASGYTLTDYYMNWMRQAPGQGLEWMGVINPYNGDTSYNQKFKGRVTMTRDTSTSTVYMELSSLRSEDTAVYYCVRDDGYYVHYFDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGKGGGGSGGGGSQVQLVQSGAEVKKPGASVKVSCKASGYTFTSYYMHWVRQAPGQGLEWMGIINPSGGRTSYAQMFQGRVTMTRDTSTSTVYMELSSLRSEDTAVYYCARDREEQWPVGGFDYWGQGTLVTVSSGGGGSGGGGSGGGGSGGGGSGGGGSDIQMTQSPSSLSASVGDRVTITCRASQSIRRYLNWYQQKPGKAPKLLIYSASNLQSGVPSRFSGSGSGTDFTLTISSLQPEDFATYYCQQSYIIPPTFGQGTKVEIK (SEQ ID NO:193) |
| Bi-LT-3 LC | DIQMTQSPSSLSASVGDRVTITCRASQDISSRLTWLQQKPEKAPKRLIYATSSLDSGVPSRFSGSGSGTDFTLTISSLQPEDFATYYCLQYASSPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO:194) |

*FIG. 32*

Improved TIGIT scfvs fused to LAG-3 antibody have good pharmacokinetic properties, similar to unfused LAG3 antibody

Bi-LT-1 and Bi-LT-3 with the improved TIGIT scFvs are homogenous and has good stability at 4° C for 7 days

Bi-LT-1 and Bi-LT-3 are more potent than the combination of parental TIGIT and LAG-3 antibodies, since they induce more IFN-γ in a SEB stimulated PBMC assay

| SEQ ID NO | Sequence | Description/Notes |
|---|---|---|
| 216 | QVQLQESGPGLVKPSQTLSLTCTVSGYSIT | T-01 HFR1 |
| 217 | WIRQPPGKGLEWIG | T-01, 02, 06, 07 HFR2 |
| 218 | RVTISVDTSKNQFSLKLSSVTAADTAVYYCAR | T-01, 06 HFR3 |
| 219 | WGQGTSVTVSS | T-01 HFR4 |
| 220 | DIQMTQSPSSLSASVGDRVTITC | T-01, 03, 04, 05, 06, 07, 10 LFR1 |
| 221 | WHQQKPGKAPKLLIY | T-01 LFR2 |
| 222 | GVPSRFSGSGSGTDFTLTISSLQPEDFATYYCQQSYSTP | T-01, 02 LFR3 |
| 223 | FGGGTKLEIKR | T-01, 06 LFR4 |
| 224 | QVKLQESGPGLVKPSQTLSLTCTVTGYSIT | T-02 HFR1 |
| 225 | RVTISVDTSKNQFSLKLSSVTAADTAVYSCAR | T-02 HFR3 |
| 226 | WGQGTLVTVSA | T-02, 06, 07 HFR4 |
| 227 | DIQMTQSPSSLSASVGDRVTIPC | T-02 LFR1 |
| 228 | WYQQKPGKAPKLLIY | T-02, 03, 04, 05, 06, 07, 10 LFR2 |
| 229 | FGEGTKLEIK | T-02 LFR4 |
| 230 | EVQLVQSGAEVKKPGATVKISCKVSGYTFT | T-03, 04 HFR1 |
| 231 | WVQQAPGKGLEWMG | T-03, 04, 05 HFR2 |
| 232 | RVTITADTSTDTAYMELSSLRSEDTAVYYCAT | T-03, 04 HFR3 |
| 233 | WGQGTLITVSVA | T-03 HFR4 |
| 234 | GVPSRFSGSGSGTDFTLTISSLQPEDFATYYC | T-03, 05, 06, 10 LFR3 |
| 235 | FGAGTKLELK | T-03, 05 LFR4 |
| 236 | WGQGTLVTVSS | T-04, 05, 08, 09, 10 HFR4 |
| 237 | GVPSRFSGSGSGTDFTFTISSLQPEDIATYYC | T-04 LFR3 |
| 238 | FGAGTKLEIK | T-04 LFR4 |
| 239 | EVQLKQSGAEVKKPGATVKISCKVSGYTFT | T-05 HFR1 |
| 240 | RVTITADTSTDTAYMELSSLRSEDTAVYFCAR | T-05 HFR3 |
| 241 | QVQLQESGPGLVKPSQTLSLTCTVSGGSVS | T-06 HFR1 |
| 242 | EVQLQESGPGLVKPSDTLSLTCAVSGYSIT | T-07 HFR1 |
| 243 | RVTMSVDTSKNQFSLKLSSVTAVDTAVYYCTR | T-07 HFR3 |
| 244 | GAPSRFSGSGSGTDFTLTISSLQPEDFGIYYC | T-07 LFR3 |
| 245 | FGGGTKLEFK | T-07 LFR4 |
| 246 | QVQLVQSGSELKKPGASVKVSCKASGYTFT | T-08 HFR1 |
| 247 | WVRQAPGQGLEWMG | T-08, 10 HFR2 |
| 248 | RFVFSLDTSVSTAYLQISSLKAEDTAVYYCAR | T-08 HFR3 |
| 249 | DVVMTQSPLSLPVTLGQPASISC | T-08 LFR1 |
| 250 | WFQQRPGQSPRVLIY | T-08 LFR2 |
| 251 | GVPDRFSGSGSGTDFTLKISRVEAEDVGVYYC | T-08 LFR3 |
| 252 | FGRGTKLEIK | T-08 LFR4 |
| 253 | QVTLKESGPTLVKPTQTLTLTCTFSGFSLS | T-09 HFR1 |
| 254 | WIRQPPGKALEWLA | T-09 HFR2 |
| 255 | RLTITKDTSKNQVVLTMTNMDPVDTATYYCAR | T-09 HFR3 |
| 256 | QAVVTQEPSLTVSPGGTVTLTC | T-09 LFR1 |
| 257 | WVQQKPGQLFRGLIG | T-09 LFR2 |
| 258 | WVPARFSGSLIGDKAALTLSGVQPEDEAEYFC | T-09 LFR3 |
| 259 | FGGGTKLTVL | T-09 LFR4 |
| 260 | QVQLVQSGAEVKKPGASVKVSCKASGYTFT | T-10 HFR1 |
| 261 | RVTMTRDTSTSTVYMELSSLRSEDTAVYYCAR | T-10 HFR3 |
| 262 | FGQGTKVEIK | T-10 LFR4 |

*FIG. 39A*

| SEQ ID NO | Sequence | Description/Notes |
|---|---|---|
| 263 | EVQLVESGGGLVQPGGSLRLSCAASGFTFS | PD-01 HFR1 |
| 264 | WVRQAPGKGLEWVS | PD-01 HFR2 |
| 265 | RFTISRDNSKNTLYLQMNSLRAEDTAVYYCAK | PD-01 HFR3 |
| 266 | WGQGTSVTVSS | PD-01 HFR4 |
| 267 | DIQMTQSPSSVSASVGDRVTITC | PD-01 LFR1 |
| 268 | WYQQKPGKAPKLLIY | PD-01, 02, 03, 04; PL-02, 03 LFR2 |
| 269 | GVPSRFSGSGSGTDFTLTISSLQPEDFATYYC | PD-01, 02, 03, 04 LFR3 |
| 270 | FGGGTKLEIK | PD-01; PL-05 LFR4 |
| 271 | QVQLVQSGAEVKKPGASVKVSCKASDYTFT | PD-02, 03, 04 HFR1 |
| 272 | WLRQAPGQGLEWMG | PD-02 HFR2 |
| 273 | RTTSTRDTSISTAYMELSRLRSDDTVVYYCTR | PD-02 HFR3 |
| 274 | WGQGTLVTVSS | PD-02, 04, 05, 06; PL-01, 02, 03, 04, 06, 07, 08 HFR4 |
| 275 | DIQMTQSPSSLSASVGDRVTFTC | PD-02, 04 LFR1 |
| 276 | FGGGTKVEIK | PD-02, 04, 05; PL-01, 04, 06, 07, 08 LFR4 |
| 277 | WVRQAPGQGLEWMG | PD-03, 04, 05, 06; PL-02, 03, 04, 08 HFR2 |
| 278 | RVTSTRDTSISTAYMELSRLRSDDTVVYYCA | PD-03, 04; PL-01 HFR3 |
| 279 | WGQGTTLTVSS | PD-03; PL-05 HFR4 |
| 280 | DIQMTQSPSSLSASVGDRVTITC | PD-03 LFR1 |
| 281 | FGAGTKLDLK | PD-03 LFR4 |
| 282 | FGGGTKVEIK | PD-04, 05; PL-01, 04, 06, 07, 08 LFR4 |
| 283 | QVQLVQSGAEVKKPGASVKVSCKASGYTFT | PD-05, 06; PL-01, 02, 03, 04, 06, 07, 08 HFR1 |
| 284 | RVTMTRDTSISTAYMELSSLRSEDTAVYYCAR | PD-05 HFR3 |
| 285 | DIVLTQSPASLAVSPGQRATITC | PD-05 LFR1 |
| 286 | WYQQKPGQPPKLLIY | PD-05 LFR2 |
| 287 | GVPARFSGSGSGTDFTLTINPVEANDTANYYC | PD-05 LFR3 |
| 288 | RVTLTADTSTSTVYMELSSLRSEDTAVYYCA | PD-06 HFR3 |
| 289 | DIQMTQSPSFLSASVGDRVTITC | PD-06 LFR1 |
| 290 | WYQQKPGKAPKALIY | PD-06 LFR2 |
| 291 | GVPSRFSGSGSGTEFTLTISSLQPEDFATYYC | PD-06 LFR3 |
| 292 | FGQGTKLEIK | PD-06 LFR4 |

*FIG. 39B*

| SEQ ID NO | Sequence | Description/Notes |
|---|---|---|
| 293 | WMKQAPGQGLEWMG | PL-01 HFR2 |
| 294 | DIQMTQSPSSLSASVGDRVTISC | PL-01, 02, 03, 04, 08 LFR1 |
| 295 | WYQQKPGKAPKLLIK | PL-01, 04, 08 LFR2 |
| 296 | GVPSRFSGSGSGTDFTLTISSLQPEDFATYFC | PL-01, 04, 08 LFR3 |
| 297 | KATMTRDKSSSTVYMELSSLRSEDTAVYYCAR | PL-02 HFR3 |
| 298 | GVPSRFSGSGSGTDFTFTISSLQPEDIATYFC | PL-02, 03 LFR3 |
| 299 | FGQGTKVEIK | PL-02, 03 LFR4 |
| 300 | RVTMTRDTSISTAYMELSRLRSDDTAVYYCAR | PL-03, 08 HFR3 |
| 301 | RVTMTRDTSTSTVYMELSSLRSEDTAVYYCAR | PL-04 HFR3 |
| 302 | QVQLQESGPGLVKPSQSLSLTCTVTGYSIT | PL-05 HFR1 |
| 303 | WIRQFPGNKLEWMG | PL-05 HFR2 |
| 304 | RISITRDTSKNQFFLQLNSVTTEDTATYYCAN | PL-05 HFR3 |
| 305 | DIVMTQSHKFMSTSVGDRVSITC | PL-05 LFR1 |
| 306 | WYQQKPGQSPKLLIF | PL-05 LFR2 |
| 307 | GVPDRFTGSGSGTDYTLTISSVQAEDLALYYC | PL-05 LFR3 |
| 308 | WVRQAPGQRLEWMGW | PL-06, 07 HFR2 |
| 309 | RVTITRDTSASTAYMELSSLRSEDTAVYYCAR | PL-06, 07 HFR3 |
| 310 | DIQMTQSPSSLSAFVGDRVTITC | PL-06 LFR1 |
| 311 | WYQQKPGKAPKLLIH | PL-06 LFR2 |
| 312 | GVPSRFSGSGSGRDFTFTISSLQPEDIATYYC | PL-06 LFR3 |
| 313 | EIVLTQSPVTLSLSPGERATLSC | PL-07 LFR1 |
| 314 | WYLQKPGQAPRLLIK | PL-07 LFR2 |
| 315 | IPARFSGSGSGSDFTLTISSLEPEDFAVYYC | PL-07 LFR3 |
| 316 | QVQLVQSGAEVKKPGASVKVSCKASGYTLT | 2L2A.1 HFR1 |
| 317 | WMRQAPGQGLEWMG | 2L2A.1 HFR2 |
| 318 | RVTMTRDTSTSTVYMELSSLRSEDTAVYYCVR | 2L2A.1 HFR3 |
| 319 | WGQGTLVTVSS | 2L2A.1, 2L2A.6, 3L1A HFR4 |
| 320 | DIQMTQSPSSLSASVGDRVTITC | 2L2A.1, 2L2A.6, 2L27B LFR1 |
| 321 | WLQQKPEKAPKRLIY | 2L2A.1 LFR2 |
| 322 | GVPSRFSGSGSGTDFTLTISSLQPEDFATYYC | 2L2A.1, 2L2A.6, 2L27B LFR3 |
| 323 | FGGGTKVEIK | 2L2A.1, 2L2A.6, 2L27B LFR4 |
| 324 | QVQLVQSGAEVKKPGASVKVSCKASGYTFT | 2L2A.6 HFR1 |
| 325 | WVRQAPGQGLEWMG | 2L2A.6 HFR2 |
| 326 | RVTMTRDTSTSTVYMELSSLRSEDTAVYYCAR | 2L2A.6 3L1A HFR3 |
| 327 | WLQQKPGKAPKRLIY | 2L2A.6, 3L1A LFR2 |
| 328 | QVQLVQSGAEVKKPGASVKVSCKASGFTFS | 2L27B HFR1 |
| 329 | WVRQAPGQGLEWMGL | 2L27B HFR2 |
| 330 | RVTMTRDTSTSTVYMELSSLRSEDTAVYFC | 2L27B HFR3 |
| 331 | FDYWDDGYYVEHFDYWGQGTLVTVSS | 2L27B HFR4 |
| 332 | WYQQKPGKAPKRLIY | 2L27B LFR2 |
| 333 | QVQLVQSGAEVKKPGASVKVSCKASGYTF | 3L1A HFR1 |
| 334 | DIQMTQSPSTLSASVGDRVTITC | 3L1A LFR1 |
| 335 | WLAWYQQKPGKAPKLLIY | 3L1A LFR2 |
| 336 | GVPSRFSGSGSGTEFTLTISSLQPDDFATYYC | 3L1A LFR3 |
| 337 | FGQGTKLEIK | 3L1A LFR4 |

*FIG. 39C*

```
                         SEQUENCE LISTING

Sequence total quantity: 337
SEQ ID NO: 1            moltype = AA  length = 6
FEATURE                 Location/Qualifiers
REGION                  1..6
                        note = Synthetic
source                  1..6
                        mol_type = protein
                        organism = synthetic construct
SEQUENCE: 1
SDYAWN                                                                    6

SEQ ID NO: 2            moltype = AA  length = 16
FEATURE                 Location/Qualifiers
REGION                  1..16
                        note = Synthetic
source                  1..16
                        mol_type = protein
                        organism = synthetic construct
SEQUENCE: 2
YISYSGSTGY NPSLKS                                                         16

SEQ ID NO: 3            moltype = AA  length = 9
FEATURE                 Location/Qualifiers
REGION                  1..9
                        note = Synthetic
source                  1..9
                        mol_type = protein
                        organism = synthetic construct
SEQUENCE: 3
RMIGYAMDY                                                                 9

SEQ ID NO: 4            moltype = AA  length = 17
FEATURE                 Location/Qualifiers
REGION                  1..17
                        note = Synthetic
source                  1..17
                        mol_type = protein
                        organism = synthetic construct
SEQUENCE: 4
YITYSGGSTS YNPSLKS                                                        17

SEQ ID NO: 5            moltype = AA  length = 9
FEATURE                 Location/Qualifiers
REGION                  1..9
                        note = Synthetic
source                  1..9
                        mol_type = protein
                        organism = synthetic construct
SEQUENCE: 5
RQIGLGFTY                                                                 9

SEQ ID NO: 6            moltype = AA  length = 5
FEATURE                 Location/Qualifiers
REGION                  1..5
                        note = Synthetic
source                  1..5
                        mol_type = protein
                        organism = synthetic construct
```

```
SEQUENCE: 6
DHTIH                                                                         5

SEQ ID NO: 7           moltype = AA  length = 17
FEATURE                Location/Qualifiers
REGION                 1..17
                       note = Synthetic
source                 1..17
                       mol_type = protein
                       organism = synthetic construct
SEQUENCE: 7
YFYPRDGSTK YNEKFKG                                                            17

SEQ ID NO: 8           moltype = AA  length = 8
FEATURE                Location/Qualifiers
REGION                 1..8
                       note = Synthetic
source                 1..8
                       mol_type = protein
                       organism = synthetic construct
SEQUENCE: 8
GMLRWFAD                                                                      8

SEQ ID NO: 9           moltype = AA  length = 17
FEATURE                Location/Qualifiers
REGION                 1..17
                       note = Synthetic
source                 1..17
                       mol_type = protein
                       organism = synthetic construct
SEQUENCE: 9
YIYPRDGSSK YNVKFKG                                                            17

SEQ ID NO: 10          moltype = AA  length = 8
FEATURE                Location/Qualifiers
REGION                 1..8
                       note = Synthetic
source                 1..8
                       mol_type = protein
                       organism = synthetic construct
SEQUENCE: 10
GMLRWFAY                                                                      8

SEQ ID NO: 11          moltype = AA  length = 5
FEATURE                Location/Qualifiers
REGION                 1..5
                       note = Synthetic
source                 1..5
                       mol_type = protein
                       organism = synthetic construct
SEQUENCE: 11
DQAIH                                                                         5

SEQ ID NO: 12          moltype = AA  length = 17
FEATURE                Location/Qualifiers
REGION                 1..17
                       note = Synthetic
source                 1..17
                       mol_type = protein
                       organism = synthetic construct
SEQUENCE: 12
YIYPRDGSTK YNETFKG                                                            17

SEQ ID NO: 13          moltype = AA  length = 16
FEATURE                Location/Qualifiers
REGION                 1..16
                       note = Synthetic
source                 1..16
                       mol_type = protein
                       organism = synthetic construct
SEQUENCE: 13
YITYSGSTSY NPSLKS                                                             16

SEQ ID NO: 14          moltype = AA  length = 9
FEATURE                Location/Qualifiers
REGION                 1..9
                       note = Synthetic
source                 1..9
                       mol_type = protein
```

```
                        organism = synthetic construct
SEQUENCE: 14
RQVGLGFAY                                                                        9

SEQ ID NO: 15           moltype = AA  length = 6
FEATURE                 Location/Qualifiers
REGION                  1..6
                        note = Synthetic
source                  1..6
                        mol_type = protein
                        organism = synthetic construct
SEQUENCE: 15
SDSAWN                                                                           6

SEQ ID NO: 16           moltype = AA  length = 16
FEATURE                 Location/Qualifiers
REGION                  1..16
                        note = Synthetic
source                  1..16
                        mol_type = protein
                        organism = synthetic construct
SEQUENCE: 16
YITYSGSTNY NPSLRS                                                               16

SEQ ID NO: 17           moltype = AA  length = 5
FEATURE                 Location/Qualifiers
REGION                  1..5
                        note = Synthetic
source                  1..5
                        mol_type = protein
                        organism = synthetic construct
SEQUENCE: 17
NYGMN                                                                            5

SEQ ID NO: 18           moltype = AA  length = 17
FEATURE                 Location/Qualifiers
REGION                  1..17
                        note = Synthetic
source                  1..17
                        mol_type = protein
                        organism = synthetic construct
SEQUENCE: 18
WINTYTGEPT YADDFKG                                                              17

SEQ ID NO: 19           moltype = AA  length = 12
FEATURE                 Location/Qualifiers
REGION                  1..12
                        note = Synthetic
source                  1..12
                        mol_type = protein
                        organism = synthetic construct
SEQUENCE: 19
APPYGYDVRF AY                                                                   12

SEQ ID NO: 20           moltype = AA  length = 7
FEATURE                 Location/Qualifiers
REGION                  1..7
                        note = Synthetic
source                  1..7
                        mol_type = protein
                        organism = synthetic construct
SEQUENCE: 20
TFAMGVG                                                                          7

SEQ ID NO: 21           moltype = AA  length = 16
FEATURE                 Location/Qualifiers
REGION                  1..16
                        note = Synthetic
source                  1..16
                        mol_type = protein
                        organism = synthetic construct
SEQUENCE: 21
HIWWDDDKYY NPALKS                                                               16

SEQ ID NO: 22           moltype = AA  length = 11
FEATURE                 Location/Qualifiers
REGION                  1..11
                        note = Synthetic
source                  1..11
```

```
                              mol_type = protein
                              organism = synthetic construct
SEQUENCE: 22
MDYSYFAWFA Y                                                              11

SEQ ID NO: 23             moltype = AA   length = 5
FEATURE                   Location/Qualifiers
REGION                    1..5
                              note = Synthetic
source                    1..5
                              mol_type = protein
                              organism = synthetic construct
SEQUENCE: 23
SYYMH                                                                      5

SEQ ID NO: 24             moltype = AA   length = 16
FEATURE                   Location/Qualifiers
REGION                    1..16
                              note = Synthetic
source                    1..16
                              mol_type = protein
                              organism = synthetic construct
SEQUENCE: 24
INPSGGRTSY AQMFQG                                                         16

SEQ ID NO: 25             moltype = AA   length = 13
FEATURE                   Location/Qualifiers
REGION                    1..13
                              note = Synthetic
source                    1..13
                              mol_type = protein
                              organism = synthetic construct
SEQUENCE: 25
DREEQWPVGG FDY                                                            13

SEQ ID NO: 26             moltype = AA   length = 11
FEATURE                   Location/Qualifiers
REGION                    1..11
                              note = Synthetic
source                    1..11
                              mol_type = protein
                              organism = synthetic construct
SEQUENCE: 26
KASQDVSTVV A                                                              11

SEQ ID NO: 27             moltype = AA   length = 7
FEATURE                   Location/Qualifiers
REGION                    1..7
                              note = Synthetic
source                    1..7
                              mol_type = protein
                              organism = synthetic construct
SEQUENCE: 27
SASYRYT                                                                    7

SEQ ID NO: 28             moltype = AA   length = 9
FEATURE                   Location/Qualifiers
REGION                    1..9
                              note = Synthetic
source                    1..9
                              mol_type = protein
                              organism = synthetic construct
SEQUENCE: 28
QQHYSTPWT                                                                  9

SEQ ID NO: 29             moltype = AA   length = 11
FEATURE                   Location/Qualifiers
REGION                    1..11
                              note = Synthetic
source                    1..11
                              mol_type = protein
                              organism = synthetic construct
SEQUENCE: 29
KASQDLSTAV A                                                              11

SEQ ID NO: 30             moltype = AA   length = 7
FEATURE                   Location/Qualifiers
REGION                    1..7
                              note = Synthetic
```

| | | |
|---|---|---|
| source | 1..7<br>mol_type = protein<br>organism = synthetic construct | |
| SEQUENCE: 30<br>SSSYRYT | | 7 |
| SEQ ID NO: 31<br>FEATURE<br>REGION<br>source | moltype = AA   length = 11<br>Location/Qualifiers<br>1..11<br>note = Synthetic<br>1..11<br>mol_type = protein<br>organism = synthetic construct | |
| SEQUENCE: 31<br>KASQDVSTTV A | | 11 |
| SEQ ID NO: 32<br>FEATURE<br>REGION<br>source | moltype = AA   length = 9<br>Location/Qualifiers<br>1..9<br>note = Synthetic<br>1..9<br>mol_type = protein<br>organism = synthetic construct | |
| SEQUENCE: 32<br>QQHYSTPLT | | 9 |
| SEQ ID NO: 33<br>FEATURE<br>REGION<br>source | moltype = AA   length = 11<br>Location/Qualifiers<br>1..11<br>note = Synthetic<br>1..11<br>mol_type = protein<br>organism = synthetic construct | |
| SEQUENCE: 33<br>KASQDVFTAV A | | 11 |
| SEQ ID NO: 34<br>FEATURE<br>REGION<br>source | moltype = AA   length = 9<br>Location/Qualifiers<br>1..9<br>note = Synthetic<br>1..9<br>mol_type = protein<br>organism = synthetic construct | |
| SEQUENCE: 34<br>QQHYSIPLT | | 9 |
| SEQ ID NO: 35<br>FEATURE<br>REGION<br>source | moltype = AA   length = 11<br>Location/Qualifiers<br>1..11<br>note = Synthetic<br>1..11<br>mol_type = protein<br>organism = synthetic construct | |
| SEQUENCE: 35<br>KASQDVSTAV A | | 11 |
| SEQ ID NO: 36<br>FEATURE<br>REGION<br>source | moltype = AA   length = 7<br>Location/Qualifiers<br>1..7<br>note = Synthetic<br>1..7<br>mol_type = protein<br>organism = synthetic construct | |
| SEQUENCE: 36<br>SASYHYT | | 7 |
| SEQ ID NO: 37<br>FEATURE<br>REGION<br>source | moltype = AA   length = 7<br>Location/Qualifiers<br>1..7<br>note = Synthetic<br>1..7<br>mol_type = protein<br>organism = synthetic construct | |
| SEQUENCE: 37<br>SASYRFT | | 7 |
| SEQ ID NO: 38<br>FEATURE<br>REGION | moltype = AA   length = 9<br>Location/Qualifiers<br>1..9 | |

```
                            note = Synthetic
source                      1..9
                            mol_type = protein
                            organism = synthetic construct
SEQUENCE: 38
QHHYSTPWT                                                                        9

SEQ ID NO: 39               moltype = AA  length = 16
FEATURE                     Location/Qualifiers
REGION                      1..16
                            note = Synthetic
source                      1..16
                            mol_type = protein
                            organism = synthetic construct
SEQUENCE: 39
RSSQSIVHSN GNTYLE                                                               16

SEQ ID NO: 40               moltype = AA  length = 7
FEATURE                     Location/Qualifiers
REGION                      1..7
                            note = Synthetic
source                      1..7
                            mol_type = protein
                            organism = synthetic construct
SEQUENCE: 40
KVSDRFS                                                                          7

SEQ ID NO: 41               moltype = AA  length = 9
FEATURE                     Location/Qualifiers
REGION                      1..9
                            note = Synthetic
source                      1..9
                            mol_type = protein
                            organism = synthetic construct
SEQUENCE: 41
FQGSHVPWT                                                                        9

SEQ ID NO: 42               moltype = AA  length = 14
FEATURE                     Location/Qualifiers
REGION                      1..14
                            note = Synthetic
source                      1..14
                            mol_type = protein
                            organism = synthetic construct
SEQUENCE: 42
RSSTGAVTTS NYAN                                                                 14

SEQ ID NO: 43               moltype = AA  length = 7
FEATURE                     Location/Qualifiers
REGION                      1..7
                            note = Synthetic
source                      1..7
                            mol_type = protein
                            organism = synthetic construct
SEQUENCE: 43
GTNNRAP                                                                          7

SEQ ID NO: 44               moltype = AA  length = 9
FEATURE                     Location/Qualifiers
REGION                      1..9
                            note = Synthetic
source                      1..9
                            mol_type = protein
                            organism = synthetic construct
SEQUENCE: 44
ALWYSNHWV                                                                        9

SEQ ID NO: 45               moltype = AA  length = 11
FEATURE                     Location/Qualifiers
REGION                      1..11
                            note = Synthetic
source                      1..11
                            mol_type = protein
                            organism = synthetic construct
SEQUENCE: 45
RASQSIRRYL N                                                                    11

SEQ ID NO: 46               moltype = AA  length = 7
FEATURE                     Location/Qualifiers
```

```
REGION                      1..7
                            note = Synthetic
source                      1..7
                            mol_type = protein
                            organism = synthetic construct
SEQUENCE: 46
SASNLQS                                                              7

SEQ ID NO: 47               moltype = AA   length = 9
FEATURE                     Location/Qualifiers
REGION                      1..9
                            note = Synthetic
source                      1..9
                            mol_type = protein
                            organism = synthetic construct
SEQUENCE: 47
QQSYIIPPT                                                            9

SEQ ID NO: 48               moltype = AA   length = 118
FEATURE                     Location/Qualifiers
REGION                      1..118
                            note = Synthetic
source                      1..118
                            mol_type = protein
                            organism = synthetic construct
SEQUENCE: 48
QVQLQESGPG LVKPSQTLSL TCTVSGYSIT SDYAWNWIRQ PPGKGLEWIG YISYSGSTGY     60
NPSLKSRVTI SVDTSKNQFS LKLSSVTAAD TAVYYCARRM IGYAMDYWGQ GTSVTVSS     118

SEQ ID NO: 49               moltype = AA   length = 115
FEATURE                     Location/Qualifiers
REGION                      1..115
                            note = Synthetic
source                      1..115
                            mol_type = protein
                            organism = synthetic construct
SEQUENCE: 49
DIQMTQSPSS LSASVGDRVT ITCKASQDVS TVVAWHQQKP GKAPKLLIYS ASYRYTGVPS     60
RFSGSGSGTD FTLTISSLQP EDFATYYCQQ SYSTPQQHYS TPWTFGGGTK LEIKR        115

SEQ ID NO: 50               moltype = AA   length = 118
FEATURE                     Location/Qualifiers
REGION                      1..118
                            note = Synthetic
source                      1..118
                            mol_type = protein
                            organism = synthetic construct
SEQUENCE: 50
QVKLQESGPG LVKPSQTLSL TCTVTGYSIT SDYAWNWIRQ PPGKGLEWIG YITYSGGTSY     60
NPSLKSRVTI SVDTSKNQFS LKLSSVTAAD TAVYSCARRQ IGLGFTYWGQ GTLVTVSA     118

SEQ ID NO: 51               moltype = AA   length = 114
FEATURE                     Location/Qualifiers
REGION                      1..114
                            note = Synthetic
source                      1..114
                            mol_type = protein
                            organism = synthetic construct
SEQUENCE: 51
DIQMTQSPSS LSASVGDRVT IPCKASQDLS TAVAWYQQKP GKAPKLLIYS SSYRYTGVPS     60
RFSGSGSGTD FTLTISSLQP EDFATYYCQQ SYSTPQQHYS TPWTFGEGTK LEIK         114

SEQ ID NO: 52               moltype = AA   length = 118
FEATURE                     Location/Qualifiers
REGION                      1..118
                            note = Synthetic
source                      1..118
                            mol_type = protein
                            organism = synthetic construct
SEQUENCE: 52
EVQLVQSGAE VKKPGATVKI SCKVSGYTFT DHTIHWVQQA PGKGLEWMGY FYPRDGSTKY     60
NEKFKGRVTI TADTSTDTAY MELSSLRSED TAVYYCATGM LRWFADWGQG TLITVSVA    118

SEQ ID NO: 53               moltype = AA   length = 107
FEATURE                     Location/Qualifiers
REGION                      1..107
                            note = Synthetic
source                      1..107
                            mol_type = protein
```

```
                              organism = synthetic construct
SEQUENCE: 53
DIQMTQSPSS LSASVGDRVT ITCKASQDVS TTVAWYQQKP GKAPKLLIYS ASYRYTGVPS    60
RFSGSGSGTD FTLTISSLQP EDFATYYCQQ HYSTPLTFGA GTKLELK                 107

SEQ ID NO: 54         moltype = AA   length = 117
FEATURE               Location/Qualifiers
REGION                1..117
                      note = Synthetic
source                1..117
                      mol_type = protein
                      organism = synthetic construct
SEQUENCE: 54
EVQLVQSGAE VKKPGATVKI SCKVSGYTFT DHTIHWVQQA PGKGLEWMGY IYPRDGSSKY    60
NVKFKGRVTI TADTSTDTAY MELSSLRSED TAVYYCATGM LRWFAYWGQG TLVTVSS      117

SEQ ID NO: 55         moltype = AA   length = 107
FEATURE               Location/Qualifiers
REGION                1..107
                      note = Synthetic
source                1..107
                      mol_type = protein
                      organism = synthetic construct
SEQUENCE: 55
DIQMTQSPSS LSASVGDRVT ITCKASQDVF TAVAWYQQKP GKAPKLLIYS ASYRYTGVPS    60
RFSGSGSGTD FTFTISSLQP EDIATYYCQQ HYSIPLTFGA GTKLEIK                 107

SEQ ID NO: 56         moltype = AA   length = 117
FEATURE               Location/Qualifiers
REGION                1..117
                      note = Synthetic
source                1..117
                      mol_type = protein
                      organism = synthetic construct
SEQUENCE: 56
EVQLKQSGAE VKKPGATVKI SCKVSGYTFT DQAIHWVQQA PGKGLEWMGY IYPRDGSTKY    60
NETFKGRVTI TADTSTDTAY MELSSLRSED TAVYFCARGM LRWFAYWGQG TLVTVSS      117

SEQ ID NO: 57         moltype = AA   length = 107
FEATURE               Location/Qualifiers
REGION                1..107
                      note = Synthetic
source                1..107
                      mol_type = protein
                      organism = synthetic construct
SEQUENCE: 57
DIQMTQSPSS LSASVGDRVT ITCKASQDVS TAVAWYQQKP GKAPKLLIYS ASYRYTGVPS    60
RFSGSGSGTD FTLTISSLQP EDFATYYCQQ HYSTPLTFGA GTKLELK                 107

SEQ ID NO: 58         moltype = AA   length = 118
FEATURE               Location/Qualifiers
REGION                1..118
                      note = Synthetic
source                1..118
                      mol_type = protein
                      organism = synthetic construct
SEQUENCE: 58
QVQLQESGPG LVKPSQTLSL TCTVSGGSVS SDYAWNWIRQ PPGKGLEWIG YITYSGSTSY    60
NPSLKSRVTI SVDTSKNQFS LKLSSVTAAD TAVYYCARRQ VGLGFAYWGQ GTLVTVSA    118

SEQ ID NO: 59         moltype = AA   length = 107
FEATURE               Location/Qualifiers
REGION                1..107
                      note = Synthetic
source                1..107
                      mol_type = protein
                      organism = synthetic construct
SEQUENCE: 59
DIQMTQSPSS LSASVGDRVT ITCKASQDVS TAVAWYQQKP GKAPKLLIYS ASYHYTGVPS    60
RFSGSGSGTD FTLTISSLQP EDFATYYCQQ HYSTPWTFGG GTKLEIK                 107

SEQ ID NO: 60         moltype = AA   length = 118
FEATURE               Location/Qualifiers
REGION                1..118
                      note = Synthetic
source                1..118
                      mol_type = protein
                      organism = synthetic construct
SEQUENCE: 60
```

```
EVQLQESGPG LVKPSDTLSL TCAVSGYSIT SDSAWNWIRQ PPGKGLEWIG YITYSGSTNY    60
NPSLRSRVTM SVDTSKNQFS LKLSSVTAVD TAVYYCTRRQ VGLGFAYWGQ GTLVTVSA     118

SEQ ID NO: 61          moltype = AA  length = 107
FEATURE                Location/Qualifiers
REGION                 1..107
                       note = Synthetic
source                 1..107
                       mol_type = protein
                       organism = synthetic construct
SEQUENCE: 61
DIQMTQSPSS LSASVGDRVT ITCKASQDVS TAVAWYQQKP GKAPKLLIYS ASYRFTGAPS    60
RFSGSGSGTD FTLTISSLQP EDFGIYYCQH HYSTPWTFGG GTKLEFK                 107

SEQ ID NO: 62          moltype = AA  length = 121
FEATURE                Location/Qualifiers
REGION                 1..121
                       note = Synthetic
source                 1..121
                       mol_type = protein
                       organism = synthetic construct
SEQUENCE: 62
QVQLVQSGSE LKKPGASVKV SCKASGYTFT NYGMNWVRQA PGQGLEWMGW INTYTGEPTY    60
ADDFKGRFVF SLDTSVSTAY LQISSLKAED TAVYYCARAP PYGYDVRFAY WGQGTLVTVS   120
S                                                                  121

SEQ ID NO: 63          moltype = AA  length = 112
FEATURE                Location/Qualifiers
REGION                 1..112
                       note = Synthetic
source                 1..112
                       mol_type = protein
                       organism = synthetic construct
SEQUENCE: 63
DVVMTQSPLS LPVTLGQPAS ISCRSSQSIV HSNGNTYLEW FQQRPGQSPR VLIYKVSDRF    60
SGVPDRFSGS GSGTDFTLKI SRVEAEDVGV YYCFQGSHVP WTFGRGTKLE IK           112

SEQ ID NO: 64          moltype = AA  length = 121
FEATURE                Location/Qualifiers
REGION                 1..121
                       note = Synthetic
source                 1..121
                       mol_type = protein
                       organism = synthetic construct
SEQUENCE: 64
QVTLKESGPT LVKPTQTLTL TCTFSGFSLS TFAMGVGWIR QPPGKALEWL AHIWWDDDKY    60
YNPALKSRLT ITKDTSKNQV VLTMTNMDPV DTATYYCARM DYSYFAWFAY WGQGTLVTVS   120
S                                                                  121

SEQ ID NO: 65          moltype = AA  length = 109
FEATURE                Location/Qualifiers
REGION                 1..109
                       note = Synthetic
source                 1..109
                       mol_type = protein
                       organism = synthetic construct
SEQUENCE: 65
QAVVTQEPSL TVSPGGTVTL TCRSSTGAVT TSNYANWVQQ KPGQLFRGLI GGTNNRAPWV    60
PARFSGSLIG DKAALTLSGV QPEDEAEYFC ALWYSNHWVF GGGTKLTVL               109

SEQ ID NO: 66          moltype = AA  length = 122
FEATURE                Location/Qualifiers
REGION                 1..122
                       note = Synthetic
source                 1..122
                       mol_type = protein
                       organism = synthetic construct
SEQUENCE: 66
QVQLVQSGAE VKKPGASVKV SCKASGYTFT SYYMHWVRQA PGQGLEWMGI INPSGGRTSY    60
AQMFQGRVTM TRDTSTSTVY MELSSLRSED TAVYYCARDR EEQWPVGGFD YWGQGTLVTV   120
SS                                                                 122

SEQ ID NO: 67          moltype = AA  length = 107
FEATURE                Location/Qualifiers
REGION                 1..107
                       note = Synthetic
source                 1..107
                       mol_type = protein
                       organism = synthetic construct
```

```
SEQUENCE: 67
DIQMTQSPSS LSASVGDRVT ITCRASQSIR RYLNWYQQKP GKAPKLLIYS ASNLQSGVPS    60
RFSGSGSGTD FTLTISSLQP EDFATYYCQQ SYIIPPTFGQ GTKVEIR                107

SEQ ID NO: 68           moltype = AA   length = 5
FEATURE                 Location/Qualifiers
REGION                  1..5
                        note = Synthetic
source                  1..5
                        mol_type = protein
                        organism = synthetic construct
SEQUENCE: 68
NFLMS                                                                 5

SEQ ID NO: 69           moltype = AA   length = 17
FEATURE                 Location/Qualifiers
REGION                  1..17
                        note = Synthetic
source                  1..17
                        mol_type = protein
                        organism = synthetic construct
SEQUENCE: 69
TISGGGRDTY YVDSVKG                                                   17

SEQ ID NO: 70           moltype = AA   length = 8
FEATURE                 Location/Qualifiers
REGION                  1..8
                        note = Synthetic
source                  1..8
                        mol_type = protein
                        organism = synthetic construct
SEQUENCE: 70
RTTYSMDY                                                              8

SEQ ID NO: 71           moltype = AA   length = 5
FEATURE                 Location/Qualifiers
REGION                  1..5
                        note = Synthetic
source                  1..5
                        mol_type = protein
                        organism = synthetic construct
SEQUENCE: 71
NSYLY                                                                 5

SEQ ID NO: 72           moltype = AA   length = 17
FEATURE                 Location/Qualifiers
REGION                  1..17
                        note = Synthetic
source                  1..17
                        mol_type = protein
                        organism = synthetic construct
SEQUENCE: 72
GINPSNGGTN FNEKFKT                                                   17

SEQ ID NO: 73           moltype = AA   length = 11
FEATURE                 Location/Qualifiers
REGION                  1..11
                        note = Synthetic
source                  1..11
                        mol_type = protein
                        organism = synthetic construct
SEQUENCE: 73
RDYNYDGGFD S                                                         11

SEQ ID NO: 74           moltype = AA   length = 5
FEATURE                 Location/Qualifiers
REGION                  1..5
                        note = Synthetic
source                  1..5
                        mol_type = protein
                        organism = synthetic construct
SEQUENCE: 74
NSYIY                                                                 5

SEQ ID NO: 75           moltype = AA   length = 12
FEATURE                 Location/Qualifiers
REGION                  1..12
                        note = Synthetic
source                  1..12
```

-continued

```
                        mol_type = protein
                        organism = synthetic construct
SEQUENCE: 75
RRDYRYDGGF DS                                                    12

SEQ ID NO: 76           moltype = AA   length = 5
FEATURE                 Location/Qualifiers
REGION                  1..5
                        note = Synthetic
source                  1..5
                        mol_type = protein
                        organism = synthetic construct
SEQUENCE: 76
TYYIY                                                             5

SEQ ID NO: 77           moltype = AA   length = 17
FEATURE                 Location/Qualifiers
REGION                  1..17
                        note = Synthetic
source                  1..17
                        mol_type = protein
                        organism = synthetic construct
SEQUENCE: 77
GINPGNGGTN FNEKFKI                                               17

SEQ ID NO: 78           moltype = AA   length = 11
FEATURE                 Location/Qualifiers
REGION                  1..11
                        note = Synthetic
source                  1..11
                        mol_type = protein
                        organism = synthetic construct
SEQUENCE: 78
RYHGYDGGLD Y                                                     11

SEQ ID NO: 79           moltype = AA   length = 5
FEATURE                 Location/Qualifiers
REGION                  1..5
                        note = Synthetic
source                  1..5
                        mol_type = protein
                        organism = synthetic construct
SEQUENCE: 79
SYYIH                                                             5

SEQ ID NO: 80           moltype = AA   length = 17
FEATURE                 Location/Qualifiers
REGION                  1..17
                        note = Synthetic
source                  1..17
                        mol_type = protein
                        organism = synthetic construct
SEQUENCE: 80
WIFPGSGNSK YNENFKG                                               17

SEQ ID NO: 81           moltype = AA   length = 9
FEATURE                 Location/Qualifiers
REGION                  1..9
                        note = Synthetic
source                  1..9
                        mol_type = protein
                        organism = synthetic construct
SEQUENCE: 81
SETYDYGDY                                                         9

SEQ ID NO: 82           moltype = AA   length = 11
FEATURE                 Location/Qualifiers
REGION                  1..11
                        note = Synthetic
source                  1..11
                        mol_type = protein
                        organism = synthetic construct
SEQUENCE: 82
LASQTIGTWL A                                                     11

SEQ ID NO: 83           moltype = AA   length = 7
FEATURE                 Location/Qualifiers
REGION                  1..7
                        note = Synthetic
```

```
source                  1..7
                        mol_type = protein
                        organism = synthetic construct
SEQUENCE: 83
AATSLAD                                                                   7

SEQ ID NO: 84           moltype = AA  length = 9
FEATURE                 Location/Qualifiers
REGION                  1..9
                        note = Synthetic
source                  1..9
                        mol_type = protein
                        organism = synthetic construct
SEQUENCE: 84
QQFYSIPWT                                                                 9

SEQ ID NO: 85           moltype = AA  length = 12
FEATURE                 Location/Qualifiers
REGION                  1..12
                        note = Synthetic
source                  1..12
                        mol_type = protein
                        organism = synthetic construct
SEQUENCE: 85
RASSTLYSNY LH                                                            12

SEQ ID NO: 86           moltype = AA  length = 7
FEATURE                 Location/Qualifiers
REGION                  1..7
                        note = Synthetic
source                  1..7
                        mol_type = protein
                        organism = synthetic construct
SEQUENCE: 86
RASFLAS                                                                   7

SEQ ID NO: 87           moltype = AA  length = 9
FEATURE                 Location/Qualifiers
REGION                  1..9
                        note = Synthetic
source                  1..9
                        mol_type = protein
                        organism = synthetic construct
SEQUENCE: 87
QQGSSIPLT                                                                 9

SEQ ID NO: 88           moltype = AA  length = 12
FEATURE                 Location/Qualifiers
REGION                  1..12
                        note = Synthetic
source                  1..12
                        mol_type = protein
                        organism = synthetic construct
SEQUENCE: 88
SASSSLYSSY LH                                                            12

SEQ ID NO: 89           moltype = AA  length = 12
FEATURE                 Location/Qualifiers
REGION                  1..12
                        note = Synthetic
source                  1..12
                        mol_type = protein
                        organism = synthetic construct
SEQUENCE: 89
RASSSLYSNY LH                                                            12

SEQ ID NO: 90           moltype = AA  length = 15
FEATURE                 Location/Qualifiers
REGION                  1..15
                        note = Synthetic
source                  1..15
                        mol_type = protein
                        organism = synthetic construct
SEQUENCE: 90
RASKSVSTSG FSYIH                                                         15

SEQ ID NO: 91           moltype = AA  length = 7
FEATURE                 Location/Qualifiers
REGION                  1..7
```

```
                             note = Synthetic
source                   1..7
                             mol_type = protein
                             organism = synthetic construct
SEQUENCE: 91
LASNLES                                                                              7

SEQ ID NO: 92            moltype = AA  length = 9
FEATURE                  Location/Qualifiers
REGION                   1..9
                             note = Synthetic
source                   1..9
                             mol_type = protein
                             organism = synthetic construct
SEQUENCE: 92
QHTWELPNT                                                                            9

SEQ ID NO: 93            moltype = AA  length = 11
FEATURE                  Location/Qualifiers
REGION                   1..11
                             note = Synthetic
source                   1..11
                             mol_type = protein
                             organism = synthetic construct
SEQUENCE: 93
KASQNVGTNV A                                                                        11

SEQ ID NO: 94            moltype = AA  length = 7
FEATURE                  Location/Qualifiers
REGION                   1..7
                             note = Synthetic
source                   1..7
                             mol_type = protein
                             organism = synthetic construct
SEQUENCE: 94
SASYRYS                                                                              7

SEQ ID NO: 95            moltype = AA  length = 9
FEATURE                  Location/Qualifiers
REGION                   1..9
                             note = Synthetic
source                   1..9
                             mol_type = protein
                             organism = synthetic construct
SEQUENCE: 95
QQYYSYPYT                                                                            9

SEQ ID NO: 96            moltype = AA  length = 117
FEATURE                  Location/Qualifiers
REGION                   1..117
                             note = Synthetic
source                   1..117
                             mol_type = protein
                             organism = synthetic construct
SEQUENCE: 96
EVQLVESGGG LVQPGGSLRL SCAASGFTFS NFLMSWVRQA PGKGLEWVST ISGGGRDTYY                    60
VDSVKGRFTI SRDNSKNTLY LQMNSLRAED TAVYYCAKRT TYSMDYWGQG TSVTVSS                      117

SEQ ID NO: 97            moltype = AA  length = 107
FEATURE                  Location/Qualifiers
REGION                   1..107
                             note = Synthetic
source                   1..107
                             mol_type = protein
                             organism = synthetic construct
SEQUENCE: 97
DIQMTQSPSS VSASVGDRVT ITCLASQTIG TWLAWYQQKP GKAPKLLIYA ATSLADGVPS                    60
RFSGSGSGTD FTLTISSLQP EDFATYYCQQ FYSIPWTFGG GTKLEIK                                 107

SEQ ID NO: 98            moltype = AA  length = 120
FEATURE                  Location/Qualifiers
REGION                   1..120
                             note = Synthetic
source                   1..120
                             mol_type = protein
                             organism = synthetic construct
SEQUENCE: 98
QVQLVQSGAE VKKPGASVKV SCKASDYTFT NSYLYWLRQA PGQGLEWMGG INPSNGGTNF                    60
NEKFKTRTTS TRDTSISTAY MELSRLRSDD TVVYYCTRRD YNYDGGFDSW GQGTLVTVSS                   120
```

```
SEQ ID NO: 99            moltype = AA  length = 108
FEATURE                  Location/Qualifiers
REGION                   1..108
                         note = Synthetic
source                   1..108
                         mol_type = protein
                         organism = synthetic construct
SEQUENCE: 99
DIQMTQSPSS LSASVGDRVT FTCRASSTLY SNYLHWYQQK PGKAPKLLIY RASFLASGVP   60
SRFSGSGSGT DFTLTISSLQ PEDFATYYCQ QGSSIPLTFG GGTKVEIK               108

SEQ ID NO: 100           moltype = AA  length = 120
FEATURE                  Location/Qualifiers
REGION                   1..120
                         note = Synthetic
source                   1..120
                         mol_type = protein
                         organism = synthetic construct
SEQUENCE: 100
QVQLVQSGAE VKKPGASVKV SCKASDYTFT NSYIYWVRQA PGQGLEWMGG INPSNGGTNF   60
NEKFKTRVTS TRDTSISTAY MELSRLRSDD TVVYYCARRD YRYDGGFDSW GQGTTLTVSS  120

SEQ ID NO: 101           moltype = AA  length = 108
FEATURE                  Location/Qualifiers
REGION                   1..108
                         note = Synthetic
source                   1..108
                         mol_type = protein
                         organism = synthetic construct
SEQUENCE: 101
DIQMTQSPSS LSASVGDRVT ITCSASSSLY SSYLHWYQQK PGKAPKLLIY RASFLASGVP   60
SRFSGSGSGT DFTLTISSLQ PEDFATYYCQ QGSSIPLTFG AGTKLDLK               108

SEQ ID NO: 102           moltype = AA  length = 120
FEATURE                  Location/Qualifiers
REGION                   1..120
                         note = Synthetic
source                   1..120
                         mol_type = protein
                         organism = synthetic construct
SEQUENCE: 102
QVQLVQSGAE VKKPGASVKV SCKASDYTFT NSYIYWVRQA PGQGLEWMGG INPSNGGTNF   60
NEKFKTRVTS TRDTSISTAY MELSRLRSDD TVVYYCARRD YNYDGGFDSW GQGTLVTVSS  120

SEQ ID NO: 103           moltype = AA  length = 108
FEATURE                  Location/Qualifiers
REGION                   1..108
                         note = Synthetic
source                   1..108
                         mol_type = protein
                         organism = synthetic construct
SEQUENCE: 103
DIQMTQSPSS LSASVGDRVT FTCRASSSLY SNYLHWYQQK PGKAPKLLIY RASFLASGVP   60
SRFSGSGSGT DFTLTISSLQ PEDFATYYCQ QGSSIPLTFG GGTKVEIK               108

SEQ ID NO: 104           moltype = AA  length = 120
FEATURE                  Location/Qualifiers
REGION                   1..120
                         note = Synthetic
source                   1..120
                         mol_type = protein
                         organism = synthetic construct
SEQUENCE: 104
QVQLVQSGAE VKKPGASVKV SCKASGYTFT TYYIYWVRQA PGQGLEWMGG INPGNGGTNF   60
NEKFKIRVTM TRDTSISTAY MELSSLRSED TAVYYCARRY HGYDGGLDYW GQGTLVTVSS  120

SEQ ID NO: 105           moltype = AA  length = 111
FEATURE                  Location/Qualifiers
REGION                   1..111
                         note = Synthetic
source                   1..111
                         mol_type = protein
                         organism = synthetic construct
SEQUENCE: 105
DIVLTQSPAS LAVSPGQRAT ITCRASKSVS TSGFSYIHWY QQKPGQPPKL LIYLASNLES   60
GVPARFSGSG SGTDFTLTIN PVEANDTANY YCQHTWELPN TFGGGTKVEI K           111

SEQ ID NO: 106           moltype = AA  length = 117
```

```
FEATURE              Location/Qualifiers
REGION               1..117
                     note = Synthetic
source               1..117
                     mol_type = protein
                     organism = synthetic construct
SEQUENCE: 106
QVQLVQSGAE VKKPGASVKV SCKASGYTFT SYYIHWVRQA PGQGLEWMGW IFPGSGNSKY    60
NENFKGRVTL TADTSTSTVY MELSSLRSED TAVYYCASET YDYGDYWGQG TLVTVSS      117

SEQ ID NO: 107       moltype = AA  length = 107
FEATURE              Location/Qualifiers
REGION               1..107
                     note = Synthetic
source               1..107
                     mol_type = protein
                     organism = synthetic construct
SEQUENCE: 107
DIQMTQSPSF LSASVGDRVT ITCKASQNVG TNVAWYQQKP GKAPKALIYS ASYRYSGVPS    60
RFSGSGSGTE FTLTISSLQP EDFATYYCQQ YYSYPYTFGQ GTKLEIK                 107

SEQ ID NO: 108       moltype = AA  length = 5
FEATURE              Location/Qualifiers
REGION               1..5
                     note = Synthetic
source               1..5
                     mol_type = protein
                     organism = synthetic construct
SEQUENCE: 108
NYWMH                                                                 5

SEQ ID NO: 109       moltype = AA  length = 17
FEATURE              Location/Qualifiers
REGION               1..17
                     note = Synthetic
source               1..17
                     mol_type = protein
                     organism = synthetic construct
SEQUENCE: 109
MIHPNTNNYN YNEKFKS                                                   17

SEQ ID NO: 110       moltype = AA  length = 12
FEATURE              Location/Qualifiers
REGION               1..12
                     note = Synthetic
source               1..12
                     mol_type = protein
                     organism = synthetic construct
SEQUENCE: 110
SDYGSSPYYF DY                                                        12

SEQ ID NO: 111       moltype = AA  length = 5
FEATURE              Location/Qualifiers
REGION               1..5
                     note = Synthetic
source               1..5
                     mol_type = protein
                     organism = synthetic construct
SEQUENCE: 111
SYWMH                                                                 5

SEQ ID NO: 112       moltype = AA  length = 17
FEATURE              Location/Qualifiers
REGION               1..17
                     note = Synthetic
source               1..17
                     mol_type = protein
                     organism = synthetic construct
SEQUENCE: 112
MIHPNVGSTN YNEKFKS                                                   17

SEQ ID NO: 113       moltype = AA  length = 12
FEATURE              Location/Qualifiers
REGION               1..12
                     note = Synthetic
source               1..12
                     mol_type = protein
                     organism = synthetic construct
SEQUENCE: 113
```

```
SRYGSSPYYF DY                                                             12

SEQ ID NO: 114          moltype = AA  length = 17
FEATURE                 Location/Qualifiers
REGION                  1..17
                        note = Synthetic
source                  1..17
                        mol_type = protein
                        organism = synthetic construct
SEQUENCE: 114
MIHPNSGGNN YNEKFKS                                                        17

SEQ ID NO: 115          moltype = AA  length = 12
FEATURE                 Location/Qualifiers
REGION                  1..12
                        note = Synthetic
source                  1..12
                        mol_type = protein
                        organism = synthetic construct
SEQUENCE: 115
SWYGSSPYYF DY                                                             12

SEQ ID NO: 116          moltype = AA  length = 17
FEATURE                 Location/Qualifiers
REGION                  1..17
                        note = Synthetic
source                  1..17
                        mol_type = protein
                        organism = synthetic construct
SEQUENCE: 116
MIHPTGVSTD YNEKFKS                                                        17

SEQ ID NO: 117          moltype = AA  length = 6
FEATURE                 Location/Qualifiers
REGION                  1..6
                        note = Synthetic
source                  1..6
                        mol_type = protein
                        organism = synthetic construct
SEQUENCE: 117
SDYAWN                                                                    6

SEQ ID NO: 118          moltype = AA  length = 16
FEATURE                 Location/Qualifiers
REGION                  1..16
                        note = Synthetic
source                  1..16
                        mol_type = protein
                        organism = synthetic construct
SEQUENCE: 118
YISDSGSTSY NPSLKS                                                         16

SEQ ID NO: 119          moltype = AA  length = 11
FEATURE                 Location/Qualifiers
REGION                  1..11
                        note = Synthetic
source                  1..11
                        mol_type = protein
                        organism = synthetic construct
SEQUENCE: 119
SFLRLRSYFD H                                                              11

SEQ ID NO: 120          moltype = AA  length = 5
FEATURE                 Location/Qualifiers
REGION                  1..5
                        note = Synthetic
source                  1..5
                        mol_type = protein
                        organism = synthetic construct
SEQUENCE: 120
SYGIN                                                                     5

SEQ ID NO: 121          moltype = AA  length = 17
FEATURE                 Location/Qualifiers
REGION                  1..17
                        note = Synthetic
source                  1..17
                        mol_type = protein
                        organism = synthetic construct
```

```
SEQUENCE: 121
CIYIGNDYTN YNEKFKG                                                             17

SEQ ID NO: 122         moltype = AA   length = 9
FEATURE                Location/Qualifiers
REGION                 1..9
                       note = Synthetic
source                 1..9
                       mol_type = protein
                       organism = synthetic construct
SEQUENCE: 122
AYYGSRVDY                                                                       9

SEQ ID NO: 123         moltype = AA   length = 11
FEATURE                Location/Qualifiers
REGION                 1..11
                       note = Synthetic
source                 1..11
                       mol_type = protein
                       organism = synthetic construct
SEQUENCE: 123
RASQDIDNYL N                                                                   11

SEQ ID NO: 124         moltype = AA   length = 7
FEATURE                Location/Qualifiers
REGION                 1..7
                       note = Synthetic
source                 1..7
                       mol_type = protein
                       organism = synthetic construct
SEQUENCE: 124
YTSRLHS                                                                         7

SEQ ID NO: 125         moltype = AA   length = 9
FEATURE                Location/Qualifiers
REGION                 1..9
                       note = Synthetic
source                 1..9
                       mol_type = protein
                       organism = synthetic construct
SEQUENCE: 125
QQGYTLPWT                                                                       9

SEQ ID NO: 126         moltype = AA   length = 11
FEATURE                Location/Qualifiers
REGION                 1..11
                       note = Synthetic
source                 1..11
                       mol_type = protein
                       organism = synthetic construct
SEQUENCE: 126
RASQDISNYL N                                                                   11

SEQ ID NO: 127         moltype = AA   length = 7
FEATURE                Location/Qualifiers
REGION                 1..7
                       note = Synthetic
source                 1..7
                       mol_type = protein
                       organism = synthetic construct
SEQUENCE: 127
YTSRLQS                                                                         7

SEQ ID NO: 128         moltype = AA   length = 9
FEATURE                Location/Qualifiers
REGION                 1..9
                       note = Synthetic
source                 1..9
                       mol_type = protein
                       organism = synthetic construct
SEQUENCE: 128
QQGNTLPWT                                                                       9

SEQ ID NO: 129         moltype = AA   length = 9
FEATURE                Location/Qualifiers
REGION                 1..9
                       note = Synthetic
source                 1..9
                       mol_type = protein
```

```
                        organism = synthetic construct
SEQUENCE: 129
QQGDTLPWT                                                                       9

SEQ ID NO: 130          moltype = AA  length = 11
FEATURE                 Location/Qualifiers
REGION                  1..11
                        note = Synthetic
source                  1..11
                        mol_type = protein
                        organism = synthetic construct
SEQUENCE: 130
KASQDVNVAV A                                                                   11

SEQ ID NO: 131          moltype = AA  length = 7
FEATURE                 Location/Qualifiers
REGION                  1..7
                        note = Synthetic
source                  1..7
                        mol_type = protein
                        organism = synthetic construct
SEQUENCE: 131
WASTRHI                                                                         7

SEQ ID NO: 132          moltype = AA  length = 9
FEATURE                 Location/Qualifiers
REGION                  1..9
                        note = Synthetic
source                  1..9
                        mol_type = protein
                        organism = synthetic construct
SEQUENCE: 132
QQHYSTPYT                                                                       9

SEQ ID NO: 133          moltype = AA  length = 11
FEATURE                 Location/Qualifiers
REGION                  1..11
                        note = Synthetic
source                  1..11
                        mol_type = protein
                        organism = synthetic construct
SEQUENCE: 133
KASQDINKYI A                                                                   11

SEQ ID NO: 134          moltype = AA  length = 7
FEATURE                 Location/Qualifiers
REGION                  1..7
                        note = Synthetic
source                  1..7
                        mol_type = protein
                        organism = synthetic construct
SEQUENCE: 134
YTSTLQP                                                                         7

SEQ ID NO: 135          moltype = AA  length = 8
FEATURE                 Location/Qualifiers
REGION                  1..8
                        note = Synthetic
source                  1..8
                        mol_type = protein
                        organism = synthetic construct
SEQUENCE: 135
LQYDNLYT                                                                        8

SEQ ID NO: 136          moltype = AA  length = 8
FEATURE                 Location/Qualifiers
REGION                  1..8
                        note = Synthetic
source                  1..8
                        mol_type = protein
                        organism = synthetic construct
SEQUENCE: 136
QSISDYLH                                                                        8

SEQ ID NO: 137          moltype = AA  length = 8
FEATURE                 Location/Qualifiers
REGION                  1..8
                        note = Synthetic
source                  1..8
```

```
                        mol_type = protein
                        organism = synthetic construct
SEQUENCE: 137
CASQSISG                                                                8

SEQ ID NO: 138          moltype = AA    length = 9
FEATURE                 Location/Qualifiers
REGION                  1..9
                        note = Synthetic
source                  1..9
                        mol_type = protein
                        organism = synthetic construct
SEQUENCE: 138
QNGHSFPYT                                                               9

SEQ ID NO: 139          moltype = AA    length = 121
FEATURE                 Location/Qualifiers
REGION                  1..121
                        note = Synthetic
source                  1..121
                        mol_type = protein
                        organism = synthetic construct
SEQUENCE: 139
QVQLVQSGAE VKKPGASVKV SCKASGYTFT NYWMHWMKQA PGQGLEWMGM IHPNTNNYNY        60
NEKFKSRVTS TRDTSISTAY MELSRLRSDD TVVYYCARSD YGSSPYYFDY WGQGTLVTVS       120
S                                                                     121

SEQ ID NO: 140          moltype = AA    length = 107
FEATURE                 Location/Qualifiers
REGION                  1..107
                        note = Synthetic
source                  1..107
                        mol_type = protein
                        organism = synthetic construct
SEQUENCE: 140
DIQMTQSPSS LSASVGDRVT ISCRASQDID NYLNWYQQKP GKAPKLLIKY TSRLHSGVPS        60
RFSGSGSGTD FTLTISSLQP EDFATYFCQQ GYTLPWTFGG GTKVEIK                     107

SEQ ID NO: 141          moltype = AA    length = 121
FEATURE                 Location/Qualifiers
REGION                  1..121
                        note = Synthetic
source                  1..121
                        mol_type = protein
                        organism = synthetic construct
SEQUENCE: 141
QVQLVQSGAE VKKPGASVKV SCKASGYTFT SYWMHWVRQA PGQGLEWMGM IHPNVGSTNY        60
NEKFKSKATM TRDKSSSTVY MELSSLRSED TAVYYCARSR YGSSPYYFDY WGQGTLVTVS       120
S                                                                     121

SEQ ID NO: 142          moltype = AA    length = 107
FEATURE                 Location/Qualifiers
REGION                  1..107
                        note = Synthetic
source                  1..107
                        mol_type = protein
                        organism = synthetic construct
SEQUENCE: 142
DIQMTQSPSS LSASVGDRVT ISCRASQDIS NYLNWYQQKP GKAPKLLIYY TSRLQSGVPS        60
RFSGSGSGTD FTFTISSLQP EDIATYFCQQ GNTLPWTFGG GTKVEIK                     107

SEQ ID NO: 143          moltype = AA    length = 121
FEATURE                 Location/Qualifiers
REGION                  1..121
                        note = Synthetic
source                  1..121
                        mol_type = protein
                        organism = synthetic construct
SEQUENCE: 143
QVQLVQSGAE VKKPGASVKV SCKASGYTFT SYWMHWVRQA PGQGLEWMGM IHPNSGGNNY        60
NEKFKSRVTM TRDTSISTAY MELSRLRSDD TAVYYCARSW YGSSPYYFDY WGQGTLVTVS       120
S                                                                     121

SEQ ID NO: 144          moltype = AA    length = 107
FEATURE                 Location/Qualifiers
REGION                  1..107
                        note = Synthetic
source                  1..107
                        mol_type = protein
```

```
                        organism = synthetic construct
SEQUENCE: 144
DIQMTQSPSS LSASVGDRVT ISCRASQDIS NYLNWYQQKP GKAPKLLIYY TSRLHSGVPS    60
RFSGSGSGTD FTFTISSLQP EDIATYFCQQ GNTLPWTFGQ GTKVEIK                 107

SEQ ID NO: 145          moltype = AA   length = 121
FEATURE                 Location/Qualifiers
REGION                  1..121
                        note = Synthetic
source                  1..121
                        mol_type = protein
                        organism = synthetic construct
SEQUENCE: 145
QVQLVQSGAE VKKPGASVKV SCKASGYTFT SYWMHWVRQA PGQGLEWMGM IHPTGVSTDY    60
NEKFKSRVTM TRDTSTSTVY MELSSLRSED TAVYYCARSD YGSSPYYFDY WGQGTLVTVS   120
S                                                                  121

SEQ ID NO: 146          moltype = AA   length = 107
FEATURE                 Location/Qualifiers
REGION                  1..107
                        note = Synthetic
source                  1..107
                        mol_type = protein
                        organism = synthetic construct
SEQUENCE: 146
DIQMTQSPSS LSASVGDRVT ISCRASQDIS NYLNWYQQKP GKAPKLLIKY TSRLHSGVPS    60
RFSGSGSGTD FTLTISSLQP EDFATYFCQQ GDTLPWTFGG GTKVEIK                 107

SEQ ID NO: 147          moltype = AA   length = 120
FEATURE                 Location/Qualifiers
REGION                  1..120
                        note = Synthetic
source                  1..120
                        mol_type = protein
                        organism = synthetic construct
SEQUENCE: 147
DVQLQESGPG LVKPSQSLSL TCTVTGYSIT SDYAWNWIRQ FPGNKLEWMG YISDSGSTSY    60
NPSLKSRISI TRDTSKNQFF LQLNSVTTED TATYYCANSF LRLRSYFDHW GQGTTLTVSS   120

SEQ ID NO: 148          moltype = AA   length = 107
FEATURE                 Location/Qualifiers
REGION                  1..107
                        note = Synthetic
source                  1..107
                        mol_type = protein
                        organism = synthetic construct
SEQUENCE: 148
DIVMTQSHKF MSTSVGDRVS ITCKASQDVN VAVAWYQQKP GQSPKLLIFW ASTRHIGVPD    60
RFTGSGSGTD YTLTISSVQA EDLALYYCQQ HYSTPYTFGG GTKLEIK                 107

SEQ ID NO: 149          moltype = AA   length = 119
FEATURE                 Location/Qualifiers
REGION                  1..119
                        note = Synthetic
source                  1..119
                        mol_type = protein
                        organism = synthetic construct
SEQUENCE: 149
QVQLVQSGAE VKKPGASVKV SCKASGYTFT SYGINWVRQA PGQRLEWMGW CIYIGNDYTN    60
YNEKFKGRVT ITRDTSASTA YMELSSLRSE DTAVYYCARA YYGSRVDYWG QGTLVTVSS    119

SEQ ID NO: 150          moltype = AA   length = 106
FEATURE                 Location/Qualifiers
REGION                  1..106
                        note = Synthetic
source                  1..106
                        mol_type = protein
                        organism = synthetic construct
SEQUENCE: 150
DIQMTQSPSS LSAFVGDRVT ITCKASQDIN KYIAWYQQKP GKAPKLLIHY TSTLQPGVPS    60
RFSGSGSGRD FTFTISSLQP EDIATYYCLQ YDNLYTFGGG TKVEIK                  106

SEQ ID NO: 151          moltype = AA   length = 119
FEATURE                 Location/Qualifiers
REGION                  1..119
                        note = Synthetic
source                  1..119
                        mol_type = protein
                        organism = synthetic construct
```

```
SEQUENCE: 151
QVQLVQSGAE VKKPGASVKV SCKASGYTFT SYGINWVRQA PGQRLEWMGW CIYIGNDYTN    60
YNEKFKGRVT ITRDTSASTA YMELSSLRSE DTAVYYCARA YYGSRVDYWG QGTLVTVSS    119

SEQ ID NO: 152          moltype = AA   length = 104
FEATURE                 Location/Qualifiers
REGION                  1..104
                        note = Synthetic
source                  1..104
                        mol_type = protein
                        organism = synthetic construct
SEQUENCE: 152
EIVLTQSPVT LSLSPGERAT LSCQSISDYL HWYLQKPGQA PRLLIKCASQ SISGIPARFS    60
GSGSGSDFTL TISSLEPEDF AVYYCQNGHS FPYTFGGGTK VEIK                    104

SEQ ID NO: 153          moltype = AA   length = 121
FEATURE                 Location/Qualifiers
REGION                  1..121
                        note = Synthetic
source                  1..121
                        mol_type = protein
                        organism = synthetic construct
SEQUENCE: 153
QVQLVQSGAE VKKPGASVKV SCKASGYTFT SYWMHWVRQA PGQGLEWMGM IHPNSGGNNY    60
NEKFKSRVTM TRDTSISTAY MELSRLRSDD TAVYYCARSW YGSSPYYFDY WGQGTLVTVS    120
S                                                                   121

SEQ ID NO: 154          moltype = AA   length = 107
FEATURE                 Location/Qualifiers
REGION                  1..107
                        note = Synthetic
source                  1..107
                        mol_type = protein
                        organism = synthetic construct
SEQUENCE: 154
DIQMTQSPSS LSASVGDRVT ISCRASQDID NYLNWYQQKP GKAPKLLIKY TSRLHSGVPS    60
RFSGSGSGTD FTLTISSLQP EDFATYFCQQ GYTLPWTFGG GTKVEIK                 107

SEQ ID NO: 155          moltype = AA   length = 327
FEATURE                 Location/Qualifiers
REGION                  1..327
                        note = Synthetic
source                  1..327
                        mol_type = protein
                        organism = synthetic construct
SEQUENCE: 155
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFLGGPSV    120
FLFPPKPKDT LMISRTPEVT CVVVDVSQED PEVQFNWYVD GVEVHNAKTK PREEQFNSTY    180
RVVSVLTVLH QDWLNGKEYK CKVSNKGLPS SIEKTISKAK GQPREPQVYT LPPSQEEMTK    240
NQVSLTCLVK GFYPSDIAVE WESNGQPENN YKTTPPVLDS DGSFFLYSRL TVDKSRWQEG    300
NVFSCSVMHE ALHNHYTQKS LSLSLGK                                       327

SEQ ID NO: 156          moltype = AA   length = 330
FEATURE                 Location/Qualifiers
REGION                  1..330
                        note = Synthetic
source                  1..330
                        mol_type = protein
                        organism = synthetic construct
SEQUENCE: 156
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
PSVFLFPPKP KDTLMISRTP EVTCVVVDVS HEDPEVKFNW YVDGVEVHNA KTKPREEQYA    180
STYRVVSVLT VLHQDWLNGK EYKCKVSNKA LPAPIEKTIS KAKGQPREPQ VYTLPPSREE    240
MTKNQVSLTC LVKGFYPSDI AVEWESNGQP ENNYKTTPPV LDSDGSFFLY SKLTVDKSRW    300
QQGNVFSCSV MHEALHNHYT QKSLSLSPGK                                    330

SEQ ID NO: 157          moltype = AA   length = 330
FEATURE                 Location/Qualifiers
REGION                  1..330
                        note = Synthetic
source                  1..330
                        mol_type = protein
                        organism = synthetic construct
SEQUENCE: 157
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLGG    120
PSVFLFPPKP KDTLMISRTP EVTCVVVDVS HEDPEVKFNW YVDGVEVHNA KTKPREEQYN    180
```

```
STYRVVSVLT VLHQDWLNGK EYKCKVSNKA LPAPIEKTIS KAKGQPREPQ VYTLPPSREE    240
MTKNQVSLTC LVKGFYPSDI AVEWESNGQP ENNYKTTPPV LDSDGSFFLY SKLTVDKSRW    300
QQGNVFSCSV MHEALHNHYT QKSLSLSPGA                                    330

SEQ ID NO: 158         moltype = AA   length = 698
FEATURE                Location/Qualifiers
REGION                 1..698
                       note = Synthetic
source                 1..698
                       mol_type = protein
                       organism = synthetic construct
SEQUENCE: 158
EVQLVESGGG LVQPGGSLRL SCAASGFTFS NFLMSWVRQA PGKGLEWVST ISGGGRDTYY     60
VDSVKGRFTI SRDNSKNTLY LQMNSLRAED TAVYYCAKRT TYSMDYWGQG TSVTVSSAST    120
KGPSVFPLAP CSRSTSESTA ALGCLVKDYF PEPVTVSWNS GALTSGVHTF PAVLQSSGLY    180
SLSSVVTVPS SSLGTKTYTC NVDHKPSNTK VDKRVESKYG PPCPPCPAPE FLGGPSVFLF    240
PPKPKDTLMI SRTPEVTCVV VDVSQEDPEV QFNWYVDGVE VHNAKTKPRE EQFNSTYRVV    300
SVLTVLHQDW LNGKEYKCKV SNKGLPSSIE KTISKAKGQP REPQVYTLPP SQEEMTKNQV    360
SLTCLVKGFY PSDIAVEWES NGQPENNYKT TPPVLDSDGS FFLYSRLTVD KSRWQEGNVF    420
SCSVMHEALH NHYTQKSLSL SLGKGGGGSG GGGSQVQLVQ SGAEVKKPGA SVKVSCKASG    480
YTFTSYYMHW VRQAPGQGLE WMGIINPSGG RTSYAQMFQG RVTMTRDTST STVYMELSSL    540
RSEDTAVYYC ARDREEQWPV GGFDYWGQGT LVTVSSGGGG SGGGGSGGGG SDIQMTQSPS    600
SLSASVGDRV TITCRASQSI RRYLNWYQQK PGKAPKLLIY SASNLQSGVP SRFSGSGSGT    660
DFTLTISSLQ PEDFATYYCQ QSYIIPPTFG QGTKVEIK                            698

SEQ ID NO: 159         moltype = AA   length = 214
FEATURE                Location/Qualifiers
REGION                 1..214
                       note = Synthetic
source                 1..214
                       mol_type = protein
                       organism = synthetic construct
SEQUENCE: 159
DIQMTQSPSS VSASVGDRVT ITCLASQTIG TWLAWYQQKP GKAPKLLIDA ATSLADGVPS     60
RFSGSGSGTD FTLTISSLQP EDFATYYCQQ FYSIPWTFGG GTKLEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 160         moltype = AA   length = 698
FEATURE                Location/Qualifiers
REGION                 1..698
                       note = Synthetic
source                 1..698
                       mol_type = protein
                       organism = synthetic construct
SEQUENCE: 160
QVQLVQSGAE VKKPGASVKV SCKASGYTFT SYYIHWVRQA PGQGLEWMGW IFPGSGNSKY     60
NENFKGRVTL TADTSTSTVY MELSSLRSED TAVYYCASET YDYGDYWGQG TLVTVSSAST    120
KGPSVFPLAP CSRSTSESTA ALGCLVKDYF PEPVTVSWNS GALTSGVHTF PAVLQSSGLY    180
SLSSVVTVPS SSLGTKTYTC NVDHKPSNTK VDKRVESKYG PPCPPCPAPE FLGGPSVFLF    240
PPKPKDTLMI SRTPEVTCVV VDVSQEDPEV QFNWYVDGVE VHNAKTKPRE EQFNSTYRVV    300
SVLTVLHQDW LNGKEYKCKV SNKGLPSSIE KTISKAKGQP REPQVYTLPP SQEEMTKNQV    360
SLTCLVKGFY PSDIAVEWES NGQPENNYKT TPPVLDSDGS FFLYSRLTVD KSRWQEGNVF    420
SCSVMHEALH NHYTQKSLSL SLGKGGGGSG GGGSQVQLVQ SGAEVKKPGA SVKVSCKASG    480
YTFTSYYMHW VRQAPGQGLE WMGIINPSGG RTSYAQMFQG RVTMTRDTST STVYMELSSL    540
RSEDTAVYYC ARDREEQWPV GGFDYWGQGT LVTVSSGGGG SGGGGSGGGG SDIQMTQSPS    600
SLSASVGDRV TITCRASQSI RRYLNWYQQK PGKAPKLLIY SASNLQSGVP SRFSGSGSGT    660
DFTLTISSLQ PEDFATYYCQ QSYIIPPTFG QGTKVEIK                            698

SEQ ID NO: 161         moltype = AA   length = 214
FEATURE                Location/Qualifiers
REGION                 1..214
                       note = Synthetic
source                 1..214
                       mol_type = protein
                       organism = synthetic construct
SEQUENCE: 161
DIQMTQSPSF LSASVGDRVT ITCKASQNVG TNVAWYQQKP GKAPKALIYS ASYRYSGVPS     60
RFSGSGSGTE FTLTISSLQP EDFATYYCQQ YYSYPYTFGQ GTKLEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 162         moltype = AA   length = 713
FEATURE                Location/Qualifiers
REGION                 1..713
                       note = Synthetic
source                 1..713
                       mol_type = protein
                       organism = synthetic construct
```

-continued

```
SEQUENCE: 162
QVQLVQSGAE VKKPGASVKV SCKASGYTFT SYYIHWVRQA PGQGLEWMGW IFPGSGNSKY    60
NENFKGRVTL TADTSTSTVY MELSSLRSED TAVYYCASET YDYGDYWGQG TLVTVSSAST   120
KGPSVFPLAP CSRSTSESTA ALGCLVKDYF PEPVTVSWNS GALTSGVHTF PAVLQSSGLY   180
SLSSVVTVPS SSLGTKTYTC NVDHKPSNTK VDKRVESKYG PPCPPCPAPE FLGGPSVFLF   240
PPKPKDTLMI SRTPEVTCVV VDVSQEDPEV QFNWYVDGVE VHNAKTKPRE EQFNSTYRVV   300
SVLTVLHQDW LNGKEYKCKV SNKGLPSSIE KTISKAKGQP REPQVYTLPP SQEEMTKNQV   360
SLTCLVKGFY PSDIAVEWES NGQPENNYKT TPPVLDSDGS FFLYSRLTVD KSRWQEGNVF   420
SCSVMHEALH NHYTQKSLSL SLGKGGGGSG GGGSQVQLVQ SGAEVKKPGA SVKVSCKASG   480
YTFTSYYMHW VRQAPGQGLE WMGIINPSGG RTSYAQMFQG RVTMTRDTST STVYMELSSL   540
RSEDTAVYYC ARDREEQWPV GGFDYWGQGT LVTVSSGGGG SGGGGSGGGG SGGGGSGGGG   600
SGGGGSDIQM TQSPSSLSAS VGDRVTITCR ASQSIRRYLN WYQQKPGKAP KLLIYSASNL   660
QSGVPSRFSG SGSGTDFTLT ISSLQPEDFA TYYCQQSYII PPTFGQGTKV EIK          713

SEQ ID NO: 163          moltype = AA   length = 5
FEATURE                 Location/Qualifiers
REGION                  1..5
                        note = Synthetic
source                  1..5
                        mol_type = protein
                        organism = synthetic construct
SEQUENCE: 163
DYYMN                                                                 5

SEQ ID NO: 164          moltype = AA   length = 17
FEATURE                 Location/Qualifiers
REGION                  1..17
                        note = Synthetic
source                  1..17
                        mol_type = protein
                        organism = synthetic construct
SEQUENCE: 164
VINPYNGDTS YNQKFKG                                                   17

SEQ ID NO: 165          moltype = AA   length = 11
FEATURE                 Location/Qualifiers
REGION                  1..11
                        note = Synthetic
source                  1..11
                        mol_type = protein
                        organism = synthetic construct
SEQUENCE: 165
DDGYYVHYFD Y                                                         11

SEQ ID NO: 166          moltype = AA   length = 5
FEATURE                 Location/Qualifiers
REGION                  1..5
                        note = Synthetic
source                  1..5
                        mol_type = protein
                        organism = synthetic construct
SEQUENCE: 166
HYYMN                                                                 5

SEQ ID NO: 167          moltype = AA   length = 17
FEATURE                 Location/Qualifiers
REGION                  1..17
                        note = Synthetic
source                  1..17
                        mol_type = protein
                        organism = synthetic construct
SEQUENCE: 167
LINPYNGDTA YNQKFKD                                                   17

SEQ ID NO: 168          moltype = AA   length = 10
FEATURE                 Location/Qualifiers
REGION                  1..10
                        note = Synthetic
source                  1..10
                        mol_type = protein
                        organism = synthetic construct
SEQUENCE: 168
TRDDGYYVEH                                                           10

SEQ ID NO: 169          moltype = AA   length = 6
FEATURE                 Location/Qualifiers
REGION                  1..6
                        note = Synthetic
source                  1..6
```

```
                        mol_type = protein
                        organism = synthetic construct
SEQUENCE: 169
TAYTIH                                                              6

SEQ ID NO: 170          moltype = AA   length = 17
FEATURE                 Location/Qualifiers
REGION                  1..17
                        note = Synthetic
source                  1..17
                        mol_type = protein
                        organism = synthetic construct
SEQUENCE: 170
WLYPGNDNIM YNENFKD                                                  17

SEQ ID NO: 171          moltype = AA   length = 9
FEATURE                 Location/Qualifiers
REGION                  1..9
                        note = Synthetic
source                  1..9
                        mol_type = protein
                        organism = synthetic construct
SEQUENCE: 171
HEDWGPLDY                                                           9

SEQ ID NO: 172          moltype = AA   length = 11
FEATURE                 Location/Qualifiers
REGION                  1..11
                        note = Synthetic
source                  1..11
                        mol_type = protein
                        organism = synthetic construct
SEQUENCE: 172
RASQDISSRL T                                                        11

SEQ ID NO: 173          moltype = AA   length = 7
FEATURE                 Location/Qualifiers
REGION                  1..7
                        note = Synthetic
source                  1..7
                        mol_type = protein
                        organism = synthetic construct
SEQUENCE: 173
ATSSLDS                                                             7

SEQ ID NO: 174          moltype = AA   length = 9
FEATURE                 Location/Qualifiers
REGION                  1..9
                        note = Synthetic
source                  1..9
                        mol_type = protein
                        organism = synthetic construct
SEQUENCE: 174
LQYASSPLT                                                           9

SEQ ID NO: 175          moltype = AA   length = 11
FEATURE                 Location/Qualifiers
REGION                  1..11
                        note = Synthetic
source                  1..11
                        mol_type = protein
                        organism = synthetic construct
SEQUENCE: 175
RASQDIGSRL N                                                        11

SEQ ID NO: 176          moltype = AA   length = 9
FEATURE                 Location/Qualifiers
REGION                  1..9
                        note = Synthetic
source                  1..9
                        mol_type = protein
                        organism = synthetic construct
SEQUENCE: 176
LQYASSPPT                                                           9

SEQ ID NO: 177          moltype = AA   length = 8
FEATURE                 Location/Qualifiers
REGION                  1..8
                        note = Synthetic
```

```
source                      1..8
                            mol_type = protein
                            organism = synthetic construct
SEQUENCE: 177
RASQSISS                                                                    8

SEQ ID NO: 178              moltype = AA  length = 7
FEATURE                     Location/Qualifiers
REGION                      1..7
                            note = Synthetic
source                      1..7
                            mol_type = protein
                            organism = synthetic construct
SEQUENCE: 178
RASNLES                                                                     7

SEQ ID NO: 179              moltype = AA  length = 9
FEATURE                     Location/Qualifiers
REGION                      1..9
                            note = Synthetic
source                      1..9
                            mol_type = protein
                            organism = synthetic construct
SEQUENCE: 179
QQSNGLPYT                                                                   9

SEQ ID NO: 180              moltype = AA  length = 120
FEATURE                     Location/Qualifiers
REGION                      1..120
                            note = Synthetic
source                      1..120
                            mol_type = protein
                            organism = synthetic construct
SEQUENCE: 180
QVQLVQSGAE VKKPGASVKV SCKASGYTLT DYYMNWMRQA PGQGLEWMGV INPYNGDTSY           60
NQKFKGRVTM TRDTSTSTVY MELSSLRSED TAVYYCVRDD GYYVHYFDYW GQGTLVTVSS          120

SEQ ID NO: 181              moltype = AA  length = 107
FEATURE                     Location/Qualifiers
REGION                      1..107
                            note = Synthetic
source                      1..107
                            mol_type = protein
                            organism = synthetic construct
SEQUENCE: 181
DIQMTQSPSS LSASVGDRVT ITCRASQDIS SRLTWLQQEP EKAPKRLIYA TSSLDSGVPK           60
RFSGSGSGTD FTLTISSLQP EDFATYYCLQ YASSPLTFGG GTKVEIK                       107

SEQ ID NO: 182              moltype = AA  length = 120
FEATURE                     Location/Qualifiers
REGION                      1..120
                            note = Synthetic
source                      1..120
                            mol_type = protein
                            organism = synthetic construct
SEQUENCE: 182
QVQLVQSGAE VKKPGASVKV SCKASGYTFT DYYMNWVRQA PGQGLEWMGV INPYNGDTSY           60
NQKFKGRVTM TRDTSTSTVY MELSSLRSED TAVYYCARDD GYYVHYFDYW GQGTLVTVSS          120

SEQ ID NO: 183              moltype = AA  length = 107
FEATURE                     Location/Qualifiers
REGION                      1..107
                            note = Synthetic
source                      1..107
                            mol_type = protein
                            organism = synthetic construct
SEQUENCE: 183
DIQMTQSPSS LSASVGDRVT ITCRASQDIS SRLTWLQQKP GKAPKRLIYA TSSLDSGVPS           60
RFSGSGSGTD FTLTISSLQP EDFATYYCLQ YASSPLTFGG GTKVEIK                       107

SEQ ID NO: 184              moltype = AA  length = 132
FEATURE                     Location/Qualifiers
REGION                      1..132
                            note = Synthetic
source                      1..132
                            mol_type = protein
                            organism = synthetic construct
SEQUENCE: 184
QVQLVQSGAE VKKPGASVKV SCKASGFTFS HYYMNWVRQA PGQGLEWMGL INPYNGDTAY           60
```

```
NQKFKDRVTM TRDTSTSTVY MELSSLRSED TAVYFCTRDD GYYVEHFDYW DDGYYVEHFD    120
YWGQGTLVTV SS                                                      132

SEQ ID NO: 185           moltype = AA   length = 107
FEATURE                  Location/Qualifiers
REGION                   1..107
                         note = Synthetic
source                   1..107
                         mol_type = protein
                         organism = synthetic construct
SEQUENCE: 185
DIQMTQSPSS LSASVGDRVT ITCRASQDIG SRLNWYQQKP GKAPKRLIYA TSSLDSGVPS    60
RFSGSGSGTD FTLTISSLQP EDFATYYCLQ YASSPPTFGG GTKVEIK                107

SEQ ID NO: 186           moltype = AA   length = 118
FEATURE                  Location/Qualifiers
REGION                   1..118
                         note = Synthetic
source                   1..118
                         mol_type = protein
                         organism = synthetic construct
SEQUENCE: 186
QVQLVQSGAE VKKPGASVKV SCKASGYTFT AYTIHWVRQA PGQGLEWMGW LYPGNDNIMY    60
NENFKDRVTM TRDTSTSTVY MELSSLRSED TAVYYCARHE DWGPLDYWGQ GTLVTVSS     118

SEQ ID NO: 187           moltype = AA   length = 107
FEATURE                  Location/Qualifiers
REGION                   1..107
                         note = Synthetic
source                   1..107
                         mol_type = protein
                         organism = synthetic construct
SEQUENCE: 187
DIQMTQSPST LSASVGDRVT ITCRASQSIS SWLAWYQQKP GKAPKLLIYR ASNLESGVPS    60
RFSGSGSGTE FTLTISSLQP DDFATYYCQQ SNGLPYTFGQ GTKLEIK                107

SEQ ID NO: 188           moltype = AA   length = 15
FEATURE                  Location/Qualifiers
REGION                   1..15
                         note = Synthetic
source                   1..15
                         mol_type = protein
                         organism = synthetic construct
SEQUENCE: 188
GGGGSGGGGS GGGGS                                                    15

SEQ ID NO: 189           moltype = AA   length = 20
FEATURE                  Location/Qualifiers
REGION                   1..20
                         note = Synthetic
source                   1..20
                         mol_type = protein
                         organism = synthetic construct
SEQUENCE: 189
GGGGSGGGGS GGGGSGGGGS                                               20

SEQ ID NO: 190           moltype = AA   length = 25
FEATURE                  Location/Qualifiers
REGION                   1..25
                         note = Synthetic
source                   1..25
                         mol_type = protein
                         organism = synthetic construct
SEQUENCE: 190
GGGGSGGGGS GGGGSGGGGS GGGGS                                         25

SEQ ID NO: 191           moltype = AA   length = 30
FEATURE                  Location/Qualifiers
REGION                   1..30
                         note = Synthetic
source                   1..30
                         mol_type = protein
                         organism = synthetic construct
SEQUENCE: 191
GGGGSGGGGS GGGGSGGGGS GGGGSGGGGS                                    30

SEQ ID NO: 192           moltype = AA   length = 706
FEATURE                  Location/Qualifiers
REGION                   1..706
```

```
                            note = Synthetic
source                      1..706
                            mol_type = protein
                            organism = synthetic construct
SEQUENCE: 192
QVQLVQSGAE VKKPGASVKV SCKASGYTLT DYYMNWMRQA PGQGLEWMGV INPYNGDTSY   60
NQKFKGRVTM TRDTSTSTVY MELSSLRSED TAVYYCVRDD GYYVHYFDYW GQGTLVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGKGGG GSGGGGSQVQ LVQSGAEVKK PGASVKVSCK  480
ASGYTFTSYY MHWVRQAPGQ GLEWMGIINP SGGRTSYAQM FQGRVTMTRD TSTSTVYMEL  540
SSLRSEDTAV YYCARDREEQ WPVGGFDYWG QGTLVTVSSG GGGSGGGGSG GGGSGGGGSD  600
IQMTQSPSSL SASVGDRVTI TCRASQSIRR YLNWYQQKPG KAPKLLIYSA SNLQSGVPSR  660
FSGSGSGTDF TLTISSLQPE DFATYYCQQS YIIPPTFGQG TKVEIK                706

SEQ ID NO: 193              moltype = AA    length = 716
FEATURE                     Location/Qualifiers
REGION                      1..716
                            note = Synthetic
source                      1..716
                            mol_type = protein
                            organism = synthetic construct
SEQUENCE: 193
QVQLVQSGAE VKKPGASVKV SCKASGYTLT DYYMNWMRQA PGQGLEWMGV INPYNGDTSY   60
NQKFKGRVTM TRDTSTSTVY MELSSLRSED TAVYYCVRDD GYYVHYFDYW GQGTLVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGKGGG GSGGGGSQVQ LVQSGAEVKK PGASVKVSCK  480
ASGYTFTSYY MHWVRQAPGQ GLEWMGIINP SGGRTSYAQM FQGRVTMTRD TSTSTVYMEL  540
SSLRSEDTAV YYCARDREEQ WPVGGFDYWG QGTLVTVSSG GGGSGGGGSG GGGSGGGGSG  600
GGGSGGGGSD IQMTQSPSSL SASVGDRVTI TCRASQSIRR YLNWYQQKPG KAPKLLIYSA  660
SNLQSGVPSR FSGSGSGTDF TLTISSLQPE DFATYYCQQS YIIPPTFGQG TKVEIK      716

SEQ ID NO: 194              moltype = AA    length = 214
FEATURE                     Location/Qualifiers
REGION                      1..214
                            note = Synthetic
source                      1..214
                            mol_type = protein
                            organism = synthetic construct
SEQUENCE: 194
DIQMTQSPSS LSASVGDRVT ITCRASQDIS SRLTWLQQKP EKAPKRLIYA TSSLDSGVPS   60
RFSGSGSGTD FTLTISSLQP EDFATYYCLQ YASSPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 195              moltype = AA    length = 227
FEATURE                     Location/Qualifiers
REGION                      1..227
                            note = Synthetic
source                      1..227
                            mol_type = protein
                            organism = synthetic construct
SEQUENCE: 195
DKTHTCPPCP APELLGGPDV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PEEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 196              moltype = AA    length = 227
FEATURE                     Location/Qualifiers
REGION                      1..227
                            note = Synthetic
source                      1..227
                            mol_type = protein
                            organism = synthetic construct
SEQUENCE: 196
DKTHTCPPCP APELLGGPSV FLFPPKPKDT LMISRTPEVT CVVVDVSHED PEVKFNWYVD   60
GVEVHNAKTK PREEQYASTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 197              moltype = AA    length = 225
```

```
FEATURE                 Location/Qualifiers
REGION                  1..225
                        note = Synthetic
source                  1..225
                        mol_type = protein
                        organism = synthetic construct
SEQUENCE: 197
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ   120
PREPQVYTLP PSQEEMTKNQ VSLTCLVKGF YPSDIAVEWE SNGQPENNYK TTPPVLDSDG   180
SFFLYSRLTV DKSRWQQGNV FSCSVMHEAL HNHYTQKSLS LSLGK                  225

SEQ ID NO: 198          moltype = AA   length = 232
FEATURE                 Location/Qualifiers
REGION                  1..232
                        note = Synthetic
source                  1..232
                        mol_type = protein
                        organism = synthetic construct
SEQUENCE: 198
DKTVERKCCV ECPPCPAPPV AGPSVFLFPP KPKDTLMISR TPEVTCVVVD VSHEDPEVQF    60
NWYVDGVEVH NAKTKPREEQ FNSTFRVVSV LTVVHQDWLN GKEYKCKVSN KGLPAPIEKT   120
ISKTKGQPRE PQVYTLPPSR EEMTKNQVSL TCLVKGFYPS DIAVEWESNG QPENNYKTTP   180
PMLDSDGSFF LYSKLTVDKS RWQQGNVFSC SVMHEALHNH YTQKSLSLSP GK           232

SEQ ID NO: 199          moltype = AA   length = 226
FEATURE                 Location/Qualifiers
REGION                  1..226
                        note = Synthetic
source                  1..226
                        mol_type = protein
                        organism = synthetic construct
SEQUENCE: 199
DKTHTCPPCP APELLGGPDV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PEEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPG                 226

SEQ ID NO: 200          moltype = AA   length = 226
FEATURE                 Location/Qualifiers
REGION                  1..226
                        note = Synthetic
source                  1..226
                        mol_type = protein
                        organism = synthetic construct
SEQUENCE: 200
DKTHTCPPCP APELLGGPSV FLFPPKPKDT LMISRTPEVT CVVVDVSHED PEVKFNWYVD    60
GVEVHNAKTK PREEQYASTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPG                 226

SEQ ID NO: 201          moltype = AA   length = 224
FEATURE                 Location/Qualifiers
REGION                  1..224
                        note = Synthetic
source                  1..224
                        mol_type = protein
                        organism = synthetic construct
SEQUENCE: 201
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ   120
PREPQVYTLP PSQEEMTKNQ VSLTCLVKGF YPSDIAVEWE SNGQPENNYK TTPPVLDSDG   180
SFFLYSRLTV DKSRWQQGNV FSCSVMHEAL HNHYTQKSLS LSLG                   224

SEQ ID NO: 202          moltype = AA   length = 231
FEATURE                 Location/Qualifiers
REGION                  1..231
                        note = Synthetic
source                  1..231
                        mol_type = protein
                        organism = synthetic construct
SEQUENCE: 202
DKTVERKCCV ECPPCPAPPV AGPSVFLFPP KPKDTLMISR TPEVTCVVVD VSHEDPEVQF    60
NWYVDGVEVH NAKTKPREEQ FNSTFRVVSV LTVVHQDWLN GKEYKCKVSN KGLPAPIEKT   120
ISKTKGQPRE PQVYTLPPSR EEMTKNQVSL TCLVKGFYPS DIAVEWESNG QPENNYKTTP   180
PMLDSDGSFF LYSKLTVDKS RWQQGNVFSC SVMHEALHNH YTQKSLSLSP G            231

SEQ ID NO: 203          moltype = AA   length = 447
FEATURE                 Location/Qualifiers
```

```
REGION                  1..447
                        note = Synthetic
source                  1..447
                        mol_type = protein
                        organism = synthetic construct
SEQUENCE: 203
EVQLQQSGPV LVKPGASVKM SCKASGYTLT DYYMNWMKQS HGKSLEWIGV INPYNGDTSC    60
NQKFKGKATL TADKSSSTAY MELNSLTSDD SAVYYCVRDD GYYVHYFDYW GQGTTLTVSS   120
ASTKGPSVFP LAPCSRSTSE STAALGCLVK DYFPEPVTVS WNSGALTSGV HTFPAVLQSS   180
GLYSLSSVVT VPSSSLGTKT YTCNVDHKPS NTKVDKRVES KYGPPCPPCP APEFLGGPSV   240
FLFPPKPKDT LMISRTPEVT CVVVDVSQED PEVQFNWYVD GVEVHNAKTK PREEQFNSTY   300
RVVSVLTVLH QDWLNGKEYK CKVSNKGLPS SIEKTISKAK GQPREPQVYT LPPSQEEMTK   360
NQVSLTCLVK GFYPSDIAVE WESNGQPENN YKTTPPVLDS DGSFFLYSRL TVDKSRWQEG   420
NVFSCSVMHE ALHNHYTQKS LSLSLGK                                       447

SEQ ID NO: 204          moltype = AA  length = 214
FEATURE                 Location/Qualifiers
REGION                  1..214
                        note = Synthetic
source                  1..214
                        mol_type = protein
                        organism = synthetic construct
SEQUENCE: 204
DIQMTQSPSS LSASLGERVT LTCRASQDIS SRLTWQQEP DGTIKRLIYA TSSLDSGVPK     60
RFNGSRSGSD YSLTISSLES EDFVDYYCLQ YASSPLTFGA GTKLELKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 205          moltype = AA  length = 330
FEATURE                 Location/Qualifiers
REGION                  1..330
                        note = Synthetic
source                  1..330
                        mol_type = protein
                        organism = synthetic construct
SEQUENCE: 205
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 206          moltype = AA  length = 330
FEATURE                 Location/Qualifiers
REGION                  1..330
                        note = Synthetic
source                  1..330
                        mol_type = protein
                        organism = synthetic construct
SEQUENCE: 206
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYA   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 207          moltype = AA  length = 327
FEATURE                 Location/Qualifiers
REGION                  1..327
                        note = Synthetic
source                  1..327
                        mol_type = protein
                        organism = synthetic construct
SEQUENCE: 207
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQQG   300
NVFSCSVMHE ALHNHYTQKS LSLSLGK                                       327

SEQ ID NO: 208          moltype = AA  length = 326
FEATURE                 Location/Qualifiers
REGION                  1..326
                        note = Synthetic
source                  1..326
                        mol_type = protein
```

```
                          organism = synthetic construct
SEQUENCE: 208
ASTKGPSVFP LAPCSRSTSE STAALGCLVK DYFPEPVTVS WNSGALTSGV HTFPAVLQSS    60
GLYSLSSVVT VPSSNFGTQT YTCNVDHKPS NTKVDKTVER KCCVECPCCP APPVAGPSVF   120
LFPPKPKDTL MISRTPEVTC VVVDVSHEDP EVQFNWYVDG VEVHNAKTKP REEQFNSTFR   180
VVSVLTVVHQ DWLNGKEYKC KVSNKGLPAP IEKTISKTKG QPREPQVYTL PPSREEMTKN   240
QVSLTCLVKG FYPSDISVEW ESNGQPENNY KTTPPMLDSD GSFFLYSKLT VDKSRWQQGN   300
VFSCSVMHEA LHNHYTQKSL SLSPGK                                        326

SEQ ID NO: 209           moltype = AA  length = 329
FEATURE                  Location/Qualifiers
REGION                   1..329
                          note = Synthetic
source                   1..329
                          mol_type = protein
                          organism = synthetic construct
SEQUENCE: 209
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                     329

SEQ ID NO: 210           moltype = AA  length = 329
FEATURE                  Location/Qualifiers
REGION                   1..329
                          note = Synthetic
source                   1..329
                          mol_type = protein
                          organism = synthetic construct
SEQUENCE: 210
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYA   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                     329

SEQ ID NO: 211           moltype = AA  length = 326
FEATURE                  Location/Qualifiers
REGION                   1..326
                          note = Synthetic
source                   1..326
                          mol_type = protein
                          organism = synthetic construct
SEQUENCE: 211
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQQG   300
NVFSCSVMHE ALHNHYTQKS LSLSLG                                        326

SEQ ID NO: 212           moltype = AA  length = 325
FEATURE                  Location/Qualifiers
REGION                   1..325
                          note = Synthetic
source                   1..325
                          mol_type = protein
                          organism = synthetic construct
SEQUENCE: 212
ASTKGPSVFP LAPCSRSTSE STAALGCLVK DYFPEPVTVS WNSGALTSGV HTFPAVLQSS    60
GLYSLSSVVT VPSSNFGTQT YTCNVDHKPS NTKVDKTVER KCCVECPCCP APPVAGPSVF   120
LFPPKPKDTL MISRTPEVTC VVVDVSHEDP EVQFNWYVDG VEVHNAKTKP REEQFNSTFR   180
VVSVLTVVHQ DWLNGKEYKC KVSNKGLPAP IEKTISKTKG QPREPQVYTL PPSREEMTKN   240
QVSLTCLVKG FYPSDISVEW ESNGQPENNY KTTPPMLDSD GSFFLYSKLT VDKSRWQQGN   300
VFSCSVMHEA LHNHYTQKSL SLSPG                                         325

SEQ ID NO: 213           moltype = AA  length = 330
FEATURE                  Location/Qualifiers
REGION                   1..330
                          note = Synthetic
source                   1..330
                          mol_type = protein
                          organism = synthetic construct
SEQUENCE: 213
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
```

```
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPGA                                    330

SEQ ID NO: 214          moltype = AA   length = 330
FEATURE                 Location/Qualifiers
REGION                  1..330
                        note = Synthetic
source                  1..330
                        mol_type = protein
                        organism = synthetic construct
SEQUENCE: 214
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKKVEP KSCDKTHTCP PCPAPELLGG    120
PSVFLFPPKP KDTLMISRTP EVTCVVVDVS HEDPEVKFNW YVDGVEVHNA KTKPREEQYA    180
STYRVVSVLT VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPGA                                    330

SEQ ID NO: 215          moltype = AA   length = 327
FEATURE                 Location/Qualifiers
REGION                  1..327
                        note = Synthetic
source                  1..327
                        mol_type = protein
                        organism = synthetic construct
SEQUENCE: 215
ASTKGPSVFP LAPCSRSTSE STAALGCLVK DYFPEPVTVS WNSGALTSGV HTFPAVLQSS     60
GLYSLSSVVT VPSSSLGTKT YTCNVDHKPS NTKVDKRVES KYGPPCPPCP APEFLGGPSV    120
FLFPPKPKDT LMISRTPEVT CVVVDVSQED PEVQFNWYVD GVEVHNAKTK PREEQFNSTY    180
RVVSVLTVLH QDWLNGKEYK CKVSNKGLPS SIEKTISKAK GQPREPQVYT LPPSQEEMTK    240
NQVSLTCLVK GFYPSDIAVE WESNGQPENN YKTTPPVLDS DGSFFLYSRL TVDKSRWQQG    300
NVFSCSVMHE ALHNHYTQKS LSLSLGA                                       327

SEQ ID NO: 216          moltype = AA   length = 30
FEATURE                 Location/Qualifiers
REGION                  1..30
                        note = Synthetic
source                  1..30
                        mol_type = protein
                        organism = synthetic construct
SEQUENCE: 216
QVQLQESGPG LVKPSQTLSL TCTVSGYSIT                                     30

SEQ ID NO: 217          moltype = AA   length = 14
FEATURE                 Location/Qualifiers
REGION                  1..14
                        note = Synthetic
source                  1..14
                        mol_type = protein
                        organism = synthetic construct
SEQUENCE: 217
WIRQPPGKGL EWIG                                                      14

SEQ ID NO: 218          moltype = AA   length = 32
FEATURE                 Location/Qualifiers
REGION                  1..32
                        note = Synthetic
source                  1..32
                        mol_type = protein
                        organism = synthetic construct
SEQUENCE: 218
RVTISVDTSK NQFSLKLSSV TAADTAVYYC AR                                  32

SEQ ID NO: 219          moltype = AA   length = 11
FEATURE                 Location/Qualifiers
REGION                  1..11
                        note = Synthetic
source                  1..11
                        mol_type = protein
                        organism = synthetic construct
SEQUENCE: 219
WGQGTSVTVS S                                                         11

SEQ ID NO: 220          moltype = AA   length = 23
FEATURE                 Location/Qualifiers
REGION                  1..23
                        note = Synthetic
```

```
source                  1..23
                        mol_type = protein
                        organism = synthetic construct
SEQUENCE: 220
DIQMTQSPSS LSASVGDRVT ITC                                               23

SEQ ID NO: 221          moltype = AA  length = 15
FEATURE                 Location/Qualifiers
REGION                  1..15
                        note = Synthetic
source                  1..15
                        mol_type = protein
                        organism = synthetic construct
SEQUENCE: 221
WHQQKPGKAP KLLIY                                                        15

SEQ ID NO: 222          moltype = AA  length = 39
FEATURE                 Location/Qualifiers
REGION                  1..39
                        note = Synthetic
source                  1..39
                        mol_type = protein
                        organism = synthetic construct
SEQUENCE: 222
GVPSRFSGSG SGTDFTLTIS SLQPEDFATY YCQQSYSTP                               39

SEQ ID NO: 223          moltype = AA  length = 11
FEATURE                 Location/Qualifiers
REGION                  1..11
                        note = Synthetic
source                  1..11
                        mol_type = protein
                        organism = synthetic construct
SEQUENCE: 223
FGGGTKLEIK R                                                            11

SEQ ID NO: 224          moltype = AA  length = 30
FEATURE                 Location/Qualifiers
REGION                  1..30
                        note = Synthetic
source                  1..30
                        mol_type = protein
                        organism = synthetic construct
SEQUENCE: 224
QVKLQESGPG LVKPSQTLSL TCTVTGYSIT                                         30

SEQ ID NO: 225          moltype = AA  length = 32
FEATURE                 Location/Qualifiers
REGION                  1..32
                        note = Synthetic
source                  1..32
                        mol_type = protein
                        organism = synthetic construct
SEQUENCE: 225
RVTISVDTSK NQFSLKLSSV TAADTAVYSC AR                                      32

SEQ ID NO: 226          moltype = AA  length = 11
FEATURE                 Location/Qualifiers
REGION                  1..11
                        note = Synthetic
source                  1..11
                        mol_type = protein
                        organism = synthetic construct
SEQUENCE: 226
WGQGTLVTVS A                                                            11

SEQ ID NO: 227          moltype = AA  length = 23
FEATURE                 Location/Qualifiers
REGION                  1..23
                        note = Synthetic
source                  1..23
                        mol_type = protein
                        organism = synthetic construct
SEQUENCE: 227
DIQMTQSPSS LSASVGDRVT IPC                                               23

SEQ ID NO: 228          moltype = AA  length = 15
FEATURE                 Location/Qualifiers
REGION                  1..15
```

-continued

```
                        note = Synthetic
source                  1..15
                        mol_type = protein
                        organism = synthetic construct
SEQUENCE: 228
WYQQKPGKAP KLLIY                                                          15

SEQ ID NO: 229          moltype = AA  length = 10
FEATURE                 Location/Qualifiers
REGION                  1..10
                        note = Synthetic
source                  1..10
                        mol_type = protein
                        organism = synthetic construct
SEQUENCE: 229
FGEGTKLEIK                                                                10

SEQ ID NO: 230          moltype = AA  length = 30
FEATURE                 Location/Qualifiers
REGION                  1..30
                        note = Synthetic
source                  1..30
                        mol_type = protein
                        organism = synthetic construct
SEQUENCE: 230
EVQLVQSGAE VKKPGATVKI SCKVSGYTFT                                          30

SEQ ID NO: 231          moltype = AA  length = 14
FEATURE                 Location/Qualifiers
REGION                  1..14
                        note = Synthetic
source                  1..14
                        mol_type = protein
                        organism = synthetic construct
SEQUENCE: 231
WVQQAPGKGL EWMG                                                           14

SEQ ID NO: 232          moltype = AA  length = 32
FEATURE                 Location/Qualifiers
REGION                  1..32
                        note = Synthetic
source                  1..32
                        mol_type = protein
                        organism = synthetic construct
SEQUENCE: 232
RVTITADTST DTAYMELSSL RSEDTAVYYC AT                                       32

SEQ ID NO: 233          moltype = AA  length = 12
FEATURE                 Location/Qualifiers
REGION                  1..12
                        note = Synthetic
source                  1..12
                        mol_type = protein
                        organism = synthetic construct
SEQUENCE: 233
WGQGTLITVS VA                                                             12

SEQ ID NO: 234          moltype = AA  length = 32
FEATURE                 Location/Qualifiers
REGION                  1..32
                        note = Synthetic
source                  1..32
                        mol_type = protein
                        organism = synthetic construct
SEQUENCE: 234
GVPSRFSGSG SGTDFTLTIS SLQPEDFATY YC                                       32

SEQ ID NO: 235          moltype = AA  length = 10
FEATURE                 Location/Qualifiers
REGION                  1..10
                        note = Synthetic
source                  1..10
                        mol_type = protein
                        organism = synthetic construct
SEQUENCE: 235
FGAGTKLELK                                                                10

SEQ ID NO: 236          moltype = AA  length = 11
FEATURE                 Location/Qualifiers
```

```
REGION                      1..11
                            note = Synthetic
source                      1..11
                            mol_type = protein
                            organism = synthetic construct
SEQUENCE: 236
WGQGTLVTVS S                                                            11

SEQ ID NO: 237              moltype = AA  length = 32
FEATURE                     Location/Qualifiers
REGION                      1..32
                            note = Synthetic
source                      1..32
                            mol_type = protein
                            organism = synthetic construct
SEQUENCE: 237
GVPSRFSGSG SGTDFTFTIS SLQPEDIATY YC                                     32

SEQ ID NO: 238              moltype = AA  length = 10
FEATURE                     Location/Qualifiers
REGION                      1..10
                            note = Synthetic
source                      1..10
                            mol_type = protein
                            organism = synthetic construct
SEQUENCE: 238
FGAGTKLEIK                                                              10

SEQ ID NO: 239              moltype = AA  length = 30
FEATURE                     Location/Qualifiers
REGION                      1..30
                            note = Synthetic
source                      1..30
                            mol_type = protein
                            organism = synthetic construct
SEQUENCE: 239
EVQLKQSGAE VKKPGATVKI SCKVSGYTFT                                        30

SEQ ID NO: 240              moltype = AA  length = 32
FEATURE                     Location/Qualifiers
REGION                      1..32
                            note = Synthetic
source                      1..32
                            mol_type = protein
                            organism = synthetic construct
SEQUENCE: 240
RVTITADTST DTAYMELSSL RSEDTAVYFC AR                                     32

SEQ ID NO: 241              moltype = AA  length = 30
FEATURE                     Location/Qualifiers
REGION                      1..30
                            note = Synthetic
source                      1..30
                            mol_type = protein
                            organism = synthetic construct
SEQUENCE: 241
QVQLQESGPG LVKPSQTLSL TCTVSGGSVS                                        30

SEQ ID NO: 242              moltype = AA  length = 30
FEATURE                     Location/Qualifiers
REGION                      1..30
                            note = Synthetic
source                      1..30
                            mol_type = protein
                            organism = synthetic construct
SEQUENCE: 242
EVQLQESGPG LVKPSDTLSL TCAVSGYSIT                                        30

SEQ ID NO: 243              moltype = AA  length = 32
FEATURE                     Location/Qualifiers
REGION                      1..32
                            note = Synthetic
source                      1..32
                            mol_type = protein
                            organism = synthetic construct
SEQUENCE: 243
RVTMSVDTSK NQFSLKLSSV TAVDTAVYYC TR                                     32

SEQ ID NO: 244              moltype = AA  length = 32
```

```
FEATURE                 Location/Qualifiers
REGION                  1..32
                        note = Synthetic
source                  1..32
                        mol_type = protein
                        organism = synthetic construct
SEQUENCE: 244
GAPSRFSGSG SGTDFTLTIS SLQPEDFGIY YC                                  32

SEQ ID NO: 245          moltype = AA  length = 10
FEATURE                 Location/Qualifiers
REGION                  1..10
                        note = Synthetic
source                  1..10
                        mol_type = protein
                        organism = synthetic construct
SEQUENCE: 245
FGGGTKLEFK                                                           10

SEQ ID NO: 246          moltype = AA  length = 30
FEATURE                 Location/Qualifiers
REGION                  1..30
                        note = Synthetic
source                  1..30
                        mol_type = protein
                        organism = synthetic construct
SEQUENCE: 246
QVQLVQSGSE LKKPGASVKV SCKASGYTFT                                     30

SEQ ID NO: 247          moltype = AA  length = 14
FEATURE                 Location/Qualifiers
REGION                  1..14
                        note = Synthetic
source                  1..14
                        mol_type = protein
                        organism = synthetic construct
SEQUENCE: 247
WVRQAPGQGL EWMG                                                      14

SEQ ID NO: 248          moltype = AA  length = 32
FEATURE                 Location/Qualifiers
REGION                  1..32
                        note = Synthetic
source                  1..32
                        mol_type = protein
                        organism = synthetic construct
SEQUENCE: 248
RFVFSLDTSV STAYLQISSL KAEDTAVYYC AR                                  32

SEQ ID NO: 249          moltype = AA  length = 23
FEATURE                 Location/Qualifiers
REGION                  1..23
                        note = Synthetic
source                  1..23
                        mol_type = protein
                        organism = synthetic construct
SEQUENCE: 249
DVVMTQSPLS LPVTLGQPAS ISC                                            23

SEQ ID NO: 250          moltype = AA  length = 15
FEATURE                 Location/Qualifiers
REGION                  1..15
                        note = Synthetic
source                  1..15
                        mol_type = protein
                        organism = synthetic construct
SEQUENCE: 250
WFQQRPGQSP RVLIY                                                     15

SEQ ID NO: 251          moltype = AA  length = 32
FEATURE                 Location/Qualifiers
REGION                  1..32
                        note = Synthetic
source                  1..32
                        mol_type = protein
                        organism = synthetic construct
SEQUENCE: 251
GVPDRFSGSG SGTDFTLKIS RVEAEDVGVY YC                                  32
```

-continued

```
SEQ ID NO: 252          moltype = AA   length = 10
FEATURE                 Location/Qualifiers
REGION                  1..10
                        note = Synthetic
source                  1..10
                        mol_type = protein
                        organism = synthetic construct
SEQUENCE: 252
FGRGTKLEIK                                                              10

SEQ ID NO: 253          moltype = AA   length = 30
FEATURE                 Location/Qualifiers
REGION                  1..30
                        note = Synthetic
source                  1..30
                        mol_type = protein
                        organism = synthetic construct
SEQUENCE: 253
QVTLKESGPT LVKPTQTLTL TCTFSGFSLS                                        30

SEQ ID NO: 254          moltype = AA   length = 14
FEATURE                 Location/Qualifiers
REGION                  1..14
                        note = Synthetic
source                  1..14
                        mol_type = protein
                        organism = synthetic construct
SEQUENCE: 254
WIRQPPGKAL EWLA                                                         14

SEQ ID NO: 255          moltype = AA   length = 32
FEATURE                 Location/Qualifiers
REGION                  1..32
                        note = Synthetic
source                  1..32
                        mol_type = protein
                        organism = synthetic construct
SEQUENCE: 255
RLTITKDTSK NQVVLTMTNM DPVDTATYYC AR                                     32

SEQ ID NO: 256          moltype = AA   length = 22
FEATURE                 Location/Qualifiers
REGION                  1..22
                        note = Synthetic
source                  1..22
                        mol_type = protein
                        organism = synthetic construct
SEQUENCE: 256
QAVVTQEPSL TVSPGGTVTL TC                                                22

SEQ ID NO: 257          moltype = AA   length = 15
FEATURE                 Location/Qualifiers
REGION                  1..15
                        note = Synthetic
source                  1..15
                        mol_type = protein
                        organism = synthetic construct
SEQUENCE: 257
WVQQKPGQLF RGLIG                                                        15

SEQ ID NO: 258          moltype = AA   length = 32
FEATURE                 Location/Qualifiers
REGION                  1..32
                        note = Synthetic
source                  1..32
                        mol_type = protein
                        organism = synthetic construct
SEQUENCE: 258
WVPARFSGSL IGDKAALTLS GVQPEDEAEY FC                                     32

SEQ ID NO: 259          moltype = AA   length = 10
FEATURE                 Location/Qualifiers
REGION                  1..10
                        note = Synthetic
source                  1..10
                        mol_type = protein
                        organism = synthetic construct
SEQUENCE: 259
FGGGTKLTVL                                                              10
```

```
SEQ ID NO: 260          moltype = AA   length = 30
FEATURE                 Location/Qualifiers
REGION                  1..30
                        note = Synthetic
source                  1..30
                        mol_type = protein
                        organism = synthetic construct
SEQUENCE: 260
QVQLVQSGAE VKKPGASVKV SCKASGYTFT                                           30

SEQ ID NO: 261          moltype = AA   length = 32
FEATURE                 Location/Qualifiers
REGION                  1..32
                        note = Synthetic
source                  1..32
                        mol_type = protein
                        organism = synthetic construct
SEQUENCE: 261
RVTMTRDTST STVYMELSSL RSEDTAVYYC AR                                        32

SEQ ID NO: 262          moltype = AA   length = 10
FEATURE                 Location/Qualifiers
REGION                  1..10
                        note = Synthetic
source                  1..10
                        mol_type = protein
                        organism = synthetic construct
SEQUENCE: 262
FGQGTKVEIK                                                                 10

SEQ ID NO: 263          moltype = AA   length = 30
FEATURE                 Location/Qualifiers
REGION                  1..30
                        note = Synthetic
source                  1..30
                        mol_type = protein
                        organism = synthetic construct
SEQUENCE: 263
EVQLVESGGG LVQPGGSLRL SCAASGFTFS                                           30

SEQ ID NO: 264          moltype = AA   length = 14
FEATURE                 Location/Qualifiers
REGION                  1..14
                        note = Synthetic
source                  1..14
                        mol_type = protein
                        organism = synthetic construct
SEQUENCE: 264
WVRQAPGKGL EWVS                                                            14

SEQ ID NO: 265          moltype = AA   length = 32
FEATURE                 Location/Qualifiers
REGION                  1..32
                        note = Synthetic
source                  1..32
                        mol_type = protein
                        organism = synthetic construct
SEQUENCE: 265
RFTISRDNSK NTLYLQMNSL RAEDTAVYYC AK                                        32

SEQ ID NO: 266          moltype = AA   length = 11
FEATURE                 Location/Qualifiers
REGION                  1..11
                        note = Synthetic
source                  1..11
                        mol_type = protein
                        organism = synthetic construct
SEQUENCE: 266
WGQGTSVTVS S                                                               11

SEQ ID NO: 267          moltype = AA   length = 23
FEATURE                 Location/Qualifiers
REGION                  1..23
                        note = Synthetic
source                  1..23
                        mol_type = protein
                        organism = synthetic construct
SEQUENCE: 267
```

```
DIQMTQSPSS VSASVGDRVT ITC                                                23

SEQ ID NO: 268          moltype = AA   length = 15
FEATURE                 Location/Qualifiers
REGION                  1..15
                        note = Synthetic
source                  1..15
                        mol_type = protein
                        organism = synthetic construct
SEQUENCE: 268
WYQQKPGKAP KLLIY                                                         15

SEQ ID NO: 269          moltype = AA   length = 32
FEATURE                 Location/Qualifiers
REGION                  1..32
                        note = Synthetic
source                  1..32
                        mol_type = protein
                        organism = synthetic construct
SEQUENCE: 269
GVPSRFSGSG SGTDFTLTIS SLQPEDFATY YC                                      32

SEQ ID NO: 270          moltype = AA   length = 10
FEATURE                 Location/Qualifiers
REGION                  1..10
                        note = Synthetic
source                  1..10
                        mol_type = protein
                        organism = synthetic construct
SEQUENCE: 270
FGGGTKLEIK                                                               10

SEQ ID NO: 271          moltype = AA   length = 30
FEATURE                 Location/Qualifiers
REGION                  1..30
                        note = Synthetic
source                  1..30
                        mol_type = protein
                        organism = synthetic construct
SEQUENCE: 271
QVQLVQSGAE VKKPGASVKV SCKASDYTFT                                         30

SEQ ID NO: 272          moltype = AA   length = 14
FEATURE                 Location/Qualifiers
REGION                  1..14
                        note = Synthetic
source                  1..14
                        mol_type = protein
                        organism = synthetic construct
SEQUENCE: 272
WLRQAPGQGL EWMG                                                          14

SEQ ID NO: 273          moltype = AA   length = 32
FEATURE                 Location/Qualifiers
REGION                  1..32
                        note = Synthetic
source                  1..32
                        mol_type = protein
                        organism = synthetic construct
SEQUENCE: 273
RTTSTRDTSI STAYMELSRL RSDDTVVYYC TR                                      32

SEQ ID NO: 274          moltype = AA   length = 11
FEATURE                 Location/Qualifiers
REGION                  1..11
                        note = Synthetic
source                  1..11
                        mol_type = protein
                        organism = synthetic construct
SEQUENCE: 274
WGQGTLVTVS S                                                             11

SEQ ID NO: 275          moltype = AA   length = 23
FEATURE                 Location/Qualifiers
REGION                  1..23
                        note = Synthetic
source                  1..23
                        mol_type = protein
                        organism = synthetic construct
```

```
SEQUENCE: 275
DIQMTQSPSS LSASVGDRVT FTC                                                     23

SEQ ID NO: 276          moltype = AA  length = 10
FEATURE                 Location/Qualifiers
REGION                  1..10
                        note = Synthetic
source                  1..10
                        mol_type = protein
                        organism = synthetic construct
SEQUENCE: 276
FGGGTKVEIK                                                                    10

SEQ ID NO: 277          moltype = AA  length = 14
FEATURE                 Location/Qualifiers
REGION                  1..14
                        note = Synthetic
source                  1..14
                        mol_type = protein
                        organism = synthetic construct
SEQUENCE: 277
WVRQAPGQGL EWMG                                                               14

SEQ ID NO: 278          moltype = AA  length = 31
FEATURE                 Location/Qualifiers
REGION                  1..31
                        note = Synthetic
source                  1..31
                        mol_type = protein
                        organism = synthetic construct
SEQUENCE: 278
RVTSTRDTSI STAYMELSRL RSDDTVVYYC A                                            31

SEQ ID NO: 279          moltype = AA  length = 11
FEATURE                 Location/Qualifiers
REGION                  1..11
                        note = Synthetic
source                  1..11
                        mol_type = protein
                        organism = synthetic construct
SEQUENCE: 279
WGQGTTLTVS S                                                                  11

SEQ ID NO: 280          moltype = AA  length = 23
FEATURE                 Location/Qualifiers
REGION                  1..23
                        note = Synthetic
source                  1..23
                        mol_type = protein
                        organism = synthetic construct
SEQUENCE: 280
DIQMTQSPSS LSASVGDRVT ITC                                                     23

SEQ ID NO: 281          moltype = AA  length = 10
FEATURE                 Location/Qualifiers
REGION                  1..10
                        note = Synthetic
source                  1..10
                        mol_type = protein
                        organism = synthetic construct
SEQUENCE: 281
FGAGTKLDLK                                                                    10

SEQ ID NO: 282          moltype = AA  length = 10
FEATURE                 Location/Qualifiers
REGION                  1..10
                        note = Synthetic
source                  1..10
                        mol_type = protein
                        organism = synthetic construct
SEQUENCE: 282
FGGGTKVEIK                                                                    10

SEQ ID NO: 283          moltype = AA  length = 30
FEATURE                 Location/Qualifiers
REGION                  1..30
                        note = Synthetic
source                  1..30
                        mol_type = protein
```

```
                                    organism = synthetic construct
SEQUENCE: 283
QVQLVQSGAE VKKPGASVKV SCKASGYTFT                                                30

SEQ ID NO: 284          moltype = AA   length = 32
FEATURE                 Location/Qualifiers
REGION                  1..32
                        note = Synthetic
source                  1..32
                        mol_type = protein
                        organism = synthetic construct
SEQUENCE: 284
RVTMTRDTSI STAYMELSSL RSEDTAVYYC AR                                             32

SEQ ID NO: 285          moltype = AA   length = 23
FEATURE                 Location/Qualifiers
REGION                  1..23
                        note = Synthetic
source                  1..23
                        mol_type = protein
                        organism = synthetic construct
SEQUENCE: 285
DIVLTQSPAS LAVSPGQRAT ITC                                                       23

SEQ ID NO: 286          moltype = AA   length = 15
FEATURE                 Location/Qualifiers
REGION                  1..15
                        note = Synthetic
source                  1..15
                        mol_type = protein
                        organism = synthetic construct
SEQUENCE: 286
WYQQKPGQPP KLLIY                                                                15

SEQ ID NO: 287          moltype = AA   length = 32
FEATURE                 Location/Qualifiers
REGION                  1..32
                        note = Synthetic
source                  1..32
                        mol_type = protein
                        organism = synthetic construct
SEQUENCE: 287
GVPARFSGSG SGTDFTLTIN PVEANDTANY YC                                             32

SEQ ID NO: 288          moltype = AA   length = 31
FEATURE                 Location/Qualifiers
REGION                  1..31
                        note = Synthetic
source                  1..31
                        mol_type = protein
                        organism = synthetic construct
SEQUENCE: 288
RVTLTADTST STVYMELSSL RSEDTAVYYC A                                              31

SEQ ID NO: 289          moltype = AA   length = 23
FEATURE                 Location/Qualifiers
REGION                  1..23
                        note = Synthetic
source                  1..23
                        mol_type = protein
                        organism = synthetic construct
SEQUENCE: 289
DIQMTQSPSF LSASVGDRVT ITC                                                       23

SEQ ID NO: 290          moltype = AA   length = 15
FEATURE                 Location/Qualifiers
REGION                  1..15
                        note = Synthetic
source                  1..15
                        mol_type = protein
                        organism = synthetic construct
SEQUENCE: 290
WYQQKPGKAP KALIY                                                                15

SEQ ID NO: 291          moltype = AA   length = 32
FEATURE                 Location/Qualifiers
REGION                  1..32
                        note = Synthetic
source                  1..32
```

```
                        mol_type = protein
                        organism = synthetic construct
SEQUENCE: 291
GVPSRFSGSG SGTEFTLTIS SLQPEDFATY YC                             32

SEQ ID NO: 292          moltype = AA   length = 10
FEATURE                 Location/Qualifiers
REGION                  1..10
                        note = Synthetic
source                  1..10
                        mol_type = protein
                        organism = synthetic construct
SEQUENCE: 292
FGQGTKLEIK                                                      10

SEQ ID NO: 293          moltype = AA   length = 14
FEATURE                 Location/Qualifiers
REGION                  1..14
                        note = Synthetic
source                  1..14
                        mol_type = protein
                        organism = synthetic construct
SEQUENCE: 293
WMKQAPGQGL EWMG                                                 14

SEQ ID NO: 294          moltype = AA   length = 23
FEATURE                 Location/Qualifiers
REGION                  1..23
                        note = Synthetic
source                  1..23
                        mol_type = protein
                        organism = synthetic construct
SEQUENCE: 294
DIQMTQSPSS LSASVGDRVT ISC                                       23

SEQ ID NO: 295          moltype = AA   length = 15
FEATURE                 Location/Qualifiers
REGION                  1..15
                        note = Synthetic
source                  1..15
                        mol_type = protein
                        organism = synthetic construct
SEQUENCE: 295
WYQQKPGKAP KLLIK                                                15

SEQ ID NO: 296          moltype = AA   length = 32
FEATURE                 Location/Qualifiers
REGION                  1..32
                        note = Synthetic
source                  1..32
                        mol_type = protein
                        organism = synthetic construct
SEQUENCE: 296
GVPSRFSGSG SGTDFTLTIS SLQPEDFATY FC                             32

SEQ ID NO: 297          moltype = AA   length = 32
FEATURE                 Location/Qualifiers
REGION                  1..32
                        note = Synthetic
source                  1..32
                        mol_type = protein
                        organism = synthetic construct
SEQUENCE: 297
KATMTRDKSS STVYMELSSL RSEDTAVYYC AR                             32

SEQ ID NO: 298          moltype = AA   length = 32
FEATURE                 Location/Qualifiers
REGION                  1..32
                        note = Synthetic
source                  1..32
                        mol_type = protein
                        organism = synthetic construct
SEQUENCE: 298
GVPSRFSGSG SGTDFTFTIS SLQPEDIATY FC                             32

SEQ ID NO: 299          moltype = AA   length = 10
FEATURE                 Location/Qualifiers
REGION                  1..10
                        note = Synthetic
```

```
source                      1..10
                            mol_type = protein
                            organism = synthetic construct
SEQUENCE: 299
FGQGTKVEIK                                                                  10

SEQ ID NO: 300              moltype = AA   length = 32
FEATURE                     Location/Qualifiers
REGION                      1..32
                            note = Synthetic
source                      1..32
                            mol_type = protein
                            organism = synthetic construct
SEQUENCE: 300
RVTMTRDTSI STAYMELSRL RSDDTAVYYC AR                                         32

SEQ ID NO: 301              moltype = AA   length = 32
FEATURE                     Location/Qualifiers
REGION                      1..32
                            note = Synthetic
source                      1..32
                            mol_type = protein
                            organism = synthetic construct
SEQUENCE: 301
RVTMTRDTST STVYMELSSL RSEDTAVYYC AR                                         32

SEQ ID NO: 302              moltype = AA   length = 30
FEATURE                     Location/Qualifiers
REGION                      1..30
                            note = Synthetic
source                      1..30
                            mol_type = protein
                            organism = synthetic construct
SEQUENCE: 302
DVQLQESGPG LVKPSQSLSL TCTVTGYSIT                                            30

SEQ ID NO: 303              moltype = AA   length = 14
FEATURE                     Location/Qualifiers
REGION                      1..14
                            note = Synthetic
source                      1..14
                            mol_type = protein
                            organism = synthetic construct
SEQUENCE: 303
WIRQFPGNKL EWMG                                                             14

SEQ ID NO: 304              moltype = AA   length = 32
FEATURE                     Location/Qualifiers
REGION                      1..32
                            note = Synthetic
source                      1..32
                            mol_type = protein
                            organism = synthetic construct
SEQUENCE: 304
RISITRDTSK NQFFLQLNSV TTEDTATYYC AN                                         32

SEQ ID NO: 305              moltype = AA   length = 23
FEATURE                     Location/Qualifiers
REGION                      1..23
                            note = Synthetic
source                      1..23
                            mol_type = protein
                            organism = synthetic construct
SEQUENCE: 305
DIVMTQSHKF MSTSVGDRVS ITC                                                   23

SEQ ID NO: 306              moltype = AA   length = 15
FEATURE                     Location/Qualifiers
REGION                      1..15
                            note = Synthetic
source                      1..15
                            mol_type = protein
                            organism = synthetic construct
SEQUENCE: 306
WYQQKPGQSP KLLIF                                                            15

SEQ ID NO: 307              moltype = AA   length = 32
FEATURE                     Location/Qualifiers
REGION                      1..32
```

```
                              note = Synthetic
source                        1..32
                              mol_type = protein
                              organism = synthetic construct
SEQUENCE: 307
GVPDRFTGSG SGTDYTLTIS SVQAEDLALY YC                                        32

SEQ ID NO: 308                moltype = AA  length = 15
FEATURE                       Location/Qualifiers
REGION                        1..15
                              note = Synthetic
source                        1..15
                              mol_type = protein
                              organism = synthetic construct
SEQUENCE: 308
WVRQAPGQRL EWMGW                                                           15

SEQ ID NO: 309                moltype = AA  length = 32
FEATURE                       Location/Qualifiers
REGION                        1..32
                              note = Synthetic
source                        1..32
                              mol_type = protein
                              organism = synthetic construct
SEQUENCE: 309
RVTITRDTSA STAYMELSSL RSEDTAVYYC AR                                        32

SEQ ID NO: 310                moltype = AA  length = 23
FEATURE                       Location/Qualifiers
REGION                        1..23
                              note = Synthetic
source                        1..23
                              mol_type = protein
                              organism = synthetic construct
SEQUENCE: 310
DIQMTQSPSS LSAFVGDRVT ITC                                                  23

SEQ ID NO: 311                moltype = AA  length = 15
FEATURE                       Location/Qualifiers
REGION                        1..15
                              note = Synthetic
source                        1..15
                              mol_type = protein
                              organism = synthetic construct
SEQUENCE: 311
WYQQKPGKAP KLLIH                                                           15

SEQ ID NO: 312                moltype = AA  length = 32
FEATURE                       Location/Qualifiers
REGION                        1..32
                              note = Synthetic
source                        1..32
                              mol_type = protein
                              organism = synthetic construct
SEQUENCE: 312
GVPSRFSGSG SGRDFTFTIS SLQPEDIATY YC                                        32

SEQ ID NO: 313                moltype = AA  length = 23
FEATURE                       Location/Qualifiers
REGION                        1..23
                              note = Synthetic
source                        1..23
                              mol_type = protein
                              organism = synthetic construct
SEQUENCE: 313
EIVLTQSPVT LSLSPGERAT LSC                                                  23

SEQ ID NO: 314                moltype = AA  length = 15
FEATURE                       Location/Qualifiers
REGION                        1..15
                              note = Synthetic
source                        1..15
                              mol_type = protein
                              organism = synthetic construct
SEQUENCE: 314
WYLQKPGQAP RLLIK                                                           15

SEQ ID NO: 315                moltype = AA  length = 31
FEATURE                       Location/Qualifiers
```

```
REGION                  1..31
                        note = Synthetic
source                  1..31
                        mol_type = protein
                        organism = synthetic construct
SEQUENCE: 315
IPARFSGSGS GSDFTLTISS LEPEDFAVYY C                                  31

SEQ ID NO: 316          moltype = AA  length = 30
FEATURE                 Location/Qualifiers
REGION                  1..30
                        note = Synthetic
source                  1..30
                        mol_type = protein
                        organism = synthetic construct
SEQUENCE: 316
QVQLVQSGAE VKKPGASVKV SCKASGYTLT                                    30

SEQ ID NO: 317          moltype = AA  length = 14
FEATURE                 Location/Qualifiers
REGION                  1..14
                        note = Synthetic
source                  1..14
                        mol_type = protein
                        organism = synthetic construct
SEQUENCE: 317
WMRQAPGQGL EWMG                                                     14

SEQ ID NO: 318          moltype = AA  length = 32
FEATURE                 Location/Qualifiers
REGION                  1..32
                        note = Synthetic
source                  1..32
                        mol_type = protein
                        organism = synthetic construct
SEQUENCE: 318
RVTMTRDTST STVYMELSSL RSEDTAVYYC VR                                 32

SEQ ID NO: 319          moltype = AA  length = 11
FEATURE                 Location/Qualifiers
REGION                  1..11
                        note = Synthetic
source                  1..11
                        mol_type = protein
                        organism = synthetic construct
SEQUENCE: 319
WGQGTLVTVS S                                                        11

SEQ ID NO: 320          moltype = AA  length = 23
FEATURE                 Location/Qualifiers
REGION                  1..23
                        note = Synthetic
source                  1..23
                        mol_type = protein
                        organism = synthetic construct
SEQUENCE: 320
DIQMTQSPSS LSASVGDRVT ITC                                           23

SEQ ID NO: 321          moltype = AA  length = 15
FEATURE                 Location/Qualifiers
REGION                  1..15
                        note = Synthetic
source                  1..15
                        mol_type = protein
                        organism = synthetic construct
SEQUENCE: 321
WLQQKPEKAP KRLIY                                                    15

SEQ ID NO: 322          moltype = AA  length = 32
FEATURE                 Location/Qualifiers
REGION                  1..32
                        note = Synthetic
source                  1..32
                        mol_type = protein
                        organism = synthetic construct
SEQUENCE: 322
GVPSRFSGSG SGTDFTLTIS SLQPEDFATY YC                                 32

SEQ ID NO: 323          moltype = AA  length = 10
```

```
FEATURE                 Location/Qualifiers
REGION                  1..10
                        note = Synthetic
source                  1..10
                        mol_type = protein
                        organism = synthetic construct
SEQUENCE: 323
FGGGTKVEIK                                                                  10

SEQ ID NO: 324          moltype = AA  length = 30
FEATURE                 Location/Qualifiers
REGION                  1..30
                        note = Synthetic
source                  1..30
                        mol_type = protein
                        organism = synthetic construct
SEQUENCE: 324
QVQLVQSGAE VKKPGASVKV SCKASGYTFT                                            30

SEQ ID NO: 325          moltype = AA  length = 14
FEATURE                 Location/Qualifiers
REGION                  1..14
                        note = Synthetic
source                  1..14
                        mol_type = protein
                        organism = synthetic construct
SEQUENCE: 325
WVRQAPGQGL EWMG                                                             14

SEQ ID NO: 326          moltype = AA  length = 32
FEATURE                 Location/Qualifiers
REGION                  1..32
                        note = Synthetic
source                  1..32
                        mol_type = protein
                        organism = synthetic construct
SEQUENCE: 326
RVTMTRDTST STVYMELSSL RSEDTAVYYC AR                                         32

SEQ ID NO: 327          moltype = AA  length = 15
FEATURE                 Location/Qualifiers
REGION                  1..15
                        note = Synthetic
source                  1..15
                        mol_type = protein
                        organism = synthetic construct
SEQUENCE: 327
WLQQKPGKAP KRLIY                                                            15

SEQ ID NO: 328          moltype = AA  length = 30
FEATURE                 Location/Qualifiers
REGION                  1..30
                        note = Synthetic
source                  1..30
                        mol_type = protein
                        organism = synthetic construct
SEQUENCE: 328
QVQLVQSGAE VKKPGASVKV SCKASGFTFS                                            30

SEQ ID NO: 329          moltype = AA  length = 15
FEATURE                 Location/Qualifiers
REGION                  1..15
                        note = Synthetic
source                  1..15
                        mol_type = protein
                        organism = synthetic construct
SEQUENCE: 329
WVRQAPGQGL EWMGL                                                            15

SEQ ID NO: 330          moltype = AA  length = 30
FEATURE                 Location/Qualifiers
REGION                  1..30
                        note = Synthetic
source                  1..30
                        mol_type = protein
                        organism = synthetic construct
SEQUENCE: 330
RVTMTRDTST STVYMELSSL RSEDTAVYFC                                            30
```

```
SEQ ID NO: 331          moltype = AA  length = 26
FEATURE                 Location/Qualifiers
REGION                  1..26
                        note = Synthetic
source                  1..26
                        mol_type = protein
                        organism = synthetic construct
SEQUENCE: 331
FDYWDDGYYV EHFDYWGQGT LVTVSS                                        26

SEQ ID NO: 332          moltype = AA  length = 15
FEATURE                 Location/Qualifiers
REGION                  1..15
                        note = Synthetic
source                  1..15
                        mol_type = protein
                        organism = synthetic construct
SEQUENCE: 332
WYQQKPGKAP KRLIY                                                    15

SEQ ID NO: 333          moltype = AA  length = 29
FEATURE                 Location/Qualifiers
REGION                  1..29
                        note = Synthetic
source                  1..29
                        mol_type = protein
                        organism = synthetic construct
SEQUENCE: 333
QVQLVQSGAE VKKPGASVKV SCKASGYTF                                     29

SEQ ID NO: 334          moltype = AA  length = 23
FEATURE                 Location/Qualifiers
REGION                  1..23
                        note = Synthetic
source                  1..23
                        mol_type = protein
                        organism = synthetic construct
SEQUENCE: 334
DIQMTQSPST LSASVGDRVT ITC                                           23

SEQ ID NO: 335          moltype = AA  length = 18
FEATURE                 Location/Qualifiers
REGION                  1..18
                        note = Synthetic
source                  1..18
                        mol_type = protein
                        organism = synthetic construct
SEQUENCE: 335
WLAWYQQKPG KAPKLLIY                                                 18

SEQ ID NO: 336          moltype = AA  length = 32
FEATURE                 Location/Qualifiers
REGION                  1..32
                        note = Synthetic
source                  1..32
                        mol_type = protein
                        organism = synthetic construct
SEQUENCE: 336
GVPSRFSGSG SGTEFTLTIS SLQPDDFATY YC                                 32

SEQ ID NO: 337          moltype = AA  length = 10
FEATURE                 Location/Qualifiers
REGION                  1..10
                        note = Synthetic
source                  1..10
                        mol_type = protein
                        organism = synthetic construct
SEQUENCE: 337
FGQGTKLEIK                                                          10
```

BISPECIFIC ANTAGONIST COMPRISING A LAG-3 BINDING DOMAIN

This application is a Continuation of U.S. patent application Ser. No. 16/457,421, filed Jun. 28, 2019, which claims priority to U.S. Provisional Patent Application Ser. No. 62/691,658, filed Jun. 29, 2018 and U.S. Provisional Patent Application Ser. No. 62/823,989, filed Mar. 26, 2019, the contents of which are expressly incorporated herein by reference herein.

FIELD

The present application relates generally to cancer treatment and, in particular, to bispecific inhibitors capable of modulating pathways associated with tumorigenesis and tumor immunity.

BACKGROUND

The inability of the host to eliminate cancer cells remains a major problem. Although an increasing number of therapeutic monoclonal antibodies have been approved for treatment of various cancers, emergence of resistance to these antibodies is frequently observed, given the many different molecular pathways underlying cancer growth and progression to metastasis. Although the immune system is the principal mechanism of cancer prevention, cancer cells counteract immunosurveillance. Natural control mechanisms have been identified that limit T-cell activation so as to prevent collateral damage resulting from unrestrained T-cell activity. This process has been exploited by tumor cells to evade immune responses. Restoring the capacity of immune effector cells, especially T cells, to recognize and eliminate cancer is a major objective in immunotherapy.

The need exists for improved therapeutic binding antagonists or antibodies and methods of treating cancer and chronic viral infections with such reagents.

SUMMARY

One aspect of the present application relates to bispecific antitumor antagonists that comprise a first targeting domain that specifically binds to an immune checkpoint regulator; a second targeting domain in the form of an scFv that specifically binds to TIGIT; and an immunoglobulin scaffold structurally linked to the first and second targeting domains, wherein the first targeting domain is positioned at N-terminal end of the antagonist, and wherein the second targeting domain is positioned at a C-terminal end of the antagonist and is linked to the immunoglobulin scaffold through a linker. In some embodiments, linker comprises 4 or 6 copies of the amino acid sequence G4S (4× G4S and 6×G4S, respectively).

In some embodiments, the first targeting domain specifically binds to PD-1, PD-L1 or LAG-3.

Another aspect of the present application relates to humanized anti-LAG-3 antibodies that inhibit binding of ligands to LAG-3.

Another aspect of the present application relates to a method for treating a cell proliferative disorder. The method comprises administering to a subject in need thereof an effective amount of a bispecific antitumor antagonist or anti-LAG-3 antibody of the present application.

BRIEF DESCRIPTION OF THE DRAWINGS

FIG. 1 shows complementarity determining region (CDR) sequences of certain anti-TIGIT mAbs. The framework region (FR) sequences flanking the anti-TIGIT CDR sequences are listed in FIG. 39A as SEQ ID NOS: 216-262.

FIGS. 2A-2C show several embodiments of anti-TIGIT antibody variable domain sequences.

FIG. 3 shows CDR sequences of certain anti-PD-1 mAbs. The FR sequences flanking the anti-PD-1 CDR sequences are listed in FIG. 39B as SEQ ID NOS: 263-292.

FIGS. 4A-4B show several embodiments of anti-PD-1 antibody variable domain sequences.

FIG. 5 shows CDR sequences of certain anti-PD-L1 mAbs. The FR sequences flanking the anti-PD-L1 CDR sequences are listed in FIG. 39C as SEQ ID NOS: 293-315.

FIGS. 6A-6C show several embodiments of anti-PD-L1 antibody variable domain sequences.

FIG. 8 summarizes the arrangement of functional domains in the bi-specific antagonists depicted in FIGS. 7A-7C.

FIGS. 9A-9B show the heavy chain (HC) and light chain (LC) amino acid sequences corresponding to the bispecific antagonists depicted in FIGS. 7A-7C.

FIG. 19A shows the heavy chain CDR sequences corresponding to the anti-LAG-3 mAbs 2L2A.1, 2L2A.6, 2L27B and 3L1A. FIG. 19B shows the light chain CDR sequences corresponding to the anti-LAG-3 mAbs 2L2A.1, 2L2A.6, 2L27B and 3L1A. The FR sequences flanking the anti-LAG-3 CDR sequences are listed in FIG. 39C as SEQ ID NOS: 316-337.

FIG. 20 shows the VH and VL sequences of anti-LAG-3 mAbs 2L2A.1, 2L2A.6, 2L27B and 3L1A.

FIGS. 30A-30B depict two exemplary bispecific antitumor antagonists, Bi-LT-1 (FIG. 30A) and Bi-LT-3 (FIG. 30B).

FIG. 31 summarizes the arrangement of functional domains in the bi-specific antagonists depicted in FIGS. 30A-30B.

FIG. 32 show the heavy chain (HC) and light chain (LC) amino acid sequences corresponding to the bispecific antagonists depicted in FIGS. 30A-30B.

FIG. 39A shows the framework regions (FRs) corresponding to the anti-TIGIT CDRs in FIG. 1. FIG. 39B shows the FRs corresponding to the anti-PD-1 CDRs in FIG. 3.

FIG. 39C shows the FRs corresponding to the anti-PD-L1 CDRs in FIG. 5 and the FRs corresponding to the anti-LAG-3 CDR in FIGS. 19A and 19B.

DETAILED DESCRIPTION

Definitions

Figure 7A:
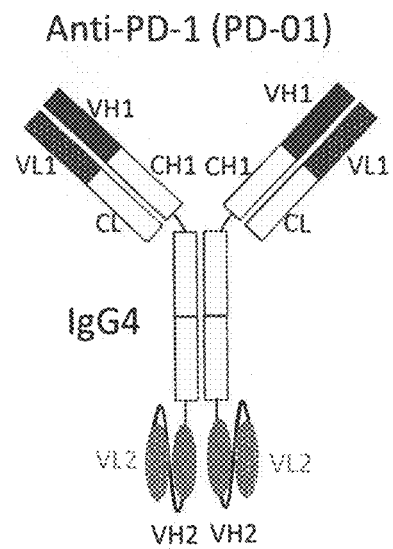
FIGS. 7A-7C depict three exemplary bispecific antitumor antagonists, Bi-TPM-93 (FIG. 7A), Bi-TPM-94A (FIG. 7B), and Bi-TPM-94B (FIG. 7C).

Herein incorporated by reference is the sequence listing filed with the USPTO as 2022-003 US3-CONT2.xml which was created on Apr. 24, 2023, and the size is 435,920 bytes.

Unless defined otherwise, all technical and scientific terms used herein have the same meanings as commonly understood by one of skill in the art to which the disclosed method and compositions belong. It must be noted that as used herein and in the appended claims, the singular forms "a," "an," and "the" include plural reference unless the context clearly dictates otherwise. Thus, for example, reference to "a peptide" includes "one or more" peptides or a "plurality" of such peptides. With respect to the teachings in the present application, any issued patent or patent application publication described in this application is expressly incorporated by reference herein.

As used herein, the term "TIGIT" refers to any form of TIGIT and variants thereof that retain at least part of the activity of TIGIT. Unless indicated differently, such as by specific reference to human TIGIT, TIGIT includes all mammalian species of native sequence TIGIT, e.g., human, canine, feline, equine, and bovine.

As used herein, the term "PD-1" refers to any form of PD-1 and variants thereof that retain at least part of the activity of PD-1. Unless indicated differently, such as by specific reference to human PD-1, PD-1 includes all mammalian species of native sequence PD-1, e.g., human, canine, feline, equine, and bovine.

As used herein, the term "PD-L1" refers to any form of PD-L1 and variants thereof that retain at least part of the activity of PD-L1. Unless indicated differently, such as by specific reference to human PD-L1, PD-L1 includes all mammalian species of native sequence PD-L1, e.g., human, canine, feline, equine, and bovine.

The term "agonist" refers to a substance which promotes (i.e., induces, causes, enhances, or increases) the biological activity or effect of another molecule. The term agonist encompasses substances which bind receptor, such as an antibody, and substances which promote receptor function without binding thereto (e.g., by activating an associated protein).

The term "antagonist" or "inhibitor" refers to a substance that prevents, blocks, inhibits, neutralizes, or reduces a biological activity or effect of another molecule, such as a receptor or ligand. An antagonist can be a monospecific antibody or a bispecific antibody.

As used herein, the term "antibody" refers to a polypeptide or a polypeptide complex that specifically recognizes and binds to an antigen through one or more immunoglobulin variable regions. An antibody can be a whole antibody, an antigen binding fragment or a single chain thereof. The term "antibody" encompasses various broad classes of polypeptides that can be distinguished biochemically. Those skilled in the art will appreciate that heavy chains are classified as alpha, delta, epsilon, gamma, and mu, or α, δ, ε, γ and μ) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are within the scope of the present disclosure, the following discussion will generally be directed to the IgG class of immunoglobulin molecules.

Antibodies of the disclosure include, but are not limited to, polyclonal, monoclonal, multispecific, bispecific, human, humanized, primatized, chimeric and single chain antibodies. Antibodies disclosed herein may be from any animal origin, including birds and mammals. Preferably, the antibodies are human, murine, rat, donkey, rabbit, goat, guinea pig, camel, llama, horse, or chicken antibodies. In some embodiments, the variable region may be condricthoid in origin (e.g., from sharks).

The terms "antibody fragment" and "antigen-binding fragment" are used with reference to a portion of an antibody, such as F(ab')2, F(ab)2, Fab', Fab, Fv, single-chain Fvs (scFv), single-chain antibodies, disulfide-linked Fvs (sdFv), fragments comprising either a VL or VH domain, fragments produced by a Fab expression library, and anti-idiotypic (anti-Id) antibodies. Regardless of structure, an antibody fragment binds with the same antigen that is recognized by the intact antibody. The term "antibody fragment" includes DARTs, and diabodies. The term "antibody fragment" also includes any synthetic or genetically engineered proteins comprising immunoglobulin variable regions that act like an antibody by binding to a specific antigen to form a complex. A "single-chain fragment variable" or "scFv" refers to a fusion protein of the variable regions of the heavy (VH) and light chains (VL) of immunoglobulins. In some aspects, the regions are connected with a short linker peptide of ten to about 25 amino acids. The linker can be rich in glycine for flexibility, as well as serine or threonine for solubility, and can either connect the N-terminus of the VH with the C-terminus of the VL, or vice versa. This protein retains the specificity of the original immunoglobulin, despite removal of the constant regions and the introduction of the linker. With regard to IgGs, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration where the light chains bracket the heavy chains starting at the mouth of the "Y" and continuing through the variable region.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention, the numbering of the constant region domains in conventional antibodies increases as they become more distal from the antigen-binding site or amino-terminus of the antibody. In conventional antibodies, the N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the VL domain and VH domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the VH and VL chains (i.e. HCDR1, HCDR2, HCDR3, LCDR1, LCDR2 and LCDR3). In some instances, e.g., certain immunoglobulin molecules are derived from camelid species or engineered based on camelid immunoglobulins. Alternatively, an immunoglobulin molecule may consist of heavy chains only with no light chains or light chains only with no heavy chains.

In naturally occurring antibodies, the six CDRs present in each antigen-binding domain are short, non-contiguous sequences of amino acids that are specifically positioned to form the antigen-binding domain as the antibody assumes its three dimensional configuration in an aqueous environment. The remainder of the amino acids in the antigen-binding domains, referred to as "framework" regions, show less inter-molecular variability. The framework regions largely adopt a 3-sheet conformation and the CDRs form loops which connect, and in some cases form part of, the 3-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined.

As used herein, the terms "VH1" and "VH2" refer to immunoglobulin heavy chain variable domains corresponding to two different binding specificities. Likewise, the terms "VL1" and "VL2" refer to light chain variable domains corresponding to two different binding specificities. When used together, it is to be understood that VH1 and VL1 regions define a common binding specificity and that VH2 and VL2 domains define a second binding specificity.

The term "framework region (FR)" as used herein refers to variable domain residues other than the CDR residues. Each variable domain typically has four FRs flanking the corresponding CDRs. For example, a VH domain typically has four HFRs: HFR1, HFR2, HFR3 and HFR4 flanking the three HCDRs in the configuration of HFR1-HCDR1-HFR2-HCDR2-HFR3-HCDR3-HFR4. Similarly, an LH domain typically has four LFRs flanking the three LCDRs in the configuration of: LFR1-LCDR1-LFR2-LCDR2-LFR3-LCDR3-LFR4. Exemplary FRs that may be utilized in the antagonists described herein are summarized in FIGS. 39A-39C.

Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

As used herein, the terms "light chain constant region" or "CL" are used interchangeably herein with reference to amino acid sequences derived from antibody light chain. Preferably, the light chain constant region comprises at least one of a constant kappa domain or constant lambda domain.

As used herein, the term "heavy chain constant region" includes amino acid sequences derived from an immunoglobulin heavy chain. A polypeptide comprising a heavy chain constant region comprises at least one of: a CH1 domain, a hinge (e.g., upper, middle, and/or lower hinge region) domain, a CH2 domain, a CH3 domain, or a variant or fragment thereof. For example, an antigen-binding polypeptide for use in the disclosure may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In some embodiments, a polypeptide of the disclosure comprises a polypeptide chain comprising a CH3 domain. Further, an antibody for use in the disclosure may lack at least a portion of a CH2 domain (e.g., all or part of a CH2 domain). It should be understood that the heavy chain constant region may be modified such that they vary in amino acid sequence from the naturally occurring immunoglobulin molecule. For example, the inventors of the present application have found that an Fc loop in the CH3 domain can tolerate or accommodate significant insertions (e.g., greater than 100 aa).

The heavy chain constant region of an antibody disclosed herein may be derived from different immunoglobulin molecules. For example, a heavy chain constant region of a polypeptide may comprise a CH1 domain derived from an IgG1 molecule and a hinge region derived from an IgG3 molecule. In another example, a heavy chain constant region can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

A "light chain-heavy chain pair" refers to the collection of a light chain and heavy chain that can form a dimer through a disulfide bond between the CL domain of the light chain and the CH1 domain of the heavy chain.

The subunit structures and three dimensional configurations of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system). The CH2 domain is unique in that it is not closely paired with another domain. Rather, two N-linked branched carbohydrate chains are interposed between the two CH2 domains of an intact native IgG molecule. The CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains.

As used herein the term "disulfide bond" includes a covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, a "variant" of antibody, antibody fragment or antibody domain refers to antibody, antibody fragment or antibody domain that (1) shares a sequence identity of at least 80%, at least 85%, at least 90%, at least 95%, at least 96%, at least 97%, at least 98% or at least 99% identity with the original antibody, antibody fragment or antibody domain, and (2) binds specifically to the same target that the original antibody, antibody fragment or antibody domain binds specifically. It should be understood that where a measure of sequence identity is presented in the form of the phrase "at least x % identical" or "at least x % identity", such an embodiment includes any and all whole number percentages equal to or above the lower limit. Further it should be understood that where an amino acid sequence is presented in the present application, it should be construed as additionally disclosing or embracing amino acid sequences having a sequence identity of at least 80%, at least 85%, at least 90%, at least 95%, at least 96%, at least 97%, at least 98% or at least 99% identity to that amino acid sequence.

As used herein, the phrase "humanized antibody" refers to an antibody derived from a non-human antibody, typically a mouse monoclonal antibody. Alternatively, a humanized antibody may be derived from a chimeric antibody that retains or substantially retains the antigen binding properties of the parental, non-human, antibody but which exhibits diminished immunogenicity as compared to the parental antibody when administered to humans.

As used herein, the phrase "chimeric antibody," refers to an antibody where the immunoreactive region or site is obtained or derived from a first species and the constant region (which may be intact, partial or modified in accordance with the instant disclosure) is obtained from a second species. In certain embodiments the target binding region or site will be from a non-human source (e.g., mouse or primate) and the constant region is human.

Included within the scope of the multispecific antibodies of the present application are various compositions and methodologies, including asymmetric IgG-like antibodies (e.g., triomab/quadroma, Trion Pharma/Fresenius Biotech); knobs-into-holes antibodies (Genentech); Cross MAbs (Roche); electrostatically matched antibodies (AMGEN); LUZ-Y (Genentech); strand exchange engineered domain (SEED) body (EMD Serono; biolonic, Merus); Fab-exchanged antibodies (Genmab), symmetric IgG-like antibodies (e.g. dual targeting (DT)-Ig (GSK/Domantis); two-in-one antibody (Genentech); crosslinked MAbs (Karmanos Cancer Center), mAb2 (F-star); Cov X-body (Cov X/Pfizer); dual variable domain (DVD)-Ig fusions (Abbott); IgG-like bispecific antibodies (Eli Lilly); Ts2Ab (Medimmune/AZ); BsAb (ZymoGenetics); HERCULES (Biogen Idec,TvAb, Roche); scFv/Fc fusions; SCORPION (Emergent BioSolutions/Trubion, ZymoGenetics/BMS); dual affinity retargeting technology (Fc-DART), MacroGenics; dual (scFv)2-Fabs (National Research Center for Antibody Medicine); F(ab)2 fusions (Medarex/AMGEN); dual-action or Bis-Fab (Genentech); Dock-and-Lock (DNL, ImmunoMedics); Fab-Fv (UCB-Celltech); scFv- and diabody-based antibodies (e.g., bispecific T cell engagers (BiTEs, Micromet); tandem diabodies (Tandab, Affimed); DARTs (MacroGenics); single-chain diabodies; TCR-like antibodies (AIT, Receptor Logics); human serum albumin scFv fusion (Merrimack); COMBODIES (Epigen Biotech); and IgG/non-IgG fusions (e.g., immunocytokines (EMDSerono, Philogen, ImmunGene, ImmunoMedics).

By "specifically binds" or "has specificity to", it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D." In some embodiments, an antibody or an antibody fragment "has specificity to" an antigen if the antibody or antibody fragment forms a complex with the antigen with a dissociation constant ($K_d$) of $10^{-6}$ M or less, $10^{-7}$ M or less, $10^{-8}$ M or less, $10^{-9}$ M or less, or $10^{-10}$ M or less.

As used herein, the phrase "chimeric antibody," refers to an antibody where the immunoreactive region or site is obtained or derived from a first species and the constant region (which may be intact, partial or modified in accordance with the instant disclosure) is obtained from a second species. In certain embodiments the target binding region or site will be from a non-human source (e.g., mouse or primate) and the constant region is human.

The term "antagonist antibody" refers to an antibody that binds to a target and prevents or reduces the biological effect of that target. In some embodiments, the term can denote an antibody that prevents the target, e.g., TIGIT, to which it is bound from performing a biological function.

As used herein, an "anti-PD-1 antagonist antibody" refers to an antibody that is able to inhibit PD-1 biological activity and/or downstream events(s) mediated by PD-1. Anti-PD-1 antagonist antibodies encompass antibodies that block, antagonize, suppress or reduce (to any degree including significantly) PD-1 biological activity, including downstream events mediated by PD-1, such as PD-1 binding and downstream signaling, inhibition of T cell proliferation, inhibition of T cell activation, inhibition of IFN secretion, inhibition of IL-2 secretion, inhibition of TNF secretion, induction of IL-10, and inhibition of anti-tumor immune responses. For purposes of the present invention, it will be explicitly understood that the term "anti-PD-1 antagonist antibody" (interchangeably termed "antagonist PD-1 antibody", "antagonist anti-PD-1 antibody" or "PD-1 antagonist antibody") encompasses all the previously identified terms, titles, and functional states and characteristics whereby PD-1 itself, a PD-1 biological activity, or the consequences of the biological activity, are substantially nullified, decreased, or neutralized in any meaningful degree. In some embodiments, an anti-PD-1 antagonist antibody binds PD-1 and upregulates an anti-tumor immune response.

As used herein, an "anti-PD-L1 antagonist antibody" refers to an antibody that is able to inhibit PD-L1 biological activity and/or downstream events(s) mediated by PD-L1. Anti-PD-L1 antagonist antibodies encompass antibodies that block, antagonize, suppress or reduce (to any degree including significantly) PD-L1 biological activity, including downstream events mediated by PD-L1, such as PD-L1 binding and downstream signaling, inhibition of T cell proliferation, inhibition of T cell activation, inhibition of IFN secretion, inhibition of IL-2 secretion, inhibition of TNF secretion, induction of IL-10, and inhibition of antitumor immune responses. For purposes of the present invention, it will be explicitly understood that the term "anti-PD-L1 antagonist antibody" (interchangeably termed "antagonist PD-L1 antibody", "antagonist anti-PD-L1 antibody" or "PD-L1 antagonist antibody") encompasses all the previously identified terms, titles, and functional states and characteristics whereby PD-L1 itself, a PD-L1 biological activity, or the consequences of the biological activity, are substantially nullified, decreased, or neutralized in any meaningful degree. In some embodiments, an anti-PD-L1 antagonist antibody binds PD-L1 and upregulates an anti-tumor immune response.

The phrase "immune checkpoint regulator" refers to a functional class of agents, which inhibit or stimulate signaling through an immune checkpoint. An "immune checkpoint regulator" includes receptors and their associated ligands, which together provide a means for inhibiting or stimulating signaling pathways that otherwise lead to T-cell activation. Exemplary immune checkpoint regulators include, but are not limited to, TIGIT and its CD155 ligand, PVR; PD-1 and its ligands, PD-L1 and PD-L2; CTLA-4 and its ligands, B7-1 and B7-2; TIM-3 and its ligand, Galectin-9; LAG-3 and its ligands, including liver sinusoidal endothelial cell lectin (LSECtin) and Galectin-3; CD122 and its CD122R ligand; CD70, B7H3, B and T lymphocyte attenuator (BTLA), and VISTA.

The phrases "checkpoint regulator antagonist", "immune checkpoint binding antagonist" and "immune checkpoint antagonist" are used interchangeably herein with reference to a class of agents that interfere with (or inhibit) the activity of an immune checkpoint regulator so that, as a result of the binding to the checkpoint regulator or its ligand, signaling through the checkpoint regulator receptor is blocked or inhibited. By inhibiting this signaling, immune-suppression can be reversed so that T cell immunity against cancer cells can be re-established or enhanced. Immune checkpoint regulator antagonists include antibody fragments, peptide inhibitors, dominant negative peptides and small molecule drugs, either in isolated forms or as part of a fusion protein or conjugate.

The phrases "immune checkpoint binding agonist" and "immune checkpoint agonist" are used interchangeably herein with reference to a class of agents that stimulate the activity of an immune checkpoint regulator so that, as a result of the binding to the checkpoint regulator or its ligand, signaling through the checkpoint regulator receptor is stimulated. By stimulating this signaling, T cell immunity against cancer cells can be re-established or enhanced. Exemplary immune checkpoint regulator agonists include, but are not limited to members of the tumor necrosis factor (TNF) receptor superfamily, such as CD27, CD40, OX40 (CD 134), glucocorticoid-induced TNFR family-related protein (GITR), and 4-1BB (CD137) and their ligands. Additional checkpoint regulator agonists belong to the B7-CD28 superfamily, including CD28 and ICOS.

The phrases "dominant-negative protein" or "dominant-negative peptide" refer to a protein or peptide derived from a wild type protein that has been genetically modified by mutation and/or deletion so that the modified protein or peptide interferes with the function of the endogenous wild-type protein from which it is derived.

The phrase "small molecule drug" refers to a molecular entity, often organic or organometallic, that is not a polymer, that has medicinal activity, and that has a molecular weight less than about 2 kDa, less than about 1 kDa, less than about 900 Da, less than about 800 Da or less than about 700 Da. The term encompasses most medicinal compounds termed "drugs" other than protein or nucleic acids, although a small peptide or nucleic acid analog can be considered a small molecule drug. Examples include chemotherapeutic anticancer drugs and enzymatic inhibitors. Small molecules drugs can be derived synthetically, semi-synthetically (i.e., from naturally occurring precursors), or biologically.

When describing polypeptide domain arrangements with hyphens between individual domains (e.g., CH2-CH3), it should be understood that the order of the listed domains is from the amino terminal end to the carboxy terminal end.

By "specifically binds" or "has specificity to", it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

The term "immunoconjugate" refers to an antibody which is fused by covalent linkage to an inhibitory peptide or small molecule drug. The peptide or small molecule drug can be linked to the C-terminus of a constant heavy chain or to the N-terminus of a variable light and/or heavy chain.

A "linker" may be used to link the peptide or small molecule drug, such as a maytansinoid, to the antitumor antagonists in a stable, covalent manner. Linkers can be susceptible to or be substantially resistant to acid-induced cleavage, light-induced cleavage, peptidase-induced cleavage, esterase-induced cleavage, and disulfide bond cleavage, at conditions under which the compound or the antibody remains active. Suitable linkers are well known in the art and include, for example, disulfide groups, thioether groups, acid labile groups, photolabile groups, peptidase labile groups and esterase labile groups. Linkers also include charged linkers, and hydrophilic forms thereof as described herein and know in the art. The immunoconjugate may further include a flexible 3-15 amino acid peptide (or spacer) between an antitumor antagonist and the peptide and/or small molecule drug.

As used herein, the term "immunoglobulin scaffold", refers to any polymer of amino acids that exhibits properties desired to support the function of an antagonist, including addition of antibody specificity, enhancement of antibody function or support of antibody structure and stability. An immunoglobulin scaffold may have one or more immunoglobulin constant regions, including CH1, CH2, and/or CH3 regions from an immunoglobulin heavy chain and/or a CL region from an immunoglobulin light chain. The immunoglobulin scaffold can be grafted with binding domains of a donor polypeptide to confer the binding specificity of the donor polypeptide onto the scaffold.

As used herein, the phrase "multispecific inhibitor" refers to a molecule comprising at least two targeting domains with different binding specificities. In some embodiments, the multispecific inhibitor is a polypeptide comprising a scaffold and two or more immunoglobulin antigen binding domains targeting different antigens or epitopes. In certain embodiments, the multispecific inhibitor is a bispecific antibody.

As used herein, the phrase "bispecific" refers to a molecule comprising at least two targeting domains with different binding specificities. Each targeting domain is capable of binding specifically to a target molecule and inhibiting a biological function of the target molecule upon binding to the target molecule. In some embodiments, the bispecific checkpoint regulator antagonist is a polymeric molecule having two or more peptides. In some embodiments, the targeting domain comprises an antigen binding domain or a CDR of an antibody. In some embodiments, the bispecific inhibitor is a bispecific antibody.

The terms "bispecific antibody," and "bispecific antagonist" are used interchangeably herein with reference to an antibody that can specifically bind two different antigens (or epitopes). In some embodiments, the bispecific antibody is a full-length antibody that binds one antigen (or epitope) on one of its two binding arms (one pair of HC/LC), and binds a different antigen (or epitope) on its second arm (a different pair of HC/LC). In these embodiments, the bispecific antibody has two distinct antigen binding arms (in both specificity and CDR sequences), and is monovalent for each antigen it binds to.

In other embodiments, the bispecific antibody is a full-length antibody that can bind two different antigens (or epitopes) in each of its two binding arms (two pairs of HC/LC) In these embodiments, the bispecific antibody has two identical antigen binding arms, with identical specificity and identical CDR sequences, and is bivalent for each antigen it binds to.

Exemplary bispecific antibodies may include asymmetric IgG-like antibodies (e.g., triomab/quadroma, Trion Pharma/Fresenius Biotech); knobs-into-holes antibodies (Genentech); Cross MAbs (Roche); electrostatically matched antibodies (AMGEN); LUZ-Y (Genentech); strand exchange engineered domain (SEED) body (EMD Serono; biolonic, Merus); Fab-exchanged antibodies (Genmab), symmetric IgG-like antibodies (e.g. dual targeting (DT)-Ig (GSK/Domantis); two-in-one antibody (Genentech); crosslinked MAbs (Karmanos Cancer Center), mAb2 (F-star); Cov X-body (Cov X/Pfizer); dual variable domain (DVD)-Ig fusions (Abbott); IgG-like bispecific antibodies (Eli Lilly); Ts2Ab (Medimmune/AZ); BsAb (ZymoGenetics); HERCULES (Biogen Idec,TvAb, Roche); scFv/Fc fusions; SCORPION (Emergent BioSolutions/Trubion, ZymoGenetics/BMS); dual affinity retargeting technology (Fc-DART), MacroGenics; dual (scFv)2-Fabs (National Research Center for Antibody Medicine); F(ab)2 fusions (Medarex/AMGEN); dual-action or Bis-Fab (Genentech); Dock-and-Lock (DNL, ImmunoMedics); Fab-Fv (UCB-Celltech); scFv- and diabody-based antibodies (e.g., bispecific T cell engagers (BiTEs, Micromet); tandem diabodies (Tandab, Affimed); DARTs (MacroGenics); single-chain diabodies; TCR-like antibodies (AIT, Receptor Logics); human serum albumin scFv fusion (Merrimack); COMBODIES (Epigen Biotech); and IgG/non-IgG fusions (e.g., immunocytokines (EMDSerono, Philogen, ImmunGene, ImmunoMedics).

The terms "treat" and "treatment" refer to the amelioration of one or more symptoms associated with a cell proliferative disorder; prevention or delay of the onset of one or more symptoms of a cell proliferative disorder; and/or lessening of the severity or frequency of one or more symptoms of cell proliferative disorder.

The phrases "to a patient in need thereof", "to a patient in need of treatment" or "a subject in need of treatment" includes subjects, such as mammalian subjects, that would benefit from administration of the antitumor antagonist of the present disclosure for treatment of a cell proliferative disorder.

The terms "therapeutically effective amount", "pharmacologically effective amount", and "physiologically effective amount" are used interchangeably to mean the amount of an antitumor antagonist that is needed to provide a threshold level of active antagonist agents in the bloodstream or in the target tissue. The precise amount will depend upon numerous factors, e.g., the particular active agent, the components and physical characteristics of the composition, intended patient population, patient considerations, and the like, and can readily be determined by one skilled in the art, based upon the information provided herein or otherwise available in the relevant literature.

The terms, "improve", "increase" or "reduce", as used in this context, indicate values or parameters relative to a baseline measurement, such as a measurement in the same individual prior to initiation of the treatment described herein, or a measurement in a control individual (or multiple control individuals) in the absence of the treatment described herein.

A "control individual" is an individual afflicted with the same cell proliferative disorder as the individual being treated, who is about the same age as the individual being treated (to ensure that the stages of the disease in the treated individual and the control individual(s) are comparable). The individual (also referred to as "patient" or "subject") being treated may be a fetus, infant, child, adolescent, or adult human with a cell proliferative disorder.

The term "cell proliferative disorder" refers to a disorder characterized by abnormal proliferation of cells. A proliferative disorder does not imply any limitation with respect to the rate of cell growth, but merely indicates loss of normal controls that affect growth and cell division. Thus, in some embodiments, cells of a proliferative disorder can have the same cell division rates as normal cells but do not respond to signals that limit such growth. Within the ambit of "cell proliferative disorder" is a neoplasm, cancer or tumor.

The term "cancer" or "tumor" refers to any one of a variety of malignant neoplasms characterized by the proliferation of cells that have the capability to invade surrounding tissue and/or metastasize to new colonization sites, and includes leukemia, lymphoma, carcinoma, melanoma, sarcoma, germ cell tumor and blastoma. Exemplary cancers for treatment with the methods of the instant disclosure include cancer of the brain, bladder, breast, cervix, colon, head and neck, kidney, lung, non-small cell lung, mesothelioma, ovary, prostate, stomach and uterus, leukemia, and medulloblastoma.

The term "leukemia" refers to progressive, malignant diseases of the blood-forming organs and is generally characterized by a distorted proliferation and development of leukocytes and their precursors in the blood and bone marrow. Exemplary leukemias include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "carcinoma" refers to the malignant growth of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "sarcoma" refers to a tumor made up of a substance like the embryonic connective tissue and is generally composed of closely packed cells embedded in a fibrillar or homogeneous substance. Exemplary sarcomas include, for example, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilns' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphomas (e.g., Non-Hodgkin Lymphoma), immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" refers to a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma subungal melanoma, and superficial spreading melanoma.

Additional cancers include, for example, Hodgkin's Disease, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, pre-malignant skin lesions, testicular cancer, thyroid cancer, neuroblastoma, esophageal cancer, genitourinary tract cancer, malignant hypercalcemia, cervical cancer, endometrial cancer, and adrenal cortical cancer.

I. Checkpoint Regulator Antagonists

In one aspect, the present application provides an antitumor antagonist comprising an immunoglobulin scaffold with (1) a pair of arms containing variable domain regions that specifically bind to a first immune checkpoint regulator and (2) a single chain (scFv) that specifically binds to a second immune checkpoint regulator.

In another aspect, the present application provides an antitumor antagonist comprising an immunoglobulin scaffold structurally linked to both a first immune checkpoint regulator antagonist, and a second immune checkpoint regulator antagonist in the form of an scFv.

In both aspects, the immunoglobulin scaffold may comprise one or more immunoglobulin constant regions, e.g., IgG CH1, CH2, and/or CH3. In certain embodiments, the immunoglobulin scaffold is an Fc (hinge-CH2-CH3).

In some embodiments, the antitumor antagonist comprises an immunoglobulin scaffold in which the N-terminal end of the antagonist includes a first immune checkpoint regulator antagonist structurally linked thereto in which the first immune checkpoint regulator antagonist specifically binds to PD-1, PD-L1, LAG-3, TIGIT, and a second immune checkpoint regulator antagonist is positioned at the C-terminal end of the antagonist as an scFv that specifically binds to PD-1, PD-L1, LAG-3 or TIGIT.

In some embodiments, the scFv comprises a linker joining heavy chain variable regions to light chain variable regions. In one embodiment, the linker comprises an amino acid sequence comprising between 3, 4, 5, 6, 7, 8, 9, or 10 copies of the amino acid sequence G4S. In another embodiment, the linker comprises an amino acid sequence set forth in either one of SEQ ID NOs: 188-191. In a more particular embodiment, the linker comprises the amino acid sequence of SEQ ID NO: 191.

In one embodiment, the anti-TIGIT scFv comprises one or more heavy chain CDRs selected from SEQ ID NOS: 1-25 and one or more light chain CDRs selected from SEQ ID NOs: 26-47.

In another embodiment, the anti-TIGIT scFv comprising heavy chain/light chain variable regions, wherein the scFv has a heavy chain variable region (HCVR) having at least 80%, at least 85%, at least 90%, at least 95%, or at least 99% identity to an amino acid sequence selected from the group consisting of SEQ ID NOS: 48, 50, 52, 54, 56, 58, 60, 62, 64, and 66 and a light chain variable region (LCVR) having at least at least 80%, at least 85%, at least 90%, at least 95%, or at least 99% to an LCVR having an amino acid sequence selected from the group consisting of SEQ ID NOS: 49, 51, 53, 55, 57, 59, 61, 63, and 67.

In a more particular embodiment, the anti-TIGIT scFv comprises an HCVR having at least 80%, at least 85%, at least 90%, at least 95%, or at least 99% identity to the amino acid sequence of SEQ ID NO:66 and an LCVR having at least 80%, at least 85%, at least 90%, at least 95%, or at least 99% to an LCVR having the amino acid sequence of SEQ ID NO:67.

In another embodiment, the anti-TIGIT scFv includes: an HCVR that comprises (1) an HCDR1 of SEQ ID NO:23, an HCDR2 of SEQ ID NO:24 and an HCDR 3 of SEQ ID NO:25 in combination with (2) an HFR1 having at least 80%, 85% or 90% identity to the amino acid sequence of SEQ ID NO:260, an HFR2 having at least 80%, 85% or 90% identity to the amino acid sequence of SEQ ID NO:247, an HFR3 having at least 80%, 85% or 90% identity to the amino acid sequence of SEQ ID NO:261, and an HFR4 having at least 80%, 85% or 90% identity to the amino acid sequence of SEQ ID NO:236; and further includes an immunoglobulin LCVR that comprises (1) an LCDR1 of SEQ ID NO:45, an LCDR2 of SEQ ID NO:46 and an LCDR 3 of SEQ ID NO:47 in combination with (2) an LFR1 having at least 80%, 85% or 90% identity to the amino acid sequence of SEQ ID NO:220, an LFR2 having at least 80%, 85% or 90% identity to the amino acid sequence of SEQ ID NO:228, an LFR3 having at least 80%, 85% or 90% identity to the amino acid sequence of SEQ ID NO:234, an LFR4 having at least 80%, 85% or 90% identity to the amino acid sequence of SEQ ID NO:262.

In another embodiment, the first targeting domain comprises one or more variable regions from an anti-PD-1 antibody, and the second targeting domain comprises an anti-TIGIT scFv as described above.

In one embodiment, the anti-PD-1 targeting domain comprises one or more heavy chain CDRs selected from SEQ ID NOS: 68-81 and/or one or more light chain CDRs selected from SEQ ID NOS: 82-95.

In another embodiment, the anti-PD-1 targeting domain comprises: an HCVR having at least 80%, at least 85%, at least 90%, at least 95%, or at least 99% identity to an amino acid sequence selected from the group consisting of SEQ ID NOS: 96, 98, 100, 102, 104, and 106; an LCVR having at least 80%, at least 85%, at least 90%, at least 95%, or at least 99% identity to an LCVR having an amino acid sequence selected from the group consisting of SEQ ID NOS: 97, 99, 101, 103, 105, and 107; or both.

In another embodiment, the anti-PD-1 targeting domain includes: an HCVR that comprises (1) an HCDR1 of SEQ ID NO:79, an HCDR2 of SEQ ID NO:80 and an HCDR 3 of SEQ ID NO:81 in combination with (2) an HFR1 having at least 80%, 85% or 90% identity to the amino acid sequence of SEQ ID NO:283, an HFR2 having at least 80%, 85% or 90% identity to the amino acid sequence of SEQ ID NO:277, an HFR3 having at least 80%, 85% or 90% identity to the amino acid sequence of SEQ ID NO:288, an HFR4 having at least 80%, 85% or 90% identity to the amino acid sequence of SEQ ID NO:274; an immunoglobulin LCVR that comprises (1) an LCDR1 of SEQ ID NO:93, an LCDR2 of SEQ ID NO:94 and an LCDR 3 of SEQ ID NO:95 in combination with (2) an LFR1 having at least 80%, 85% or 90% identity to the amino acid sequence of SEQ ID NO:289, an LFR2 having at least 80%, 85% or 90% identity to the amino acid sequence of SEQ ID NO:290, an LFR3 having at least 80%, 85% or 90% identity to the amino acid sequence of SEQ ID NO:291, and an LFR4 having at least 80%, 85% or 90% identity to the amino acid sequence of SEQ ID NO:292; or both.

In another embodiment, the anti-PD-1 targeting domain comprises an HCVR having at least 80%, at least 85%, at least 90%, at least 95%, or at least 99% identity to the amino acid sequence of SEQ ID NO:106; an LCVR having at least at least 80%, at least 85%, at least 90%, at least 95%, or at least 99% identity to the amino acid sequence of SEQ ID NO: 107; or both.

In a particular embodiment, a bispecific anti-PD-1/anti-TIGIT antagonist includes a first targeting domain comprising an HCVR having the amino acid sequence of SEQ ID NO:106 and/or an LCVR having the amino acid sequence of SEQ ID NO:107 in combination with an anti-TIGIT scFv comprising an HCVR having the amino acid sequence of SEQ ID NO:66 and an LCVR having the amino acid sequence of SEQ ID NO:67.

In a more particular embodiment, the scFv in the bispecific anti-PD-1/anti-TIGIT antagonist comprises a linker joining heavy chain variable regions to light chain variable regions in the second targeting domain, where the linker comprises the amino acid sequence of SEQ ID NO:191.

In another embodiment, the bispecific anti-PD-1/anti-TIGIT antagonist includes: an immunoglobulin heavy chain comprising the amino acid sequence of SEQ ID NO:160; an immunoglobulin light chain comprising the amino acid sequence of SEQ ID NO:161; or both.

In another embodiment, the bispecific anti-PD-1/anti-TIGIT antagonist includes: an immunoglobulin heavy chain comprising the amino acid sequence of SEQ ID NO:162; an immunoglobulin light chain comprising the amino acid sequence of SEQ ID NO:161; or both.

In another embodiment, the bispecific anti-PD-1/anti-TIGIT antagonist comprises an immunoglobulin heavy chain comprising the amino acid sequence of SEQ ID NO: 160, and an immunoglobulin light chain comprising the amino acid sequence of SEQ ID NO: 161.

In another embodiment, the first targeting domain comprises one or more variable regions from an anti-PD-L1 antibody, and the second targeting domain comprises an anti-TIGIT scFv as described above.

In one embodiment, the anti-PD-L1 targeting domain comprises one or more heavy chain CDRs selected from SEQ ID NOS: 108-122 and/or one or more light chain CDRs selected from SEQ ID NOS: 123-138.

In another embodiment, the anti-PD-L1 targeting domain comprises an HCVR having at least 80%, at least 85%, at least 90%, at least 95%, or at least 99% identity to an amino acid sequence selected from the group consisting of SEQ ID NOs: 139, 141, 143, 145, 147, 149, 151, and 153 and/or an LCVR having at least 80%, at least 85%, at least 90%, at least 95%, or at least 99% identity to an amino acid sequence selected from the group consisting of SEQ ID NOs: 140, 142, 144, 146, 148, 152, and 154.

In another embodiment, the anti-PD-L1 targeting domain comprises an HCVR having at least 80%, at least 85%, at least 90%, at least 95%, or at least 99% identity to the amino acid sequence of SEQ ID NO:153 and/or an LCDR having at least 80%, at least 85%, at least 90%, at least 95%, or at least 99% identity to an LCVR having the amino acid sequence of SEQ ID NO:154.

In another embodiment, the anti-PD-L1 targeting domain includes: an immunoglobulin HCVR that comprises (1) an HCDR1 of SEQ ID NO:111, an HCDR2 of SEQ ID NO:114 and an HCDR 3 of SEQ ID NO:115 in combination with (2) an HFR1 having at least 80%, 85% or 90% identity to the amino acid sequence of SEQ ID NO:283, an HFR2 having at least 80%, 85% or 90% identity to the amino acid sequence of SEQ ID NO:277, an HFR3 having at least 80%, 85% or 90% identity to the amino acid sequence of SEQ ID NO:300, and an HFR4 having at least 80%, 85% or 90% identity to the amino acid sequence of SEQ ID NO:274; an immunoglobulin LCVR that comprises (1) an LCDR1 of SEQ ID NO:123, an LCDR2 of SEQ ID NO:124 and an LCDR 3 of SEQ ID NO:125 in combination with (2) an LFR1 having at least 80%, 85% or 90% identity to the amino acid sequence of SEQ ID NO:294, an LFR2 having at least 80%, 85% or 90% identity to the amino acid sequence of SEQ ID NO:295, an LFR3 having at least 80%, 85% or 90% identity to the amino acid sequence of SEQ ID NO:296, and an LFR4 having at least 80%, 85% or 90% identity to the amino acid sequence of SEQ ID NO:276; or both.

In a particular embodiment, a bispecific anti-PD-L1/anti-TIGIT antagonist includes a first targeting domain comprising: an HCVR having the amino acid sequence of SEQ ID NO: 153 and/or an LCVR having the amino acid sequence of SEQ ID NO: 154 in combination with a second targeting domain in the form of an anti-TIGIT scFv comprising an HCVR having the amino acid sequence of SEQ ID NO: 66 and an LCVR having the amino acid sequence of SEQ ID NO: 67. In a more particular embodiment, the scFv in the bispecific anti-PD-L1/anti-TIGIT antagonist comprises a linker joining anti-TIGIT HCVR to the anti-TIGIT LCVR in the second targeting domain, where the linker comprises the amino acid sequence of SEQ ID NO: 191.

In another embodiment, the first targeting domain comprises one or more variable regions from an anti-LAG-3 antibody, and the second targeting domain comprises an anti-TIGIT scFv as described above.

In one embodiment, the anti-LAG-3 targeting domain comprises one or more immunoglobulin heavy chain CDRs selected from SEQ ID NOS: 163-171 and/or one or more immunoglobulin light chain CDRs selected from SEQ ID NOS: 172-178.

In another embodiment, the anti-LAG-3 targeting domain comprises an HCVR having at least 80%, at least 85%, at least 90%, at least 95%, or at least 99% identity to an amino acid sequence selected from the group consisting of SEQ ID NOs: 180, 182, 184, and 186 and/or an LCVR having at least 80%, at least 85%, at least 90%, at least 95%, or at least 99% identity to an LCVR having an amino acid sequence selected from the group consisting of SEQ ID NOs: 181, 183, 185, and 187.

In another embodiment, the anti-LAG-3 targeting domain includes: an immunoglobulin HCVR comprising (1) an HCDR1 of SEQ ID NO:163, an HCDR2 of SEQ ID NO:164 and an HCDR 3 of SEQ ID NO:165 in combination with (2) an HFR1 having at least 80%, 85% or 90% identity to the amino acid sequence of SEQ ID NO:316, an HFR2 having at least 80%, 85% or 90% identity to the amino acid sequence of SEQ ID NO:317, an HFR3 having at least 80%, 85% or 90% identity to the amino acid sequence of SEQ ID NO:318, and an HFR4 having at least 80%, 85% or 90% identity to the amino acid sequence of SEQ ID NO:319; an immunoglobulin LCVR comprising (1) an LCDR1 of SEQ ID NO:172, an LCDR2 of SEQ ID NO:173 and an LCDR 3 of SEQ ID NO:174 in combination with (2) an LFR1 having at least 80%, 85% or 90% identity to the amino acid sequence of SEQ ID NO:320, an LFR2 having at least 80%, 85% or 90% identity to the amino acid sequence of SEQ ID NO:321, an LFR3 having at least 80%, 85% or 90% identity to the amino acid sequence of SEQ ID NO:322, and an LFR4 having at least 80%, 85% or 90% identity to the amino acid sequence of SEQ ID NO:323; or both.

In another embodiment, the anti-LAG-3 targeting domain comprises an immunoglobulin HCVR having an amino acid sequence that is 90%, 95%, 99%, or 100% identical to the amino acid sequence of SEQ ID NO:180 and/or an immunoglobulin LCVR having an amino acid sequence that is 90%, 95%, 99%, or 100% identical to the amino acid sequence of SEQ ID NO:181.

In a particular embodiment, a bispecific anti-LAG-3/anti-TIGIT antagonist includes a first targeting domain comprising an HCVR having the amino acid sequence of SEQ ID NO:180 and/or an LCVR having the amino acid sequence of SEQ ID NO:181 in combination with an anti-TIGIT scFv comprising an HCVR having the amino acid sequence of SEQ ID NO: 66 and an LCVR having the sequence of SEQ ID NO:67. In a more particular embodiment, the scFv in the bispecific anti-LAG-3/anti-TIGIT antagonist comprises a linker joining anti-TIGIT HCVR to the anti-TIGIT LCVR in the second targeting domain, where the linker comprises the amino acid sequence of SEQ ID NO:189 or SEQ ID NO:191.

In one embodiment, the bispecific anti-LAG-3/anti-TIGIT antagonist includes an immunoglobulin heavy chain comprising the amino acid sequence of SEQ ID NO:192 or 193; an immunoglobulin light chain comprising the amino acid sequence of SEQ ID NO:181, or both.

Anti-LAG-3 Antibodies and Antigen Binding Fragments Thereof

In another aspect, the present application provides antibodies, including antigen-binding portions thereof, which specifically bind LAG-3. FIG. 19A shows the heavy chain CDR1, CD2 and CDR3 sequences corresponding to the anti-LAG-3 mAbs 2L2A.1, 2L2A.6, 2L27B and 3L1A. FIG. 19B shows the light chain CDR1, CD2 and CDR3 sequences corresponding to the anti-LAG-3 mAbs 2L2A.1, 2L2A.6, 2L27B and 3L1A. FIG. 20 shows the VH and VL sequences of anti-LAG-3 mAbs 2L2A.1, 2L2A.6, 2L27B and 3L1A.

In one embodiment, an anti-LAG-3 antibody or antigen-binding portion thereof includes: an immunoglobulin heavy chain CDR1 (HCDR1) having at least 80%, at least 85%, or at least 90% sequence identity to an HCDR1 amino acid sequence selected from the group consisting of SEQ ID NOs: 163, 166, and 169; an immunoglobulin heavy chain CDR2 (HCDR2) sequence having at least 80%, at least 85%, or at least 90% sequence identity to an HCDR2 amino acid sequence selected from the group consisting of SEQ ID NOs. 164, 167, and 170; an immunoglobulin heavy chain CDR3 (HCDR3) having at least 80%, at least 85%, or at least 90% sequence identity to an HCDR3 amino acid sequence selected from the group consisting of SEQ ID NOs. 165, 168, and 171; an immunoglobulin light chain CDR1 (LCDR1) having at least 80%, at least 85%, or at least 90% sequence identity to an LCDR1 amino acid sequence selected from the group consisting of SEQ ID NOs. 172, 175, and 177; an immunoglobulin light chain CDR2 (LCDR2) having at least 80%, at least 85%, or at least 90% sequence identity to an LCDR2 amino acid sequence selected from the group consisting of SEQ ID NOs. 173 and 178; and an immunoglobulin light chain CDR3 (LCDR3) having at least 80%, at least 85%, or at least 90% sequence identity to an LCDR3 amino acid sequence selected from the group consisting of SEQ ID NOs. 174, 176 and 179.

In another embodiment, an anti-LAG-3 antibody or antigen-binding portion thereof includes: an immunoglobulin HCDR1 amino acid sequence selected from the group consisting of SEQ ID NOs: 163, 166, and 169; an immunoglobulin HCDR2 amino acid sequence selected from the group consisting of SEQ ID NOs. 164, 167, and 170; an immunoglobulin HCDR3 amino acid sequence selected from the group consisting of SEQ ID NOs. 165, 168, and 171; an immunoglobulin LCDR1 amino acid sequence selected from the group consisting of SEQ ID NOs. 172, 175, and 177; an immunoglobulin LCDR2 amino acid sequence selected from the group consisting of SEQ ID NOs. 173 and 178; and an immunoglobulin LCDR3 amino acid sequence selected from the group consisting of SEQ ID NOs. 174, 176 and 179.

In another embodiment, the anti-LAG-3 antibody or antigen-binding portion thereof includes: an immunoglobulin HCVR having at least 80%, 85%, 90%, 95% or 99% identity to an amino acid sequence selected from the group consisting of SEQ ID NOS: 180, 182, 184, and 186; an immunoglobulin LCVR having at least 80%, 85%, 90%, 95% or 99% identity to an LCVR having an amino acid sequence selected from the group consisting of SEQ ID NOs. 181, 183, 185, and 187; or both.

In another embodiment, the anti-LAG-3 antibody or antigen-binding portion thereof includes: an immunoglobulin HCVR having an amino acid sequence selected from the group consisting of SEQ ID NOS: 180, 182, 184, and 186; an immunoglobulin LCVR having an amino acid sequence selected from the group consisting of SEQ ID NOs. 181, 183, 185, and 187; or both.

In another embodiment, the anti-LAG-3 antibody or antigen-binding portion thereof includes: an immunoglobulin heavy chain sequence that is at least 80%, at least 85%, at least 90%, at least 95%, at least 99%, or 100% identical to the amino acid sequence of SEQ ID NO: 180; an immunoglobulin light chain sequence that is at least 80%, at least 85%, at least 90%, at least 95%, at least 99%, or 100% identical to the amino acid sequence of SEQ ID NO:181; or both.

In a more particular embodiment, the anti-LAG-3 antibody or antigen-binding portion thereof includes: the immunoglobulin heavy chain sequence of SEQ ID NO:180; the immunoglobulin light chain sequence of SEQ ID NO:181; or both.

In another aspect, the present application provides one or more nucleic acids encoding any anti-LAG-3 antibody or any antigen-binding portion thereof as described herein.

In another aspect, the present application provides one or more expression vectors comprising one or more nucleic acids encoding any anti-LAG-3 antibody or any antigen-binding portion thereof as described herein.

In another aspect, the present application provides a host cell transformed with the one or more nucleic acids or the one or more expression vectors encoding any anti-LAG-3 antibody or any antigen-binding portion as described herein.

In another aspect, the present application provides a bispecific antitumor antagonist comprising a first targeting domain specifically binding LAG-3; and a second targeting domain specifically binding PD-1, PD-L1 or TIGIT, where the first targeting domain comprises any of the above-described LAG-3-binding portions. Preferably, the anti-LAG-3 bispecific anti-tumor antagonist includes an immunoglobulin scaffold comprising one or more IgG constant regions, e.g., CH1, CH2, CH3, and/or CL.

In some embodiments, the first targeting domain is positioned at the N-terminal end and the second targeting domain is positioned at the C-terminal end. In other embodiments, the first targeting domain is positioned at the C-terminal end and the second targeting domain is positioned at the N-terminal end. In yet other embodiments, the second targeting domain is inserted within a loop region of e.g., the CH3 domain.

In one embodiment, a bispecific antitumor antagonist comprises a first targeting domain specifically binding LAG-3, and a second targeting domain specifically binding PD-1, where the first targeting domain comprises any of the anti-LAG-3 binding fragments described above, and where the second targeting domain comprises any of the PD-1 binding fragments described below. For example, in one embodiment, the first targeting domain includes the HCVR amino acid sequence of SEQ ID NO: 180 in combination with an LCVR having the amino acid sequence of SEQ ID NO: 181, and the second targeting domain includes an HCVR having the amino acid sequence of SEQ ID NO: 106 in combination with an LCVR having the amino acid sequence of SEQ ID NO: 107. Alternatively, the second domain may be configured in the form of a PD-1 ECD.

In another embodiment, a bispecific antitumor antagonist includes a first targeting domain specifically binding LAG-3 and a second targeting domain specifically binding PD-L1, where the first targeting domain comprises any of the anti-LAG-3 binding fragments described above, and where the second targeting domain comprises any of the PD-L1 binding fragments described below. For example, in one embodiment, the first targeting domain includes an HCVR having the amino acid sequence of SEQ ID NO:180 in combination with an LCVR having the amino acid sequence of SEQ ID NO: 181, and the second targeting domain includes an HCVR having the amino acid sequence of SEQ ID NO: 153 in combination with an LCVR having the amino acid sequence of SEQ ID NO: 154.

In another embodiment, a bispecific antitumor antagonist comprises a first targeting domain specifically binding LAG-3 and a second targeting domain specifically binding TIGIT, where the first targeting domain comprises any of the anti-LAG-3 binding fragments described above, and where the second targeting domain comprises any of the TIGIT binding fragments described below. For example, in one embodiment, the first targeting domain includes an HCVR having the amino acid sequence of SEQ ID NO:180 in combination with an LCVR having the amino acid sequence of SEQ ID NO: 181, and the second targeting domain includes an HCVR having the amino acid sequence of SEQ ID NO: 66 in combination with an LCVR having the amino acid sequence of SEQ ID NO: 67. Alternatively, the second domain may be configured in the form of a TIGIT ECD.

Exemplary immunoglobulin scaffolds include, for example, a complete CH1-CH2-CH3 segment as set forth in SEQ ID NOS: 155-157 and 205-215, or an Fc (hinge-CH2-CH3) comprising the amino acid sequence set forth in any one of SEQ ID NOS: 195-202.

Anti-TIGIT Antibody and Anti-TIGIT Antibody Fragments

In some embodiments, the checkpoint regulator antagonist includes an anti-TIGIT antibody or antigen-binding fragment(s) thereof. FIG. 1 shows CDR sequences of anti-TIGIT mAbs, while FIGS. 2A-2B show several embodiments of anti-TIGIT antibody variable domain sequences for use in the present application.

In one embodiment, the anti-TIGIT antibody or antigen-binding fragment(s) thereof includes: (1) an immunoglobulin HCVR comprising three complementarity determining regions (HCDRs): HCDR1, HCDR2 and HCDR3, where the HCDR1 has an amino acid sequence that is at least 80%, at least 85%, at least 90%, at least 95%, at least 99%, or 100% identical to an amino acid sequence selected from the group consisting of SEQ ID NOS: 1, 6, 11, 15, 17, 20 and 23, where the HCDR2 has an amino acid sequence that is at least 80%, at least 85%, at least 90%, at least 95%, at least 99%, or 100% identical to an amino acid sequence selected from the group consisting of SEQ ID NOS: 2, 4, 7, 9, 12, 13, 16, 18, 21 and 24, and where the HCDR3 has an amino acid sequence that is at least 80%, at least 85%, at least 90%, at least 95%, at least 99%, or 100% identical to an amino acid sequence selected from the group consisting of SEQ ID NOS: 3, 5, 8, 10, 14, 19, 22 and 25; and (2) an immunoglobulin LCVR comprising LCDR1, LCDR2 and LCDR3 sequences, where the LCDR1 has an amino acid sequence that is at least 80%, at least 85%, at least 90%, at least 95%, at least 99%, or 100% identical to an amino acid sequence selected from the group consisting of SEQ ID NOS: 26, 29, 31, 33, 35, 39, 42 and 45, wherein the LCDR2 has an amino acid sequence that is at least 80%, at least 85%, at least 90%, at least 95%, at least 99%, or 100% identical to an amino acid sequence selected from the group consisting of SEQ ID NOS: 27, 30, 36, 37, 40, 43 and 46, and where the LCDR3 has an amino acid sequence that is at least 80%, at least 85%, at least 90%, at least 95%, at least 99%, or 100% identical to an amino acid sequence selected from the group consisting of SEQ ID NOS: 28, 32, 34, 38, 41, 44 and 47; where the antibody or the antigen-binding portion thereof binds specifically to human TIGIT.

In another embodiment, the anti-TIGIT antibody or antigen-binding fragment(s) thereof includes: (1) an immunoglobulin HCVR having an amino acid sequence that is at least 80%, at least 85%, at least 90%, at least 95%, at least 99%, or 100% identical to an amino acid sequence selected from the group consisting of SEQ ID NOs: 48, 50, 52, 54, 56, 58, 60, 62, 64, and 66; and (2) an immunoglobulin LCVR having an amino acid sequence that is at least 80%, at least 85%, at least 90%, at least 95%, at least 99%, or 100% identical to an amino acid sequence selected from the group consisting of SEQ ID NOS: 49, 51, 53, 55, 57, 59, 61, 63, 65, and 67; where the antibody or the antigen-binding portion thereof binds specifically to human TIGIT.

Anti-PD-1 Antibodies and Antigen-Binding Fragments Thereof

In some embodiments, the checkpoint regulator antagonist includes an anti-PD-1 antibody or antigen-binding fragment(s) thereof. FIG. 3 shows CDR sequences of anti-PD-1 mAbs and FIGS. 4A-4C show several embodiments of anti-PD-1 antibody variable domain sequences for use in the present application.

In one embodiment, the anti-PD-1 antibody or antigen-binding fragment(s) thereof includes: (1) an immunoglobulin HCVR comprising HCDR1, HCDR2 and HCDR3 sequences, where the HCDR1 has an amino acid sequence that is at least 80%, at least 85%, at least 90%, at least 95%, at least 99%, or 100% identical to an amino acid sequence selected from the group consisting of SEQ ID NOS: 68, 71, 74, 76, and 79, where the HCDR2 has an amino acid sequence that is at least 80%, at least 85%, at least 90%, at least 95%, at least 99%, or 100% identical to an amino acid sequence selected from the group consisting of SEQ ID NOS: 69, 72, 77, and 80, and where the HCDR3 has an amino acid sequence that is at least 80%, at least 85%, at least 90%, at least 95%, at least 99%, or 100% identical to an amino acid sequence selected from the group consisting of SEQ ID NOS: 70, 73, 75, 78, and 81; and (2) an immunoglobulin LCVR comprising LCDR1, LCDR2 and LCDR3 sequences, where the LCDR1 has an amino acid sequence that is at least 80%, at least 85%, at least 90%, at least 95%, at least 99%, or 100% identical to an amino acid sequence selected from the group consisting of SEQ ID NOS: 82, 85, 88, 89, 90, and 93, where the LCDR2 has an amino acid sequence that is at least 80%, at least 85%, at least 90%, at least 95%, at least 99%, or 100% identical to an amino acid sequence selected from the group consisting of SEQ ID NOS: 83, 86, 91, and 94, and where the LCDR3 has an amino acid sequence that is at least 80%, 85%, 90%, 95%, 99%, or 100% identical to an amino acid sequence selected from the group consisting of SEQ ID NOS: 84, 87, 92, and 95, where the antibody or the antigen-binding portion thereof binds specifically to human PD-1.

In some embodiments, the anti-PD-1 antibody or antigen-binding fragment(s) thereof include: (1) an immunoglobulin HCVR having an amino acid sequence that is at least 80%, at least 85%, at least 90%, at least 95%, at least 99%, or 100% identical to an amino acid sequence selected from the group consisting of SEQ ID NOS: 96, 98, 100, 102, 104, and 106; and (2) an immunoglobulin LCVR having an amino acid sequence that is at least 80%, at least 85%, at least 90%, at least 95%, at least 99%, or 100% identical to an amino acid sequence selected from the group consisting of SEQ ID NOS: 97, 99, 101, 103, 105, and 107, where the antibody, or the antigen-binding portion thereof, binds specifically to human PD-1.

Anti-PD-L1 Antibodies and Antigen-Binding Fragment Thereof

In some embodiments, the checkpoint regulator antagonist includes an anti-PD-L1 antibody or antigen-binding fragment(s) thereof. FIG. 5 shows CDR sequences of anti-PD-L1 mAbs and FIGS. 6A-6C show several embodiments of anti-PD-L1 antibody variable domain sequences for use in the present application.

In one embodiment, the PD-L1 antibody or antigen-binding fragment(s) thereof includes: (1) an immunoglobulin HCVR comprising HCDR1, HCDR2 and HCDR3 sequences, where the HCDR1 has an amino acid sequence that is at least 80%, at least 85%, at least 90%, at least 95%, at least 99%, or 100% identical to an amino acid sequence selected from the group consisting of SEQ ID NOS: 108, 111, 117, and 120, where the HCDR2 has an amino acid sequence that is at least 80%, at least 85%, at least 90%, at least 95%, at least 99%, or 100% identical to an amino acid sequence selected from the group consisting of SEQ ID NOS: 109, 112, 114, 116, 118, and 121, where the HCDR3 has an amino acid sequence that is at least 80%, at least 85%, at least 90%, at least 95%, at least 99%, or 100% identical to an amino acid sequence selected from the group consisting of SEQ ID NOS: 110, 113, 115, 119, and 122; and (2) an immunoglobulin LCVR, wherein the light chain variable region comprises three complementarity determining regions (LCDRs): LCDR1, LCDR2 and LCDR3, wherein the LCDR1 has an amino acid sequence that is at least 80%, at least 85%, at least 90%, at least 95%, at least 99%, or 100% identical to an amino acid sequence selected from the group consisting of SEQ ID NOS: 123, 126, 130, 133, and 136, wherein the LCDR2 has an amino acid sequence that is at least 80%, at least 85%, at least 90%, at least 95%, at least 99%, or 100% identical to an amino acid sequence selected from the group consisting of SEQ ID NOS: 124, 127, 131, 134, and 137, and wherein the LCDR3 has an amino acid sequence that is at least 80%, at least 85%, at least 90%, at least 95%, at least 99%, or 100% identical to an amino acid sequence selected from the group consisting of SEQ ID NOS: 125, 128, 129, 132, 135, and 138, wherein the antibody, or the antigen-binding portion thereof, binds specifically to human PD-L1.

In some embodiments, the PD-L1 antibody or antigen-binding fragment(s) thereof include: (1) an immunoglobulin HCVR having an amino acid sequence that is at least 80%, at least 85%, at least 90%, at least 95%, at least 99%, or 100% identical to an amino acid sequence selected from the group consisting of SEQ ID NOS: 139, 141, 143, 145, 147, 149, 151, and 153; and (2) an immunoglobulin LCVR having an amino acid sequence that is at least 80%, at least 85%, at least 90%, at least 95%, at least 99%, or 100% identical to an amino acid sequence selected from the group consisting of SEQ ID NOS: 140, 142, 144, 146, 148, 150, 152 and 154, where the antibody, or the antigen-binding portion thereof, binds specifically to human PD-L1.

II. Miscellaneous Embodiments

The HCVRs and LCVRs described herein may be linked to an immunoglobulin scaffold. In some embodiments, the immunological scaffold is configured as an IgG1, IgG2 or IgG4. The immunoglobulin scaffold may include CH1-CH2-CH3 regions or it may include a naturally-occurring Fc region or a non-naturally occurring or mutated Fc region, e.g., an effectorless or mostly effectorless Fc (e.g., human IgG2 or IgG4) or, alternatively, an Fc with enhanced binding to one or more activating Fc receptors (FcTRI, FcTRIIa or FcTRIIIa) so as to enhance $T_{reg}$ depletion in the tumor environment. Accordingly, in certain embodiments the anti-TIGIT, anti-PD-1, anti-PD-L1, anti-LAG-3, HCVRs and LCVRs described herein may be linked to an Fc comprising one or more modifications, typically to alter one or more functional properties of the antibody, such as serum half-life, complement fixation, Fc receptor binding, and/or antigen-dependent cellular cytotoxicity.

In one embodiment, the immunoglobulin scaffold for use in the present application includes a CH1-CH2-CH3 region having an amino acid sequence set forth in SEQ ID NOs: 155-157 and 205-215. In another embodiment, the immunoglobulin scaffold includes or substantially consists of an Fc receptor, such as one having the amino acid sequence set forth in any one of SEQ ID NOs: 195-202.

Furthermore, an antibody described herein may be chemically modified (e.g., one or more chemical moieties can be attached to the antibody) or it may be modified to alter its glycosylation, to alter one or more functional properties of the antibody. More specifically, in certain embodiments, the antibodies in the present application may include modifications in the Fc region in order to generate an Fc variant with (a) increased or decreased antibody-dependent cell-mediated cytotoxicity (ADCC), (b) increased or decreased complement mediated cytotoxicity (CDC), (c) increased or decreased affinity for C1q and/or (d) increased or decreased affinity for a Fc receptor relative to the parent Fc. Such Fc region variants will generally comprise at least one amino acid modification in the Fc region. Combining amino acid modifications is thought to be particularly desirable. For example, the variant Fc region may include two, three, four, five, etc. substitutions therein, e.g., of the specific Fc region positions identified herein.

For uses where effector function is to be avoided altogether, e.g., when antigen binding alone is sufficient to generate the desired therapeutic benefit, and effector function only leads to (or increases the risk of) undesired side effects, IgG4 antibodies may be used, or antibodies or fragments lacking the Fc region or a substantial portion thereof can be devised, or the Fc may be mutated to eliminate glycosylation altogether (e.g., N297A). Alternatively, a hybrid construct of human IgG2 (CH1 domain and hinge region) and human IgG4 (CH2 and CH3 domains) may be generated that is devoid of effector function, lacking the ability to bind FcTRs (like IgG2) and activate complement (like IgG4). When using an IgG4 constant domain, it is usually preferable to include the substitution S228P, which mimics the hinge sequence in IgG1 and thereby stabilizes IgG4 molecules, reducing Fab-arm exchange between the therapeutic antibody and endogenous IgG4 in the patient being treated.

In preferred embodiments, the the first and second targeting domains are presented in a humanized immunoglobulin scaffold. Additionally, the IgG scaffold may have a N297A or K447A amino acid substitution.

In certain embodiments, the anti-TIGIT, anti-PD-1, anti-PD-L1, anti-LAG-3, or fragments thereof may be modified to increase its biological half-life. Various approaches may be employed, including e.g., that increase the binding affinity of the Fc region for FcRn. In one embodiment, the antibody is altered within the CH1 or CL region to contain a salvage receptor binding epitope taken from two loops of a CH2 domain of an Fc region of an IgG, as described in U.S. Pat. Nos. 5,869,046 and 6,121,022. The numbering of residues in the Fc region is that of the EU index. Sequence variants disclosed herein are provided with reference to the residue number followed by the amino acid that is substituted in place of the naturally occurring amino acid, optionally preceded by the naturally occurring residue at that position. Where multiple amino acids may be present at a given position, e.g., if sequences differ between naturally occurring isotypes, or if multiple mutations may be substituted at the position, they are separated by slashes (e.g., "X/Y/Z").

Exemplary Fc variants that increase binding to FcRn and/or improve pharmacokinetic properties include substitutions at positions 259, 308, and 434, including for example 259I, 308F, 428L, 428M, 434S, 434H, 434F, 434Y, and 434M. Other variants that increase Fc binding to FcRn include: 250E, 250Q, 428L, 428F, 250Q/428L (Hinton et al., 2004, J. Biol. Chem. 279(8): 6213-6216, Hinton et al. 2006 Journal of Immunology 176:346-356), 256A, 272A, 305A, 307A, 311A, 312A, 378Q, 380A, 382A, 434A (Shields et al. (2001) J. Biol. Chem., 276(9):6591-6604), 252F, 252Y, 252W, 254T, 256Q, 256E, 256D, 433R, 434F, 434Y, 252Y/254T/256E, 433K/434F/436H (Dall'Acqua et al. (2002) J. Immunol., 169:5171-5180, Dall'Acqua et al. (2006) J. Biol. Chem., 281:23514-23524, and U.S. Pat. No. 8,367,805.

Modification of certain conserved residues in IgG Fc (I253, H310, Q311, H433, N434), such as the N434A variant (Yeung et al. (2009) J. Immunol. 182:7663), have been proposed as a way to increase FcRn affinity, thus increasing the half-life of the antibody in circulation (WO 98/023289). The combination Fc variant comprising M428L and N434S has been shown to increase FcRn binding and increase serum half-life up to five-fold (Zalevsky et al. (2010) Nat. Biotechnol. 28:157). The combination Fc variant comprising T307A, E380A and N434A modifications also extends half-life of IgG1 antibodies (Petkova et al. (2006) Int. Immunol. 18:1759). In addition, combination Fc variants comprising M252Y-M428L, M428L-N434H, M428L-N434F, M428L-N434Y, M428L-N434A, M428L-N434M, and M428L-N434S variants have also been shown to extend half-life (U.S. 2006/173170). Further, a combination Fc variant comprising M252Y, S254T and T256E was reported to increase half-life-nearly 4-fold.

Dall'Acqua et al. (2006) J. Biol. Chem. 281:23514.

The bispecific antitumor antagonists of the present application may be constructed with an IgG backbone. More specifically, any of the bispecific antagonists of the present application may be constructed with an IgG1 or IgG4 backbone. Use of an IgG1 backbone is preferable for cancer treatment where a target is present on antigen presenting cells that can mediate antibody-dependent cell-mediated cytotoxicity (ADCC). Use of an IgG4 backbone allows targeting of antigen where antigen binding alone is sufficient to generate the desired therapeutic benefits. IgG4-based antagonists preclude undesirable effector functions associated with e.g., IgG1 antibodies, including FcTR binding and complement activation.

Homodimers and Heterodimers

One of the challenges for efficiently producing bispecific antibody preparations concerns mispairing of heavy and light chains, when co-expressing chains of different binding specificities. Table 1 lists several amino acid substitution options for overcoming mispairing between heavy chains of different binding specificities, which "enforce" or preferentially promote correct association between desired heavy chains. Any approach to prevent or reduce mispairing between heavy chains may be used to make the bispecific antitumor antagonists according to the present disclosure.

The "knobs-into-hole" (KiH) approach relies on modifications of the interface between the two CH3 domains where most interactions occur. Typically, a bulky residue is introduced into the CH3 domain of one antibody heavy chain and acts similarly to a key. In the other heavy chain, a "hole" is formed that is able to accommodate this bulky residue, mimicking a lock. The resulting heterodimeric Fc-part can be further stabilized by artificial disulfide bridges.

An alternative approach is based on charged residues with ionic interactions or steric complementarity. This includes altering the charge polarity in the CH3 interface so that co-expression of electrostatically matched Fc domains support favorable attractive interactions and heterodimer formation while retaining the hydrophobic core, whereas unfavorable repulsive charge interactions suppress homodimerization. See Table 1. The amino acid numbering in Table 1 follows the Kabat numbering scheme and can be applied to heavy chain amino acid sequences of the antibodies described herein.

In some embodiments, an immunological scaffold may be substituted with another dimer structure containing, for example, leucine zipper (LZ) domains. A leucine zipper is a common three-dimensional structural motif in proteins, typically as part of a DNA-binding domain in various transcription factors. A single LZ typically contains 4-5 leucine residues at approximately 7-residue intervals, which forms an amphipathic alpha helix with a hydrophobic region running along one side. In a particular embodiment, a heterodimeric protein scaffold comprises a LZ from the c-jun transcription factor associated with a LZ from the c-fos transcription factor. Although c-jun is known to form jun-jun homodimers and c-fos does not form homodimers, the formation of jun-fos heterodimers is greatly favored over jun-jun homodimers.

A leucine zipper domain may be incorporated in place of CH2-CH3 sequences in the protein scaffold or it may be placed at the carboxy terminal end of the two heavy chains in the bispecific antitumor antagonist. In the case of the latter, a furin cleavage site may be introduced between the carboxy terminal end of CH3 and the amino terminal end of the leucine zipper. This can facilitate furin-mediated cleavage of the leucine zipper following the heterodimerization step when co-expressing the heavy and light chains of the bi-specific antitumor antagonist in an appropriate mammalian cell expression system (see Wranik et al., J. Biol. Chem., 287(5):43331-43339, 2012).

TABLE 1

| Type | HC1 | HC2 |
| --- | --- | --- |
| Knobs-into-holes | Y349C, T366S, L368A, Y407V | S354C, T366W |
| Ionic, electrostatic | S183E, E356K, E357K, D399K | S183K, K370E, K409D, K439E |
| Ionic, electrostatic | K392D, K409D | E356K, D399K |
| HA-TF substitutions | S364H, F405A | Y349T, T394F |
| HF-TA substitutions | S364H, T394F | Y349T, F405A |
| Leucine zipper heterodimer | human c-Jun leucine zipper | human c-fos leucine zipper |

The amino acid numbering in Table 1 follows the Kabat numbering scheme and can be applied to heavy chain amino acid sequences of the antibodies described herein. The mutations described in Table 1 may be applied to the sequence (published or otherwise) of any immunoglobulin IgG1 heavy chain, as well as other immunoglobulin classes, and subclasses (or isotypes) therein.

When co-expressing heavy and light chains of monospecific, bi-specific antibodies, a light chain of one binding specificity can also mispair with a heavy chain of a different binding specificity. Therefore, in certain embodiments, portions of the heavy chain, light chain or both may be modified relative to the "wild-type" antibody chains from which they are derived to prevent or reduce mispairing of both heavy chain constant regions to one another, as well mispairing of light chain constant regions to their heavy chain counterparts.

The light chain mispairing problem can be addressed in several ways. In some embodiments, sterically complementary mutations and/or disulfide bridges may be incorporated into the two VL/VH interfaces. In other embodiments, mutations can be incorporated based on ionic or electrostatic interactions. In some embodiments, light chain mispairing may be prevented or reduced by employing a first arm with an S183E mutation in the CH1 domain of the heavy chain and an S176K mutation in the CL domain of the light chain. A second arm may include an S183K mutation in the in the CH1 domain of the heavy chain and an S176E mutation in the CL domain of the light chain. In other embodiments, a "CrossMab" approach is employed, where one arm in the bispecific antitumor antagonist (e.g., Fab) is left untouched, but in the other arm containing the other binding specificity, one or more domains in the light chain are swapped with one or more domains in the heavy chain at the heavy chain:light chain interface.

Methods, immunoglobulin domain sequences, including specific mutations for preventing mispairing of heavy and light chains as disclosed above are further described in U.S. Patent Application Publication Nos. 2014/0243505, 2013/0022601.

Conjugates

In certain embodiments, the antitumor antagonists of the present application are chemically conjugated to one or more peptides and/or small molecule drugs. The peptides or small molecule drug can be the same or different. The peptides or small molecule drugs can be attached, for example to reduced SH groups and/or to carbohydrate side chains. Methods for making covalent or non-covalent conjugates of peptides or small molecule drugs with antibodies are known in the art and any such known method may be utilized.

In some embodiments the peptide or small molecule drug is attached to the hinge region of a reduced antibody component via disulfide bond formation. Alternatively, such agents can be attached using a heterobifunctional cross-linkers, such as N-succinyl 3-(2-pyridyldithio)propionate (SPDP). General techniques for such conjugation are well-known in the art. In some embodiments, the peptide or small molecule drug is conjugated via a carbohydrate moiety in the Fc region of the antibody. The carbohydrate group can be used to increase the loading of the same agent that is bound to a thiol group, or the carbohydrate moiety can be used to bind a different therapeutic or diagnostic agent. Methods for conjugating peptide inhibitors or small molecule drugs to antibodies via antibody carbohydrate moieties are well-known to those of skill in the art. For example, in one embodiment, the method involves reacting an antibody component having an oxidized carbohydrate portion with a carrier polymer that has at least one free amine function. This reaction results in an initial Schiff base (imine) linkage, which can be stabilized by reduction to a secondary amine to form the final conjugate. Exemplary methods for conjugating small molecule drugs and peptides to antibodies are described in U.S. Patent Application Publication No. 2014/0356385.

Preferably, the antitumor antagonists in the present disclosure retain certain desirable characteristics and pharmacokinetic properties of antibodies, including a desirable in vitro and in vivo stability (e.g., lone half-life and shelf-life stability), efficient delivery into desired target cells, increased affinity for binding partners, desirable antibody-dependent cell-mediated cytotoxicity and complement-dependent cytotoxicity, and reduced renal clearance or excretion. Accordingly, careful attention to size and need for particular constant region effector functions may be considered in the design of the antitumor antagonists.

The anti-TIGIT, anti-PD-1 and anti-PD-L1 inhibitors, including monospecific, bispecific antitumor antagonists therefrom, may range in size from 50 kD to 300 kD, from 50 kD to 250 kD, from 60 kD to 250 kD, from 80 kDa to 250 kD, from 100 kD to 250 kD, from 125 kD to 250 kD, from 150 kD to 250 kD, from 60 kD to 225 kD, from 75 kD to 225 kD, from 100 kD to 225 kD, from 125 kD to 225 kD, from 150 kD to 225 kD, from 60 kD to 200 kD, from 75 kD to 200 kD, from 100 kD to 125 kD to 200 kD, from 150 kD to 200 kD, from 60 kD to 150 kD, from 75 kD to 150 kD, from 100 kD to 150 kD, from 60 kD to 125 kD, from 75 kD to 125 kD, from 75 kD to 100 kD, or any range encompassed by any combination of whole numbers listed in the above cited ranges or any ranges specified by any combination of whole numbers between any of the above cited ranges.

Kits

The present application further provides a kit comprising any one or more of the checkpoint regulator antagonist or antitumor antagonist of the present application. In some embodiments, the kit further contains additional components, including syringes and needles for administration, as well as reagents, including secondary antibodies for detection, and additional human antibodies described herein for use in combination therapies therewith. A kit typically includes a label and/or instructions indicating the intended use of the contents of the kit. The label or instruction may include any writing, or recorded material supplied on or with the kit, or which otherwise accompanies the kit.

III. Methods of Using the Antitumor Antagonists

The antitumor antagonists of the present application have numerous in vitro and in vivo utilities including, for example, enhancement of immune responses and treatment of cancers, infectious diseases or autoimmune diseases.

In certain embodiments, the present application provides a method for treating: a cell proliferative disorder; a method of reducing or depleting regulatory T cells in a tumor; a method for treating a microbial infection; or a method for treating an immunological disorder, where the method comprises administering to a subject in need thereof an effective amount of an antitumor antagonist according to the present application.

In some embodiments, the antitumor antagonists of the present application are administered to cells in culture, in vitro or ex vivo, or to human subjects, e.g., in vivo, to enhance immunity in a variety of diseases. Accordingly, provided herein are methods of modifying an immune response in a subject comprising administering to the subject an antibody or antigen-binding fragment thereof as described herein such that the immune response in the subject is enhanced, stimulated or up-regulated. Preferred subjects include human patients in whom enhancement of an immune response would be desirable. The methods are particularly suitable for treating human patients having a disorder that can be treated by augmenting an immune response (e.g., the T-cell mediated immune response). The methods are particularly suitable for treatment of cancer or chronic infections in vivo. For example, the anti-TIGIT, anti-PD-1, anti-PD-L1 or anti-LAG-3 compositions may be administered together with an antigen of interest or the antigen may already be present in the subject to be treated (e.g., a tumor-bearing or virus-bearing subject) to enhance antigen-specific immunity. When anti-TIGIT antibodies are administered together with another agent, the two can be administered separately or simultaneously.

In some embodiments, the checkpoint regulator antagonist used in the above-described method is an anti-TIGIT, anti-PD-1, anti-PD-L1 antibody, anti-LAG-3 antibody, a fragment thereof, or combination thereof. In some embodiments, the checkpoint regulator antagonist is a monospecific or bispecific antibody.

In some embodiments, the checkpoint regulator antagonist or antitumor antagonist is in the form of an antibody or antibody fragment. In some embodiments, the antibodies described herein are human or humanized antibodies.

Also encompassed are methods for detecting and/or measuring the presence of human TIGIT, human PD-1, human PD-L1 or human LAG3 in a sample comprising contacting the sample, and a control sample, with a human monoclonal antibody thereof, or an antigen binding fragment thereof, which specifically binds to human TIGIT, human PD-1 or human PD-L1 under conditions that allow for formation of a complex between the antibody or fragment thereof and human TIGIT, human PD-1 or human PD-L1. The formation of a complex is then detected, wherein a difference in complex formation between the sample compared to the control sample is indicative the presence of human TIGIT antigen in the sample.

Given the ability of anti-TIGIT, anti-PD-1, anti-PD-L1 and anti-LAG-3 antibodies to block inhibition or co-inhibition of T cell responses, e.g., antigen-specific T cell responses, provided herein are in vitro and in vivo methods of using the antibodies described herein to stimulate, enhance or upregulate antigen-specific T cell responses, e.g., anti-tumor T cell responses. In certain embodiments, CD3 stimulation is also provided (e.g., by co-incubation with a cell expressing membrane CD3), which stimulation can be provided at the same time, before, or after treatment with an anti-TIGIT, anti-PD-1, anti-PD-L1 or anti-LAG-3 antibody. For example, the present application provides a method of enhancing an antigen-specific T cell response comprising contacting a T cell with an anti-TIGIT, anti-PD-1, anti-PD-L1 or anti-LAG-3 antibody described herein, and optionally with CD3, such that an antigen-specific T cell response is enhanced, e.g., by removal of a TIGIT, PD-1, PD-L1 or LAG-3 mediated inhibitory effect. Any suitable indicator of an antigen-specific T cell response can be used to measure the antigen-specific T cell response. Non-limiting examples of such suitable indicators include increased T cell proliferation in the presence of the antibody and/or increase cytokine production in the presence of the antibody. In a preferred embodiment, interleukin-2 and/or interferon-.gamma. production by the antigen-specific T cell is enhanced.

Further encompassed are methods for enhancing an immune response (e.g., an antigen-specific T cell response) in a subject comprising administering an anti-TIGIT antibody, an anti-PD-1 antibody, an anti-PD-L1 antibody, an anti-LAG-3 antibody, or a bi-specific antitumor antagonist described herein to the subject such that an immune response (e.g., an antigen-specific T cell response) in the subject is enhanced. In a preferred embodiment, the subject is a tumor-bearing subject and an immune response against the tumor is enhanced. A tumor may be a solid tumor or a liquid tumor, e.g., a hematological malignancy. In certain embodiments, a tumor is an immunogenic tumor. In other embodiments, a tumor is non-immunogenic. In certain embodiments, a tumor is PD-L1 positive. In other embodiments a tumor is PD-L1 negative. A subject may also be a virus-bearing subject in which an immune response against the virus is enhanced as a consequence of administering an anti-TIGIT antibody, anti-PD-1 antibody, anti-PD-L1 antibody, anti-LAG-3 antibody, monospecific antitumor antagonist or bispecific antitumor antagonist, as described herein.

In one embodiment, a method for inhibiting the growth of tumor cells in a subject comprises administering to the subject an anti-TIGIT antibody, anti-PD-1 antibody, anti-PD-L1 antibody, anti-LAG-3 antibody or bispecific antitumor antagonist described herein such that growth of the tumor is inhibited in the subject. Also provided are methods of treating chronic viral infection in a subject comprising administering to the subject an anti-TIGIT antibody, anti-PD-1 antibody, anti-PD-L1 antibody, anti-LAG-3 antibody or bispecific antitumor antagonist as described herein such that the chronic viral infection is treated in the subject.

Also encompassed herein are methods for depleting $T_{reg}$ cells from the tumor microenvironment of a subject with a tumor, e.g., cancerous tumor, comprising administering to the subject a therapeutically effective amount of an anti-TIGIT antibody, anti-PD-1 antibody, anti-PD-L1 antibody, anti-LAG-3 antibody, or bispecific antitumor antagonist described herein that comprises an Fc that stimulates depletion of $T_{reg}$ cells in the tumor microenvironment. An Fc may, e.g., be an Fc with effector function or enhanced effector function, such as binding or having enhanced binding to one or more activating Fc receptors.

In a preferred embodiment, $T_{reg}$ depletion occurs without significant depletion or inhibition of $T_{eff}$ in the tumor microenvironment, and without significant depletion or inhibition of Teff cells and $T_{reg}$ cells outside of the tumor microenvironment. In certain embodiments, the subject has higher levels of TIGIT on $T_{reg}$ cells than on $T_{eff}$ cells, e.g., in the tumor microenvironment. In certain embodiments, anti-TIGIT antibodies or antagonists may deplete $T_{regs}$ in tumors and/or $T_{regs}$ in tumor infiltrating lymphocytes (TILs). For example, in the CT26 tumor model, an anti-mouse TIGIT antibody formatted as a mouse IgG2a (which exhibits effector function) partially depleted both Treg and CD8$^+$ T cells, but did not deplete CD4$^+$ T cells. An effectorless counterpart anti-TIGIT antibody, formatted as a mouse IgG1 D265A, did not deplete T cells.

When considering whether or not to employ Fc effector function or an effectorless anti-TIGIT antibody, due consideration must be given to the tradeoff between depletion of $T_{regs}$, which may enhance anti-tumor immune response, and depletion of CD8$^+$ T cells, which would eliminate some of the cells needed to actually kill tumor cells. Although depletion of $T_{regs}$ might be expected to enhance anti-tumor activity, recent studies have demonstrated that ligation of TIGIT on TIGIT$^+$ $T_{regs}$ promotes $T_{reg}$ cell-mediated suppression of $T_{eff}$ cell proliferation (Joller et al. (2014) Immunity 40:569), suggesting that blocking of TIGIT signaling (e.g., using an antagonist anti-TIGIT antibody of the present invention) might also enhance anti-tumor activity. Accordingly, it may be most efficacious to use an antagonist anti-TIGIT antibody lacking effector function, which: i) blocks TIGIT signaling in $T_{regs}$ thus reducing their immunosuppressive activity; ii) activates anti-tumor CD8$^+$ T cells by blocking TIGIT's inhibitory effects, while at the same time avoiding their effector-function-mediated depletion; and iii) enhances DNAM-mediated activation by allowing DNAM to bind to PVR (CD155, the TIGIT ligand) that would otherwise have been bound by TIGIT (and by reducing direct TIGIT-DNAM interactions) (Johnston et al. (2014) Cancer Cell 26:923). The same is applicable to use of anti-PD-1 antibodies, anti-PD-L1 antibodies or bispecific antitumor antagonists.

In certain embodiments, an anti-TIGIT antibody, anti-PD-1 antibody, anti-PD-L1 antibody, anti-LAG-3 antibody or bispecific antitumor antagonist described herein is given to a subject as an adjunctive therapy. Treatment of cancer patient with an anti-TIGIT antibody, anti-PD-1 antibody, anti-PD-L1 antibody, anti-LAG-3 antibody or bispecific antitumor antagonist according to the present application may lead to a long-term durable response relative to the current standard of care; long term survival of at least 1, 2, 3, 4, 5, 10 or more years, recurrence free survival of at least 1, 2, 3, 4, 5, or 10 or more years. In certain embodiments, treatment of a cancer patient with an anti-TIGIT antibody, anti-PD-1 antibody, anti-PD-L1 antibody, anti-LAG-3 antibody or bispecific antitumor antagonist prevents recurrence of cancer or delays recurrence of cancer by, e.g., 1, 2, 3, 4, 5, or 10 or more years. An anti-TIGIT, anti-PD-1, anti-PD-L1 and/or anti-LAG-3 treatment can be used as a primary or secondary line of treatment.

In certain preferred embodiments, the subject has a cell proliferative disease or cancer. Blocking of PVR/Nectin-2 signaling through TIGIT by anti-TIGIT antibodies can enhance the immune response to cancerous cells in the patient. Similarly, blocking of Provided herein are methods for treating a subject having cancer, comprising administering to the subject an anti-TIGIT, anti-PD-1, anti-PD-L1, anti-LAG-3 or bispecific antitumor antagonist thereof as described herein, such that the subject is treated, e.g., such that growth of cancerous tumors is inhibited or reduced and/or that the tumors regress. An anti-TIGIT anti-PD-1, anti-PD-L1, anti-LAG-3 or bispecific antitumor antagonist thereof as described herein can be used alone to inhibit the growth of cancerous tumors. Alternatively, any of these antitumor antagonists can be used in conjunction with another agent, e.g., other anti-cancer targets, immunogenic agents, standard cancer treatments, or other antibodies, as described below.

Accordingly, provided herein are methods of treating cancer, e.g., by inhibiting growth of tumor cells, in a subject, comprising administering to the subject a therapeutically effective amount of an anti-TIGIT, anti-PD-1, anti-PD-L1 or anti-LAG-3 antagonist, or a bispecific antitumor antagonist, as described herein. Preferably, the antibody is a human anti-TIGIT, anti-PD-1, anti-PD-L1 or anti-LAG-3 antibody comprising the anti-TIGIT, anti-PD-1, anti-PD-L1 or anti-LAG-3 HCVRs and LCVR described herein, or it may be a chimeric, humanized, or non-human anti-hu TIGIT, anti-hu PD-1, anti-PD-L1 antibody or anti-LAG-3 antibody, e.g., a chimeric, humanized, or non-human anti-TIGIT, anti-PD-1, anti-PD-L1 or anti-LAG-3 antibody that competes for binding with, or binds to the same epitope as, at least one of the anti-TIGIT, anti-PD-1, anti-PD-L1 or anti-LAG-3 antibodies described herein.

Cancers whose growth may be inhibited using the antibodies of the invention include cancers typically responsive to immunotherapy. Non-limiting examples of cancers for treatment include squamous cell carcinoma, small-cell lung cancer, non-small cell lung cancer, squamous non-small cell lung cancer (NSCLC), non NSCLC, glioma, gastrointestinal cancer, renal cancer (e.g. clear cell carcinoma), ovarian cancer, liver cancer, colorectal cancer, endometrial cancer, kidney cancer (e.g., renal cell carcinoma (RCC)), prostate cancer (e.g. hormone refractory prostate adenocarcinoma), thyroid cancer, neuroblastoma, pancreatic cancer, glioblastoma (glioblastoma multiforme), cervical cancer, stomach cancer, bladder cancer, hepatoma, breast cancer, colon carcinoma, and head and neck cancer (or carcinoma), gastric cancer, germ cell tumor, pediatric sarcoma, sinonasal natural killer, melanoma (e.g., metastatic malignant melanoma, such as cutaneous or intraocular malignant melanoma), bone cancer, skin cancer, uterine cancer, cancer of the anal region, testicular cancer, carcinoma of the fallopian tubes, carcinoma of the endometrium, carcinoma of the cervix, carcinoma of the vulva, carcinoma of the vagina, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, cancer of the ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally-induced cancers including those induced by asbestos, virus-related cancers (e.g., human papilloma virus (HPV)-related tumor), and hematologic malignancies derived from either of the two major blood cell lineages, i.e., the myeloid cell line (which produces granulocytes, erythrocytes, thrombocytes, macrophages and mast cells) or lymphoid cell line (which produces B, T, NK and plasma cells), such as all types of leukemias, lymphomas, and myelomas, e.g., acute, chronic, lymphocytic and/or myelogenous leukemias, such as acute leukemia (ALL), acute myelogenous leukemia (AML), chronic lymphocytic leukemia (CLL), and chronic myelogenous leukemia (CML), undifferentiated AML (MO), myeloblastic leukemia (M1), myeloblastic leukemia (M2; with cell maturation), promyelocytic leukemia (M3 or M3 variant [M3V]), myelomonocytic leukemia (M4 or M4 variant with eosinophilia [M4E]), monocytic leukemia (M5), erythroleukemia (M6), megakaryoblastic leukemia (M7), isolated granulocytic sarcoma, and chloroma; lymphomas, such as Hodgkin's lymphoma (HL), non-Hodgkin's lymphoma (NEIL), B-cell lymphomas, T-cell lymphomas, lymphoplasmacytoid lymphoma, monocytoid B-cell lymphoma, mucosa-associated lymphoid tissue (MALT) lymphoma, anaplastic (e.g., Ki 1+) large-cell lymphoma, adult T-cell lymphoma/leukemia, mantle cell lymphoma, angio immunoblastic T-cell lymphoma, angiocentric lymphoma, intestinal T-cell lymphoma, primary mediastinal B-cell lymphoma, precursor T-lymphoblastic lymphoma, T-lymphoblastic; and lymphoma/leukemia (T-Lbly/T-ALL), peripheral T-cell lymphoma, lymphoblastic lymphoma, post-transplantation lymphoproliferative disorder, true histiocytic lymphoma, primary central nervous system lymphoma, primary effusion lymphoma, lymphoblastic lymphoma (LBL), hematopoietic tumors of lymphoid lineage, acute lymphoblastic leukemia, diffuse large B-cell lymphoma, Burkitt's lymphoma, follicular lymphoma, diffuse histiocytic lymphoma (DHL), immunoblastic large cell lymphoma, precursor B-lymphoblastic lymphoma, cutaneous T-cell lymphoma (CTLC) (also called mycosis fungoides or Sezary syndrome), and lymphoplasmacytoid lymphoma (LPL) with Waldenstrom's macroglobulinemia; myelomas, such as IgG myeloma, light chain myeloma, nonsecretory myeloma, smoldering myeloma (also called indolent myeloma), solitary plasmocytoma, and multiple myelomas, chronic lymphocytic leukemia (CLL), hairy cell lymphoma; hematopoietic tumors of myeloid lineage, tumors of mesenchymal origin, including fibrosarcoma and rhabdomyoscarcoma; seminoma, teratocarcinoma, tumors of the central and peripheral nervous, including astrocytoma, schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma, hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; a/d T-NHL hepatosplenic lymphoma; peripheral/post-thymic T cell lymphoma (pleomorphic and immunoblastic subtypes); angiocentric (nasal) T-cell lymphoma; cancer of the head or neck, renal cancer, rectal cancer, cancer of the thyroid gland; acute myeloid lymphoma, as well as any combinations of said cancers. The methods described herein may also be used for treatment of metastatic cancers, refractory cancers (e.g., cancers refractory to previous immunotherapy, e.g., with a blocking CTLA-4 or PD-1 antibody), and recurrent cancers.

An anti-TIGIT, anti-PD-1 antibody, anti-PD-L1 antibody, anti-LAG-3 antibody or bispecific antitumor antagonist can be administered alone, in combination with another antitumor antagonist, or concurrently with another antitumor antagonist. An anti-TIGIT, anti-PD-1 antibody, anti-LAG-3 antibody or bispecific antitumor antagonist can also be administered in combination, or concurrently with, an immunogenic agent, such as cancerous cells, tumor vaccines, purified tumor antigens (including recombinant proteins, peptides, and carbohydrate molecules), cells transfected with genes encoding immune stimulating cytokines, in a cancer vaccine strategy (He et al. (2004) J. Immunol. 173:4919-28), or an oncolytic virus.

Many experimental strategies for vaccination against tumors have been devised. In one of these strategies, a vaccine is prepared using autologous or allogeneic tumor cells. Some of these cellular vaccines have been shown to be most effective when the tumor cells are transduced to express GM-CSF. GM-CSF has been shown to be a potent activator of antigen presentation for tumor vaccination (Dranoff et al. (1993) Proc. Natl. Acad. Sci. U.S.A. 90: 3539-43). Cancer vaccines have been shown to enhance effector T-cell infiltration into the tumors in preclinical models. The major types of cancer vaccines include peptide vaccines, vector-based antigen specific vaccines, whole-cell vaccines, and dendritic cell vaccines. All vaccine-based therapies are designed to deliver either single or multiple antigenic epitopes or antigens from the whole cells to the patients and induce tumor-specific effector T cells. Thus, a vaccine-based therapy may be the most efficient way to induce T-cell infiltration into the tumor.

The study of gene expression and large scale gene expression patterns in various tumors has led to the definition of so called tumor specific antigens (Rosenberg, S A (1999) Immunity 10: 281-7). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host.

TIGIT, PD-1, PD-L1 and/or LAG-3 inhibition may be used in conjunction with a collection of recombinant proteins and/or peptides expressed in a tumor in order to generate an immune response to these proteins. Such proteins may be viewed by the immune system as self-antigens and are therefore tolerant to them. The tumor antigen can include the protein telomerase, which is required for the synthesis of telomeres of chromosomes and which is expressed in more than 85% of human cancers and in only a limited number of somatic tissues (Kim et al. (1994) Science 266: 2011-2013). Tumor antigens can also be "neo-antigens" expressed in cancer cells because of somatic mutations that alter protein sequence or create fusion proteins between two unrelated sequences (i.e., bcr-abl in the Philadelphia chromosome), or idiotype from B cell tumors.

Non-limiting examples of tumor vaccines include sipuleucel-T (Provenge®), an FDA-approved tumor vaccine for metastatic prostate cancer; tumor cells transfected to express the cytokine granulocyte macrophage colony-stimulating factor (GM-CSF), such as the whole cell GM-CSF-secreting irradiated, allogeneic pancreatic cancer vaccine (GVAX; Johns Hopkins); a multi-peptide vaccine consisting of immunogenic peptides derived from breast cancer antigens, neu, legumain, and p-catenin, which prolonged the vaccine-induced progression-free survival of breast tumor-bearing mice when administered in combination with anti-PD-1 antibody (Karyampudi L. et al. (2014) Cancer Res 74:2974-2985); peptides of melanoma antigens, such as peptides of gp100, MAGE antigens, Trp-2, MARTI and/or tyrosinase, or. Other tumor vaccines include proteins from viruses implicated in human cancers such as human papilloma viruses (HPV)(e.g., Gardasil®, Gardasil 9@, and Cervarix®; hepatitis B virus (e.g., Engerix-B and Recombivax HB); hepatitis C virus (HCV), Kaposi's sarcoma associated herpes sarcoma virus (KSHV). Another form of tumor specific antigen that can be used in conjunction with TIGIT inhibition is purified heat shock proteins (HSP) isolated from the tumor tissue itself. These heat shock proteins contain fragments of proteins from the tumor cells and these HSPs are highly efficient at delivery to antigen presenting cells for eliciting tumor immunity. Talimogene laherparepvec (T-VEC, or Imlygic®) is an FDA-approved oncolytic virus for the treatment of some patients with metastatic melanoma that cannot be surgically removed.

Dendritic cells (DC) are potent antigen presenting cells that can be used to prime antigen-specific responses. DC's can be produced ex vivo and loaded with various protein and peptide antigens, as well as tumor cell extracts (Nestle et al. (1998) Nature Medicine 4: 328-332). DCs can also be transduced by genetic means to express these tumor antigens as well. DCs have also been fused directly to tumor cells for the purposes of immunization (Kugler et al. (2000) Nature Medicine 6:332-336). As a method of vaccination, DC immunization may be effectively combined with TIGIT blocking to activate (unleash) more potent anti-tumor responses.

TIGIT, PD-1, PD-L1 and/or LAG-3 inhibition can also be combined with standard cancer treatments (e.g., surgery, radiation, and chemotherapy). In particular, TIGIT, PD-1, PD-L1 and/or LAG-3 inhibition can be effectively combined with chemotherapeutic regimes. In these instances, it may be possible to reduce the dose of chemotherapeutic reagent administered (Mokyr et al. (1998) Cancer Research 58: 5301-5304). An example of such a combination is an anti-tumor antagonist in combination with decarbazine for the treatment of melanoma. Another example of such a combination is a checkpoint regulator antagonist or antitumor antagonist in combination with interleukin-2 (IL-2) for the treatment of melanoma. For example, the scientific rationale behind the combined use of TIGIT, PD-1, PD-L1 and/or LAG-3 inhibition and chemotherapy to promote cell death is a consequence of the cytotoxic action of most chemotherapeutic compounds, should result in increased levels of tumor antigen in the antigen presentation pathway. Other combination therapies that may result in synergy with TIGIT, PD-1, PD-L1 and/or LAG-3 inhibition through cell death are radiation, surgery, and hormone deprivation. Each of these protocols creates a source of tumor antigen in the host. Angiogenesis inhibitors can also be combined with TIGIT, PD-1, PD-L1 and/or LAG-3 inhibition. Inhibition of angiogenesis leads to tumor cell death, which may feed tumor antigen into host antigen presentation pathways.

The anti-TIGIT antibodies, anti-PD-1 antibodies, anti-PD-L1 antibodies, anti-LAG-3 antibodies, and bispecific antitumor antagonists described herein may also be used in combination with bispecific antibodies that target Fcα or Fcγ receptor-expressing effectors cells to tumor cells (see, e.g., U.S. Pat. Nos. 5,922,845 and 5,837,243). Bispecific antibodies can be used to target two separate antigens. For example anti-Fc receptor/antitumor antigen (e.g., Her-2/neu) bispecific antibodies have been used to target macrophages to sites of tumor. This targeting may more effectively activate tumor specific responses. The T cell arm of these responses would be augmented by the inhibition of TIGIT, PD-1, PD-L1 and/or LAG-3. Alternatively, antigen may be delivered directly to DCs by the use of bispecific antibodies that bind to tumor antigen and a dendritic cell specific cell surface marker.

Tumors evade host immune surveillance by a large variety of mechanisms. Many of these mechanisms may be overcome by the inactivation of immunosuppressive proteins expressed by the tumors. These include among others TGF-β, IL-10, and Fas ligand. Antibodies to each of these entities can be used in combination with the antitumor antagonists described herein to counteract the effects of the immunosuppressive agent and favor tumor immune responses by the host.

Other antibodies that activate host immune responsiveness can be used in combination with the antitumor antagonists described herein. These include molecules on the surface of dendritic cells that activate DC function and antigen presentation. Anti-CD40 antibodies are able to substitute effectively for T cell helper activity (Ridge et al. (1998) Nature 393: 474-478) and can be used in conjunction with anti-TIGIT antibodies. Activating antibodies to T cell costimulatory molecules, such as OX-40 (Weinberg et al. (2000) Immunol 164: 2160-2169), CD137/4-1BB (Melero et al. (1997) Nature Medicine 3: 682-685 (1997), and ICOS (Hutloff et al. (1999) Nature 397: 262-266) may also provide for increased levels of T cell activation. In addition, inhibitors of other immune checkpoint regulators may also be used in conjunction with other antitumor antagonists described herein, as further described below.

Bone marrow transplantation is currently being used to treat a variety of tumors of hematopoietic origin. While graft versus host disease is a consequence of this treatment, TIGIT inhibition may be used to increase the effectiveness of the donor engrafted tumor specific T cells by reducing graft vs. tumor responses.

Ex vivo activation and expansion of antigen specific T cells and adoptive transfer of these cells into recipients in order to stimulate antigen-specific T cells against cancers or viral infections in the presence of anti-TIGIT antibodies can increase the frequency and activity of the adoptively transferred T cells.

There are also several experimental treatment protocols that involve ex vivo activation and expansion of antigen specific T cells and adoptive transfer of these cells into recipients in order to stimulate antigen-specific T cells against tumor (Greenberg & Riddell (1999) Science 285: 546-51). These methods can also be used to activate T cell responses to infectious agents such as CMV. Ex vivo activation in the presence of anti-TIGIT antibodies can increase the frequency and activity of the adoptively transferred T cells.

In certain embodiments, an antitumor antagonist described herein may be administered to a subject with an infectious disease, especially chronic infections. In this case, similar to its application to cancer, antibody-mediated TIGIT, PD-1, PD-L1 and/or LAG-3 inhibition can be used alone, or as an adjuvant, in combination with vaccines, to enhance immune responsiveness to pathogens, toxins, and self-antigens. Exemplary pathogens for which this therapeutic approach can be applied include, but are not limited to, HIV, Hepatitis (A, B, & C), Influenza, Herpes, Giardia, Malaria, *Leishmania, Staphylococcus aureus*, and *Pseudomonas aeruginosa*. TIGIT, PD-1, PD-L1 and/or LAG-3 inhibition is particularly useful against established infections by agents such as HIV that present novel or altered antigens over the course of the infections. Administration of the anti-TIGIT antibodies, anti-PD-1 antibodies, anti-PD-L1 antibodies or bispecific antitumor antagonists can allow for recognition of these antigens as foreign so as to provoke an appropriate T cell response.

Other pathogenic viruses causing infections treatable by the methods described herein include HIV, hepatitis (A, B, or C), herpesvirus infections (e.g., VZV, HSV-1, HAV-6, HSV-II, and CMV, Epstein Barr virus), and infections caused by an adenovirus, influenza virus, flavivirus, echoviruses, rhinoviruses, coxsackie viruses, coronaviruses, respiratory syncytial viruses, mumps viruses, rotavirus, measles virus, rubella virus, parvovirus, vaccinia virus, HTLV virus, dengue virus, papillomavirus, molluscum virus, poliovirus, rabies virus, JC virus, arboviral encephalitis virus, or combination thereof.

Exemplary pathogenic bacteria or diseases caused therefrom which may be treatable by the methods described herein include *Chlamydia, Rickettsia*, Mycobacteria, Staphylococci, Streptococci, Pneumonococci, Meningococci and Gonococci, *Klebsiella, Proteus, Serratia, Pseudomonas, Legionella, Diphtheria, Salmonella*, Bacilli, Cholera, Leptospirosis tetanus, botulism, anthrax, plague, and Lyme disease.

Exemplary pathogenic fungi causing infections treatable by the methods described herein include *Candida* (e.g., *albicans, krusei, glabrata, tropicalis*, etc.), *Cryptococcus neoformans, Aspergillus* (e.g., *fumigatus, niger*, etc.), Mucorales (e.g., *mucor, absidia, rhizopus*), *Sporothrix schenkii, Blastomyces dermatitidis, Paracoccidioides brasiliensis, Coccidioides immitis* and *Histoplasma capsulatum*.

Exemplary pathogenic parasites causing infections treatable by the methods described herein include *Entamoeba histolytica, Balantidium coli, Naegleria fowleri, Acanthamoeba* sp., *Giardia Zambia, Cryptosporidium* sp., *Pneumocystis carinii, Plasmodium vivax, Babesia microti, Trypanosoma brucei, Trypanosoma cruzi, Leishmania donovani, Toxoplasma gondii, Nippostrongylus brasiliensis*.

In all of the above methods, TIGIT, PD-1, PD-L1 and/or LAG-3 inhibition can be combined with other forms of immunotherapy, such as cytokine treatment (e.g., interferons, GM-CSF, G-CSF, IL-2), or bispecific antibody therapy using two different binding specificities to provide enhanced presentation of tumor antigens.

Anti-TIGIT antibodies, anti-PD-1 antibodies, anti-PD-L1 antibodies, anti-LAG-3 antibodies and bispecific antitumor antagonists described herein can be used to enhance antigen-specific immune responses by co-administration of one or more of any of these antibodies with an antigen of interest (e.g., a vaccine). Accordingly, provided herein are methods of enhancing an immune response to an antigen in a subject, comprising administering to the subject: (i) the antigen; and (ii) an anti-TIGIT antibody, anti-PD-1 antibody, anti-PD-L1 antibody, anti-LAG-3 antibody or bispecific antitumor antagonist, or combination thereof, such that an immune response to the antigen in the subject is enhanced. The antigen can be, for example, a tumor antigen, a viral antigen, a bacterial antigen or an antigen from a pathogen. Non-limiting examples of such antigens include those discussed in the sections above, such as the tumor antigens (or tumor vaccines) discussed above, or antigens from the viruses, bacteria or other pathogens described above.

In certain embodiments, a peptide or fusion protein comprising the epitope to which an anti-TIGIT antibody, anti-PD-1 antibody, anti-PD-L1 antibody, LAG-3 antibody or bispecific antitumor antagonist binds may be used as a vaccine instead of, or in addition to, the antitumor antagonist(s).

Suitable routes of administering the antibody compositions (e.g., human monoclonal antibodies, multi-specific antibodies or antagonists and immunoconjugates) described herein in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

Combination Therapies

In another aspect, the present application provides combination therapies for enhancing an antigen-specific T cell response in a subject. In one embodiment, the method includes contacting a T cell with an anti-TIGIT antibody, anti-PD-1 antibody, anti-PD-L1 antibody, anti-LAG-3 antibody, antibody fragment thereof or bispecific antitumor antagonist in combination with a second antibody, antibody fragment, antagonist or drug such that an antigen-specific T cell response or apoptotic pathway is enhanced. For example, in some embodiments, the first antibody or antibody fragment specifically binds TIGIT and the second antibody or antibody fragment specifically binds to PD-1, PD-L1 or LAG-3.

In a related aspect, a method of reducing or depleting regulatory T cells in a tumor of a subject in need thereof includes administering an effective amount of an antibody or antibody fragment in combination with a second antibody, antibody fragment, antagonist or drug such that the number of regulatory T cells in the subject is reduced.

In some embodiments, the subject has a cell proliferative disease or cancer as described herein.

In other embodiments, the subject has a chronic viral infection, inflammatory disease or autoimmune disease as described herein.

The provision of two distinct signals to T-cells is a widely accepted model for lymphocyte activation of resting T lymphocytes by antigen-presenting cells (APCs). This model further provides for the discrimination of self from non-self and immune tolerance. The primary signal, or antigen specific signal, is transduced through the T-cell receptor (TCR) following recognition of foreign antigen peptide presented in the context of the major histocompatibility-complex (MHC). The second or co-stimulatory signal is delivered to T-cells by co-stimulatory molecules expressed on antigen-presenting cells (APCs). This induces T-cells to promote clonal expansion, cytokine secretion and effector function. In the absence of co-stimulation, T-cells can become refractory to antigen stimulation, which results in a tolerogenic response to either foreign or endogenous antigens.

In the two-signal model, T-cells receive both positive co-stimulatory and negative co-inhibitory signals. The regulation of such positive and negative signals is critical to maximize the host's protective immune responses, while maintaining immune tolerance and preventing autoimmunity. Negative signals seem necessary for induction of T-cell tolerance, while positive signals promote T-cell activation. Both co-stimulatory and co-inhibitory signals are provided to antigen-exposed T cells, and the interplay between co-stimulatory and co-inhibitory signals is essential to controlling the magnitude of an immune response. Further, the signals provided to the T cells change as an infection or immune provocation is cleared, worsens, or persists, and these changes powerfully affect the responding T cells and re-shape the immune response.

The mechanism of co-stimulation is of therapeutic interest because the manipulation of co-stimulatory signals has shown to provide a means to either enhance or terminate cell-based immune response. Recently, it has been discovered that T cell dysfunction or anergy can occur concurrently with an induced and sustained expression of immune checkpoint regulators, such as programmed death 1 polypeptide (PD-1) and its ligands, PD-L1 and PD-L2. PD-L1 is overexpressed in many cancers and is often associated with poor prognosis (Thompson R H et al., Cancer Res 2006, 66(7): 3381). Further, the majority of tumor infiltrating T lymphocytes predominantly express PD-1, in contrast to T lymphocytes in normal tissues and peripheral blood T lymphocytes indicating that up-regulation of PD-1 on tumor-reactive T cells can contribute to impaired antitumor immune responses (Blood 2009 114(8):1537). This may be due to exploitation of PD-L1 signaling mediated by PD-L1 expressing tumor cells interacting with PD-1 expressing T cells to result in attenuation of T cell activation and evasion of immune surveillance. Inhibition of the PD-L1/PD-1 interaction provides a means to enhance T cell immunity, including CD8+ T cell-mediated killing of cancer cells and tumors. Similar enhancements to T cell immunity have been observed by inhibiting the binding of PD-L1 to the binding partner B7-1. Consequently, therapeutic targeting of PD-1 and other immune checkpoint regulators are an area of intense interest.

Combining inhibition of TIGIT, PD-1, PD-L1 and/or LAG-3 signaling with other signaling pathways deregulated in tumor cells can provide a means for enhance treatment efficacy. In recent years, a number of immune checkpoint regulators in the form of receptors and their ligands have been identified. One important family of membrane-bound ligands that bind to co-stimulatory or co-inhibitory receptors is the B7 family, which includes CTLA-4 and its ligands, B7-1 and B7-2; PD-1 and its ligands, PD-L1 (B7-H1) and PD-L2 (B7-DC); B7-H2 (ICOS-L), B7-H3, B7-H4, B7-H5 (VISTA), and B7-H6. Additional immune checkpoint antagonists include, but are not limited to TIM-3 and its ligand, Galectin-9; LAG-3 and its ligands, including liver sinusoidal endothelial cell lectin (LSECtin) and Galectin-3; CD122 and its CD122R ligand; CD70, B7H3, B and T lymphocyte attenuator (BTLA), and VISTA (Le Mercier et al. (2015) Front. Immunol., (6), Article 418). In addition, a number of checkpoint regulator antagonists have been identified and tested in various clinical and pre-clinical models and/or approved by the FDA (Kyi et al., FEBS Letters, 588:368-376 (2014). The concept of inhibitory receptor blockade, also known as immune checkpoint blockade, has been validated by virtue of e.g., the FDA approval of the PD-1 inhibitors, nivolumab and pembrolizumab, as well as the anti-CTLA-4 antibody, ipilimumab for metastatic melanoma.

An immune checkpoint antagonist modulates or interferes with the activity of the immune checkpoint regulator so that, as a result of the binding to the checkpoint regulator or its ligand, signaling through the checkpoint regulator receptor is blocked or inhibited. By inhibiting this signaling, immune-suppression can be reversed so that T cell immunity against cancer cells can be re-established or enhanced. In contrast, an immune checkpoint agonist (of e.g., a costimulatory molecule) stimulates the activity of an immune checkpoint regulator so that, as a result of the binding to the checkpoint regulator or its ligand, signaling through the checkpoint regulator receptor is stimulated. By stimulating this signaling, T cell immunity against cancer cells can be re-established or enhanced.

Accordingly, in one embodiment, a method for stimulating an immune response in a subject comprises administering to the subject an anti-TIGIT antibody, anti-PD-1 antibody, anti-PD-L1 antibody, anti-LAG-3 antibody, antibody fragment(s) thereof (e.g., anti-TIGIT HCVR and/LCVRs) or bispecific antitumor antagonist described herein in combination with another immune checkpoint regulator described herein above, such that an immune response is stimulated in the subject, for example to inhibit tumor growth or to stimulate an anti-viral response.

In one embodiment, an anti-TIGIT antibody, anti-PD-1 antibody, anti-PD-L1 antibody, anti-LAG-3 antibody, antibody fragment(s) thereof, or bispecific antitumor antagonist, according to the present application is administered in combination with another immune checkpoint regulator, either as separate antibodies or in multi-specific antibody comprising binding specificities to multiple products. Generally, an anti-TIGIT antibody, anti-PD-1 antibody, anti-PD-L1 antibody, anti-LAG-3 antibody, or bispecific antitumor antagonist, described herein can be combined to stimulate an immune response with (i) an antagonist of the IgSF family protein, B7 family or TNF family that inhibit T cell activation, or antagonist of a cytokine that inhibits T cell activation (e.g., IL-6, IL-10, TGF-β, VEGF, or other immunosuppressive cytokines) and/or (ii) an agonist of a stimulatory receptors of the IgSF family, B7 family or TNF family or of cytokines to stimulate T cell activation, for stimulating an immune response.

In one embodiment, the subject is administered an anti-TIGIT antibody or HCVR and/or LCVR fragments thereof in combination with an anti-PD-1 antibody or PD-1 antagonist. In another embodiment, the subject is administered is administered an anti-TIGIT antibody or HCVR and/or LCVR fragments thereof in combination with an anti-PD-L1 antibody or PD-L1 antagonist. In another embodiment, the subject is administered an anti-TIGIT antibody or HCVR and/or LCVR fragments thereof in combination with an anti-CTLA-4 antibody or CTLA-4 antagonist.

In certain embodiments, only subjects with a cancer exhibiting high expression of a ligand for an immune checkpoint regulator are selected for combination treatment with the anti-TIGIT, anti-PD-1, anti-PD-L1 and/or anti-LAG-3 antibody, fragment thereof, or any of the bispecific antagonists of the present application. By way of example, in one embodiment, a subject with a cancer exhibiting high expression of PVR (CD155) and/or Nectin-2 (CD112) and/or low expression PD-L1 may be selected for monotherapy with anti-TIGIT antibodies, fragments thereof, or TIGIT antagonists of the present application, or combination therapy with a PD-1 antagonist or other immune checkpoint regulator.

The anti-TIGIT antibody, anti-PD-1 antibody, anti-PD-L1 antibody may be administered separately from the second antibody, antibody fragment or antagonist, or a multispecific antibody or antagonist may be administered comprising at least one binding specificity for TIGIT and a second binding specificity for the other targeted product. Further, the anti-TIGIT, anti-PD-1 antibody, anti-PD-L1 antibody, anti-LAG-3 antibody or bi-specific antagonist in accordance with the present application may be co-administered with one or more additional agents, e.g., antibodies, antagonists, or drugs in amount(s) effective in stimulating an immune response and/or apoptosis so as to further enhance, stimulate or upregulate an immune response and/or apoptosis in a subject.

In some embodiments, the anti-TIGIT, anti-PD-1, anti-PD-L1 or anti-LAG-3 antibody or fragment(s) thereof is administered subsequent to treatment with a different antitumor antagonist. For example, in one embodiment, anti-TIGIT, anti-PD-1, anti-PD-L1 or anti-LAG-3 antibodies may be administered only after treatment with a PD-1/PD-L1 antagonist has failed, has led to incomplete therapeutic response, or there has been recurrence of the tumor or relapse (or "PD-1 failure"). In some embodiments, cancers exhibiting such failures may be screened for expression of e.g., PVR and/or Nectin-2 and only those having high level expression are treated with an anti-TIGIT, anti-PD-1, anti-PD-L1 or anti-LAG-3 antibody, fragment or antagonist of the present application.

In one embodiment, the anti-TIGIT, anti-PD-1, anti-PD-L1 or anti-LAG-3 antibody or fragment(s) thereof are administered in combination with a PD-1, PD-L1, PD-L2, TIGIT, or LAG-3 antagonist.

Other anti-PD-1 antibodies include, but are not limited to, nivolumab (BMS-936558, MDX-1106, OPDIVO™), a humanized immunoglobulin G4 (IgG4) mAb (Bristol-Myers Squibb); pembrolizumab (MK-3475, lambrolizumab, KEYTRUDA™)(Merck); pidilizumab (CT-011)(Medivation); and AMP-224 (Merck). Anti-PD-1 antibodies are commercially available, for example from ABCAM (AB137132), BIOLEGEND™ (EH12.2H7, RMP1-14) and AFFYMETRIX EBIOSCIENCE (J105, J116, MIH4).

Other anti-PD-L1 antibodies include atezolizumab (MPDL3280A, RG7446), a fully human IgG4 mAb Genentech/Roche); BMS-936559 (MDX-1105), a fully humanized IgG4 mAb (Bristol-Myers Squibb); MEDI4736, a humanized IgG antibody (Medimmune/AstraZeneca); and MSB0010718C, a fully human IgG4 monoclonal antibody (Merck, EMD Serono).

Exemplary anti-CTLA-4 antibodies for use in accordance with the present methods include ipilimumab, trevilizumab and tremelimumab.

In certain embodiments, the antitumor antagonist is a dominant negative protein of the immune checkpoint regulator. In particular embodiments, the dominant negative protein comprises an extracellular domain derived from a member selected from the group consisting of PD-L1, PD-L2, PD-1, B7-1, B7-2, B7H3, CTLA-4, LAG-3, TIM-3, TIGIT, BTLA, VISTA, CD70, and combinations thereof. In certain particular embodiments, these extracellular domains are fused to an immunoglobulin constant region or Fc receptor in the presently described antibodies. Such mutants can bind to the endogenous receptor so as to form a complex that is deficient in signaling. In certain embodiments, the extracellular domain is fused to an immunoglobulin constant region or Fc fragment or to a monomer in the oligomeric protein complex.

In certain embodiments, a dominant negative PD-L1 antagonist comprises an extracellular domain of PD-1. An exemplary dominant negative protein is AMP-224 (co-developed by Glaxo Smith Kline and Amplimmune), a recombinant fusion protein comprising the extracellular domain of PD-L2 and the Fc region of human IgG. In another embodiment, a dominant-negative PD-L1 antagonist includes one or more mutation(s) in PD-1 preventing its ability to bind PD-L1.

Exemplary immune checkpoint regulator agonists include, but are not limited to members of the tumor necrosis factor (TNF) receptor superfamily, such as CD27, CD40, OX40, GITR and 4-1BB (CD137) and their ligands, or members of the B7-CD28 superfamily, including CD28 and ICOS (CD278). Additional checkpoint regulator agonists include CD2, CDS, ICAM-1, LFA-1 (CD11a/CD18), CD30, BAFFR, HVEM, CD7, LIGHT, NKG2C, SLAMF7, NKp80, CD160, B7-H3, CD83 ligand. Immune checkpoint agonists can include antibodies or soluble fusion protein agonists comprising one or more costimulatory domains. Agonist antibodies include, but are not limited to anti-CD40 mAbs, such as CP-870,893, lucatumumab, and dacetuzumab; anti-CD137 mAbs, such as BMS-663513 urelumab, and PF-05082566; anti-OX40 mAbs; anti-GITR mAbs, such as TRX518; anti-CD27 mAbs, such as CDX-1127; and anti-ICOS mAbs.

Exemplary GITR agonists include, e.g., GITR fusion proteins and anti-GITR antibodies (e.g., bivalent anti-GITR antibodies) such as, e.g., a GITR fusion protein described in U.S. Pat. Nos. 6,111,090 and 8,586,023; European Patent No.: 090505B1, U.S. Pat. No. PCT Publication Nos.: WO 2010/003118 and 2011/090754. Anti-GITR antibodies are described in, e.g., in U.S. Pat. Nos. 7,025,962, 7,618,632, 7,812,135, 8,388,967, and 8,591,886; European Patent Nos.: 1947183B1 and 1866339; PCT Publication Nos.: WO 2011/028683, WO 2013/039954, WO2005/007190, WO 2007/133822, WO2005/055808, WO 99/40196, WO 2001/03720, WO99/20758, WO2006/083289, WO 2005/115451, WO 2011/051726. An exemplary anti-GITR antibody is TRX518.

Another family of membrane bound ligands that bind to co-stimulatory or co-inhibitory receptors is the TNF family of molecules that bind to cognate TNF receptor family members, which include CD40 and CD40L, OX-40, OX-40L, CD70, CD27L, CD30, CD30L, 4-1BBL, CD137/4-1BB, TRAIL/Apo2-L, TRAILR1/DR4, TRAILR2/DR5, TRAILR3, TRAILR4, OPG, RANK, RANKL, TWEAKR/Fni4, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNF γ, TNFR2, TNFα, LTβR, Lymphotoxin α 1(32, FAS, FASL, RELT, DR6, TROY, NGFR (see, e.g., Tansey, M. G. et al. (2009) Drug Discovery Today, 14(23-24):1082-1088).

Immune checkpoint agonists or costimulatory molecules include cell surface molecules other than antigen receptors or their ligands that are required for an efficient immune response, and include, but are not limited to MHC class I molecules, MHC class II molecules, TNF receptor proteins, immunoglobulin-like proteins, cytokine receptors, integrins, signaling lymphocytic activation molecules (SLAM proteins), activating NK cell receptors, BTLA, Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD 11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAMI, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

In one aspect, T cell responses can be stimulated by a combination of the anti-TIGIT, anti-PD-1, anti-PD-L1 or anti-LAG-3 mAbs of the present invention and one or more of (i) an antagonist of a protein that inhibits T cell activation (e.g., immune checkpoint inhibitors), such as CTLA-4, PD-1, PD-L1, PD-L2, LAG-3, TIM-3, Galectin 9, CEACAM-1, BTLA, CD69, Galectin-1, CD113, GPR56, VISTA, 2B4, CD48, GARP, PD-1H, LAIR1, TIM-1, CD96 and TIM-4, and (ii) an agonist of a protein that stimulates T cell activation such as B7-1, B7-2, CD28, 4-1BB (CD137), 4-1BBL, ICOS, CD40, ICOS-L, OX40, OX40L, GITR, GITRL, CD70, CD27, CD40, DR3 and CD28H.

Exemplary agents that modulate one of the above proteins and may be combined with the anti-TIGIT antibodies, anti-PD-1 antibodies, anti-PD-L1 antibodies, and/or anti-LAG-3 antibodies of the present application for treating cancer, include: YERVOY™/ipilimumab or tremelimumab (to CTLA-4), galiximab (to B7.1), OPDIVO™/nivolumab/BMS-936558 (to PD-1), pidilizumab/CT-011 (to PD-1), KEYTRUDA™/pembrolizumab/MK-3475 (to PD-1), AMP224 (to B7-DC/PD-L2), BMS-936559 (to B7-H1), MPDL3280A (to B7-H1), MEDI-570 (to ICOS), AMG557 (to B7H2), MGA271 (to B7H3), IMP321 (to LAG-3), urelumab/BMS-663513 and PF-05082566 (to CD137/4-1BB), CDX-1127 (to CD27), MEDI-6383 and MEDI-6469 (to OX40), RG-7888 (to OX40L), Atacicept (to TACI), CP-870893 (to CD40), lucatumumab (to CD40), dacetuzumab (to CD40), and muromonab-CD3 (to CD3).

Other molecules that can be combined with the antitumor antagonists described herein for the treatment of cancer include antagonists of inhibitory receptors on NK cells or agonists of activating receptors on NK cells. For example, antagonist anti-TIGIT, anti-PD-1, and/or anti-PD-L1 antibodies can be combined with antagonists of KIR (e.g., lirilumab), CSF-1R antagonists, such as RG7155.

Tumors evade host immune surveillance by a large variety of mechanisms. Many of these mechanisms may be overcome by the inactivation of immunosuppressive proteins expressed by the tumors. These include among others TGF-β, IL-10, and Fas ligand. Antibodies to each of these entities can be used in combination with the antitumor antagonists described herein to counteract the effects of the immunosuppressive agent and favor tumor immune responses by the host.

Other antibodies that activate host immune responsiveness can be used in combination with the antitumor antagonists described herein. These include molecules on the surface of dendritic cells that activate DC function and antigen presentation. Anti-CD40 antibodies are able to substitute effectively for T cell helper activity and can be used in conjunction with the antitumor antagonists described herein. Activating antibodies to T cell costimulatory molecules such as OX-40, CD137/4-1BB, and ICOS may also provide for increased levels of T cell activation.

In certain embodiments, the antitumor antagonists described herein can be co-administered with one or other more therapeutic agents, e.g., anti-cancer agents, radiotoxic agents or an immunosuppressive agent. Such co-administration can solve problems due to development of resistance to drugs, changes in the antigenicity of the tumor cells that would render them unreactive to the antibody, and toxicities (by administering lower doses of one or more agents).

The antitumor antagonists described herein can be linked to the agent (as an immuno-complex) or can be administered separate from the agent. In the latter case (separate administration), the antibody can be administered before, after or concurrently with the agent or can be co-administered with other known therapies, e.g., an anti-cancer therapy, e.g., radiation.

The antitumor antagonists described herein may be co-administered with one or more anti-cancer agents so as to provide two anti-cancer agents operating synergistically via different mechanisms to yield a cytotoxic effect in human cancer cells.

The antitumor antagonists described herein may be combined with an anti-cancer agent, such an alkylating agent; an anthracycline antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; a phosphatidylinositol-3-kinase (PI3K) inhibitor; an Akt inhibitor; a mammalian target of rapamycin (mTOR) inhibitor; a proteasomal inhibitor; a poly(ADP-ribose) polymerase (PARP) inhibitor; a Ras/MAPK pathway inhibitor; a centrosome declustering agent; a multi-kinase inhibitor; a serine/threonine kinase inhibitor; a tyrosine kinase inhibitor; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase or a protein methyltransferase), a cytidine analogue or combination thereof.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); thiotepa (Thioplex); bendamustine (Treanda); or streptozocin (Zanosar).

Exemplary anthracycline antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but are not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan); cetuximab (Erbitux); panitumumab (Vectibix); tositumomab/iodine131 tositumomab (Bexxar); alemtuzumab (Campath); ibritumomab (Zevalin; In-111; Y-90 Zevalin); gemtuzumab (Mylotarg); eculizumab (Soliris) ordenosumab.

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033); matuzumab (Emd7200) or EKB-569.

Exemplary HER2 inhibitors include, but are not limited to, trastuzumab (Herceptin); lapatinib (Tykerb) or AC-480.

Exemplary histone deacetylase inhibitors include, but are not limited to, vorinostat (Zolinza), valproic acid, romidepsin, entinostat abexinostat, givinostat, and mocetinostat.

Exemplary hormones include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepilone (Ixempra); nocodazole; epothilone; vinorelbine (Navelbine); camptothecin (CPT); irinotecan (Camptosar); topotecan (Hycamtin); amsacrine or lamellarin D (LAM-D).

Exemplary phosphatidyl-inositol-3 kinase (PI3K) inhibitors include wortmannin an irreversible inhibitor of PI3K, demethoxyviridin a derivative of wortmannin, LY294002, a reversible inhibitor of PI3K; BKM120 (Buparlisib); Idelalisib (a PI3K Delta inhibitor); duvelisib (IPI-145, an inhibitor of PI3K delta and gamma); alpelisib (BYL719), an alpha-specific PI3K inhibitor; TGR 1202 (previously known as RP5264), an oral PI3K delta inhibitor; and copanlisib (BAY 80-6946), an inhibitor PI3Kα,δ isoforms predominantly.

Exemplary Akt inhibitors include, but are not limited to miltefosine, AZD5363, GDC-0068, MK2206, Perifosine, RX-0201, PBI-05204, GSK2141795, and SR13668.

Exemplary MTOR inhibitors include, but are not limited to, everolimus (Afinitor) or temsirolimus (Torisel); rapamune, ridaforolimus; deforolimus (AP23573), AZD8055 (AstraZeneca), OSI-027 (OSI), INK-128, BEZ235, PI-103, Torin1, PP242, PP30, Ku-0063794, WAY-600, WYE-687, WYE-354, and CC-223.

Exemplary proteasomal inhibitors include, but are not limited to, bortezomib (PS-341), ixazomib (MLN 2238), MLN 9708, delanzomib (CEP-18770), carfilzomib (PR-171), YU101, oprozomib (ONX-0912), marizomib (NPI-0052), and disufiram.

Exemplary PARP inhibitors include, but are not limited to, olaparib, iniparib, velaparib, BMN-673, BSI-201, AG014699, ABT-888, GPI21016, MK4827, INO-1001, CEP-9722, PJ-34, Tiq-A, Phen, PF-01367338 and combinations thereof.

Exemplary Ras/MAPK pathway inhibitors include, but are not limited to, trametinib, selumetinib, cobimetinib, CI-1040, PD0325901, AS703026, R04987655, R05068760, AZD6244, GSK1120212, TAK-733, U0126, MEK162, and GDC-0973.

Exemplary centrosome declustering agents include, but are not limited to, griseofulvin; noscapine, noscapine derivatives, such as brominated noscapine (e.g., 9-bromonoscapine), reduced bromonoscapine (RBN), N-(3-brormobenzyl) noscapine, aminonoscapine and water-soluble derivatives thereof, CW069; the phenanthridene-derived poly(ADP-ribose) polymerase inhibitor, PJ-34; N2-(3-pyridylmethyl)-5-nitro-2-furamide, N2-(2-thienylmethyl)-5-nitro-2-furamide, and N2-benzyl-5-nitro-2-furamide.

Exemplary multi-kinase inhibitors include, but are not limited to, regorafenib; sorafenib (Nexavar); sunitinib (Sutent); BIBW 2992; E7080; Zd6474; PKC-412; motesanib; or AP24534.

Exemplary serine/threonine kinase inhibitors include, but are not limited to, ruboxistaurin; eril/easudil hydrochloride; flavopiridol; seliciclib (CYC202; Roscovitrine); SNS-032 (BMS-387032); Pkc412; bryostatin; KAI-9803; SF1126; VX-680; Azd1152; Arry-142886 (AZD-6244); SCIO-469; GW681323; CC-401; CEP-1347 or PD 332991.

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); CEP-701; SU5614; MLN518; XL999; VX-322; Azd0530; BMS-354825; SKI-606 CP-690; AG-490; WHI-P154; WHI-P131; AC-220; or AMG888.

Exemplary VEGF/VEGFR inhibitors include, but are not limited to, bevacizumab (Avastin); sorafenib (Nexavar); sunitinib (Sutent); ranibizumab; pegaptanib; or vandetinib.

Exemplary microtubule targeting drugs include, but are not limited to, paclitaxel, docetaxel, vincristin, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxol.

Exemplary general chemotherapeutic, anti-neoplastic, anti-proliferative agents include, but are not limited to, altretamine (Hexalen); isotretinoin (Accutane; Amnesteem; Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Revlimid); bexarotene (Targretin); thalidomide (Thalomid); temsirolimus (Torisel); arsenic trioxide (Trisenox); verteporfin (Visudyne); mimosine (Leucenol); (1M tegafur-0.4 M 5-chloro-2,4-dihydroxypyrimidine-1 M potassium oxonate) or lovastatin.

In certain embodiments, TIGIT, PD-1, PD-L1 and/or LAG-3 inhibition is combined with standard cancer treatments (e.g., surgery, radiation, and chemotherapy). TIGIT, PD-1, PD-L1 and/or LAG-3 inhibition can be effectively combined with chemotherapeutic regimes. In these instances, it may be possible to reduce the dose of chemotherapeutic reagent administered. An example of such a combination is an anti-TIGIT, anti-PD-1, anti-PD-L1 or anti-LAG-3 antibody in combination with decarbazine for the treatment of melanoma. Another example of such a combination is an anti-TIGIT, anti-PD-1, anti-PD-L1 or anti-LAG-3 antibody in combination with interleukin-2 (IL-2) for the treatment of melanoma. It is believed that the combined use of TIGIT, PD-1, PD-L1 and/or LAG-3 inhibition and chemotherapy can enhance apoptosis and increase tumor antigen presentation for cytotoxic immunity. Other synergistic combination therapies include TIGIT, PD-1, PD-L1 and/or LAG-3 inhibition through cell death when used in combination with radiation, surgery or hormone deprivation. Each of these protocols creates a source of tumor antigen in the host.

In certain embodiments, the checkpoint regulator antagonists described herein can be used in multi-specific antagonists or in combination with bispecific antibodies targeting Fcα or Fcγ receptor-expressing effector cells to tumor cells (see, e.g., U.S. Pat. Nos. 5,922,845 and 5,837,243). Bispecific antibodies can be used to target two separate antigens. For example anti-Fc receptor/anti-tumor antigen (e.g., Her-2/neu) bispecific antibodies have been used to target macrophages to cancer cells or tumors. This targeting may more effectively activate tumor specific responses. The T cell arm of these responses would be augmented by the inhibition of TIGIT, PD-1, PD-L1 and/or LAG-3. Alternatively, antigen may be delivered directly to DCs by the use of bispecific antibodies that bind to tumor antigen and a dendritic cell specific cell surface marker.

IV. Nucleic Acids and Host Cells for Expressing Checkpoint Regulator

In another aspect, the present application provides nucleic acids encoding the antitumor antagonists of the present application, including the heavy and light chains, as well as expression vectors comprising such nucleic acids. In particular, the nucleic acids encode one or more HCDRs, LCDRs, HCVRs and/or LCVRs corresponding to any of the antibodies, antagonists or fragments described herein.

Thus, in one aspect, the present application provides one or more nucleic acids encoding any of the antitumor antagonists, antibodies or antigen-binding portions thereof as described herein.

In another aspect, the present application provides one or more expression vectors comprising the one or more nucleic acids encoding any of the antitumor antagonists, antibodies or antigen-binding portions thereof as described herein.

In another aspect, the present application provides a host cell transformed with the one or more expression vectors comprising the one or more nucleic acids encoding any of the antitumor antagonists, antibodies or antigen-binding portions thereof as described herein.

DNA(s) encoding antigen binding sites can be isolated and sequenced from a monoclonal antibody produced in hybridoma cells using conventional procedures (e.g., by using oligonucleotide probes that are capable of binding specifically to genes encoding the heavy and light chains of the monoclonal antibodies). Alternatively, amino acid sequences from immunoglobulins of interest may be determined by direct protein sequencing, and suitable encoding nucleotide sequences can be designed according to a universal codon table. In other cases, nucleotide and amino acid sequences of antigen binding sites or other immunoglobulin sequences, including constant regions, hinge regions and the like may be obtained from published sources well known in the art.

Expression vectors encoding a particular monospecific or bispecific anti-tumor antagonist may be used to synthesize the antitumor antagonists of the present disclosure in cultured cells in vitro or they may be directly administered to a patient to express the anti-tumor antagonist in vivo or ex vivo. As used herein, an "expression vector" refers to a viral or non-viral vector comprising a polynucleotide encoding one or more polypeptide chains corresponding to the monospecific or bispecific antitumor antagonists of the present disclosure in a form suitable for expression from the polynucleotide(s) in a host cell for antibody preparation purposes or for direct administration as a therapeutic agent.

A nucleic acid sequence is "operably linked" to another nucleic acid sequence when the former is placed into a functional relationship with the latter. For example, a DNA for a presequence or signal peptide is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a signal peptide, contiguous and in reading phase. However, enhancers do not have to be contiguous. Linking is accomplished by ligation at convenient restriction sites. If such sites do not exist, synthetic oligonucleotide adaptors or linkers may be used in accordance with conventional practice.

Nucleic acid sequences for expressing the antitumor antagonists typically include an amino terminal signal peptide sequence, which is removed from the mature protein. Since the signal peptide sequences can affect the levels of expression, the polynucleotides may encode any one of a variety of different N-terminal signal peptide sequences. It will be appreciated by those skilled in the art that the design of the expression vector can depend on such factors as the choice of the host cell to be transformed, the level of expression of protein desired, and the like.

The above described "regulatory sequences" refer to DNA sequences necessary for the expression of an operably linked coding sequence in one or more host organisms. The term "regulatory sequences" is intended to include promoters, enhancers and other expression control elements (e.g., polyadenylation signals). Regulatory sequences include those which direct constitutive expression of a nucleotide sequence in many types of host cells or those which direct expression of the nucleotide sequence only in certain host cells (e.g., tissue-specific regulatory sequences). Expression vectors generally contain sequences for transcriptional termination, and may additionally contain one or more elements positively affecting mRNA stability.

The expression vector contains one or more transcriptional regulatory elements, including promoters and/or enhancers, for directing the expression of antitumor antagonists. A promoter comprises a DNA sequence that functions to initiate transcription from a relatively fixed location in regard to the transcription start site. A promoter contains core elements required for basic interaction of RNA polymerase and transcription factors, and may operate in conjunction with other upstream elements and response elements.

As used herein, the term "promoter" is to be taken in its broadest context and includes transcriptional regulatory elements (TREs) from genomic genes or chimeric TREs therefrom, including the TATA box or initiator element for accurate transcription initiation, with or without additional TREs (i.e., upstream activating sequences, transcription factor binding sites, enhancers, and silencers) which regulate activation or repression of genes operably linked thereto in response to developmental and/or external stimuli, and trans-acting regulatory proteins or nucleic acids. A promoter may contain a genomic fragment or it may contain a chimera of one or more TREs combined together.

Preferred promoters are those capable of directing high-level expression in a target cell of interest. The promoters may include constitutive promoters (e.g., HCMV, SV40, elongation factor-1α (EF-1α)) or those exhibiting preferential expression in a particular cell type of interest. Enhancers generally refer to DNA sequences that function away from the transcription start site and can be either 5' or 3' to the transcription unit. Furthermore, enhancers can be within an intron as well as within the coding sequence. They are usually between 10 and 300 bp in length, and they function in cis. Enhancers function to increase and/or regulate transcription from nearby promoters. Preferred enhancers are those directing high-level expression in the antibody producing cell. Cell or tissue-specific transcriptional regulatory elements (TREs) can be incorporated into expression vectors to restrict expression to desired cell types. Pol III promoters (H1 or U6) are particularly useful for expressing shRNAs from which siRNAs are expressed. An expression vector may be designed to facilitate expression of the antitumor antagonist in one or more cell types.

In certain embodiments, one or more expression vectors may be engineered to express both the antitumor antagonist and one or more siRNA targeting the Tie2 pathway, the VEGF pathway or an immune checkpoint regulator.

An siRNA is a double-stranded RNA that can be engineered to induce sequence-specific post-transcriptional gene silencing of mRNAs. Synthetically produced siRNAs structurally mimic the types of siRNAs normally processed in cells by the enzyme Dicer. When expressed from an expression vector, the expression vector is engineered to transcribe a short double-stranded hairpin-like RNA (shRNA) that is processed into a targeted siRNA inside the cell. Synthetic siRNAs and shRNAs may be designed using well known algorithms and synthesized using a conventional DNA/RNA synthesizer.

To co-express the individual chains of the antitumor antagonist, a suitable splice donor and splice acceptor sequences may be incorporated for expressing both products. Alternatively, an internal ribosome binding sequence (IRES) or a 2A peptide sequence, may be employed for expressing multiple products from one promoter. An IRES provides a structure to which the ribosome can bind that does not need to be at the 5' end of the mRNA. It can therefore direct a ribosome to initiate translation at a second initiation codon within a mRNA, allowing more than one polypeptide to be produced from a single mRNA. A 2A peptide contains short sequences mediating co-translational self-cleavage of the peptides upstream and downstream from the 2A site, allowing production of two different proteins from a single transcript in equimolar amounts. CHYSEL is a non-limiting example of a 2A peptide, which causes a translating eukaryotic ribosome to release the growing polypeptide chain that it is synthesizing without dissociating from the mRNA. The ribosome continues translating, thereby producing a second polypeptide.

An expression vector may comprise a viral vector or a non-viral vector. A viral vectors may be derived from an adeno-associated virus (AAV), adenovirus, herpesvirus, vaccinia virus, poliovirus, poxvirus, a retrovirus (including a lentivirus, such as HIV-1 and HIV-2), Sindbis and other RNA viruses, alphavirus, astrovirus, coronavirus, orthomyxovirus, papovavirus, paramyxovirus, parvovirus, picornavirus, togaviruses and the like. A non-viral vector is simply a "naked" expression vector that is not packaged with virally derived components (e.g., capsids and/or envelopes).

In certain cases, these vectors may be engineered to target certain diseases or cell populations by using the targeting characteristics inherent to the virus vector or engineered into the virus vector. Specific cells may be "targeted" for delivery of polynucleotides, as well as expression. Thus, the term "targeting", in this case, may be based on the use of endogenous or heterologous binding agents in the form of capsids, envelope proteins, antibodies for delivery to specific cells, the use of tissue-specific regulatory elements for restricting expression to specific subset(s) of cells, or both.

In some embodiments, expression of the antibody chains is under the control of the regulatory element such as a tissue specific or ubiquitous promoter. In some embodiments, a ubiquitous promoter such as a CMV promoter, CMV-chicken beta-actin hybrid (CAG) promoter, a tissue specific or tumor-specific promoter to control the expression of a particular antibody heavy or light chain or single-chain derivative therefrom.

Non-viral expression vectors can be utilized for non-viral gene transfer, either by direct injection of naked DNA or by encapsulating the antitumor antagonist-encoding polynucleotides in liposomes, microparticles, microcapsules, virus-like particles, or erythrocyte ghosts. Such compositions can be further linked by chemical conjugation to targeting domains to facilitate targeted delivery and/or entry of nucleic acids into desired cells of interest. In addition, plasmid vectors may be incubated with synthetic gene transfer molecules such as polymeric DNA-binding cations like polylysine, protamine, and albumin, and linked to cell targeting ligands such as asialoorosomucoid, insulin, galactose, lactose or transferrin.

Alternatively, naked DNA may be employed. Uptake efficiency of naked DNA may be improved by compaction or by using biodegradable latex beads. Such delivery may be improved further by treating the beads to increase hydrophobicity and thereby facilitate disruption of the endosome and release of the DNA into the cytoplasm.

V. Methods for Producing Monospecific or Multispecific Antibodies

In another aspect, the present application provides host cells transformed with the anti-TIGIT, anti-PD-1, anti-PD-L1 and/or anti-LAG-3 HCVRs and/or LCVRs, encoding nucleic acids or expression vectors, or nucleic acids/expression vectors encoding the monospecific or bi-specific antitumor antagonist of the present application. The host cells can be any bacterial or eukaryotic cell capable of expressing the anti-TIGIT, anti-PD-1, anti-PD-L1 and/or anti-LAG-3 HCVRs and/or LCVRs encoding nucleic acids or expression vectors or any of the other co-administered antibodies or antagonists described herein.

In another aspect, a method of producing an antitumor antagonist comprises culturing a host cell transformed with one or more anti-TIGIT, anti-PD-1, anti-PD-L1 and/or anti-LAG-3 HCVRs and/or LCVRs encoding nucleic acids or expression vectors under conditions that allows production of the antibody or fragment, and purifying the antibody from the cell.

In a further aspect, the present application provides a method for producing an antibody comprising culturing a cell transiently or stably expressing one or more constructs encoding one or more polypeptide chains in the antibody; and purifying the antibody from the cultured cells. Any cell capable of producing a functional antibody may be used. In preferred embodiments, the antibody-expressing cell is of eukaryotic or mammalian origin, preferably a human cell. Cells from various tissue cell types may be used to express the antibodies. In other embodiments, the cell is a yeast cell, an insect cell or a bacterial cell. Preferably, the antibody-producing cell is stably transformed with a vector expressing the antibody.

One or more expression vectors encoding the antibody heavy or light chains can be introduced into a cell by any conventional method, such as by naked DNA technique, cationic lipid-mediated transfection, polymer-mediated transfection, peptide-mediated transfection, virus-mediated infection, physical or chemical agents or treatments, electroporation, etc. In addition, cells may be transfected with one or more expression vectors for expressing the antibody along with a selectable marker facilitating selection of stably transformed clones expressing the antibody. The antibodies produced by such cells may be collected and/or purified according to techniques known in the art, such as by centrifugation, chromatography, etc.

Examples of suitable selectable markers for mammalian cells include dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are CHO DHFR$^-$ cells and mouse LTK$^-$ cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, mycophenolic acid, or hygromycin. The three examples employ bacterial genes under eukaryotic control to convey resistance to the appropriate drug G418 or neomycin (geneticin), xgpt (mycophenolic acid) or hygromycin, respectively. Others include the neomycin analog G418 and puromycin.

Exemplary antibody-expressing cells include human Jurkat, human embryonic kidney (HEK) 293, Chinese hamster ovary (CHO) cells, mouse WEHI fibrosarcoma cells, as well as unicellular protozoan species, such as *Leishmania tarentolae*. In addition, stably transformed, antibody producing cell lines may be produced using primary cells immortalized with c-myc or other immortalizing agents.

In one embodiment, the cell line comprises a stably transformed *Leishmania* cell line, such as *Leishmania tarentolae*. *Leishmania* are known to provide a robust, fast-growing unicellular host for high level expression of eukaryotic proteins exhibiting mammalian-type glycosylation patterns. A commercially available *Leishmania* eukaryotic expression kit is available (Jena Bioscience GmbH, Jena, Germany).

In some embodiments, the cell line expresses at least 1 mg, at least 2 mg, at least 5 mg, at least 10 mg, at least 20 mg, at least 50 mg, at least 100 mg, at least 200 mg, at least 300 mg, at least 400 mg, or at least 500 mg of the antibody/liter of culture.

The antibodies in the present application may be isolated from antibody expressing cells following culture and maintenance in any appropriate culture medium, such as RPMI, DMEM, and AIM V©. The antibodies can be purified using conventional protein purification methodologies (e.g., affinity purification, chromatography, etc.), including the use of Protein-A or Protein-G immunoaffinity purification. In some embodiments, antibodies are engineered for secretion into culture supernatants for isolation therefrom.

VI. Pharmaceutical Compositions and Methods of Treatment

Another aspect of the present application relates to pharmaceutical compositions and methods for treating a cell proliferative disorder, such as cancer, chronic infections, or immunologically compromised disease states. In one embodiment, the pharmaceutical composition comprises one or more antitumor antagonists of the present application. In some embodiments, the antitumor antagonist(s) comprise one or more checkpoint regulator antagonists, such as anti-T cell Ig and ITIM domain (TIGIT) inhibitors, PD-1 inhibitors, PD-L1 inhibitors and LAG-3 inhibitors. The antagonist(s) are formulated together with a pharmaceutically acceptable carrier. Pharmaceutical composition of the present application may include one or more different antibodies, one or more multispecific antibodies, one or more immunoconjugates, or a combination thereof as described herein.

As described above, methods for using the pharmaceutical compositions described herein comprise administering to a subject in need thereof an effective amount of the pharmaceutical composition according to the present disclosure.

Any suitable route or mode of administration can be employed for providing the patient with a therapeutically or prophylactically effective dose of the antibody or antagonist. Exemplary routes or modes of administration include parenteral (e.g., intravenous, intraarterial, intramuscular, subcutaneous, intratumoral), oral, topical (nasal, transdermal, intradermal or intraocular), mucosal (e.g., nasal, sublingual, buccal, rectal, vaginal), inhalation, intralymphatic, intraspinal, intracranial, intraperitoneal, intratracheal, intravesical, intrathecal, enteral, intrapulmonary, intralymphatic, intracavital, intraorbital, intracapsular and transurethral, as well as local delivery by catheter or stent.

A pharmaceutical composition comprising an antibody or antagonist in accordance with the present disclosure may be formulated in any pharmaceutically acceptable carrier(s) or excipient(s). As used herein, the term "pharmaceutically acceptable carrier" includes any and all solvents, dispersion media, coatings, antibacterial and antifungal agents, isotonic and absorption delaying agents, and the like that are physiologically compatible. Pharmaceutical compositions may comprise suitable solid or gel phase carriers or excipients. Exemplary carriers or excipients include but are not limited to, calcium carbonate, calcium phosphate, various sugars, starches, cellulose derivatives, gelatin, and polymers such as polyethylene glycols. Exemplary pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the therapeutic agents.

The antitumor antagonist can be incorporated into a pharmaceutical composition suitable for parenteral administration. Suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, argi- nine, can be included as 0-0.05% polysorbate-80 (optimally 0.005-0.01%). Additional surfactants include but are not limited to polysorbate 20 and BRIJ surfactants.

Therapeutic antitumor antagonist preparations can be lyophilized and stored as sterile powders, preferably under vacuum, and then reconstituted in bacteriostatic water (containing, for example, benzyl alcohol preservative) or in sterile water prior to injection. Pharmaceutical composition may be formulated for parenteral administration by injection e.g., by bolus injection or continuous infusion.

The therapeutic agents in the pharmaceutical compositions may be formulated in a "therapeutically effective amount" or a "prophylactically effective amount". A "therapeutically effective amount" refers to an amount effective, at dosages and for periods of time necessary, to achieve the desired therapeutic result. A therapeutically effective amount of the recombinant vector may vary depending on the condition to be treated, the severity and course of the condition, the mode of administration, whether the antibody or agent is administered for preventive or therapeutic purposes, the bioavailability of the particular agent(s), the ability of the antitumor antagonist to elicit a desired response in the individual, previous therapy, the age, weight and sex of the patient, the patient's clinical history and response to the antibody, the type of the antitumor antagonist used, discretion of the attending physician, etc. A therapeutically effective amount is also one in which any toxic or detrimental effects of the recombinant vector is outweighed by the therapeutically beneficial effects. A "prophylactically effective amount" refers to an amount effective, at dosages and for periods of time necessary, to achieve the desired prophylactic result.

Preferably, the polypeptide domains in the antitumor antagonist are derived from the same host in which they are to be administered in order to reduce inflammatory responses against the administered therapeutic agents.

The antitumor antagonist is suitably administered to the patent at one time or over a series of treatments and may be administered to the patient at any time from diagnosis onwards. The antitumor antagonist may be administered as the sole treatment or in conjunction with other drugs or therapies useful in treating the condition in question.

As a general proposition, a therapeutically effective amount or prophylactically effective amount of the antitumor antagonist will be administered in a range from about 1 ng/kg body weight/day to about 100 mg/kg body weight/day whether by one or more administrations. In a particular embodiment, each antitumor antagonist is administered in the range of from about 1 ng/kg body weight/day to about 10 mg/kg body weight/day, about 1 ng/kg body weight/day to about 1 mg/kg body weight/day, about 1 ng/kg body weight/day to about 100 µg/kg body weight/day, about 1 ng/kg body weight/day to about 10 µg/kg body weight/day, about 1 ng/kg body weight/day to about 1 µg/kg body weight/day, about 1 ng/kg body weight/day to about 100 ng/kg body weight/day, about 1 ng/kg body weight/day to about 10 ng/kg body weight/day, about 10 ng/kg body weight/day to about 100 mg/kg body weight/day, about 10 ng/kg body weight/day to about 10 mg/kg body weight/day, about 10 ng/kg body weight/day to about 1 mg/kg body weight/day, about 10 ng/kg body weight/day to about 100 µg/kg body weight/day, about 10 ng/kg body weight/day to about 10 µg/kg body weight/day, about 10 ng/kg body weight/day to about 1 µg/kg body weight/day, 10 ng/kg body weight/day to about 100 ng/kg body weight/day, about 100 ng/kg body weight/day to about 100 mg/kg body weight/day, about 100 ng/kg body weight/day to about 10 mg/kg body weight/day, about 100 ng/kg body weight/day to about 1 mg/kg body weight/day, about 100 ng/kg body weight/day to about 100 g/kg body weight/day, about 100 ng/kg body weight/day to about 10 μg/kg body weight/day, about 100 ng/kg body weight/day to about 1 μg/kg body weight/day, about 1 μg/kg body weight/day to about 100 mg/kg body weight/day, about 1 μg/kg body weight/day to about 10 mg/kg body weight/day, about 1 μg/kg body weight/day to about 1 mg/kg body weight/day, about 1 μg/kg body weight/day to about 100 μg/kg body weight/day, about 1 μg/kg body weight/day to about 10 μg/kg body weight/day, about 10 μg/kg body weight/day to about 100 mg/kg body weight/day, about 10 μg/kg body weight/day to about 10 mg/kg body weight/day, about 10 μg/kg body weight/day to about 1 mg/kg body weight/day, about 10 μg/kg body weight/day to about 100 μg/kg body weight/day, about 100 μg/kg body weight/day to about 100 mg/kg body weight/day, about 100 μg/kg body weight/day to about 10 mg/kg body weight/day, about 100 μg/kg body weight/day to about 1 mg/kg body weight/day, about 1 mg/kg body weight/day to about 100 mg/kg body weight/day, about 1 mg/kg body weight/day to about 10 mg/kg body weight/day, about 10 mg/kg body weight/day to about 100 mg/kg body weight/day.

In other embodiments, the antitumor antagonist is administered at a dose of 500 g to 20 g every three days, or 25 mg/kg body weight every three days.

In other embodiments, each antitumor antagonist is administered in the range of about 10 ng to about 100 ng per individual administration, about 10 ng to about 1 μg per individual administration, about 10 ng to about 10 μg per individual administration, about 10 ng to about 100 μg per individual administration, about 10 ng to about 1 mg per individual administration, about 10 ng to about 10 mg per individual administration, about 10 ng to about 100 mg per individual administration, about 10 ng to about 1000 mg per injection, about 10 ng to about 10,000 mg per individual administration, about 100 ng to about 1 μg per individual administration, about 100 ng to about 10 μg per individual administration, about 100 ng to about 100 μg per individual administration, about 100 ng to about 1 mg per individual administration, about 100 ng to about 10 mg per individual administration, about 100 ng to about 100 mg per individual administration, about 100 ng to about 1000 mg per injection, about 100 ng to about 10,000 mg per individual administration, about 1 μg to about 10 μg per individual administration, about 1 μg to about 100 μg per individual administration, about 1 μg to about 1 mg per individual administration, about 1 μg to about 10 mg per individual administration, about 1 μg to about 100 mg per individual administration, about 1 μg to about 1000 mg per injection, about 1 μg to about 10,000 mg per individual administration, about 10 μg to about 100 μg per individual administration, about 10 μg to about 1 mg per individual administration, about 10 μg to about 10 mg per individual administration, about 10 μg to about 100 mg per individual administration, about 10 μg to about 1000 mg per injection, about 10 μg to about 10,000 mg per individual administration, about 100 μg to about 1 mg per individual administration, about 100 g to about 10 mg per individual administration, about 100 μg to about 100 mg per individual administration, about 100 μg to about 1000 mg per injection, about 100 μg to about 10,000 mg per individual administration, about 1 mg to about 10 mg per individual administration, about 1 mg to about 100 mg per individual administration, about 1 mg to about 1000 mg per injection, about 1 mg to about 10,000 mg per individual administration, about 10 mg to about 100 mg per individual administration, about 10 mg to about 1000 mg per injection, about 10 mg to about 10,000 mg per individual administration, about 100 mg to about 1000 mg per injection, about 100 mg to about 10,000 mg per individual administration and about 1000 mg to about 10,000 mg per individual administration. The antitumor antagonist may be administered daily, every 2, 3, 4, 5, 6 or 7 days, or every 1, 2, 3 or 4 weeks.

In other particular embodiments, the amount of the antitumor antagonist may be administered at a dose of about 0.0006 mg/day, 0.001 mg/day, 0.003 mg/day, 0.006 mg/day, 0.01 mg/day, 0.03 mg/day, 0.06 mg/day, 0.1 mg/day, 0.3 mg/day, 0.6 mg/day, 1 mg/day, 3 mg/day, 6 mg/day, 10 mg/day, 30 mg/day, 60 mg/day, 100 mg/day, 300 mg/day, 600 mg/day, 1000 mg/day, 2000 mg/day, 5000 mg/day or 10,000 mg/day. As expected, the dosage will be dependent on the condition, size, age and condition of the patient.

In certain embodiments, the coding sequences for a antitumor antagonist are incorporated into a suitable expression vector (e.g., viral or non-viral vector) for expressing an effective amount of the antitumor antagonist in patient with a cell proliferative disorder. In certain embodiments comprising administration of e.g., one or more recombinant AAV (rAAV) viruses, the pharmaceutical composition may comprise the rAAVs in an amount comprising at least $10^{10}$, at least $10^{11}$, at least $10^{12}$, at least $10^{13}$, or at least $10^{14}$ genome copies (GC) or recombinant viral particles per kg, or any range thereof. In certain embodiments, the pharmaceutical composition comprises an effective amount of the recombinant virus, such as rAAV, in an amount comprising at least $10^{10}$, at least $10^{11}$, at least $10^{12}$, at least $10^{13}$, at least $10^{14}$, at least $10^{15}$ genome copies or recombinant viral particles genome copies per subject, or any range thereof.

Dosages can be tested in several art-accepted animal models suitable for any particular cell proliferative disorder.

Delivery methodologies may also include the use of polycationic condensed DNA linked or unlinked to killed viruses, ligand linked DNA, liposomes, eukaryotic cell delivery vehicles cells, deposition of photopolymerized hydrogel materials, use of a handheld gene transfer particle gun, ionizing radiation, nucleic charge neutralization or fusion with cell membranes, particle mediated gene transfer and the like.

The present invention is further illustrated by the following examples which should not be construed as limiting. The contents of all references, patents and published patent applications cited throughout this application, as well as the Figures and Tables are incorporated herein by reference.

EXAMPLES

Example 1: Generation of Monoclonal Antibodies

Monoclonal antibodies (mAbs) of the present application are generated and screened using techniques well known in the art, see, e.g., Harlow and Lane (1988) *Antibodies, A Labortory Manual*, Cold Spring Harbor Publications, New York. The antigen specific hybridoma mAbs are cloned, sequenced and engineered using techniques well known in the art, see e.g., Lo. B. K. C Methods in Molecular Biology™. Volume 248 2004. Antibody Engineering.

FIG. 1 shows CDR sequences of anti-TIGIT mAbs. FIGS. 2A-2B show several embodiments of anti-TIGIT antibody variable domain sequences. FIG. 3 shows CDR sequences of anti-PD-1 mAbs. FIGS. 4A-4C show several embodiments of anti-PD-1 antibody variable domain sequences. FIG. 5 shows CDR sequences of anti-PD-L1 mAbs. FIGS. 6A-6C show several embodiments of anti-PD-L1 antibody variable domain sequences.

Example 2: Design of Bispecific Anti-PD-1 Antibodies with Anti-TIGIT scFv

Figure 7B:
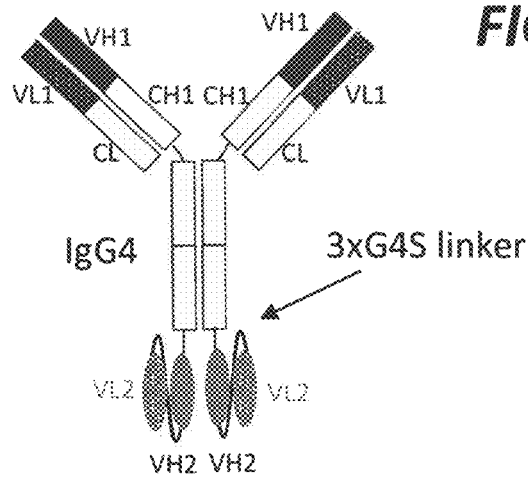
Figure 7C:
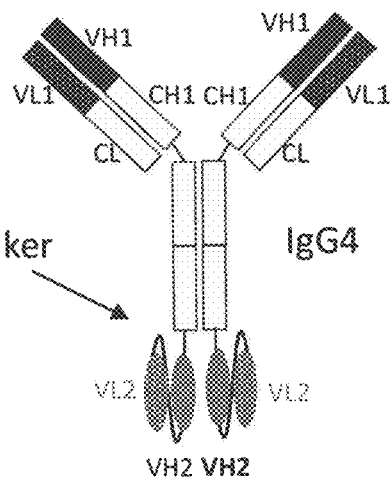

FIGS. 7A-7C show three exemplary bispecific antitumor antagonists, Bi-TPM-93 (FIG. 7A), Bi-TPM-94A (FIG. 7B), and Bi-TPM-94B (FIG. 7C). These antagonists contain an anti-PD-1 (PD-01) antibody backbone (FIG. 7A) or an anti-PD-1 (PD-06/2P17) antibody backbone (FIGS. 7A, 7B) along with an anti-TIGIT scFv with heavy chain and light chain variable regions from the anti-TIGIT mAb T-10/B21 separated by a 3×G4S linker (FIGS. 7A, 7B) or a 6×G4S linker (FIG. 7C).

FIG. 8 shows functional domain sequences present in the bispecific antibodies depicted in FIGS. 7A-7C.

FIGS. 9A-9B show exemplary heavy chain (HC) and light chain (LC) sequences corresponding to the bispecific antibodies depicted in FIGS. 7A-7C.

Figure 10:
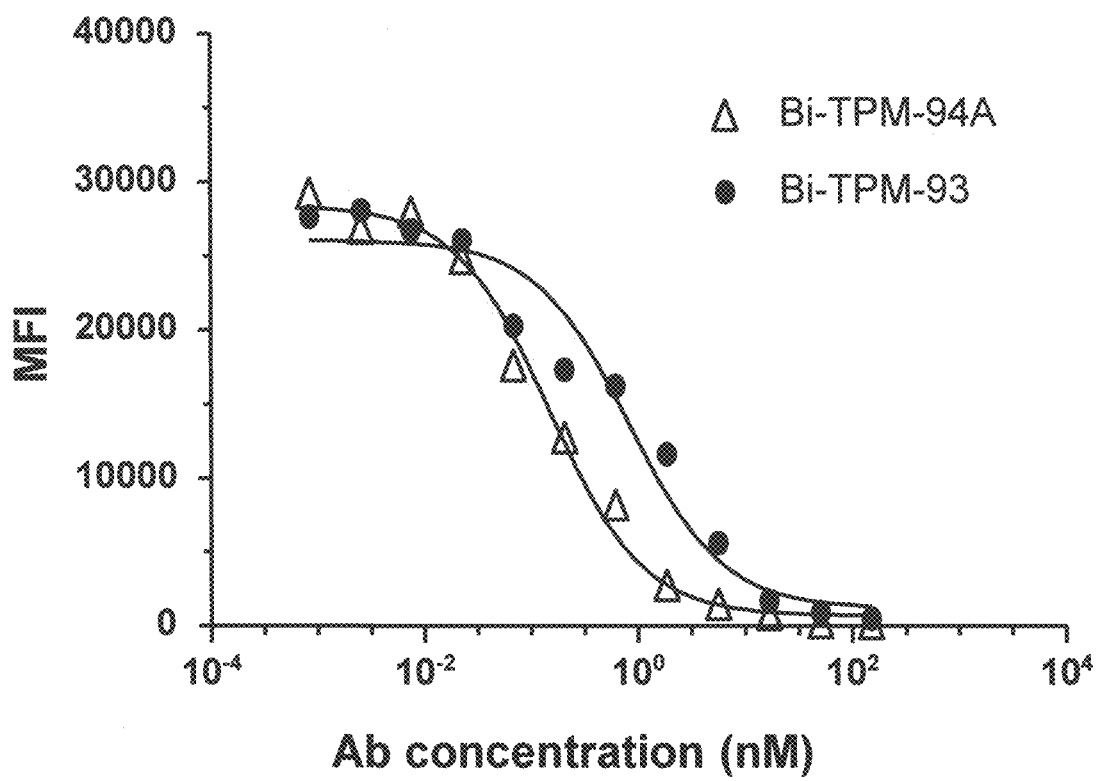
FIG. 10 depicts a blocking assay showing that Bi-TPM-94A blocks the interaction between PD-1 and its ligand (IC50=0.15 nM), PD-L1 better than Bi-TPM-93 (IC50=0.83 nM).

Example 3: Expression and Functional Characterization of Bispecific Anti-PD-1/Anti-TIGIT Antibodies To evaluate the PD-1 blocking ability of Bi-TPM-93 and Bi-TPM-94A, a PD-1 IC50 assay was conducted in which serial dilutions of the bispecific mAbs were incubated at 4° C. for 30 mins with human PD-1 transfected CHOK1 cells and 7 μg/ml FITC labeled human PD-L1-Fc protein, followed by washing and fixation of the cells prior to analysis with an iQue intellicyt system. The results of this assay in FIG. 10 show that Bi-TPM-94 containing VH and VL sequences from PD-06/2P17 blocks the interaction between PD-1 and its ligand, PD-L1 better (IC50=0.15 nM) than Bi-TPM-93 containing VH and VL sequences from PD-O1 (IC50=0.83 nM).

Figure 11:
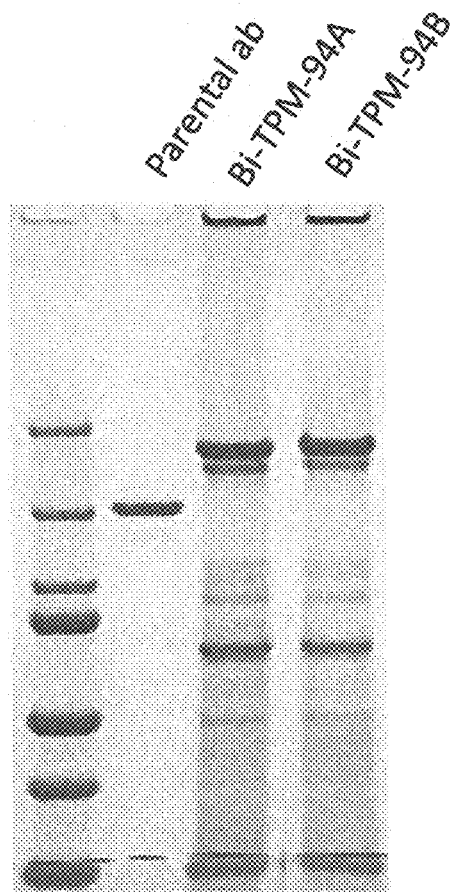
FIG. 11 shows a non-reducing PAGE analysis of Bi-TPM-94A and Bi-TPM-94B transiently expressed in human embryonic kidney (HEK) 293 cells.

FIG. 11 shows a non reducing PAGE analysis demonstrating robust transient expression of both Bi-TPM-94A and Bi-TPM-94B in human embryonic kidney (HEK) 293 cells.

To evaluate the degree of homogeneity of the antagonist species corresponding to Bi-TPM93, Bi-TPM-94A, and Bi-TPM-94B, the samples were purified and subjected to a size-exclusion ultra-high performance liquid chromatography (SE-UHPLC) analysis. Purification of the samples was carried out as follows. First, harvested cell culture fluids (HCCFs) were subjected to 0.2 m filtration following by affinity purification using Hitrap Protein A HP chromatography (GE Healthcare) at 1 mL/min. Following affinity purification, the material was subjected to cation exchange (CEX) chromatography using Sepax Proteomix® SCX-NP5 columns with gradient elution at 0.8 mL/min. The amounts of aggregate (high molecular weight, HMW), dimer, and low molecular weight (LMW) fragments were determined by SE-UPLC using Tosoh TSKgel UP-G3000SWXL columns.

Figure 12:
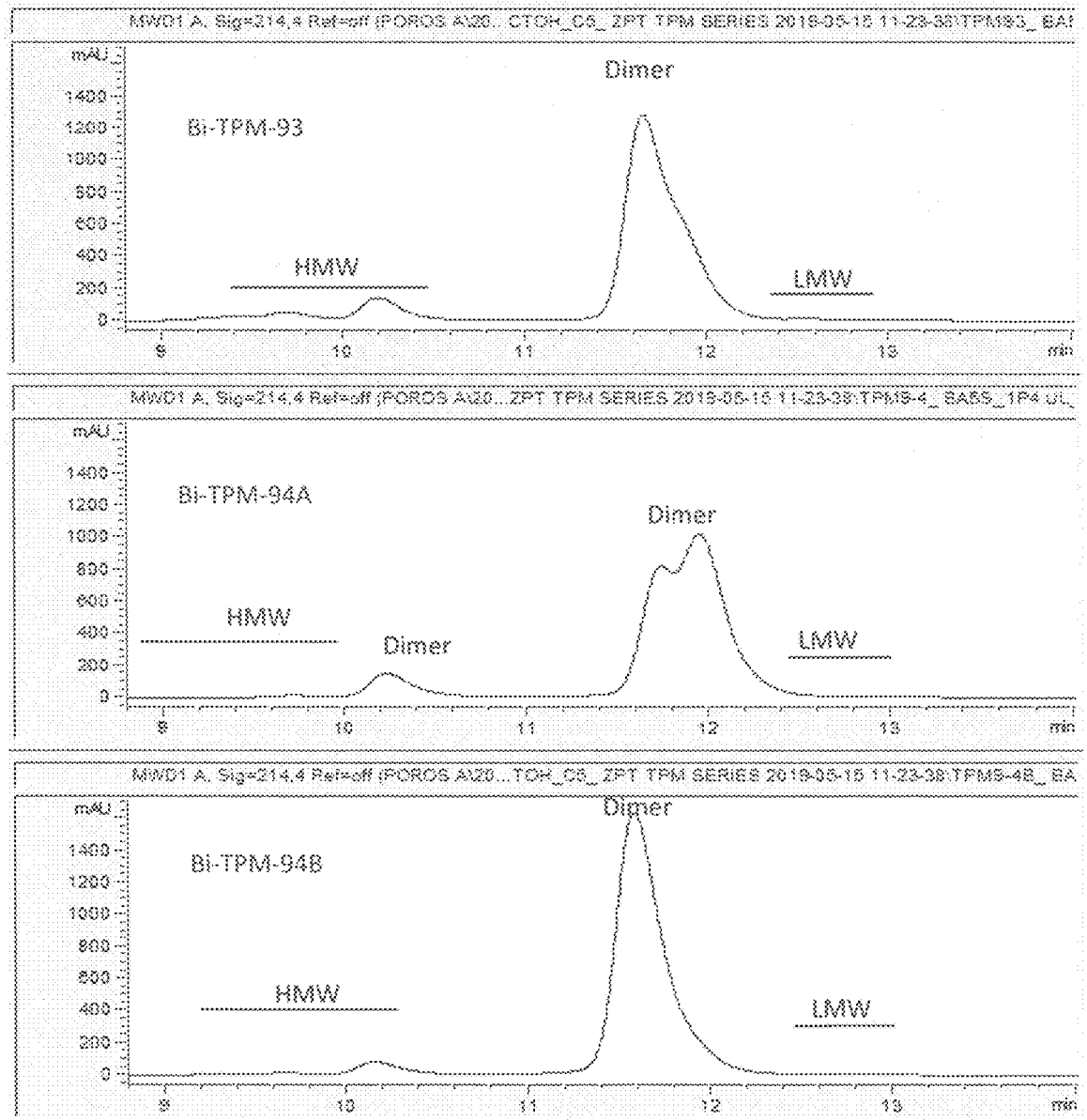
FIG. 12 shows a size-exclusion ultra-high performance liquid chromatography (SE-UHPLC) analysis illustrating species heterogeneity in Bi-TPM-93 and Bi-TPM-94, which is eliminated by linker modification in Bi-TPM-94B.

The results of this analysis (FIG. 12) unexpectedly revealed a level of species heterogeneity in Bi-TPM 93 and Bi-TPM-94A that was eliminated by linker modification in Bi-TPM-94B, i.e., increasing the length of linker from 3×G4S to 6×G4S.

To evaluate the binding affinities and kinetics of binding to His tagged human PD-1 by Bi-TPM-94A, Bi-TPM-94B, and a parental anti-PD-1 benchmark (BM) mAb, bio-layer interferometry was carried out using the Octet RED96 system (ForteBio). Briefly, 20 nM of the bispecific antagonist were loaded onto anti-human IgG capture biosensors. Association of analyte (His tagged human PD-1 protein or His tagged human TIGIT protein) was observed by placing the biosensors in wells containing serial dilution of His tagged PD-1 or His tagged TIGIT for 5 mins. Dissociation was measured after transfer of the biosensors into kinetic buffer alone and monitoring of the interferometry signal for 10 minutes. The observed on and off rates ($K_a$ and $K_d$) were fit using a 11 binding global fit model comprising at least 5 concentrations tested, followed by calculation of the equilibrium binding constant $K_D$.

Figure 13A:
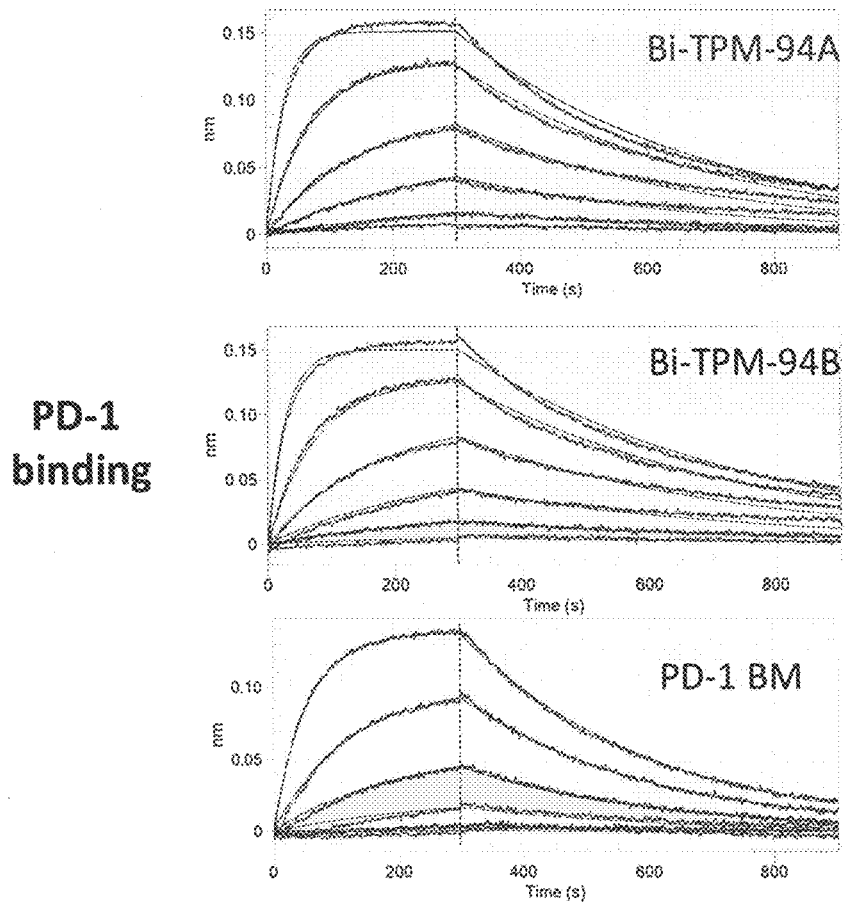
FIG. 13A shows that the binding affinities of Bi-TPM-94A and Bi-TPM-94B for PD-1 are stronger than the binding affinity of a benchmark anti-PD-1 antibody for PD-1.
Figure 13B:
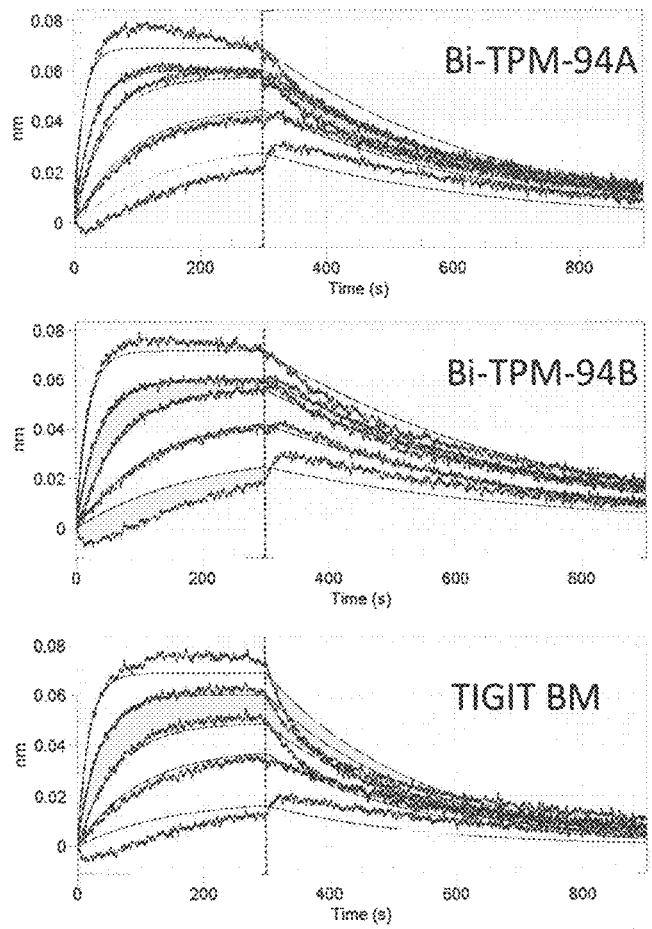
FIG. 13B shows that the binding affinities of Bi-TPM-94A and Bi-TPM-94B for TIGIT are stronger than the binding affinity of a benchmark anti-TIGIT antibody for TIGIT.

The results of this analysis in FIG. 13A show that the binding affinities of Bi-TPM-94A and Bi-TPM-94B to PD-1 are stronger than the binding affinity of a benchmark anti-PD-1 antibody to PD-1. Likewise, FIG. 13B shows that the binding affinities of Bi-TPM-94A and Bi-TPM-94A to TIGIT are stronger than the binding affinity of a benchmark anti-TIGIT antibody to TIGIT.

Figure 14A:
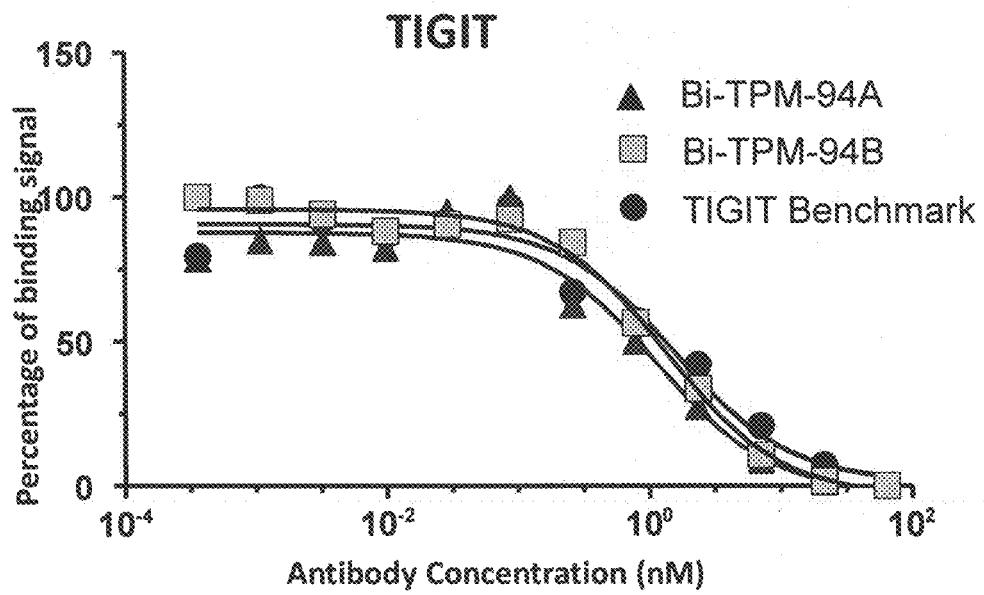
FIGS. 14A-14B show Bi-TPM-94A and Bi-TPM-94B potently block both TIGIT binding to its ligand, human PVR (CD155) (FIG. 14A) and block PD-1 binding to its ligand, PD-L1 (FIG. 14B).
Figure 14B:
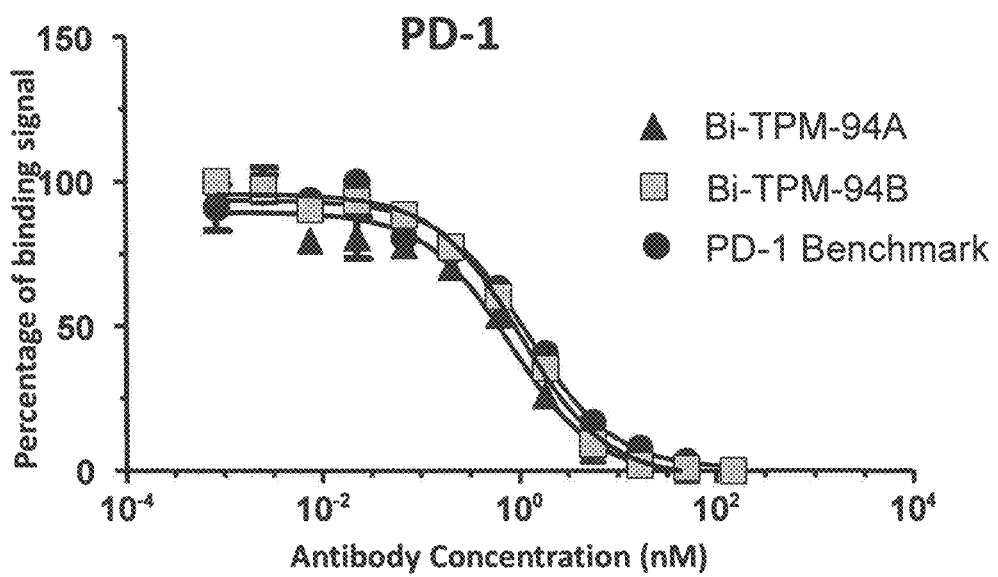

A blocking assay using CHO cells stabley expressing TIGIT and 1 ug/ml biotinylated PVR-muFc was used to compare Bi-TPM-94A and Bi-TPM-94B ability to block the binding of TIGIT to its PVR ligand TIGIT. Briefly, cells were incubated with biotinylated PVR-Fc and the Bi-TPM molecules, washed and bound PVR-muFc was detected with PE streptavidin using in the iQue Intellicyt system. FIG. 14A shows, both molecules similarly block the binding of TIGIT and PVR. Similarly, both molecules can block the binding of PD-1 to its PD-L1 ligand (FIG. 14B). The results of these assay further revealed that Bi-TPM-94A and Bi-TPM-94B exhibited IC50 values slightly better than corresponding anti-TIGIT and anti-PD-1 benchmark (BM) antibodies.

Figure 15:
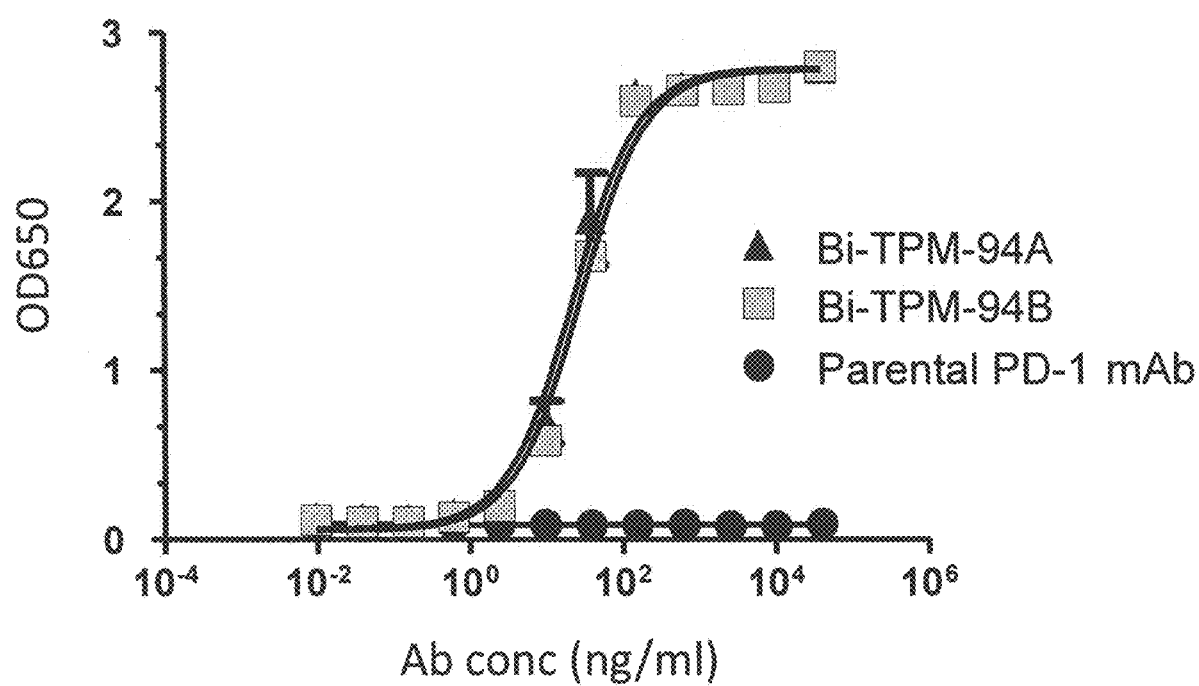
FIG. 15 shows the results of an ELISA assay demonstrating simultaneous binding of PD-1 and TIGIT by Bi-TPM-94A and Bi-TPM-94B in which huPD-1-Fc coated 96 well plates were incubated with serially diluted samples of Bi-TPM-94A and Bi-TPM-94B, followed by His-tagged huTIGIT protein, whereby bound molecules were detected using HRP-conjugated anti-His tag Ab and TMB substrate.

To determine whether Bi-TPM-94A and Bi-TPM-94B can bind both PD-1 and TIGIT simultaneously, huPD-1-Fc-coated (5 μg/ml) 96 well ELISA plates were blocked with 1% BSA in PBS and incubated for 2 hours with serial dilutions of the anti-PD-1/anti-TIGIT bi-specific antibodies, followed by addition and incubation for 2 hours with His-tagged huTIGIT protein. After washing, HRP conjugated anti-His tag Ab and TMB substrate were added as detection agents and quantified with a Perkin Elmer multimode plate reader. The results of this assay in FIG. 15 show simultaneous binding of PD-1 and TIGIT by Bi-TPM-94A and Bi-TPM-94B.

To evaluate the ability of Bi-TPM-94B to induce IFN-7 production, 250,000 human PBMCs from donors screened for CMV antigen reactivity, i.e., Donor 287 (FIG. 16A) and Donor 401 (FIG. 16B) were stimulated with 0.1 μg/ml of CMV-infected cell lysates (lanes 2-7) to stimulate CMV reactive T cells or not stimulated with CMV-infected cell lysates (lane 1). Shp-77 cells were co-cultured with the PBMCs to provide an immune function inhibitory environment and further incubated with human IgG (lane 3), parental anti-TIGIT mAb B21-35 (lane 4), parental anti-PD-1 mAb 2P17 (lane 5), parental anti-TIGIT mAb B21-35 in combination with parental anti-PD-1 mAb 2P17 (lane 6), or Bi-TPM-94B (lane 7). 5 days later, cell culture supernatants were examined for IFN-7 production by ELISA.

Figure 16A:
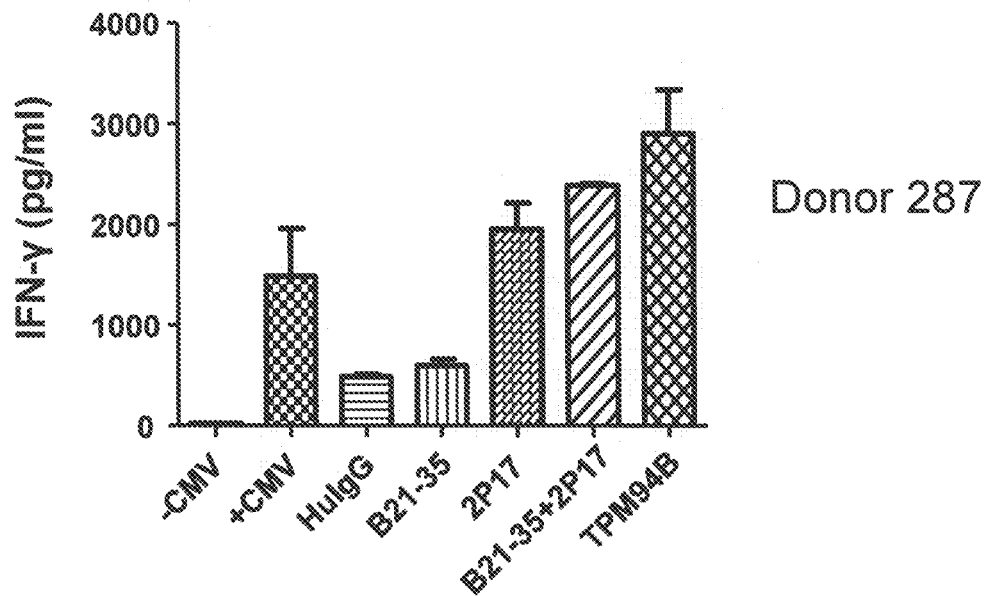
FIGS. 16A-16B show increased IFN-7 secretion from human PBMCs (Donor 287, FIG. 16A; Donor 401, FIG. 16B) with Bi-TPM-94B relative to the individual or combination of parental anti-PD-1 and anti-TIGIT antibodies, as well as the negative controls.
Figure 16B:
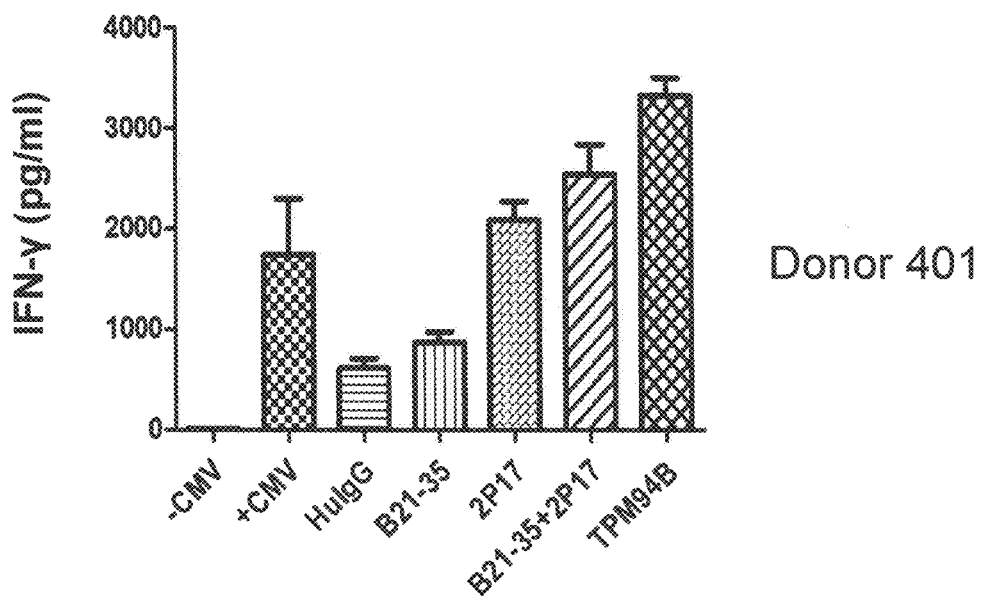

The results of this analysis in FIGS. 16A-16B show increased IFN-7 secretion from human PBMCs (Donor 287, FIG. 16A; Donor 401, FIG. 16B) with Bi-TPM-94B relative to the monospecific parental mAbs or the combination of monospecific parental anti-PD-1 and anti-TIGIT antibodies, as well as the negative controls.

To evaluate the ability of Bi-TPM-94B to induce T cell proliferation, 250,000 human PBMCs from the Donor 287 (FIG. 17A) and Donor 401 (FIG. 17B) were stimulated with 0.1 μg/ml of CMV-infected cell lysates for 2 days to stimulate CMV reactive T cells and then labeled with carboxyfluorescein succinimidyl ester (CFSE). The CFSE-labeled PBMCs were then co-cultured with Shp-77 cells to provide an immune function inhibitory environment and further incubated with human IgG (lane 1), parental anti-TIGIT mAb B21-35 (lane 2), parental anti-PD-1 mAb 2P17 (lane 3), parental anti-TIGIT mAb B21-35 in combination with parental anti-PD-1 mAb 2P17 (lane 4), or Bi-TPM-94B (lane 5). 5 days later, CSFE signal on CD3+ T cells were analyzed with an iQue intellicyt system and a proliferation index was calculated, based on the loss of CFSE signal.

Figure 17A:
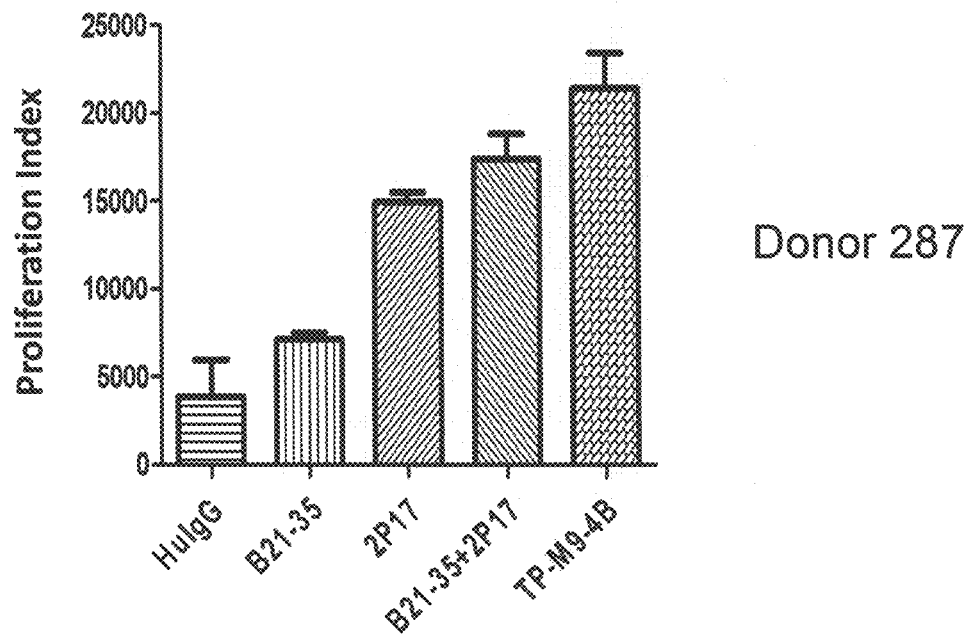
FIGS. 17A-17B show that Bi-TPM-94B enhances proliferation of primary human T cells from Donor 287 PBMCs (FIG. 17A) and Donor 401 PBMCs (FIG. 17B) to a greater extent than the individual or combination of parental anti-PD-1 and anti-TIGIT antibodies, as well as the negative controls.
Figure 17B:
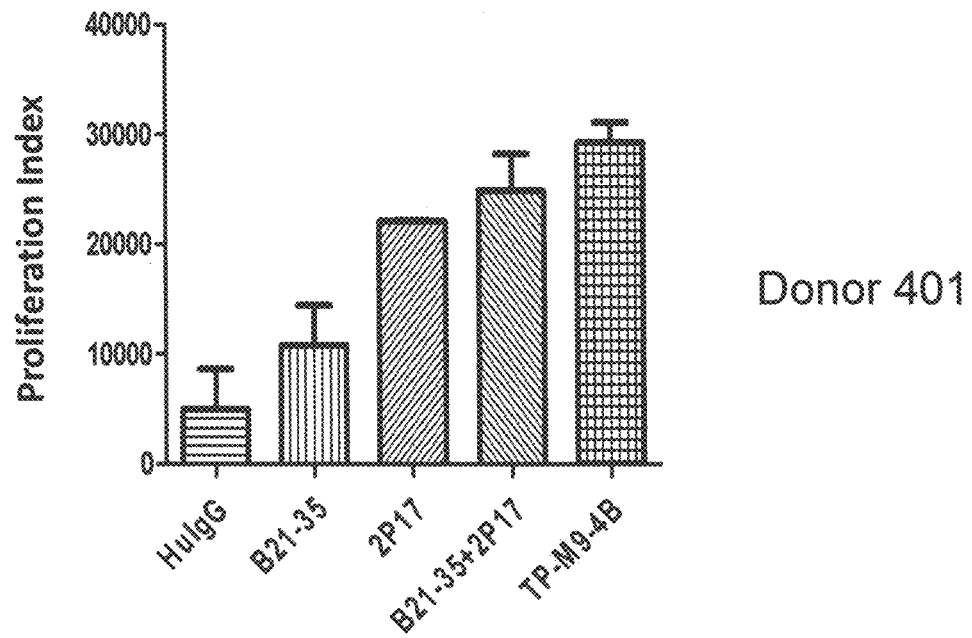

The results of this analysis in FIGS. 17A-17B show that Bi-TPM-94B enhances proliferation of primary human T cells from Donor 287 PBMCs (FIG. 17A) and Donor 401 PBMCs (FIG. 17B) to a greater extent than the individual or combination of parental anti-PD-1 and anti-TIGIT antibodies, as well as the negative controls.

To evaluate the pharmacokinetic properties of Bi-TPM-94A and Bi-TPM-94B in vivo, a pharmacokinetic profile was generated. Briefly, 10 mg/kg of Bi-TMP-94A or Bi-TPM-94B was intravenously injected into the tail vein of 6-10 week old female CD1 mice (n=2 mice). Serum was harvested at 3 minutes, 3 hours, 1 day, 3 days, 7 days and 10 days post injection. To detect the antibodies in the serum, 96 well ELISA plates were coated with 5 μg/ml goat anti-human IgG (Fc specific) F(ab')2 fragment (Sigma, #SAB3701274) and then blocked with 5% milk in PBS. Following the blocking step, both the mouse serum and purified Bi-TPM-94A or Bi-TPM-94B molecules (as a standards) were serially diluted in 5% milk, and were then added to the plate and incubated for 2 hr. After the incubation, the wells were washed and then incubated with Peroxidase AffiniPure Mouse Anti-Human IgG Fcγ Fragment Specific (Jackson ImmunoResearch #209-035-098) and TMB-ELISA Substrate Solution (Thermo Scientific #34029) and quantified by OD650 signal with a Perkin Elmer multimode plate reader.

Figure 18:
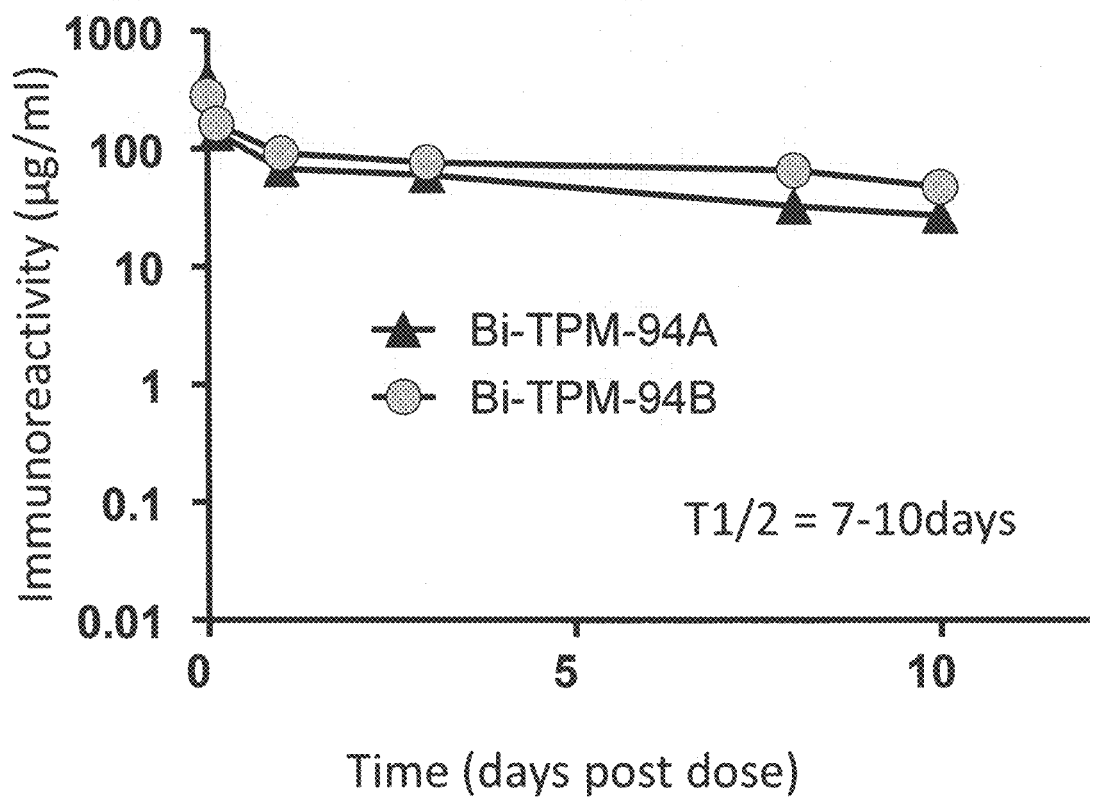
FIG. 18 is a pharmacokinetic profile showing that Bi-TPM-94A and Bi-TPM-94B have similar in vivo half-lives ($T_{1/2}$) following a tail vein injection into 6-10 week old female CD1 mice. The bispecific antagonists were recovered from serum taken at various times post-injection and subjected to analysis by ELISA.

The results of this analysis in FIG. 18 showed that the half-life (Tvz) of the bispecific antagonist Bi-TPM-94A and Bi-TMP-94B are 7-10 days. Thus, the Bi-TPM-94A and B molecules have the improved property of higher affinity binding as compared to Bi-TPM-93, and Bi-TPM-94B, with the extended G4S linker in the anti-TIGIT scfv, is further improved as compared to Bi-TPM-93 and Bi-TPM-94A with regards to homogeneity.

Example 4: Identification and Functional Characterization of Anti-LAG-3 Monoclonal Antibodies In another aspect, the present application relates to the screening and characterization of monoclonal antibodies or the antigen-binding portions thereof that specifically bind to the human immune checkpoint regulator, LAG-3. FIG. 19A shows the heavy chain CDR1, CD2 and CDR3 sequences corresponding to the anti-LAG-3 mAbs 2L2A.1, 2L2A.6, 2L27B and 3L1A that were isolated. FIG. 19B shows the light chain CDR1, CD2 and CDR3 sequences corresponding to the anti-LAG-3 mAbs 2L2A.1, 2L2A.6, 2L27B and 3L1A. FIG. 20 shows the VH and VL sequences of anti-LAG-3 mAbs 2L2A.1, 2L2A.6, 2L27B and 3L1A.

Figure 21A:
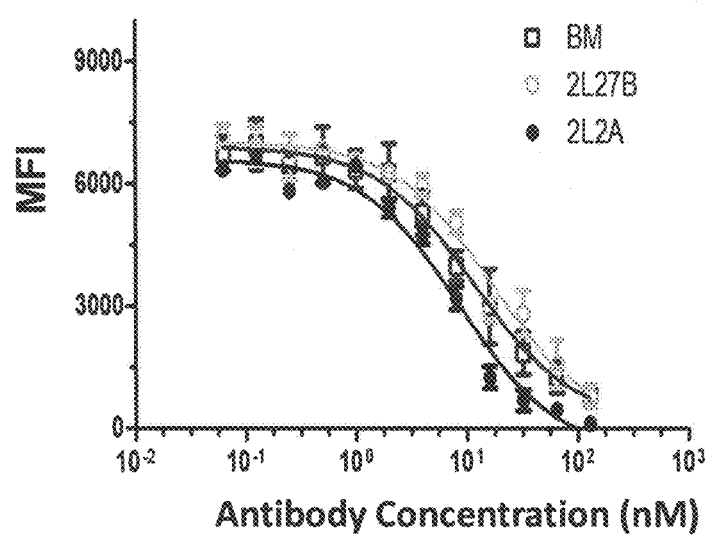
FIGS. 21A-21B show the results of assays confirming the ability of the anti-LAG-3 mAbs to block LAG-3 binding.
Figure 21B:
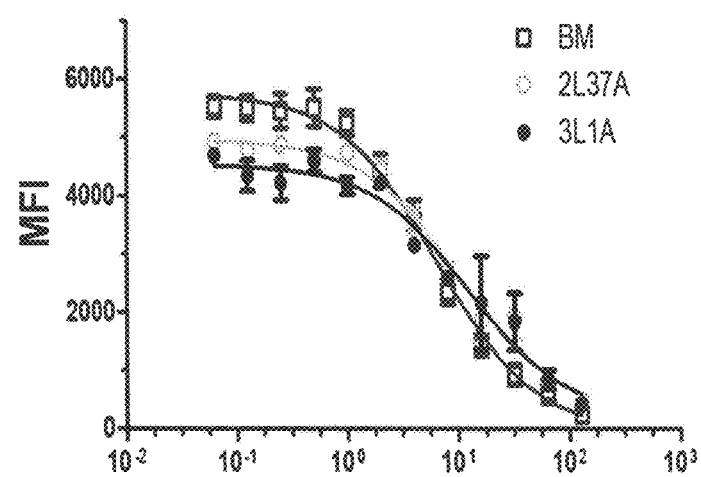

A blocking assay was carried out to show that the mAbs 2L2A and 2L27B (FIG. 21A) and 2L37A and 3L1A (FIG. 21B) to block the interaction between human LAG-3 and its major ligand, major histocompatibility complex II (MHC II) antigen expressed on Raji cells. Briefly, 2-fold serial dilutions of the mAbs 2L2A and 2L27B (FIG. 21A) and 2L37A and 3L1A (FIG. 21B) were prepared. The serial dilutions and human LAG-3-huFc were incubated for 30 mins at room temperature and then added to Raji cells and further incubated for 30 minutes on ice. Then, Raji cells were washed and LAG-3-huFc binding on Raji cells was detected with anti-human IgG PE. Cells were fixed prior to analysis with an iQue Intellicyt system. The results of this analysis in FIGS. 21A-21B confirm the ability of the mouse anti-LAG-3 mAbs to block the interaction between LAG-3 and its major ligand, major histocompatibility complex II (MHC II) antigen to a degree comparable to that of an anti-LAG-3 benchmark (BM) mAb.

The above-described blocking assay was further used to calculate IC50 values reflecting inhibition of binding of LAG-3 to MHC II by anti-LAG-3 antibodies, specifically, a humanized anti-LAG-3 variant, 2L2A.1, an anti-LAG-3 benchmark (BM) antibody (BMS-986016, Bristol-Myers Squibb), and a chimeric 2L2A antibody comprising mouse 2L2A CDRs in a human Ig.

Figure 22:
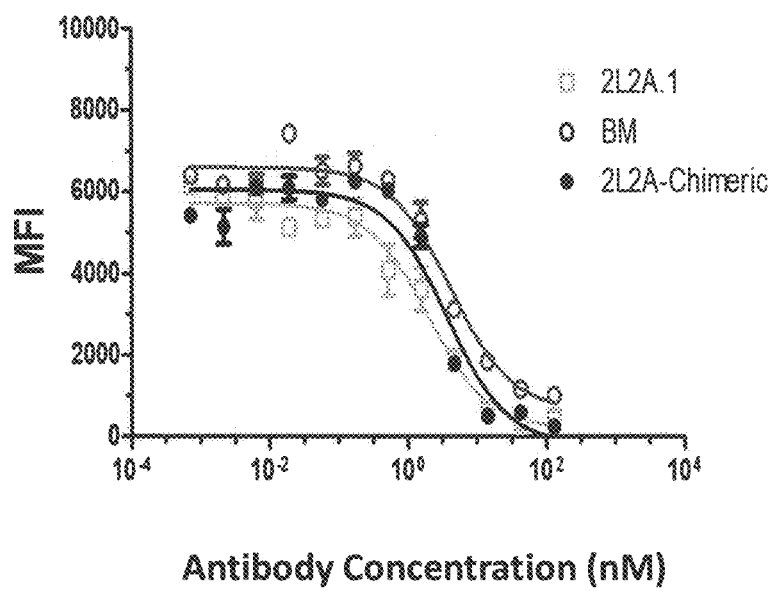
FIG. 22 shows the results of a cell-based blocking assay measuring the ability of the anti-LAG-3 mAb 2L2A.1, a benchmark (BM) anti-LAG-3 mAb, and a chimeric 2L2A antibody (SEQ ID NOS: 203 and 204) to block the interaction between LAG-3-muFc and its major ligand, major histocompatibility complex (MHC) antigen expressed on Raji cells. The assay data was used to calculate IC50 values (nm) depicted.

The results of these assay in FIG. 22 show that the humanized anti-LAG-3 mAb 2L2A.1 is a better blocker than the the BM mAb and the chimeric 2L2A antibody comprising mouse 2L2A CDRs in a human Ig as reflected in the lower IC50 value obtained.

Figure 23A:
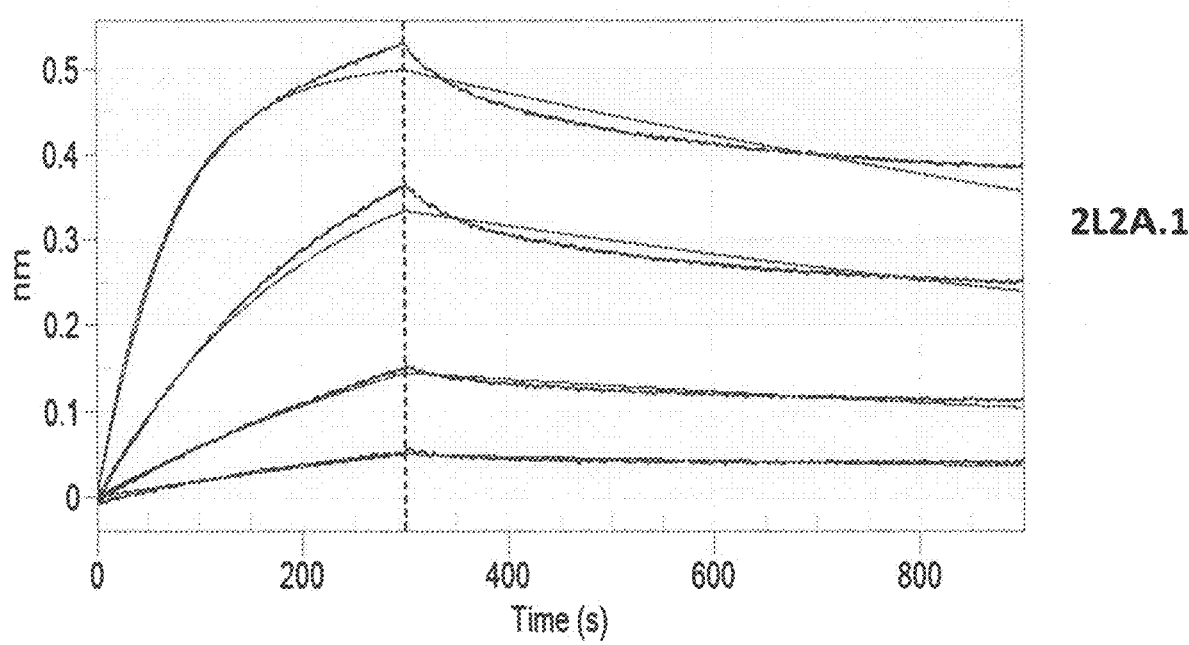
FIGS. 23A-23B show affinity analysis of anti-LAG-3 2L2A.1 mAb for binding human LAG-3-His (FIG. 23A) or human LAG-3-mIgG2a (FIG. 23B) as determined by surface plasmon resonance (SPR), along with corresponding binding affinity constants.
Figure 23B:
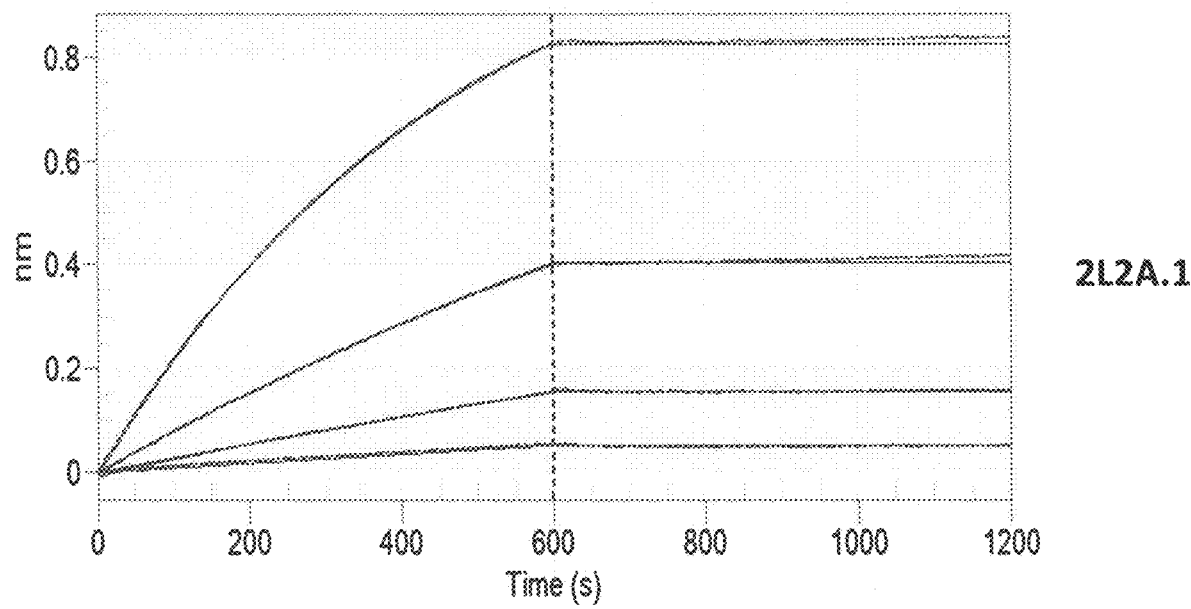

To evaluate the binding affinities and kinetics of binding to His tagged human LAG-3 by the anti-LAG-3 mAb 2L2A.1, bio-layer interferometry was carried out using the Octet RED96 system (ForteBio), essentially as described above in Example 3 above with reference to FIGS. 13A-13B as determined by surface plasmon resonance (SPR), along with corresponding binding affinity constants. FIG. 23A shows the binding affinities of the humanized 2L2A.1 antibody to His-tagged human LAG-3. FIG. 23B similarly shows the binding affinity constants for binding of the humanized 2L2A.1 antibody to human LAG-3 fused to mouse IgG2a (huLAG-3-mIgG2a).

Figure 24:
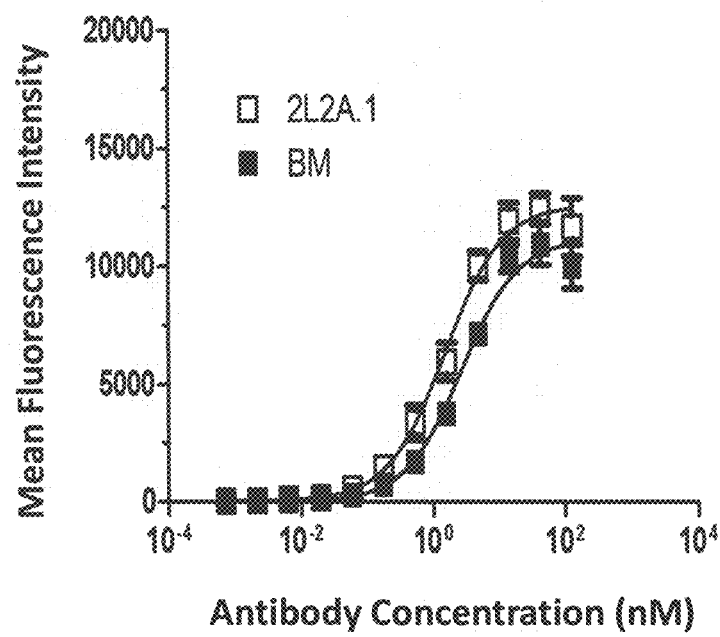
FIG. 24 depicts the binding of anti-LAG-3 mAb variant, 2L2A.1 or a benchmark antibody (BM) to LAG-3, including the half maximal effective concentrations ($EC_{50}$) producing a response halfway between the baseline and the maximum.

To further evaluate the ability of 2L2A.1 to bind human LAG-3, serial dilutions of 2L2A.1 or a LAG-3 benchmark (BM) antibody were added to CHO-K1 cells (20,000 cells/well) expressing human LAG-3. The mixtures were incubated at 4° C. for 20 min, washed 3 times, and stained with the secondary antibody, PE labeled F(ab')2-Goat anti-human IgG Fc (Thermo Scientific #H10104) by incubation at 4° C. for 20 min. Cells were washed and resuspended in 7AAD solution and fixed in 10% neutral buffered formalin solution for 15 minutes before analysis with the iQue Intellicyt system. Corresponding EC50 values reflecting the half maximal effective concentrations ($EC_{50}$) producing a response halfway between the baseline and maximum response with respect to binding human LAG-3 were also determined. As shown in FIG. 24, the results show that 2L2A.1 has a higher affinity of binding for human LAG-3 than the BM antibody.

Figure 25:
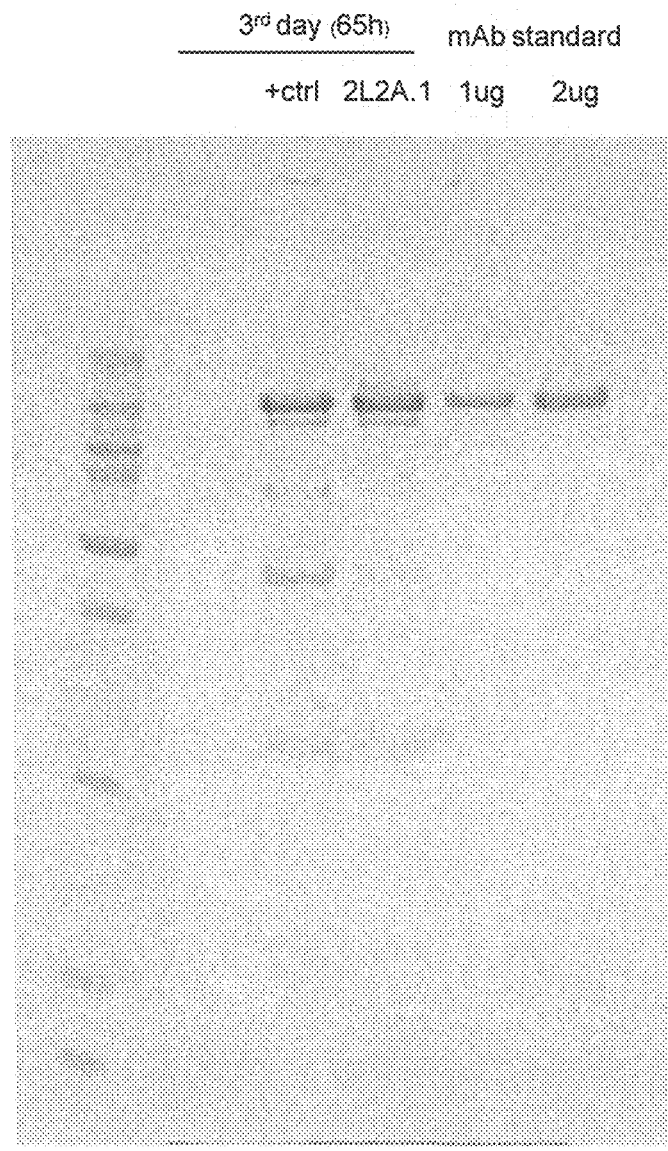
FIG. 25 shows a non-denaturing polyacrylamide gel (PAGE) analysis of humanized anti-LAG-3 mAb variant 2L2A.1 transiently expressed by HEK293. The positive control is HybPL1 (1PL 11 CDRg-VH:1PL25 CDRg-VL).

FIG. 25 shows a non-denaturing polyacrylamide gel (PAGE) analysis demonstrating robust expression of humanized anti-LAG-3 mAb variant 2L2A.1 in transiently expressed human embryonic kidney (HEK) 293 cells as compared to a control (ctrl) antibody.

Figure 26:
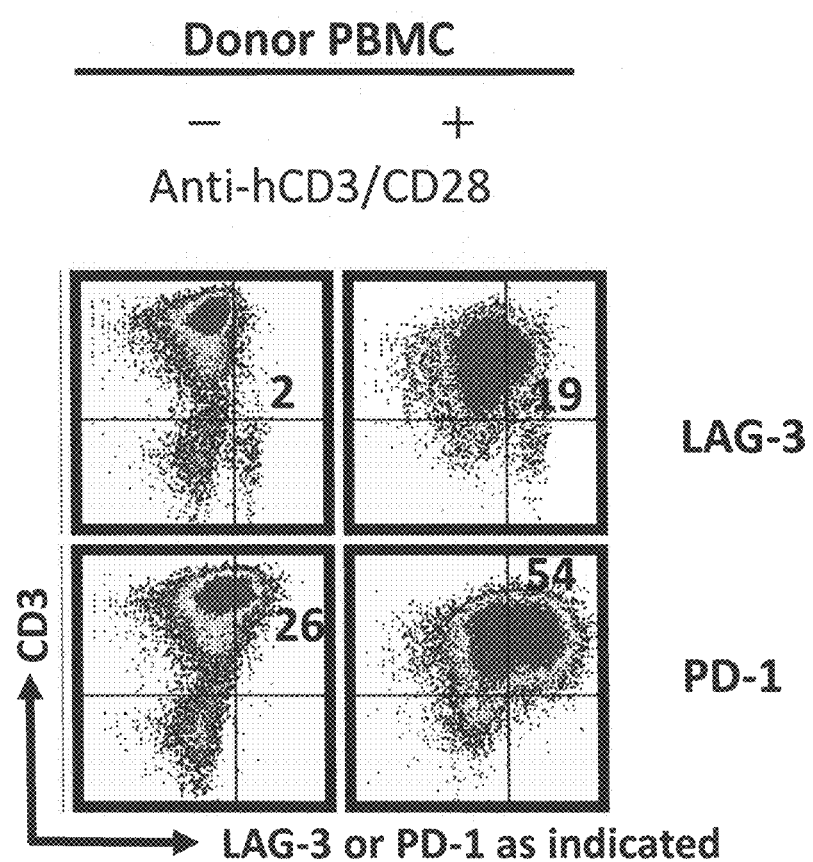
FIG. 26 is a FACS analysis showing co-expression of LAG-3 and PD-1 in activated human CD3$^+$ T cells.

To evaluate whether LAG-3 and PD-1 are coexpressed in activated human CD3+ T cells, FACS analysis was carried out on donor PBMCs activated with anti-human CD3/CD28. The results of this analysis in FIG. 26 confirmed the co-expression of LAG-3 and PD-1 by human PBMCs activated with Staphylococcal enterotoxin B (SEB).

Figure 27A:
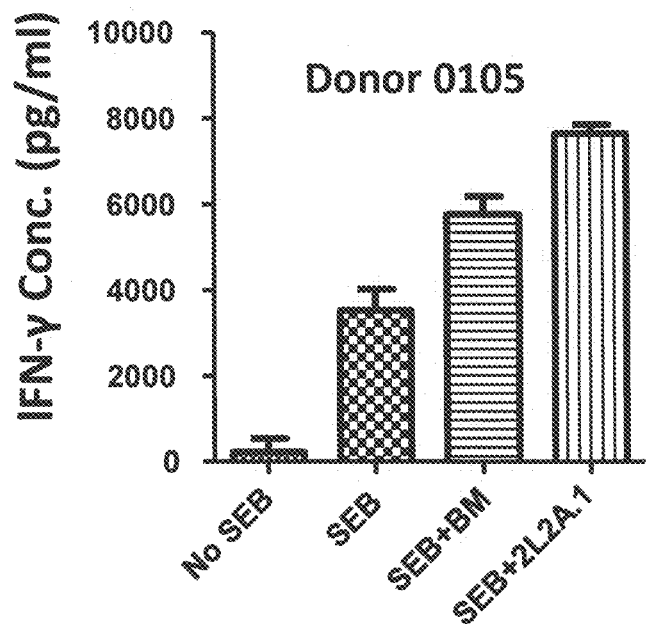
FIGS. 27A-27B show IFN-7 production, PBMCs from two donors (Donor 0105, FIG. 27A; Donor 0817, FIG. 27B) were stimulated with Staphylococcal enterotoxin B (SEB; lanes 2-4) or not stimulated with SEB (lane 1) in a 96 well plate. Following stimulation, the donor PBMCs were incubated with: no antibody (lanes 1, 2), an anti-LAG-3 benchmark (BM) antibody (lane 3), or the anti-LAG-3 mAb, 2L2A.1. The results of this assay showed that 2L2A.1 induces more IFN-7 production in both donor PBMCs than the anti-LAG-3 benchmark antibody.
Figure 27B:
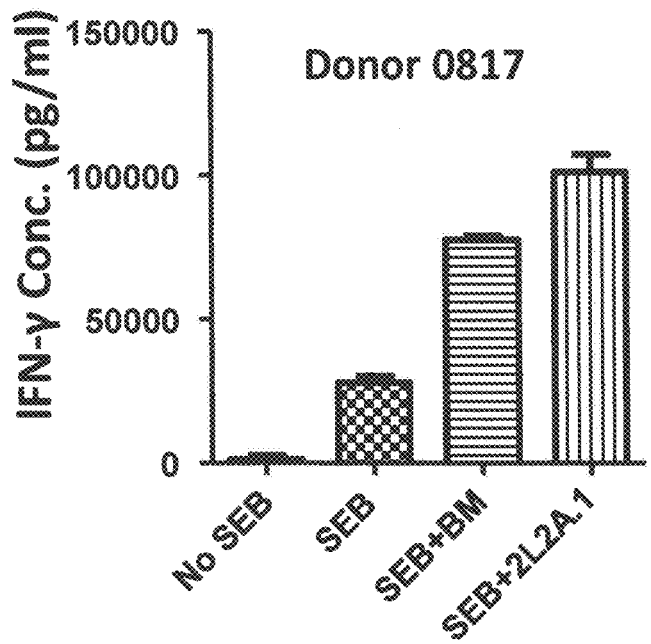

To evaluate the ability of 2L2A.1 to induce IFN-γ production, 100,000 human PBMCs from two donors, i.e., Donor 0105 (FIG. 27A) and Donor 0817 (FIG. 27B) were plated on a 96-well ELISA plate. PBMCs were either not stimulated (lane 1) or stimulated with 0.5 µg/ml of Staphylococcal enterotoxin B (SEB; lanes 2-4). To the stimulated cells, Benchmark (BM) anti-LAG-3 mAb (lane 3), the 2L2A.1 mAb (lane 4), or an isotype-matched control antibody (lane 2), were added and incubated at 37° C. for 5 days. Cell culture supernatants were then examined for IFN-7 production by ELISA. The results in FIGS. 27A-27B show increased IFN-7 secretion from both human donor PBMCs with 2L2A.1 relative to the anti-LAG-3 BM.

Figure 28A:
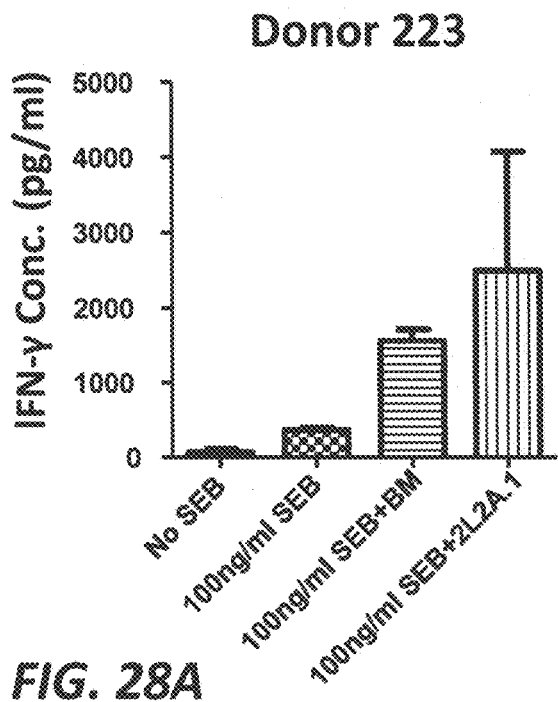
FIGS. 28A-28C show increased IFN-7 production from three donor human PBMCs (Donor 223, FIG. 28A; Donor 224, FIG. 28B; Donor 225, FIG. 28C) stimulated with SEB (lanes 2-4) or not stimulated with SEB (lane 1). In addition, the donor PBMCs were incubated with: no antibody (lanes 1, 2), an anti-LAG-3 benchmark (BM) antibody (lane 3) or with the anti-LAG-3 mAb 2L2A.1.
Figure 28B:
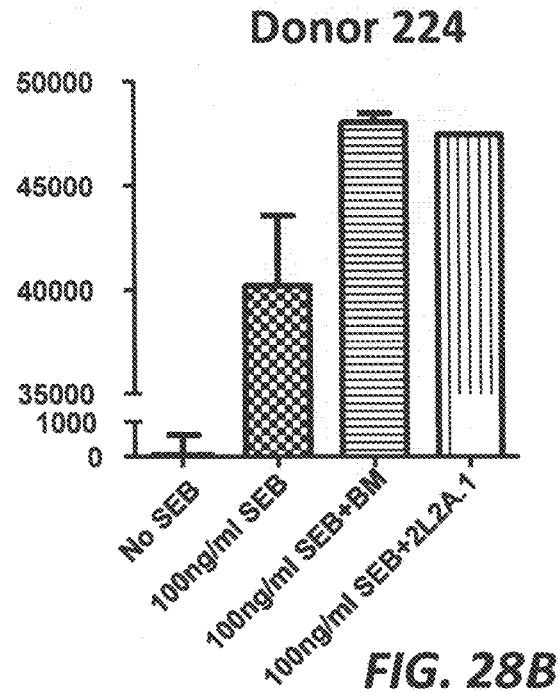
Figure 28C:
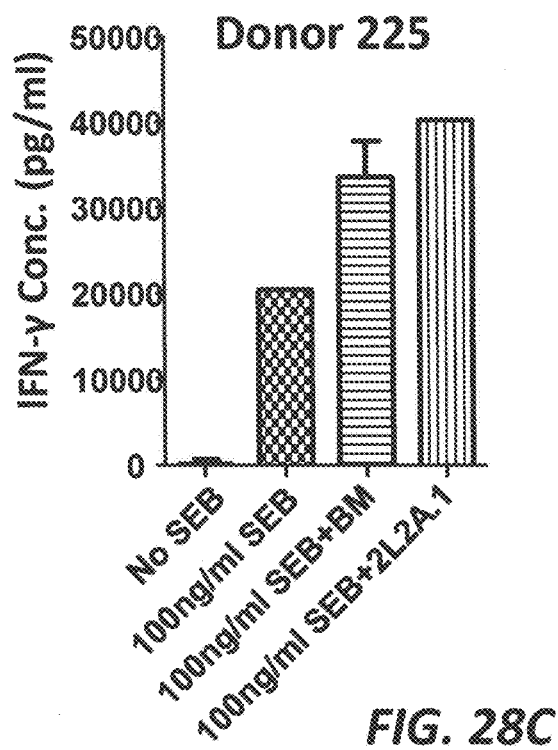
Figure 29A:
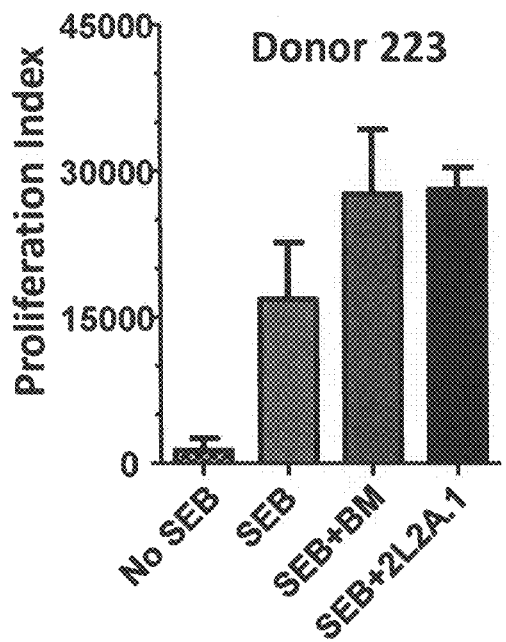
FIGS. 29A-29C show that the anti-LAG-3 mAb 2L2A.1 enhances proliferation of primary human T cells from Donor 223 (FIG. 29A), Donor 224 (FIG. 29B) and Donor 225 (FIG. 29C) to a greater extent than the benchmark anti-LAG-3 antibody.
Figure 29B:
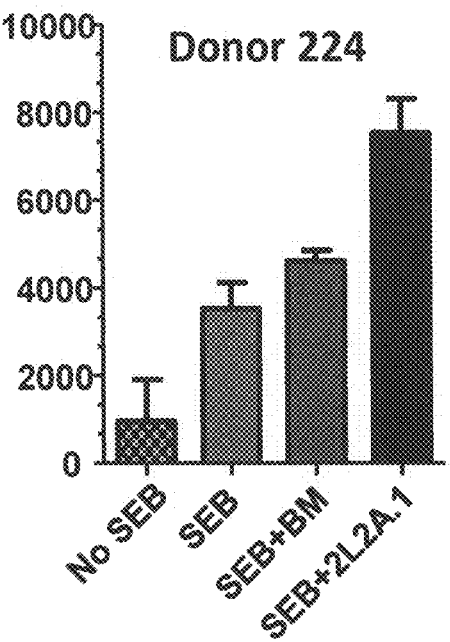
Figure 29C:
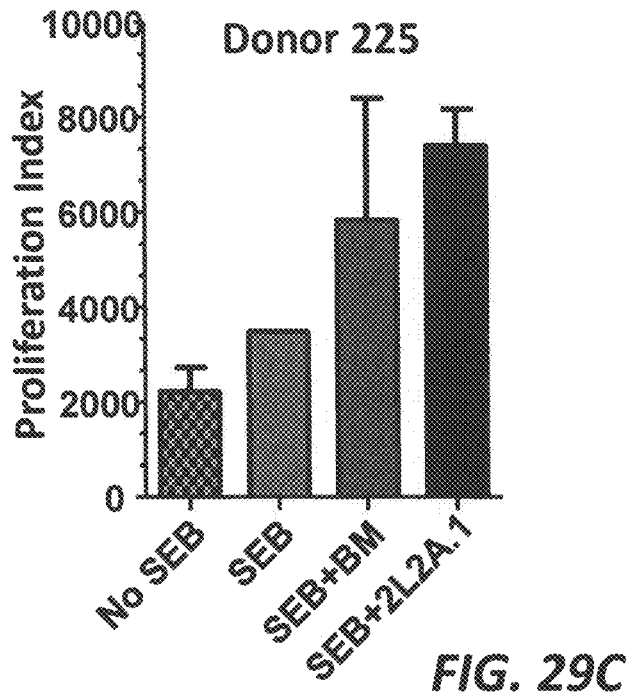

A similar analysis was done, but also assessed proliferation of the PBMCs with 3 additional donor PBMCs, Donor 223 (FIG. 28A), Donor 224 (FIG. 28B), and Donor 225 (FIG. 28C). The results in FIGS. 28A-28B further establish increased IFN-7 secretion from human donor PBMCs with 2L2A.1 relative to the anti-LAG-3 BM. To assess proliferation, the 3 donor PBMCs were labeled with CSFE, stimulated with 100 ng/ml SEB, and Benchmark (BM) anti-LAG-3 mAb (lane 3), the 2L2A.1 mAb (lane 4), or an isotype-matched control antibody (lane 2), were added. The PBMC mixtures were incubated at 37° C. for 5 days, and loss of CFSE signal on CD4 T cells were quantified by FACS to generate a Proliferation Index. The results shown in FIGS. 29A and 29B establish that 2L2A.1 can induce more primary T cell proliferation than a benchmark (BM) anti-LAG-3 mAb.

Example 5: Design and Functional Characterization of Bispecific Anti-LAG-3/Anti-TIGIT scFv Antagonist Based on the design and characterization of the bispecific anti-PD-1/anti-TIGIT scFv described in Example 1, it was of interest to evaluate whether the benefits in manufacturability and functionality of this design can be extended to an analogous bispecific anti-LAG-3/anti-TIGIT scFv design. FIGS. 30A-30B depict two exemplary bispecific antitumor antagonists, Bi-LT-1, with the extended scfv linker 4×G4S (FIG. 30A) and Bi-LT-3, with the extended scfv linker 6×G4S (FIG. 30B). FIG. 31 summarizes the arrangement of functional domains in the bispecific antagonists depicted in FIGS. 30A-30B. FIG. 32 show the heavy chain (HC) and light chain (LC) amino acid sequences corresponding to the bispecific antagonists depicted in FIGS. 30A-30B.

To evaluate the ability of the bispecific antitumor antagonists, Bi-LT-1 and Bi-LT-3 to block the interaction between TIGIT and its ligand, human PVR (CD155), and additionally block the interaction between LAG-3 and its major ligand, major histocompatibility complex II (MHC II) antigen, cell-based blocking assays were carried as follows.

Figure 33A:
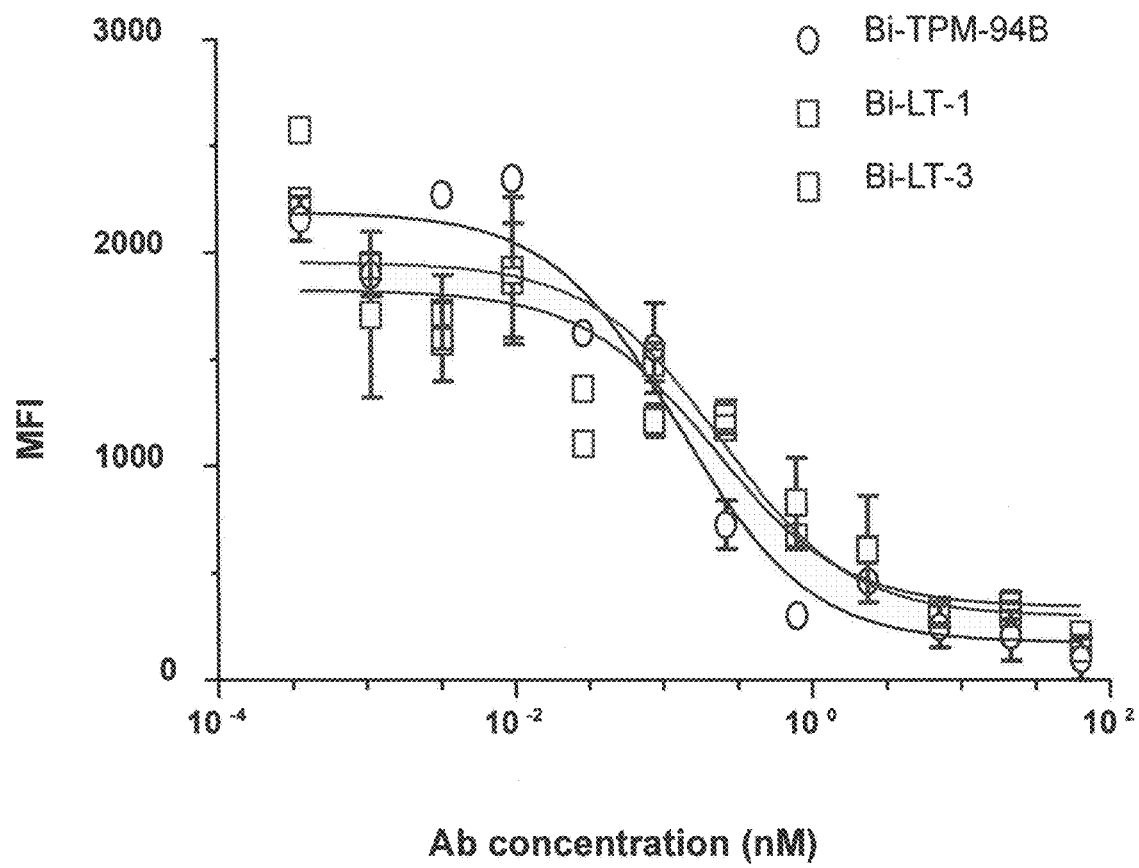
FIGS. 33A-33B shows the results of a cell-based blocking assay measuring the ability of the bispecific antagonists, LT-1 and LT-3, and the bispecific antagonist, Bi-TPM-94B or an anti-LAG-3 benchmark mAb to block the interaction between LAG-3-muFc and its major ligand, major histocompatibility complex (MHC) antigen expressed on Raji cells (FIG. 33A) or block the interaction between TIGIT and its ligand, human PVR (CD155) (FIG. 33B). The assay data was used to calculate IC50 values (nm) depicted.

Briefly, to show that Bi-LT-1 and Bi-LT-3 can block the interaction between TIGIT and its ligand, human PVR (CD155), a cell-based blocking assay was carried out in which serial dilutions of Bi-LT-1, Bi-LT-3, or Bi-TPM-94B (described in Example 1 above) were incubated with human TIGIT-transfected CHOKI cells and CD155/PVR-mouse IgG2a for 30 minutes on ice. CD155/PVR-mouse IgG2a binding on CHOKI cells was detected with anti-mouse IgG PE. Cells were fixed prior to analysis with an iQue intellicyt system. The results from this assay are shown in FIG. 33A and reveal that Bi-LT-1 and Bi-LT-3, with the extended scfv linkers retain their bioactivity for TIGIT.

Figure 33B:
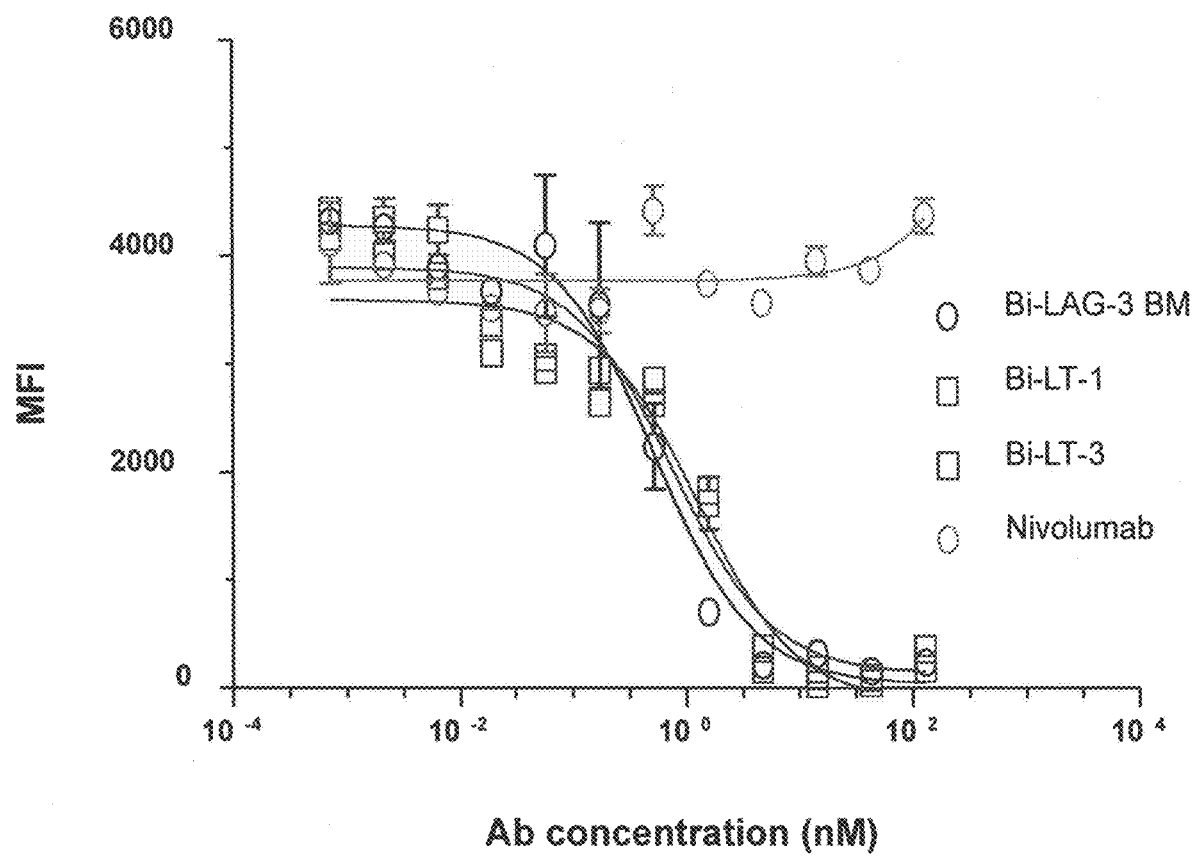

To show that the bispecific antitumor antagonists, Bi-LT-1 and Bi-LT-3 can also block the interaction between LAG-3 and its major ligand, major histocompatibility complex II (MHC II) antigen a cell-based blocking assay was carried out in which serial dilutions of Bi-LT-1, Bi-LT-3, or an anti-LAG-3 benchmark (BM) antibody were incubated with LAG-3-mouse IgG2a for 30 mins at room temperature, added to Raji cells, and further incubated for 30 minutes on ice. The Raji cells were then washed, and LAG-3-mouse IgG2a binding on Raji cells was detected with anti-mouse IgG PE. Cells were fixed prior to analysis with an iQue intellicyt system. The results of this assay are shown in FIG. 33B indicate that Bi-LT-1 and Bi-LT-1 retain their bioactivity for LAG-3 similar to the benchmark anti-LAG3 antibody. The assay data was further used to calculate IC50 values (nm) depicted, which are comparable to the IC50 value for the anti-LAG-3 benchmark (BM) antibody. Taken together, the results in FIGS. 33A and 33B establish that Bi-LT-1 and Bi-LT-3 retain their bioactivity for both TIGIT and LAG-3.

Figure 34:
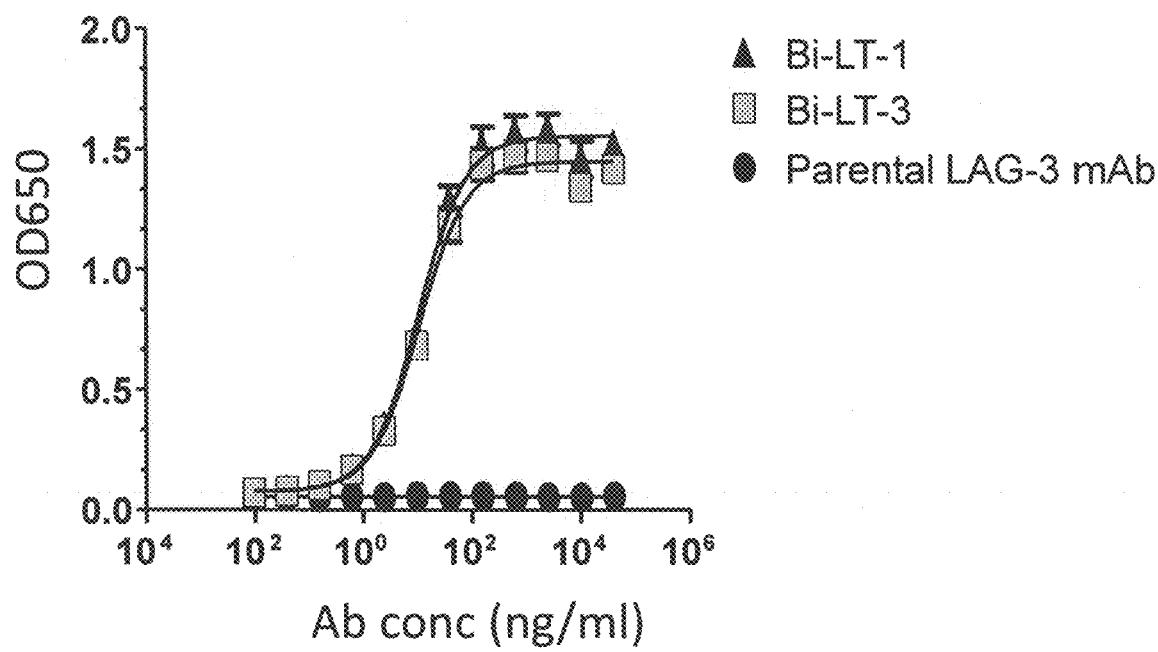
FIG. 34 shows the results of an ELISA assay demonstrating simultaneous binding of LAG-3 and TIGIT by Bi-LT-1, Bi-LT-3 or the parental anti-LAG-3 mAb in which LAG-3-muFc coated 96 well plates were incubated with serially diluted samples of Bi-LT-1, Bi-LT-3 or the parental anti-LAG-3 mAb, followed by His-tagged huTIGIT protein, whereby bound molecules were detected using HRP-conjugated anti-His tag HRP and TMB substrate. The assay data was used to calculate EC50 values (nm) depicted.
Figure 35A:
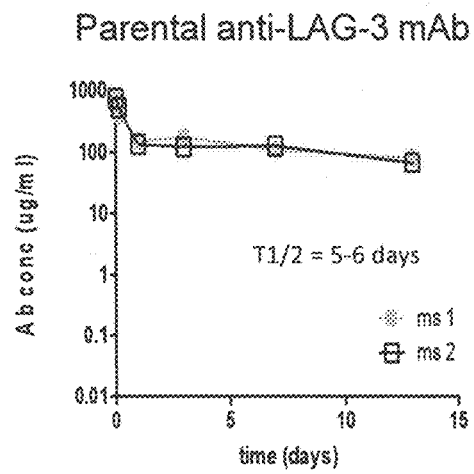
FIGS. 35A-35D depict pharmacokinetic profiles and in vivo half-lives ($T_{1/2}$) corresponding to the parental anti-LAG-3 mAb (FIG. 35A), an anti-LAG-3 benchmark mAb (FIG. 35B), Bi-LT-1 (FIG. 35C), or Bi-LT-3 (FIG. 35D) following a tail vein injection into 6-10 week old female CD1 mice. The antibodies and bispecific antagonists were recovered from serum taken at various times post-injection and subjected to analysis by ELISA. The $T_{1/2}$ for parental anti-LAG-3 mAb, Bi-LT-1 and Bi-LT-3 are five to six days, the $T_{1/2}$ for anti-LAG-3 BM mAb is either 2 days (mouse 3) or 7 days (mouse 4).
Figure 35B:
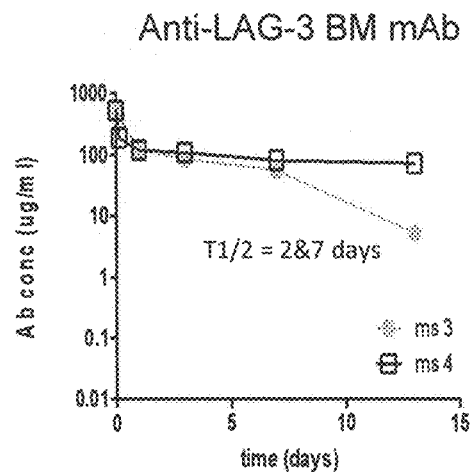
Figure 35C:
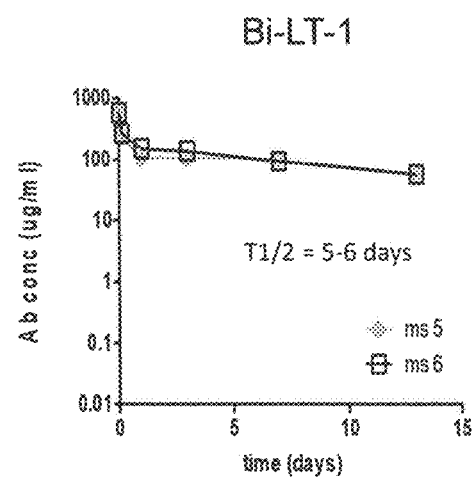
Figure 35D:
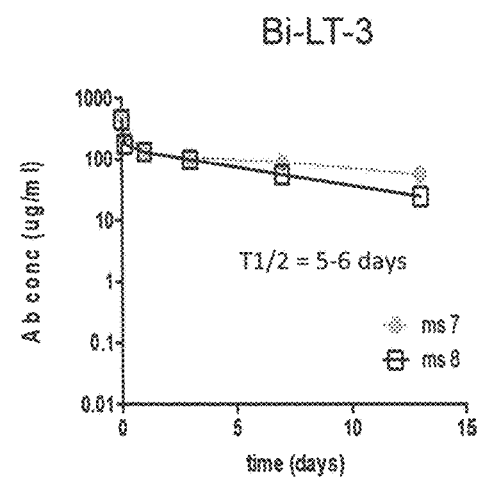

To see whether Bi-LT-1 and Bi-LT-3 can simultaneously bind both LAG-3 and TIGIT, 5 µg/ml LAG-3-mIgG was coated on an ELISA plate at 4° C. overnight and then blocked before adding serial dilutions of LT-1, LT-3 or a parental LAG-3 mAb. Following a 1 hr incubation at room temperature, the plate was washed and 500 ng/ml His tagged HuTIGIT was added and incubated for 1 hr at room temperature. Plate bound His tagged HuTIGIT was then detected using anti-His tag HRP and a TMB substrate. This results of this assay in FIG. 34 demonstrate that Bi-LT-1 and Bi-LT-3 can simultaneously bind both LAG-3 and TIGIT.

FIGS. 35A-35D depict pharmacokinetic profiles and in vivo half-lives ($T_{1/2}$) corresponding to the parental anti-LAG-3 mAb (FIG. 35A), an anti-LAG-3 benchmark mAb (FIG. 35B), Bi-LT-1 (FIG. 35C), or Bi-LT-3 (FIG. 35D) following a tail vein injection into 6-10 week old female CD1 mice. The antibodies and bispecific antagonists were recovered from serum taken at various times post-injection and subjected to analysis by ELISA. The results indicate both Bi-LT-1 and Bi-LT-3 have similar pharmacokinetics as compared to the anti-LAG3 parental antibody and to the benchmark antibody, with half-lives (T½) of 5-6 days.

Figure 36A:
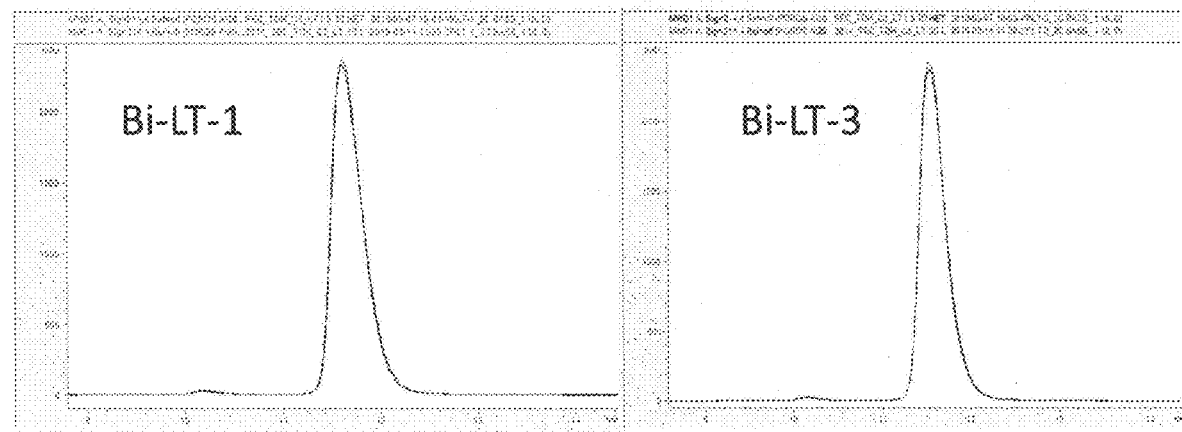
FIG. 36A shows a size exclusion chromatography (SEC) profile of Bi-LT-1 and Bi-LT-3 showing homogeneity and good stability at 4° C. after 7 days.
Figure 36B:
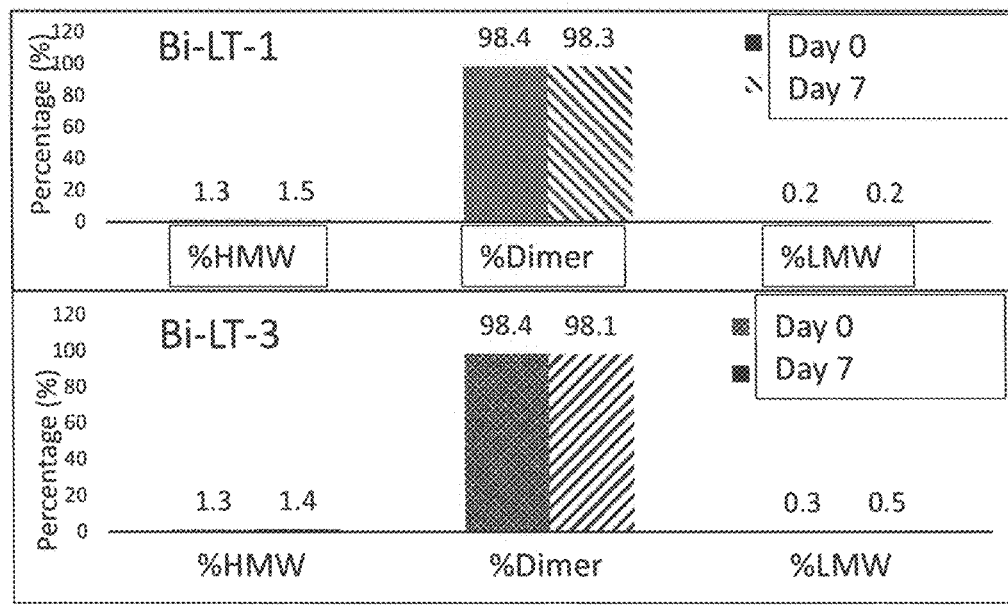
FIG. 36B shows a size-exclusion ultra-high performance liquid chromatography (SE-UHPLC) analysis illustrating species homogeneity of protein A purified Bi-LT-1 and Bi-LT-3, as reflected in low levels of high molecular weight (HMW) species at Day 0 and Day 7 (1.3%, 1.5% respectively for Bi-LT-1 and 1.3%, 1.4%, respectively for Bi-LT-3) and low molecular weight (LMW) species at Day 0 and Day 7 (0.2%, 0.2%, respectively for Bi-LT-1 and 0.3%, 0.5%, respectively for Bi-LT-3) in comparison to dimer species at Day 0 and Day 7 (98.4%, 98.3%, respectively for Bi-LT-1 and 98.4%, 98.1%, respectively for Bi-LT-3).

To evaluate species homogeneity and stability of protein A purified Bi-LT-1 and Bi-LT-3, a size exclusion chromatography (SEC) profile of Bi-LT-1 and Bi-LT-3 was generated as described above. The results of this analysis in FIG. 36A are consistent with both of the extended scfv linkers creating species homogeneity and good stability after 7 days at 4° C. FIG. 36B shows a size-exclusion ultra-high performance liquid chromatography (SE-UHPLC) analysis carried out as described above. The results from this analysis are consistent with the species homogeneity observed in FIG. 36A, as reflected in low levels of high molecular weight (HMW) species at Day 0 and Day 7 (1.3%, 1.5%, respectively for Bi-LT-1 and 1.3%, 1.4%, respectively for Bi-LT-3) and low molecular weight (LMW) species at Day 0 and Day 7 (0.2%, 0.2%, respectively, for Bi-LT-1 and 0.3%, 0.5%, respectively for Bi-LT-3) in comparison to dimer species at Day 0 and Day 7 (98.4%, 98.3%, respectively for Bi-LT-1 and 98.4%, 98.1%, respectively for Bi-LT-3).

Figure 37A:
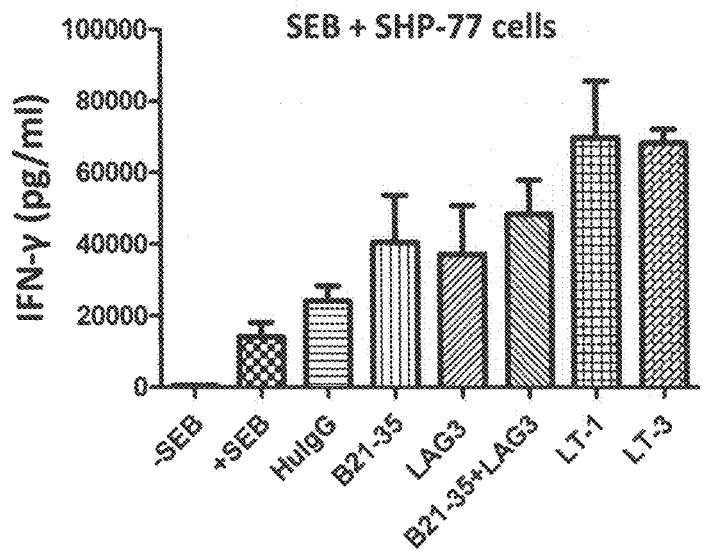
FIGS. 37A-37B show IFN-7 production from human PBMCs stimulated with Staphylococcal enterotoxin B (SEB; lanes 2-8) or not stimulated with SEB (lane 1) in the presence of SHP-77 cells (FIG. 37A) or H358 cells (FIG. 37B), followed by incubation with: no antibody (lanes 1, 2); human IgG (lane 3); parental anti-TIGIT B21-35 mAb (lane 4); parental anti-LAG-3 2L2A.1 mAb (lane 5); parental mAbs, anti-TIGIT B21-35 and anti-LAG-3 2L2A.1 mAb (lane 6); Bi-LT-1 (lane 7); and Bi-LT-3 (lane 8).
Figure 37B:
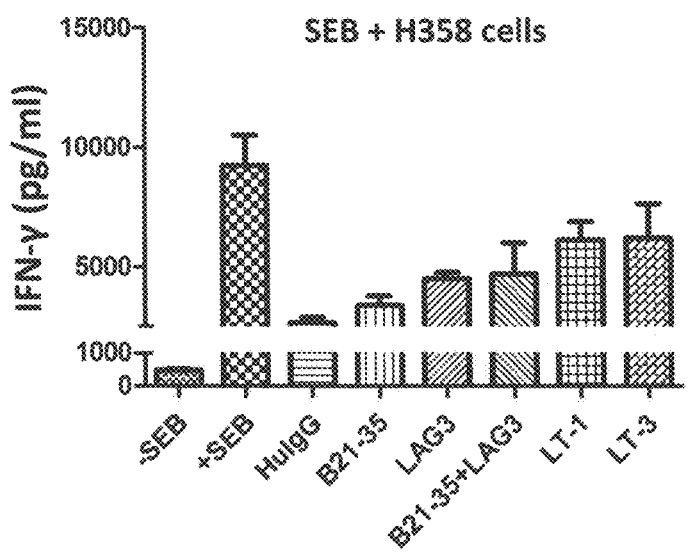

To evaluate the ability of Bi-LT-1 and Bi-LT-3 to induce IFN-7 production, human PBMCs were stimulated with 100 ng/ml SEB in the presence of either SHP-77 cells (FIG. 37A) or H358 cells (FIG. 37B) to provide an immune suppressive signal. Human IgG control (lane 3), anti-TIGIT mAb (B21-35) alone (lane 4), anti-LAG-3 mAb alone (lane 5), a combination of anti-TIGIT mAb and anti-LAG-3 mAb (lane 6), Bi-LT-1 (lane 7), or Bi-LT-3 (lane 8) were then added to rescue T cell function (FIGS. 37A, 37B). 4 days later, cell culture supernatants were collected and examined for IFN-γ level by ELISA. The results of these analyses in FIGS. 37A and 37B show that LT-1 and LT-3 are more potent than the combination of parental TIGIT and LAG-3 antibodies.

Figure 38:
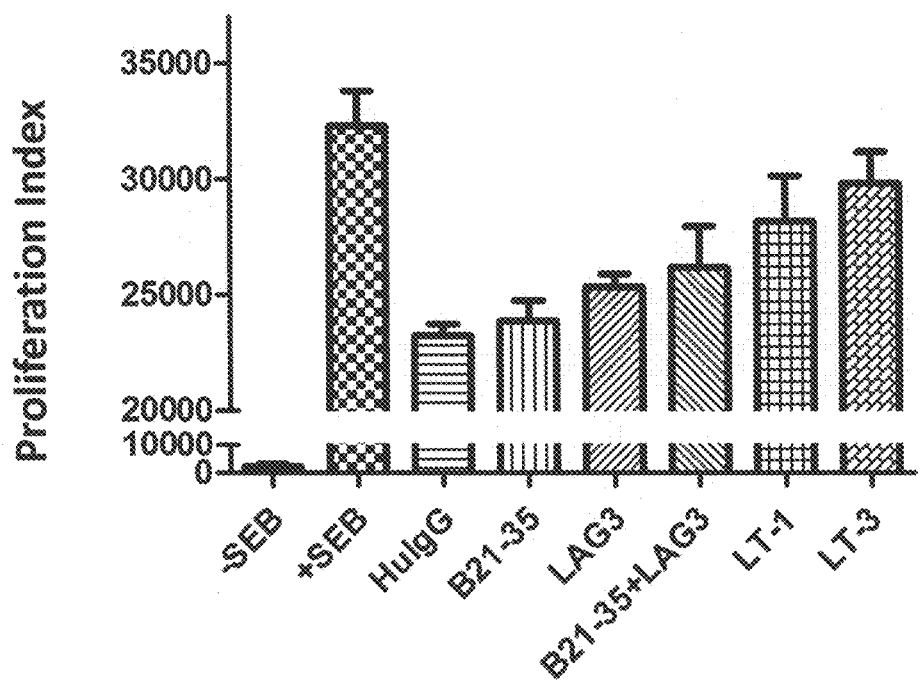
FIG. 38 shows the proliferation of CD4 T cells from human PBMCs stimulated with SEB in the presence of SHP-77 cells (lanes 2-8) and human IgG control (lane 3), anti-TIGIT mAb B21-35 (lane 4), anti-LAG-3 mAb (lane 5), the combination of anti-TIGIT mAb and anti-LAG-3 mAb (lane 6), Bi-LT-1 (lane 7) or Bi-LT-3 (lane 8).

FIG. 38 shows an evaluation of the ability of Bi-LT-1 and Bi-LT-3 to induce proliferation of CD4 T cells. Human PMBC were labeled with CSFE and then stimulated with 100 ng/ml SEB, in the presence of SHP-77 cells to provide immune suppressive signal. 128 nM human IgG control (lane 3), anti-TIGIT mAb B21-35 (lane 4), anti-LAG-3 mAb (lane 5), the combination of anti-TIGIT mAb and anti-LAG-3 mAb (lane 6), Bi-LT-1 (lane 7) or Bi-LT-3 (lane 8) were used to rescue T cell function. 5 days later, loss of CFSE signal on CD4 T cells was quantified by FACS to determine the Proliferation Index. Similar to the increased stimulation of IFNγ over the parental antibodies and the combination of the 2 parental antibodies, both Bi-LT-1 and Bi-LT-3 have increased ability to stimulate proliferation of human CD4 T cells.

The above description is for the purpose of teaching a person of ordinary skill in the art how to practice the present invention and is not intended to detail all those obvious modifications and variations which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A polynucleotide encoding a bispecific antagonist, wherein the bispecific antagonist comprises a first targeting domain and a second targeting domain:

wherein the first targeting domain binds specifically to human LAG-3 and comprises:

(1) an immunoglobulin HCVR comprising three HCDRs: HCDR1, HCDR2 and HCDR3, wherein the HCDR 1 comprises an amino acid sequence selected from the group consisting of SEQ ID NOS: 163, 166 and 169, wherein the HCDR2 comprises an amino acid sequence selected from the group consisting of SEQ ID NOS: 164, 167 and 170, and wherein the HCDR3 comprises an amino acid sequence selected from the group consisting of SEQ ID NOS: 165, 168 and 171; and (2) an immunoglobulin LCVR comprising three LCDRs: LCDR1, LCDR2 and LCDR3, wherein the LCD R 1 comprises an amino acid sequence selected from the group consisting of SEQ ID NOS: 172, 175 and 177, wherein the LCDR 2 comprises an amino acid sequence selected from the group consisting of SEQ ID NOS: 173 and 178, and wherein the LCDR 3 comprises an amino acid sequence selected from the group consisting of SEQ ID NOS; 174, 176 and 179.

2. The polynucleotide of claim 1, wherein the second targeting domain of the bispecific antagonist binds specifically to human TIGIT.

3. The polynucleotide of claim 2, wherein the second targeting domain the bispecific antagonist comprises:

(1) an immunoglobulin HCVR comprising three HCDRs: HCDR1, HCDR2 and HCDR3, wherein the HCDR 1 comprises an amino acid sequence selected from the group consisting of SEQ ID NOS: 1, 6, 11, 15, 17, 20 and 23, wherein the HCDR2 comprises an amino acid sequence selected from the group consisting of SEQ ID NOS: 2, 4, 7, 9, 12, 13, 16, 18, 21 and 24, and wherein the HCDR 3 comprises an amino acid sequence selected from the group consisting of SEQ ID NOS: 3, 5, 8, 10, 14, 19, 22 and 25; and (2) an immunoglobulin LCVR comprising three LCDRs: LCDR1, LCDR2 and LCDR3, wherein the LCD R 1 comprises an amino acid sequence selected from the group consisting of SEQ ID NOS: 26, 29, 31, 33, 35, 39, 42 and 45, wherein the LCDR 2 comprises an amino acid sequence selected from the group consisting of SEQ ID NOS: 27, 30, 36, 37, 40, 43 and 46, and wherein the LCDR 3 comprises an amino acid sequence selected from the group consisting of SEQ ID NOS: 28, 32, 34, 38, 41, 44 and 47.

4. The polynucleotide of claim 3, wherein the second targeting domain the bispecific antagonist comprises an HCDR 1 comprising the amino acid sequence of SEQ ID NO:23, an HCDR2 comprising the amino acid sequence of SEQ ID NO:24, an HCDR 3 comprising the amino acid sequence of SEQ ID NO:25, an LCDR 1 comprising the amino acid sequence of SEQ ID NO:45, an LCDR2 comprising the amino acid sequence of SEQ ID NO:46, and an LCDR3 comprising the amino acid sequence of SEQ ID NO:47.

5. The polynucleotide of claim 4, wherein the second targeting domain comprises a heavy chain variable region comprising the amino acid sequence of SEQ ID NO: 66 and a light chain variable region comprising the amino acid sequence of SEQ ID NO:67.

6. The polynucleotide of claim 1, wherein the second targeting domain binds specifically to human PD-1.

7. The polynucleotide of claim 6, wherein the second targeting domain comprises:

(1) an immunoglobulin HCVR comprising three complementarity determining regions (HCDRs): HCDR1, HCDR2 and HCDR3, wherein the HCDR1 comprises an amino acid sequence selected from the group consisting of SEQ ID NOS: 68, 71, 74, 76 and 79, wherein the HCDR 2 comprises an amino acid sequence selected from the group consisting of SEQ ID NOS: 69, 72, 77 and 80, and wherein the HCDR 3 comprises an amino acid sequence selected from the group consisting of SEQ ID NOS: 70, 73, 75, 78 and 81; and (2) an immunoglobulin LCVR comprising three complementarity determining regions (LCDRs): LCDR1, LCDR 2 and LCDR3, wherein the LCDR 1 comprises an amino acid sequence selected from the group consisting of SEQ ID NOS: 82, 85, 88, 89, 90 and 93, wherein the LCDR2 comprises an amino acid sequence selected from the group consisting of SEQ ID NOS: 83, 86.91 and 94, and wherein the LCDR 3 comprises an amino acid sequence selected from the group consisting of SEQ ID NOS: 84, 87, 92 and 95.

8. The polynucleotide of claim 7, wherein the second targeting domain comprises an HCDR 1 comprising the amino acid sequence of SEQ ID NO:76, an HCDR2 comprising the amino acid sequence oaf SEQ ID NO:77, an HCDR 3 comprising the amino acid sequence of SEQ ID NO:78, a LCDR 1 comprising the amino acid sequence of SEQ ID NO: 90, a LCDR 2 comprising the amino acid sequence of SEQ ID NO:91, and a LCDR3 comprising the amino acid sequence of SEQ ID NO:92.

9. The polynucleotide of claim 8, wherein the second targeting domain comprises a heavy chain variable region comprising the amino acid sequence of SEQ ID NO: 104 and a light chain variable region comprising the amino acid sequence of SEQ ID NO: 105.

10. The polynucleotide of claim 7, wherein the second targeting domain comprises an HCDR 1 comprising the amino acid sequence of SEQ ID NO:79, an HCDR2 comprising the amino acid sequence of SEQ ID NO: 80, an HCDR3 comprising the amino acid sequence of SEQ ID NO:81, a LCDR 1 comprising the amino acid sequence of SEQ ID NO: 93, a LCDR 2 comprising the amino acid sequence of SEQ ID NO;94, and a LCDR3 comprising the amino acid sequence of SEQ ID NO:95.

11. The polynucleotide of claim 10, wherein the second targeting domain comprises a heavy chain variable region comprising the amino acid sequence f SEQ ID NO: 106 and a light chain variable region comprising the amino acid sequence of SEQ ID NO: 107.

12. The polynucleotide of claim 1, wherein the second targeting domain binds specifically to human PD-L1.

13. The polynucleotide of claim 12, wherein the second targeting domain comprises:

(1) an immunoglobulin HCVR comprising three complementarity determining regions (HCDRs): HCDR1, HCDR2 and HCDR3, wherein the HCDR 1 comprises an amino acid sequence selected from the group consisting of SEQ ID NOS: 108, 111, 117 and 120, wherein the HCDR 2 comprises an amino acid sequence selected from the group consisting SEQ ID NOS: 109, 112, 114, 116, 118, 121 and 125, and wherein the HCDR 3 comprises an amino acid sequence selected from the group consisting of SEQ ID NOS: 110, 113, 115, 119 and 122; and (2) an immunoglobulin LCVR comprising three LCDRs: LCDR1, LCDR2 and LCDR3, wherein the LCD R 1 comprises an amino acid sequence selected from the group consisting of SEQ ID NOS: 123, 126, 130, 133 and 136, wherein the LCDR2 comprises an amino acid sequence selected from the group consisting of SEQ ID NOS: 126, 127, 131, 134 and 137, and wherein the LCD R 3 comprises an amino acid sequence selected from the group consisting of SEQ ID NOS: 125, 128, 129, 132, 135 and 138.

14. The polynucleotide of claim 13, wherein the second targeting domain comprises an HCDR 1 comprising the amino acid sequence of SEQ ID NO:111, an HCDR2 comprising the amino acid sequence of SEQ ID NO:114, an HCDR3 comprising the amino acid sequence of SEQ ID NO:115, a LCDR1 comprising the amino acid sequence of SEQ ID NO: 123, a LCDR2 comprising the amino acid sequence of SEQ ID NO: 124, and a LCDR3 comprising the amino acid sequence of SEQ ID NO:125.

15. The polynucleotide of claim 14, wherein the second targeting domain comprises a heavy chain variable region comprising the amino acid sequence of SEQ ID NO: 153 and a light chain variable region comprising the amino acid sequence of SEQ ID NO: 154.

16. An expression vector, comprising the polynucleotide of claim 1.

17. The expression vector of claim 16, wherein the expression vector is a non-viral vector.

18. The expression vector of claim 16, wherein the expression vector is a viral vector.

19. A method of treating a cell proliferative disorder in a subject, comprising: administering to a subject in need thereof an effective amount of the polynucleotide of claim 1.

20. A method of treating a cell proliferative disorder in a subject, comprising: administering to a subject in need thereof an effective amount of the expression vector of claim 16.

\* \* \* \* \*